US012012395B2

(12) United States Patent
Hunt et al.

(10) Patent No.: US 12,012,395 B2
(45) Date of Patent: *Jun. 18, 2024

(54) PYRIDAZINONE COMPOUNDS AND USES THEREOF

(71) Applicant: Edgewise Therapeutics, Inc., Boulder, CO (US)

(72) Inventors: Kevin Hunt, Boulder, CO (US); Kevin Koch, Boulder, CO (US); Alan Russell, Boulder, CO (US); Stephen Schlachter, Boulder, CO (US); Paul Winship, Cambridge (GB); Chris Steele, Cambridge (GB)

(73) Assignee: Edgewise Therapeutics, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/345,909

(22) Filed: Jun. 11, 2021

(65) Prior Publication Data

US 2022/0106291 A1 Apr. 7, 2022

Related U.S. Application Data

(63) Continuation of application No. 17/088,469, filed on Nov. 3, 2020, now Pat. No. 11,091,464, which is a continuation of application No. PCT/US2019/060157, filed on Nov. 6, 2019.

(60) Provisional application No. 62/756,553, filed on Nov. 6, 2018.

(51) Int. Cl.
| C07D 401/14 | (2006.01) |
| C07D 405/14 | (2006.01) |
| C07D 413/06 | (2006.01) |
| C07D 413/14 | (2006.01) |
| C07D 417/06 | (2006.01) |
| C07D 417/14 | (2006.01) |

(52) U.S. Cl.
CPC ......... C07D 401/14 (2013.01); C07D 405/14 (2013.01); C07D 413/06 (2013.01); C07D 413/14 (2013.01); C07D 417/06 (2013.01); C07D 417/14 (2013.01)

(58) Field of Classification Search
CPC .. C07D 401/14; C07D 413/14; C07D 417/14; C07D 413/06; C07D 405/14; C07D 417/06
USPC .................................................... 514/252.02
See application file for complete search history.

(56) References Cited

U.S. PATENT DOCUMENTS

| 5,698,554 | A | 12/1997 | Ishida et al. |
| 5,753,642 | A | 5/1998 | Michelotti et al. |
| 5,846,514 | A | 12/1998 | Foster et al. |
| 6,005,117 | A | 12/1999 | Wehner et al. |
| 6,334,997 | B1 | 1/2002 | Foster et al. |
| 7,763,617 | B2 | 7/2010 | Kohno et al. |
| 8,445,489 | B2 | 5/2013 | Stieber et al. |
| 8,580,781 | B2 | 11/2013 | Dorsch et al. |
| 8,604,036 | B2 | 12/2013 | Dorsch et al. |
| 8,673,916 | B2 | 3/2014 | Bacon et al. |
| 9,566,310 | B2 | 2/2017 | Burkin et al. |
| 11,091,464 | B2 * | 8/2021 | Hunt ................... C07D 413/06 |
| 11,236,065 | B2 | 2/2022 | Hunt et al. |
| 11,390,606 | B2 | 7/2022 | Hunt et al. |
| 2006/0189621 | A1 | 8/2006 | Sato et al. |
| 2010/0179148 | A1 | 7/2010 | Stieber et al. |
| 2012/0289698 | A1 | 11/2012 | Ashcraft et al. |
| 2014/0072536 | A1 | 3/2014 | Burkin et al. |
| 2014/0094457 | A1 | 4/2014 | Gardner et al. |
| 2015/0376167 | A1 | 12/2015 | Jorand-Lebrun et al. |
| 2018/0280385 | A1 | 10/2018 | Wollin et al. |
| 2018/0303821 | A1 | 10/2018 | Sonner et al. |
| 2019/0248779 | A1 | 8/2019 | Parks et al. |
| 2019/0256474 | A1 | 8/2019 | Parks et al. |
| 2021/0130327 | A1 | 5/2021 | Hunt et al. |
| 2022/0081410 | A1 | 3/2022 | Hunt et al. |
| 2023/0048816 | A1 | 2/2023 | Hunt et al. |
| 2023/0150977 | A1 | 5/2023 | Koch et al. |
| 2023/0159513 | A1 | 5/2023 | Koch et al. |

FOREIGN PATENT DOCUMENTS

| CN | 103570730 A | 2/2014 |
| CN | 108947912 A | 12/2018 |
| DE | DD-286354 A5 | 1/1991 |
| DE | 102005057924 A1 | 6/2007 |
| EP | 2611798 B1 | 4/2015 |
| EP | 3877052 A1 | 9/2021 |
| EP | 3877367 A1 | 9/2021 |
| EP | 3877376 A1 | 9/2021 |
| EP | 4149465 A1 | 3/2023 |
| EP | 4149466 A1 | 3/2023 |

(Continued)

OTHER PUBLICATIONS

Co-pending U.S. Appl. No. 18/053,332, inventor Russell; Alan, filed on Nov. 7, 2022.
Co-pending U.S. Appl. No. 18/053,343, inventor Russellalan, filed on Nov. 7, 2022.
Co-pending U.S. Appl. No. 18/053,350, inventor Russellalan, filed on Nov. 7, 2022.
Dean. Recent Advances in the Synthesis and Applications of Radiolabeled Compounds for Drug Discovery and Development. In: Curr. Pharm. Des., 6(10):110 (2000) (Preface only).
English machine translation for WO 2017/02798 (Feb. 23, 17). 49 pages.

(Continued)

*Primary Examiner* — Kahsay Habte
(74) *Attorney, Agent, or Firm* — Wilson Sonsini Goodrich & Rosati

(57) ABSTRACT

Substituted pyridazinone compounds, conjugates, and pharmaceutical compositions for use in the treatment of neuromuscular diseases, such as Duchenne Muscular Dystrophy (DMD), are disclosed herein. The disclosed compounds are useful, among other things, in the treating of DMD and modulating inflammatory inhibitors IL-1, IL-6 or TNF-α.

39 Claims, 8 Drawing Sheets

(56) References Cited

FOREIGN PATENT DOCUMENTS

| | | |
|---|---|---|
| EP | 4149467 A1 | 3/2023 |
| EP | 4149620 A1 | 3/2023 |
| EP | 4149621 A1 | 3/2023 |
| JP | S6140270 A | 2/1986 |
| JP | 2009518323 A | 5/2009 |
| JP | 2010528994 A | 8/2010 |
| JP | 2010528995 A | 8/2010 |
| JP | 2013525376 A | 6/2013 |
| JP | 2015527409 A | 9/2015 |
| JP | 2016508505 A | 3/2016 |
| JP | WO2020017587 A1 | 8/2021 |
| JP | 2022506685 A | 1/2022 |
| JP | 2022506686 A | 1/2022 |
| JP | 2022506687 A | 1/2022 |
| KR | 20150123937 A | 11/2015 |
| WO | WO-0194319 A1 | 12/2001 |
| WO | WO-2006095666 A1 | 9/2006 |
| WO | WO-2007044796 A2 | 4/2007 |
| WO | WO-2008103277 A2 | 8/2008 |
| WO | WO-2008145242 A1 | 12/2008 |
| WO | WO-2009006959 A1 | 1/2009 |
| WO | WO-2009024221 A1 | 2/2009 |
| WO | WO-2010048149 A2 | 4/2010 |
| WO | WO-2011133882 A1 | 10/2011 |
| WO | WO-2011133888 A1 | 10/2011 |
| WO | WO-2012021707 A2 | 2/2012 |
| WO | WO-2013057101 A1 | 4/2013 |
| WO | WO-2014031928 A2 | 2/2014 |
| WO | WO-2014096965 A2 | 6/2014 |
| WO | WO-2014121931 A1 | 8/2014 |
| WO | WO-2017028798 A1 | 2/2017 |
| WO | WO-2018081377 A1 | 5/2018 |
| WO | WO-2018081378 A1 | 5/2018 |
| WO | WO-2018081381 A1 | 5/2018 |
| WO | WO-2018187553 A1 | 10/2018 |
| WO | WO-2019043123 A1 | 3/2019 |
| WO | WO-2019084499 A1 | 5/2019 |
| WO | WO-2019222633 A1 | 11/2019 |
| WO | WO-2019236625 A1 | 12/2019 |
| WO | WO-2020097258 A1 | 5/2020 |
| WO | WO-2020097265 A1 | 5/2020 |
| WO | WO-2020097266 A1 | 5/2020 |
| WO | WO-2021231546 A1 | 11/2021 |
| WO | WO-2021231565 A1 | 11/2021 |
| WO | WO-2021231572 A1 | 11/2021 |
| WO | WO-2021231615 A1 | 11/2021 |
| WO | WO-2021231630 A1 | 11/2021 |
| WO | WO-2023091606 | 5/2023 |
| WO | WO2024055007 A1 | 3/2024 |

OTHER PUBLICATIONS

Evans. Synthesis of radiolabeled compounds. J Radio anal Chem 64(1-2):9-32 (1981).

Fedorak et al. A novel colon-specific steroid prodrug enhances sodium chloride absorption in rat colitis. Am. J. Physiol. 269:G210-218 (1995).

Fieser, et al. Fieser and Fieser's Reagents for Organic Synthesis. John Wiley and Sons. 1994.

George W.; Varma, Rajender S., The Synthesis of Radiolabeled Compounds via Organometallic Intermediates, Tetrahedron, 1989, 45(21), 6601-21.

Greene, et al. Protective Groups in Organic Synthesis. John Wiley & Sons, 1991.

Higuchi et al. Pro-drugs as Novel Delivery Systems, vol. 14 of the A.C.S. Symposium Series; and in Bioreversible Carriers in Drug Design, ed. Edward B. Roche, American Pharmaceutical Association and Pergamon Press (1987).

Hochhaus et al. A selective HPLC/RIA for dexamethasone and its prodrug dexamethasone- 21-sulphobenzoate sodium in biological fluids. Biomed. Chrom. 6:283-286 (1992).

Hudkins, Robert L. et al., Discovery and characterization of 6-{4-[3-(R)-2-Methylpyrrolidin-1-yl) propoxy]phenyl}-2 H -pyridazin-3-one(CEP-26401, Irdabisant): A potent, selective histamine H 3 Receptor inverse agonist, Journal of Medicinal Chemistry, vol. 54, No. 13, Jul. 14, 2011, pp. 4781-4792, XP055829893.

Larock, A. Comprehensive Organic Transformations. VCH Publishers, (1989).

Larsen et al. Prodrug forms for the sulfonamide group. I. Evaluation of N-acyl derivatives, N-sulfonylaminides, N-sulfonylsulfilimines and sulfonylureas as possible prodrug derivatives. Int. J. Pharmaceutics 37:87-95 (1987).

Larsen, et al. Prodrug forms for the sulfonamide group. Part 2. Water-soluble amino acid derivatives of N-Methyl-sulfonamides as possible prodrugs. Int. J. Pharm. 1988; 47:103-110.

Lu et al. Optimization and Synthesis of Pyridazinone Derivatives as Novel Inhibitors of Hepatitis B Virus by Inducing Genome-free Capsid Formation. ACS Infect. Dis. 2017, 3, 199-205. Published Dec. 18, 2016.

Lu et al. Optimization and Synthesis of pyridazinone derivatives as novel inhibitors of Hepatitis B virus by inducing genome-free capsid formation. Supporting information for infect. Dis. (3, 199-205), P.S1-S68. (2016).

McKinstry-Wu, et al., Discovery of a Novel General Anesthetic Chemotype Using High- throughput Screening. Anesthesiology, 2015; 122:325-33.

McLoed et al. A Glucocorticoid Prodrug Facilitates Normal Mucosal Function in Rat Colitis Without Adrenal Suppression. Gastroenterol 106:405-413 (1994).

National Center for Biotechnology Information (2022). PubChem Compound Summary for CID 7660155. Retrieved Mar. 10, 2022 from https://pubchem.ncbi.nlm.nih.gov/compound/7660155.

National Center for Biotechnology Information (2022). PubChem Compound Summary for CID 7662323. Retrieved Mar. 10, 2022 from https://pubchem.ncbi.nlm.nih.gov/compound/7662323.

National Center for Biotechnology Information (2022). PubChem Compound Summary for CID 8698959. Retrieved Mar. 10, 2022 from https://pubchem.ncbi.nlm.nih.gov/compound/8698959.

National Center for Biotechnology Information (2022). PubChem Compound Summary for CID 8698960. Retrieved Mar. 10, 2022 from https://pubchem.ncbi.nlm.nih.gov/compound/8698960.

Paquette, et al. Encyclopedia of Reagents for Organic Synthesis. John Wiley and Sons (1995).

PCT/US2019/060148 International Search Report and Written Opinion dated Apr. 2, 2020.

PCT/US2019/060155 International Search Report and Written Opinion dated Mar. 5, 2020.

PCT/US2019/060157 International Search Report and Written Opinion dated Mar. 5, 2020.

PCT/US2021/031952 International Search Report and Written Opinion dated Nov. 18, 2021.

PCT/US2021/031979 International Search Report and Written Opinion dated Aug. 13, 2021.

PCT/US2021/031989 International Search Report and Written Opinion dated Aug. 13, 2021.

PCT/US2021/032048 International Search Report and Written Opinion dated Aug. 25, 2021.

PCT/US2021/032064 International Search Report and Written Opinion dated Aug. 25, 2021.

PCT/US2022/050313 International Search Report and Written Opinion dated Feb. 8, 2023.

Pitarch et al., Etude chhimque et pharmacologique d'une serie de pyridazones substituees. European Journal of Medicinal Chemistry 9(6): 644-650 (1974).

SG11202104713R Written Opinion Report dated Jan. 4, 2023.

Sinkula et al. Rationale for design of biologically reversible drug derivatives: prodrugs. J. Pharm. Sci. 64:181-210 (1975).

U.S. Appl. No. 17/088,466 Notice of Allowance dated Aug. 26, 2021.

U.S. Appl. No. 17/088,466 Office Action dated May 7, 2021.

U.S. Appl. No. 17/088,468 Notice of Allowance dated Apr. 12, 2022.

U.S. Appl. No. 17/088,468 Office Action dated Aug. 20, 2021.

U.S. Appl. No. 17/088,468 Office Action dated May 5, 2021.

(56) References Cited

OTHER PUBLICATIONS

U.S. Appl. No. 17/088,469 Notice of Allowance dated May 6, 2021.
Yukawa, et al., Design, Synthesis, and biological evaluation of a novel series of peripheral-selective noradrenaline reuptake inhibitors—PArt 3, Bioorganic & Medicinal Chemistry 2016; 24:3716-3726.
Co-pending PCT Application No. PCT/US2023/021739, inventor Koch, Kevin, filed on May 10, 2023.
Cepeda et al., Functional Properties of Faba Bean (Vicia Faba) Protein Flour Dried by Spray Drying and Freeze Drying. Journal of Food Engineering, 36(3):303-310(1998).
Donovan et al., EDG-5506 targets fast skeletal myosin and reduces muscle damage biomarkers in a phase 1 trial in Becker muscular dystrophy (BMD). Neuromuscular Disorders, Elsevier Ltd., vol. 32, Oct. 1, 2022, abstract p. 124.
Liu et al., Pyridazinone Derivatives Displaying Highly Potent and Selective Inhibitory Activities Against C-Met Tyrosine Kinase. European journal of medicinal chemistry, 108:322-333(2016).
Miyaura, et al. Palladium-Catalyzed Cross-Coupling Reactions of Organboron Compounds. Chem. Rev., 1995; 95(7):2457-2483.
PCT/US2023/021739 International Search Report and Written Opinion dated Nov. 26, 2023.
PCT/US2023/073790 International Search Report and Written Opinion dated Dec. 13, 2023.
PubChem CID 56643059 https://pubchem.ncbi.nlm.ni.gov/compound/56643059 Date create: Feb. 29, 2012.
PubChem CID 556643068 https://pubchem.ncbi.nlm.nih.gov/compound/56643068 Date create: Feb. 29, 2012.
PubChem SID 371083532 https://pubchem.ncbi.nlm.nih.gov/substance/371083532 Source: Ambinter, Deposit Date: May 25, 2018, Available, Modify Date: May 25, 2018; CID: 51044092.
PubChem SID 371425619 https://pubchem.ncbi.nlm.nih.gov/substance/371425619 Source: Ambinter, Deposit Date: May 25, 2018, Available, Modify Date: May 25, 2018; CID: 51048704.
Registry (STN)[online], date of retrieval: Nov. 13, 2023: Dec. 7, 2011 RN:1350041-75-6, Jul. 16, 2010. RN: 1232768-39-6, Feb. 26, 2007. RN:923076-66-8, Feb. 23, 2007 RN:922973-89-5.
Salives et al., Solid-Phase Syntheses of 6-Arylpyridazin-3(2H)-Ones. J. Comb. Chem, 3:414-420 (2005).

\* cited by examiner

| | | Component | Stock Concentrations | | Final Concentrations in Specific Buffer | Reaction Concentrations |
|---|---|---|---|---|---|---|
| Total Well Volume (μL) | 50 | | Value | Unit | | |
| Buffer A (μL) | 25 | PM12 Buffer | 10 | x | 1.00 x | 1.00 x |
| | | KCl | 600 | mM | 60.00 mM | 60.00 mM |
| | | BSA | 20 | mg/mL | 0.10 mg/mL | 0.10 mg/mL |
| | | DTT | 1000 | mM | 1.00 mM | 1.00 mM |
| | | PK/LDH | 80 | mM | 0.80 mM | 0.40 mM |
| | | Rabbit Psoas Prep 11 | 5.83 | mg/mL | 0.50 mg/mL | 0.25 mg/mL |
| | | Antifoam | 1.00 | % | 0.01 % | 0.01 % |
| | | Water | | | | |
| Buffer B (μL) | 25 | PM12 Buffer | 10 | x | 1.00 x | 1.00 x |
| | | pCa Solution | 10 | x | 2.00 x | 1.00 x |
| | | KCl | 600 | mM | 60.00 mM | 60.00 mM |
| | | BSA | 20 | mg/mL | 0.10 mg/mL | 0.10 mg/mL |
| | | DTT | 1000 | mM | 1.00 mM | 1.00 mM |
| | | ATP | 100 | mM | 0.10 mM | 0.05 mM |
| | | NADH | 30 | mM | 1.00 mM | 0.50 mM |
| | | PEP | 100 | mM | 3.00 mM | 1.50 mM |
| | | Antifoam | 1.00 | % | 0.01 % | 0.01 % |
| | | Water | | | | |

FIG. 7

| | | Total Well Volume (μL) | 50 | | Number of Wells | 96 | |
|---|---|---|---|---|---|---|---|
| | | Component | Volume per well (μL) | Total Volume (μL) | Prepare Volume (μL) | | |
| Buffer A (μL) | 25 | PM12 Buffer | 2.50 | 240.00 | 312.00 | PM12 Buffer (1 x) |
| | | KCl | 2.50 | 240.00 | 312.00 | KCl (60 mM) |
| | | BSA | 0.13 | 12.00 | 15.60 | BSA (0.1 mg/mL) |
| | | DTT | 0.03 | 2.40 | 3.12 | DTT (1 mM) |
| | | PK/LDH | 0.25 | 24.00 | 31.20 | PK/LDH (0.4 mM) |
| | | Rabbit Psoas Prep 11 | 2.14 | 205.83 | 267.58 | Rabbit Psoas Prep 11 (0.25 mg/mL) |
| | | Antifoam | 0.25 | 24.00 | 31.20 | Antifoam (0.01 %) |
| | | Water | 17.21 | 1651.77 | 2147.30 | Water |
| | | | 25.00 | 2400.00 | 3120.00 | |
| Buffer B (μL) | 25 | PM12 Buffer | 2.50 | 240.00 | 312.00 | PM12 Buffer (1 x) |
| | | pCa Solution | 5.00 | 480.00 | 624.00 | pCa Solution (1 x) |
| | | KCl | 2.50 | 240.00 | 312.00 | KCl (60 mM) |
| | | BSA | 0.13 | 12.00 | 15.60 | BSA (0.1 mg/mL) |
| | | DTT | 0.03 | 2.40 | 3.12 | DTT (1 mM) |
| | | ATP | 0.03 | 2.40 | 3.12 | ATP (0.05 mM) |
| | | NADH | 0.83 | 80.00 | 104.00 | NADH (0.5 mM) |
| | | PEP | 0.75 | 72.00 | 93.60 | PEP (1.5 mM) |
| | | Antifoam | 0.25 | 24.00 | 31.20 | Antifoam (0.01 %) |
| | | Water | 12.99 | 1247.20 | 1621.36 | Water ( ) |
| | | | 25.00 | 2400.00 | 3120.00 | Total |

FIG. 8

PYRIDAZINONE COMPOUNDS AND USES THEREOF

CROSS-REFERENCE

This application is a continuation of U.S. Non-Provisional application Ser. No. 17/088,469, filed Nov. 3, 2020, which is a continuation of International Patent Application No. PCT/US2019/060157, filed Nov. 6, 2019, which claims the benefit of U.S. Provisional Application Ser. No. 62/756,553 filed Nov. 6, 2018, each of which is hereby incorporated herein by reference in its entirety.

BACKGROUND OF THE INVENTION

Skeletal muscle is the largest organ system in the human body, serving two primary purposes. The first is force production to enable muscle contraction, locomotion, and postural maintenance; the second is glucose, fatty acid and amino acid metabolism. The contraction of skeletal muscle during every-day activity and exercise is naturally connected to muscle stress, breakdown and remodeling which is important for muscle adaptation. In individuals with neuromuscular conditions, such as Duchenne Muscular Dystrophy (DMD), muscle contractions lead to continued rounds of amplified muscle breakdown that the body struggles to repair. Eventually, as patients age, a pathophysiological process emerges that leads to excess inflammation, fibrosis, and fatty deposit accumulation in the muscle, portending a steep decline in physical function and contribution to mortality.

DMD is a genetic disorder affecting skeletal muscle and is characterized by progressive muscle degeneration and weakness. There remains a need for treatments that reduce muscle breakdown in patients with neuromuscular conditions such as DMD.

SUMMARY OF THE INVENTION

The present disclosure generally relates to substituted pyridazinone compounds or salts of Formula (I), (Ia), (Ib), (Ic), (Id), (Ie), (II), or (IIa) and pharmaceutical compositions thereof. The substituted pyridazinone compounds or salts of Formula (I), (Ia), (Ib), (Ic), (Id), (Ie), (II), or (IIa) disclosed herein may be used to treat or prevent neuromuscular diseases. In some embodiments, a compound or salt of Formula (I), (Ia), (Ib), (Ic), (Id), (Ie), (II), or (IIa) is an inhibitor of skeletal muscle contraction. In some embodiments, a compound or salt of Formula (I), (Ia), (Ib), (Ic), (Id), (Ie), (II), or (IIa) is an inhibitor of myosin. In some embodiments, a compound or salt of Formula (I), (Ia), (Ib), (Ic), (Id), (Ie), (II), or (IIa) is an inhibitor of skeletal muscle myosin II.

In some aspects, methods of treating a movement disorder may comprise administering a compound or salt of any one of Formula (I), (Ia), (Ib), (Ic), (Id), (Ie), (II), (IIa), (III), or (III') to inhibit skeletal muscle myosin II. In some embodiments, said movement disorder comprises muscle spasticity. In some embodiments, said muscle spasticity may be selected from spasticity associated with multiple sclerosis, Parkinson's disease, Alzheimer's disease, or cerebral palsy, or injury, or a traumatic event such as stroke, traumatic brain injury, spinal cord injury, hypoxia, meningitis, encephalitis, phenylketonuria, or amyotrophic lateral sclerosis.

The disclosure provides compound and salts thereof for use in treating disease. In certain aspects, the disclosure provides a compound or salt of Formula (I), (Ia), (Ib), (Ic), (Id), (II) or (IIa), pharmaceutical compositions thereof as well as methods of use in the treatment of disease.

In certain aspects, the disclosure provides a compound represented by Formula (I):

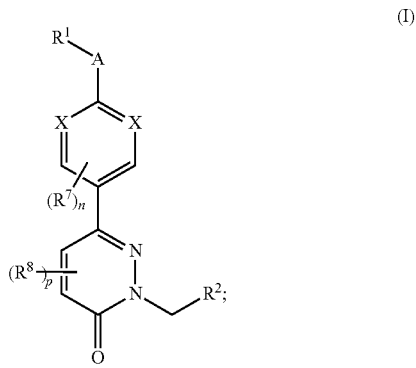

or a salt thereof, wherein:

each X is independently selected from $C(R^3)$, N, and $N^+(-O^-)$ wherein at least one X is N or $N^+(-O^-)$;

A is selected from $-O-$, $-NR^4-$, $-CR^5R^6-$, $-S-$, $-S(O)-$, and $-S(O)_2-$;

$R^1$ is selected from:

$C_{1-6}$ alkyl, $C_{2-6}$ alkenyl, and $C_{2-6}$ alkynyl, each of which is optionally substituted with one or more substituents independently selected from halogen, $-OR^{10}$, $-SR^{10}$, $-N(R^{10})_2$, $-C(O)R^{10}$, $-C(O)N(R^{10})_2$, $-N(R^{10})C(O)R^{10}$, $-C(O)OR^{10}$, $-OC(O)R^{10}$, $-N(R^{10})C(O)N(R^{10})_2$, $-OC(O)N(R^{10})_2$, $-N(R^{10})C(O)OR^{10}$, $-S(O)R^{10}$, $-S(O)_2R^{10}$, $-NO_2$, $=O$, $=S$, $=N(R^{10})$, $-CN$, $C_{3-10}$ carbocycle and 3- to 10-membered heterocycle, wherein the $C_{3-10}$ carbocycle and 3- to 10-membered heterocycle are each optionally substituted with one or more $R^9$; and $C_{3-10}$ carbocycle and 3- to 10-membered heterocycle, each of which is optionally substituted with one or more substituents independently selected from halogen, $-OR^{10}$, $-SR^{10}$, $-N(R^{10})_2$, $-C(O)R^{10}$, $-C(O)N(R^{10})_2$, $-N(R^{10})C(O)R^{10}$, $-N(R^{10})C(O)N(R^{10})_2$, $-OC(O)N(R^{10})_2$, $-N(R^{10})C(O)OR^{10}$, $-C(O)OR^{10}$, $-OC(O)R^{10}$, $-S(O)R^{10}$, $-S(O)_2R^{10}$, $-NO_2$, $=O$, $=S$, $=N(R^{10})$, $-CN$, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^9$; or $R^1$ together with $R^3$ form a 5- to 10-membered heterocycle or $C_{5-10}$ carbocycle, wherein the 5- to 10-membered heterocycle or $C_{5-10}$ carbocycle is optionally substituted with one or more $R^9$; or $R^1$ together with $R^5$ form a 3- to 10-membered heterocycle or $C_{3-10}$ carbocycle, wherein the 3- to 10-membered heterocycle or $C_{3-10}$ carbocycle is optionally substituted with one or more $R^9$; or $R^1$ together with $R^4$ form a 3- to 10-membered heterocycle, wherein the 3- to 10-membered heterocycle is optionally substituted with one or more $R^9$;

$R^2$ is a heteroaryl optionally substituted with one or more substituents independently selected from:

halogen, $-OR^{10}$, $-SR^{10}$, $-N(R^{10})_2$, $-C(O)R^{10}$, $-C(O)N(R^{10})_2$, $-N(R^{10})C(O)R^{10}$, $-N(R^{10})C(O)N(R^{10})_2$, $-OC(O)N(R^{10})_2$, $-N(R^{10})C(O)OR^{10}$, $-C(O)OR^{10}$, $-OC(O)R^{10}$, $-S(O)R^{10}$, $-S(O)_2R^{10}$, $-NO_2$, =O, =S, =N($R^{10}$), and —CN; and when $R^2$ is pyridyl or pyrimidyl, a substituent on a nitrogen atom of the pyridyl or pyrimidyl is optionally further selected from —O;

$C_{1-6}$ alkyl, $C_{2-6}$ alkenyl, and $C_{2-6}$ alkynyl, each of which is optionally substituted with one or more substituents independently selected from halogen, —$OR^{10}$, —$SR^{10}$, —N($R^{10}$)$_2$, —C(O)$R^{10}$, —C(O)N($R^{10}$)$_2$, —N($R^{10}$)C(O)$R^{10}$, —N($R^{10}$)C(O)N($R^{10}$)$_2$, —OC(O)N($R^{10}$)$_2$, —N($R^{10}$)C(O)O$R^{10}$, —C(O)O$R^{10}$, —OC(O)$R^{10}$, —S(O)$R^{10}$, —S(O)$_2R^{10}$, —NO$_2$, =O, =S, =N($R^{10}$), —CN, $C_{3-10}$ carbocycle and 3- to 10-membered heterocycle, wherein the $C_{3-10}$ carbocycle and 3- to 10-membered heterocycle are each optionally substituted with one or more $R^9$; and $C_{3-10}$ carbocycle and 3- to 10-membered heterocycle, each of which is optionally substituted with one or more $R^9$;

$R^3$, $R^5$, and $R^6$ are each independently selected from:
hydrogen, halogen, —$OR^{10}$, —$SR^{10}$, —N($R^{10}$)$_2$, —NO$_2$, and —CN; and $C_{1-6}$ alkyl optionally substituted with one or more substituents independently selected from halogen, —$OR^{10}$, —$SR^{10}$, —N($R^{10}$)$_2$, —NO$_2$, and —CN; or $R^3$ together with $R^1$ form a 5- to 10-membered heterocycle or $C_{5-10}$ carbocycle, wherein the 5- to 10-membered heterocycle or $C_{5-10}$ carbocycle is optionally substituted with one or more $R^9$; or $R^5$ together with $R^1$ form a 3- to 10-membered heterocycle or $C_{3-10}$ carbocycle, wherein the 3- to 10-membered heterocycle or $C_{3-10}$ carbocycle is optionally substituted with one or more $R^9$;

$R^4$ is independently selected from:
hydrogen; and
$C_{1-6}$ alkyl optionally substituted with one or more substituents independently selected from halogen, —$OR^{10}$, —$SR^{10}$, —N($R^{10}$)$_2$, —NO$_2$, and —CN; or $R^4$ together with $R^1$ form a 3- to 10-membered heterocycle, which is optionally substituted with one or more $R^9$;

$R^7$ and $R^8$ are independently selected from:
halogen, —$OR^{10}$, —$SR^{10}$, —N($R^{10}$)$_2$, —NO$_2$, —CN, and $C_{1-6}$ alkyl optionally substituted with one or more substituents independently selected from halogen, —$OR^{10}$, —$SR^{10}$, —N($R^{10}$)$_2$, —NO$_2$, and —CN;

each $R^9$ is independently selected from:
halogen, —$OR^{10}$, —$SR^{10}$, —N($R^{10}$)$_2$, —C(O)$R^{10}$, —C(O)N($R^{10}$)$_2$, —N($R^{10}$)C(O)$R^{10}$, —N($R^{10}$)C(O)N($R^{10}$)$_2$, —OC(O)N($R^{10}$)$_2$, —N($R^{10}$)C(O)O$R^{10}$, —C(O)O$R^{10}$, —OC(O)$R^{10}$, —S(O)$R^{10}$, —S(O)$_2R^{10}$, —NO$_2$, =O, =S, =N($R^{10}$), and —CN; and $C_{1-3}$ alkyl, $C_{2-3}$ alkenyl, and $C_{2-3}$ alkynyl, each of which is optionally substituted with one or more substituents independently selected from halogen, —$OR^{10}$, —$SR^{10}$, —N($R^{10}$)$_2$, —C(O)$R^{10}$, —C(O)N($R^{10}$)$_2$, —N($R^{10}$)C(O)$R^{10}$, —N($R^{10}$)C(O)N($R^{10}$)$_2$, —OC(O)N($R^{10}$)$_2$, —N($R^{10}$)C(O)O$R^{10}$, —C(O)O$R^{10}$, —OC(O)$R^{10}$, —S(O)$R^{10}$, —S(O)$_2R^{10}$, —NO$_2$, =O, =S, =N($R^{10}$), and —CN;

each $R^{10}$ is independently selected from:
hydrogen; and
$C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

n is 0, 1, or 2; and p is 0, 1, or 2.

In certain aspects, the disclosure provides a compound represented by Formula (II):

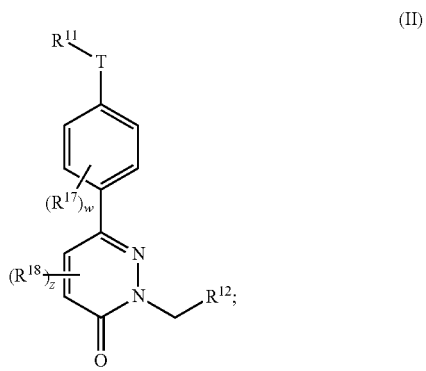

(II)

or a salt thereof, wherein:

T is selected from —O—, —$NR^{14}$—, —$CR^{15}R^{16}$—, —C(O)—, —S—, —S(O)—, and —S(O)$_2$;

$R^{11}$ is selected from:
$C_{1-5}$ haloalkyl optionally further substituted with one or more substituents independently selected from —$OR^{20}$, —$SR^{20}$, —N($R^{20}$)$_2$, —NO$_2$, =O, =S, —CN, $C_{3-10}$ carbocycle and 3- to 10-membered heterocycle, wherein the $C_{3-10}$ carbocycle and 3- to 10-membered heterocycle are each optionally substituted with one or more $R^{19}$;

$R^{12}$ is a heteroaryl optionally substituted with one or more substituents independently selected from:
halogen, —$OR^{20}$, —$SR^{20}$, —N($R^{20}$)$_2$, —C(O)$R^{20}$, —C(O)N($R^{20}$)$_2$, —N($R^{20}$)C(O)$R^{20}$, —N($R^{20}$)C(O)N($R^{20}$)$_2$, —OC(O)N($R^{20}$)$_2$, —N($R^{20}$)C(O)O$R^{20}$, —C(O)O$R^{20}$, —OC(O)$R^{20}$, —S(O)$R^{20}$, —S(O)$_2R^{20}$, —NO$_2$, =O, =S, =N($R^{20}$), —CN; and when $R^{12}$ is pyridyl or pyrimidyl, a substituent on a nitrogen atom of the pyridyl or pyrimidyl is optionally further selected from —O;

$C_{1-6}$ alkyl, $C_{2-6}$ alkenyl, $C_{2-6}$ alkynyl, each of which is optionally substituted with one or more substituents independently selected from halogen, —$OR^{20}$, —$SR^{20}$, —N($R^{20}$)$_2$, —C(O)$R^{20}$, —C(O)N($R^{20}$)$_2$, —N($R^{20}$)C(O)$R^{20}$, —N($R^{20}$)C(O)N($R^{20}$)$_2$, —OC(O)N($R^{20}$)$_2$, —N($R^{20}$)C(O)O$R^{20}$, —C(O)O$R^{20}$, —OC(O)$R^{20}$, —S(O)$R^{20}$, —S(O)$_2R^{20}$, —NO$_2$, =O, =S, =N($R^{20}$), —CN, $C_{3-10}$ carbocycle and 3- to 10-membered heterocycle, wherein the $C_{3-10}$ carbocycle and 3- to 10-membered heterocycle are each optionally substituted with one or more $R^{19}$; and $C_{3-10}$ carbocycle and 3- to 10-membered heterocycle, each of which is optionally substituted with one or more —$R^{19}$;

$R^{14}$ is selected from:
- hydrogen, and $C_{1-6}$ alkyl optionally substituted with one or more substituents independently selected from halogen, —$OR^{20}$, —$SR^{20}$, —$N(R^{20})_2$, —$NO_2$, and —CN;

each $R^{15}$ and $R^{16}$ is independently selected from:
- hydrogen, halogen, —$OR^{20}$, —$SR^{20}$, —$N(R^{20})_2$—, —$NO_2$, —CN, and $C_{1-6}$ alkyl optionally substituted with one or more substituents independently selected from halogen, —$OR^{20}$, —$SR^{20})_2$, —$N(R^{20})_2$, —$NO_2$, and —CN;

each $R^{17}$ and $R^{18}$ is independently selected from:
- halogen, —$OR^{20}$, —$SR^{20}$, —$N(R^{20})_2$, —$NO_2$, —CN, and $C_{1-6}$ alkyl optionally substituted with one or more substituents independently selected from halogen, —$OR^{20}$, —$SR^{20}$, —$N(R^{20})_2$, —$NO_2$, and —CN;

each $R^{19}$ is independently selected from:
- halogen, —$OR^{20}$, —$SR^{20}$, —$N(R^{20})_2$, —$C(O)R^{20}$, —$C(O)N(R^{20})_2$, —$N(R^{20})C(O)R^{20}$, —$N(R^{20})C(O)N(R^{20})_2$, —$OC(O)N(R^{20})_2$, —$N(R^{20})C(O)OR^{20}$, —$C(O)OR^{20}$, —$OC(O)R^{20}$, —$S(O)R^{20}$, —$S(O)_2R^{20}$, —$NO_2$, =O, =S, =$N(R^{20})$, —CN; and
- $C_{1-3}$ alkyl, $C_{2-3}$ alkenyl, $C_{2-3}$ alkynyl, each of which is optionally substituted with one or more substituents independently selected from halogen, —$OR^{20}$, —$SR^{20}$, —$N(R^{20})_2$, —$C(O)R^{20}$, —$C(O)N(R^{20})_2$, —$N(R^{20})C(O)R^{20}$, —$N(R^{20})C(O)N(R^{20})_2$, —$OC(O)N(R^{20})_2$, —$N(R^{20})C(O)OR^{20}$, —$C(O)OR^{20}$, —$OC(O)R^{20}$, —$S(O)R^{20}$, —$S(O)_2R^{20}$, —$NO_2$, =O, =S, =$N(R^{20})$, and —CN;

each $R^{20}$ is independently selected from:
- hydrogen; and
- $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =O, —O—$C_{1-6}$ alkyl, —S—$C_{1-6}$ alkyl, —$N(C_{1-6}$ alkyl)$_2$, —$NH(C_{1-6}$ alkyl), $C_{3-8}$ carbocycle, 3- to 10-membered heterocycle; and
- $C_{3-10}$ carbocycle and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl)$_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and haloalkyl;

w is 0, 1, or 2; and
z is 0, 1, or 2.

In certain aspects, the disclosure provides a method of treating activity-induced muscle damage, comprising administering to a subject in need thereof a compound or salt of Formula (III'):

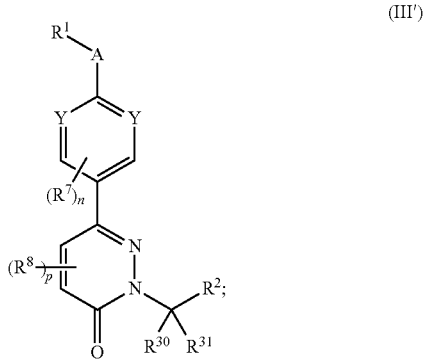

or a salt thereof, wherein:
each Y is independently selected from $C(R^3)$, N, and $N^+(—O^-)$;
A is absent or selected from —O—, —$CR^5R^6$—, —C(O)—, —S—, —S(O)—, and —$S(O)_2$—;
$R^1$ is selected from:
- $C_{1-6}$ alkyl, $C_{2-6}$ alkenyl, and $C_{2-6}$ alkynyl, each of which is optionally substituted with one or more substituents independently selected from halogen, —$OR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, —CN, $C_{3-10}$ carbocycle, and 3- to 10-membered heterocycle, wherein the $C_{3-10}$ carbocycle and 3- to 10-membered heterocycle are each optionally substituted with one or more $R^9$; and
- $C_{3-10}$ carbocycle and 3- to 10-membered heterocycle, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^1)_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN; or
- $R^1$ together with $R^3$ form a 5- to 10-membered heterocycle or $C_{5-10}$ carbocycle, wherein the 5- to 10-membered heterocycle or $C_{5-10}$ carbocycle is optionally substituted with one or more $R^9$; or $R^1$ together with $R^5$ form a 3- to 10-membered heterocycle or saturated $C_{3-10}$ carbocycle, wherein the 3- to 10-membered heterocycle or saturated $C_{3-10}$ carbocycle is optionally substituted with one or more $R^9$; or $R^1$ together with $R^4$ form a 3- to 10-membered heterocycle, wherein the 3- to 10-membered heterocycle is optionally substituted with one or more $R^9$; and
- when A is —$NR^4$—, $R^1$ is additionally selected from hydrogen, and when A is —C(O)—, $R^1$ is additionally selected from —$N(R^{10})_2$ and —$OR^{10}$;
- when A is absent $R^1$ is further selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, and —CN;

$R^2$ is a heteroaryl optionally substituted with one or more substituents independently selected from:
- halogen, —$OR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN; and when $R^2$ is pyridyl or pyrimidyl, a substituent on a nitrogen atom of the pyridyl or pyrimidyl is optionally further selected from —$O^-$;
- $C_{1-6}$ alkyl, $C_{2-6}$ alkenyl, and $C_{2-6}$ alkynyl, each of which is optionally substituted with one or more substituents independently selected from halogen, —$OR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, —CN, $C_{3-10}$ carbocycle and 3- to 10-membered heterocycle, wherein the $C_{3-10}$ carbocycle and 3- to 10-membered heterocycle are each optionally substituted with one or more $R^9$; and $C_{3-10}$ carbocycle and 3- to 10-membered heterocycle, each of which is optionally substituted with one or more $R^9$;

each $R^3$, $R^5$, and $R^6$ is independently selected from:
hydrogen, halogen, —$OR^{10}$, —$SR^{10}$, —$N(R^{10})_2$, —$NO_2$, —CN, and $C_{1-6}$ alkyl optionally substituted with one or more substituents independently selected from halogen, —$OR^{10}$, —$SR^{10}$, —$N(R^{10})_2$, —$NO_2$, and —CN; or $R^3$ together with $R^1$ form a 5- to 10-membered heterocycle or $C_{5-10}$ carbocycle, wherein the 5- to 10-membered heterocycle or $C_{5-10}$ carbocycle is optionally substituted with one or more $R^9$; $R^5$ together with $R^1$ form a 3- to 10-membered heterocycle or $C_{3-10}$ carbocycle, wherein the 3- to 10-membered heterocycle or $C_{3-10}$ carbocycle is optionally substituted with one or more $R^9$;

$R^4$ is independently selected from:
hydrogen; and
$C_{1-6}$ alkyl optionally substituted with one or more substituents independently selected from halogen, —$OR^{10}$, —$SR^{10}$, —$N(R^{10})_2$, —$NO_2$, and —CN; or $R^4$ together with $R^1$ form a 3- to 10-membered heterocycle, which is optionally substituted with one or more $R^9$;

each $R^7$ and $R^8$ is independently selected from
halogen, —$OR^{10}$, —$SR^{10}$, —$N(R^{10})_2$, —$NO_2$, —CN, and $C_{1-6}$ alkyl optionally substituted with one or more substituents independently selected from halogen, —$OR^{10}$, —$SR^{10}$, —$N(R^{10})_2$, —$NO_2$, and —CN;

each $R^9$ is independently selected from
halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, —CN; and $C_{1-3}$ alkyl, $C_{2-3}$ alkenyl, $C_{2-3}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN;

each $R^{10}$ is independently selected from
hydrogen; and
$C_{1-6}$ alkyl, $C_{2-6}$ alkenyl, $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and
$C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and haloalkyl;

$R^{30}$ and $R^{31}$ are independently selected from $R^{10}$ or $R^{30}$ and $R^{31}$ come together to form a $C_{3-7}$ carbocycle, wherein the 3- to 7-membered heterocycle, wherein $C_{3-7}$ carbocycle and 3- to 7-membered heterocycle are optionally substituted with $R^9$;

n is 0, 1, or 2; and
p is 0, 1, or 2.

In certain aspects, the disclosure provides a method of treating a neuromuscular condition or treating activity-induced muscle damage or of inhibiting muscle myosin II, comprising administering to a subject in need thereof a compound or salt of any one of Formulas (I), (Ia), (Ib), (Ic), (Id), (Ie), (II), and (IIa).

In certain aspects, the disclosure provides a method of treating a movement disorder, comprising administering to a subject in need thereof a compound or salt of any one of Formulas (I), (Ia), (Ib), (Ic), (Id), (Ie), (II), and (IIa).

In certain aspects, the disclosure provides a pharmaceutical composition comprising a compound or salt of any one Formulas (I), (Ia), (Ib), (Ic), (Id), (Ie), (II), and (IIa) or a pharmaceutically acceptable excipient.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 7 depicts Buffer A and Buffer B, stored on ice until use.

FIG. 8 depicts buffer preparation.

DETAILED DESCRIPTION OF THE INVENTION

Figure 1:
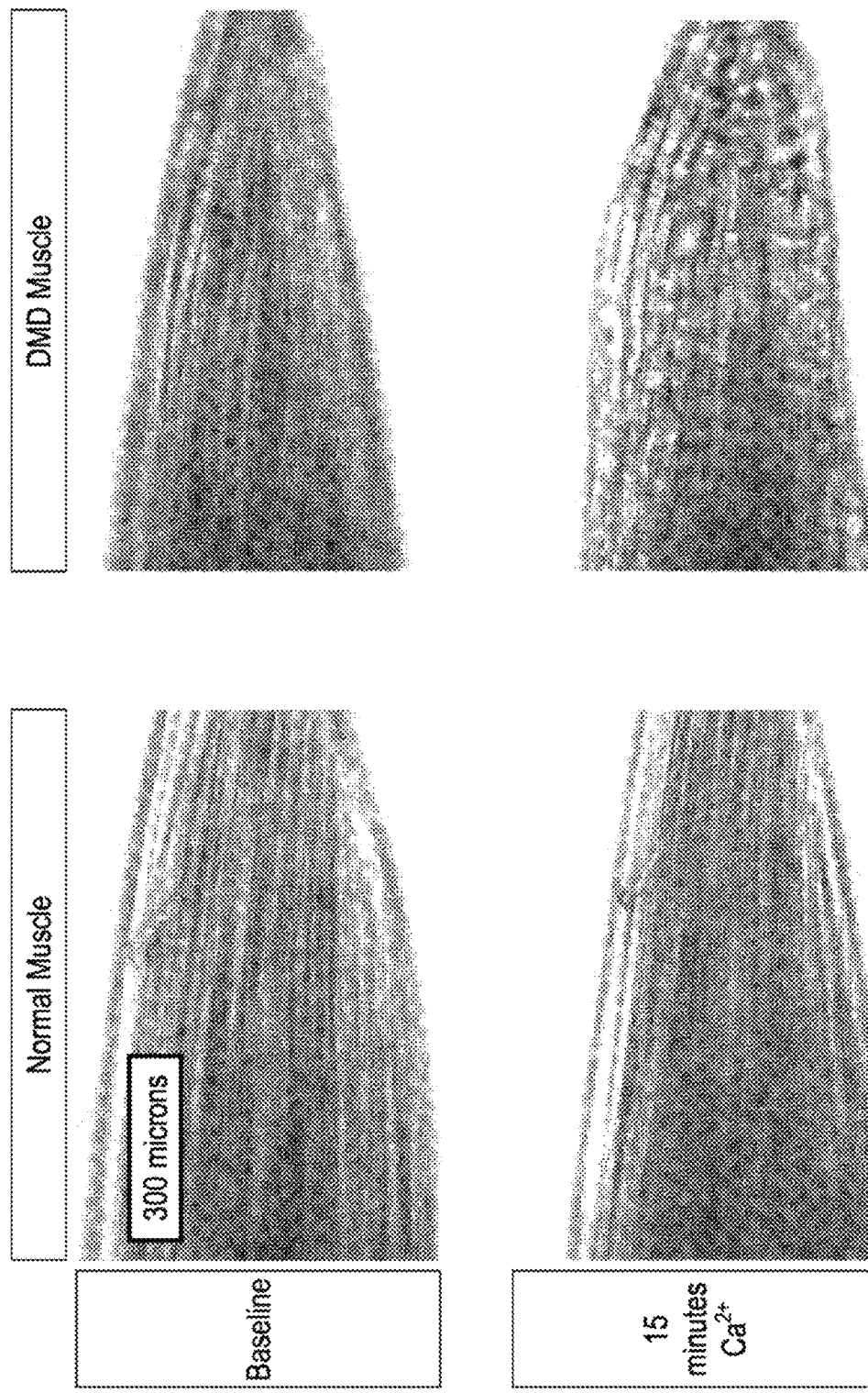
FIG. 1 depicts excessive contraction-induced injuries, which precede the inflammation and irreversible fibrosis that characterizes late-stage DMD pathology.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

In certain aspects, the disclosure provides methods for treating neuromuscular conditions through selective inhibition of fast-fiber skeletal muscle myosin. In particular, methods of the disclosure may be used in the treatment of DMD and other neuromuscular conditions.

Skeletal muscle is mainly composed of two types of fibers, slow-twitch muscle fiber (i.e., type I) and fast-twitch muscle fiber (i.e., type II). In each muscle, the two types of fibers are configured in a mosaic-like arrangement, with differences in fiber type composition in different muscles and at different points in growth and development. Slow-twitch muscle fibers have excellent aerobic energy production ability. Contraction rate of the slow-twitch muscle fiber is low but tolerance to fatigue is high. Slow-twitch muscle fibers typically have a higher concentration of mitochondria and myoglobin than do fast-twitch fibers and are surrounded by more capillaries than are fast-twitch fibers. Slow-twitch fibers contract at a slower rate due to lower myosin ATPase activity and produce less power compared to fast-twitch fibers, but they are able to maintain contractile function over longer-terms, such as in stabilization, postural control, and endurance exercises.

Fast twitch muscle fibers in humans are further divided into two main fiber types depending on the specific fast skeletal myosin they express (Type IIa, IIx/d). A third type of fast fiber (Type IIb) exists in other mammals but is rarely identified in human muscle. Fast-twitch muscle fibers have excellent anaerobic energy production ability and are able to generate high amounts of tension over a short period of time. Typically, fast-twitch muscle fibers have lower concentrations of mitochondria, myoglobin, and capillaries compared to slow-twitch fibers, and thus can fatigue more quickly. Fast-twitch muscles produce quicker force required for power and resistance activities.

The proportion of the type I and type II can vary in different individuals. For example, non-athletic individuals can have close to 50% of each muscle fiber types. Power athletes can have a higher ratio of fast-twitch fibers, e.g., 70-75% type II in sprinters. Endurance athletes can have a higher ratio of slow-twitch fibers, e.g., 70-80% in distance runners. The proportion of the type I and type II fibers can also vary depending on the age of an individual. The proportion of type II fibers, especially the type IN, can decline as an individual ages, resulting in a loss in lean muscle mass.

Figure 2:
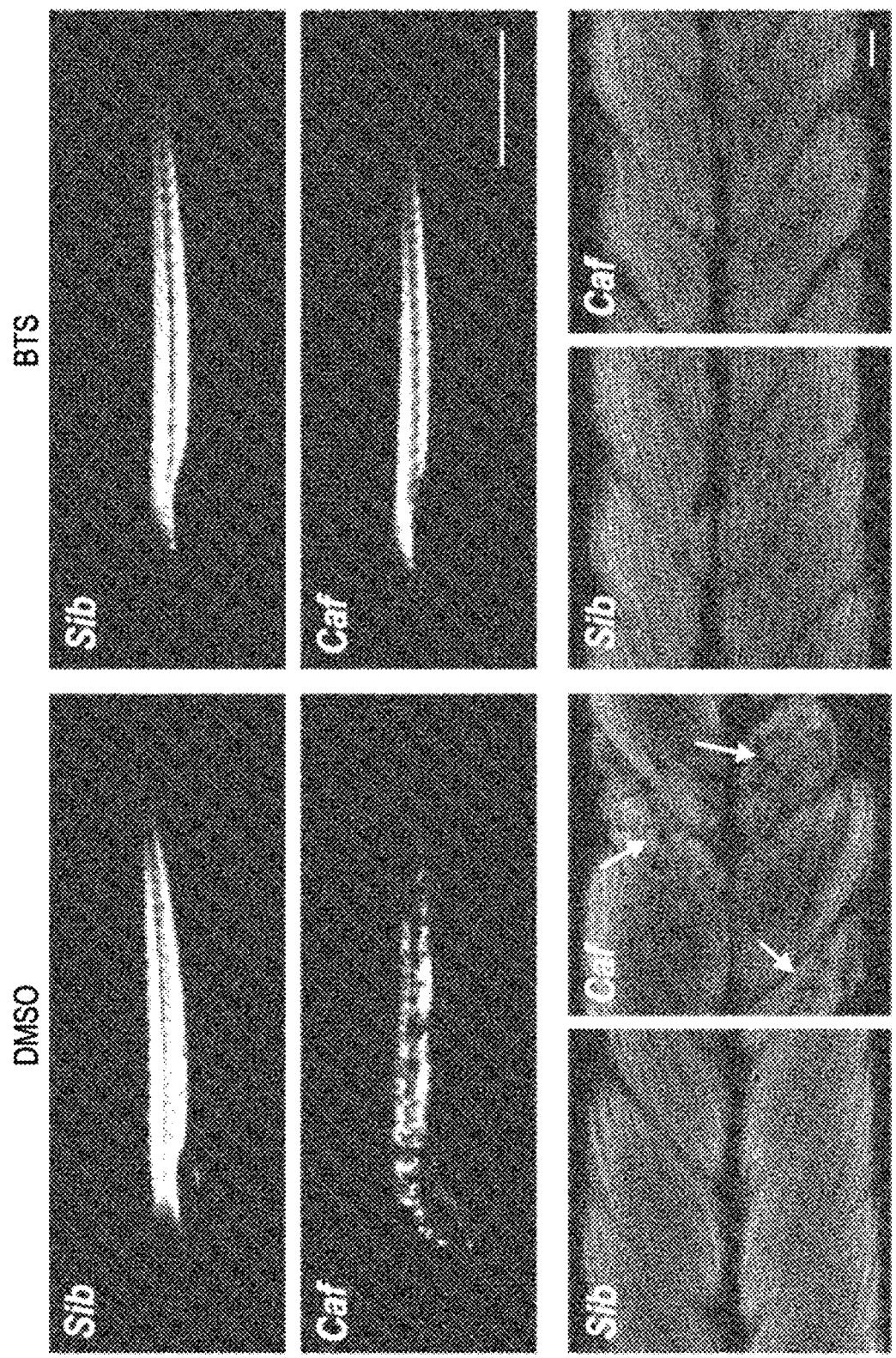
FIG. 2 depicts N-benzyl-p-tolyl-sulfonamide (BTS), an inhibitor of fast-fiber skeletal muscle myosin, has been shown to protect muscles from pathological muscle derangement in embryos from zebrafish model of DMD.

The contractile action of skeletal muscle leads to muscle damage in subjects with neuromuscular disease, e.g., DMD, and this damage appears to be more prevalent in fast fibers. It has been observed that acute force drop after lengthening injury is greater in predominantly fast type II fiber muscles compared to predominantly slow type I fiber muscles in dystrophy mouse models. It has also been demonstrated that the degree of acute force drop and histological damage in dystrophy mouse models is proportional to peak force development during lengthening injury. Excessive contraction-induced injuries, which precede the inflammation and irreversible fibrosis that characterizes late-stage DMD pathology are shown in FIG. 1 [Figure adapted: Claflin and Brooks, Am J Brooks, Physiol Cell, 2008,]. Contraction-induced muscle damage in these patients may be reduced by limiting peak force generation in type II fibers and possibly increasing reliance on healthier type I fibers. N-benzyl-p-tolyl-sulfonamide (BTS), an inhibitor of fast-fiber skeletal muscle myosin, has been shown to protect muscles from pathological muscle derangement in embryos from zebrafish model of DMD as shown in FIG. 2. [Source: Li and Amer, PLoSONE, 2015].

Inhibitors of skeletal muscle myosin that are not selective for the type II fibers may lead to excessive inhibition of skeletal muscle contraction including respiratory function and unwanted inhibition of cardiac activity as the heart shares several structural components (such as type I myosin) with type I skeletal muscle fibers. While not wishing to be bound by a particular mechanistic theory, this disclosure provides selective inhibitors of fast-fiber skeletal muscle myosin as a treatment option for DMD and other neuromuscular conditions. The targeted inhibition of type II skeletal muscle myosin may reduce skeletal muscle contractions while minimizing the impact on a subject's daily activities.

Definitions

Unless defined otherwise, all technical and scientific terms used herein have the same meaning as is commonly understood by one of skill in the art to which this invention belongs.

As used in the specification and claims, the singular form "a", "an" and "the" includes plural references unless the context clearly dictates otherwise.

The term "$C_{x-y}$" or "$C_x-C_y$" when used in conjunction with a chemical moiety, such as alkyl, alkenyl, or alkynyl is meant to include groups that contain from x to y carbons in the chain. For example, the term "$C_{1-6}$ alkyl" refers to substituted or unsubstituted saturated hydrocarbon groups, including straight-chain alkyl and branched-chain alkyl groups that contain from 1 to 6 carbons.

The terms "$C_{x-y}$ alkenyl" and "$C_{x-y}$ alkynyl" refer to substituted or unsubstituted unsaturated aliphatic groups analogous in length and possible substitution to the alkyls described above, but that contain at least one double or triple bond, respectively.

The term "carbocycle" as used herein refers to a saturated, unsaturated or aromatic ring in which each atom of the ring is carbon. Carbocycle includes 3- to 10-membered monocyclic rings, 5- to 12-membered bicyclic rings, 5- to 12-membered spiro bicycles, and 5- to 12-membered bridged rings. Each ring of a bicyclic carbocycle may be selected from saturated, unsaturated, and aromatic rings. In an exemplary embodiment, an aromatic ring, e.g., phenyl, may be fused to a saturated or unsaturated ring, e.g., cyclohexane, cyclopentane, or cyclohexene. A bicyclic carbocycle includes any combination of saturated, unsaturated and aromatic bicyclic rings, as valence permits. A bicyclic carbocycle further includes spiro bicyclic rings such as spiropentane. A bicyclic carbocycle includes any combination of ring sizes such as 3-3 spiro ring systems, 4-4 spiro ring systems, 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. Exemplary carbocycles include cyclopentyl, cyclohexyl, cyclohexenyl, adamantyl, phenyl, indanyl, naphthyl, and bicyclo[1.1.1]pentanyl.

The term "aryl" refers to an aromatic monocyclic or aromatic multicyclic hydrocarbon ring system. The aromatic monocyclic or aromatic multicyclic hydrocarbon ring system contains only hydrogen and carbon and from five to eighteen carbon atoms, where at least one of the rings in the ring system is aromatic, i.e., it contains a cyclic, delocalized (4n+2) π-electron system in accordance with the Htickel theory. The ring system from which aryl groups are derived include, but are not limited to, groups such as benzene, fluorene, indane, indene, tetralin and naphthalene.

The term "cycloalkyl" refers to a saturated ring in which each atom of the ring is carbon. Cycloalkyl may include monocyclic and polycyclic rings such as 3- to 10-membered monocyclic rings, 5- to 12-membered bicyclic rings, 5- to 12-membered spiro bicycles, and 5- to 12-membered bridged rings. In certain embodiments, a cycloalkyl comprises three to ten carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Polycyclic cycloalkyl radicals include, for example, adamantyl, spiropentane, norbornyl (i.e., bicyclo[2.2.1]heptanyl), decalinyl, 7,7 dimethyl bicyclo[2.2.1]heptanyl, bicyclo[1.1.1]pentanyl, and the like.

The term "cycloalkenyl" refers to a saturated ring in which each atom of the ring is carbon and there is at least one double bond between two ring carbons. Cycloalkenyl may include monocyclic and polycyclic rings such as 3- to 10-membered monocyclic rings, 6- to 12-membered bicyclic rings, and 5- to 12-membered bridged rings. In other embodiments, a cycloalkenyl comprises five to seven carbon atoms. The cycloalkenyl may be attached to the rest of the molecule by a single bond. Examples of monocyclic cycloalkenyls include, e.g., cyclopentenyl, cyclohexenyl, cycloheptenyl, and cyclooctenyl.

The term "halo" or, alternatively, "halogen" or "halide," means fluoro, chloro, bromo or iodo. In some embodiments, halo is fluoro, chloro, or bromo.

The term "haloalkyl" refers to an alkyl radical, as defined above, that is substituted by one or more halo radicals, for example, trifluoromethyl, dichloromethyl, bromomethyl, 2,2,2-trifluoroethyl, 1-chloromethyl-2-fluoroethyl, and the like. In some embodiments, the alkyl part of the haloalkyl radical is optionally further substituted as described herein.

The term "heterocycle" as used herein refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, 5- to 12-membered spiro bicycles, and 5- to 12-membered bridged rings. A bicyclic heterocycle includes any combination of saturated, unsaturated and aromatic bicyclic rings, as valence permits. In an exemplary embodiment, an aromatic ring, e.g., pyridyl, may be fused to a saturated or unsaturated ring, e.g., cyclohexane, cyclopentane, morpholine, piperidine or cyclohexene. A bicyclic heterocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. A bicyclic heterocycle further includes spiro bicyclic rings, e.g., 5 to 12-membered spiro bicycles, such as 2-oxa-6-azaspiro[3.3]heptane.

The term "heteroaryl" refers to a radical derived from a 5 to 18 membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is aromatic, i.e., it contains a cyclic, delocalized (4n+2) π-electron system in accordance with the Mickel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzoxazolyl, benzo[d]thiazolyl, benzothiadiazolyl, benzo[b][1,4]dioxepinyl, benzo[b][1,4] oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl).

The term "heterocycloalkyl" refers to a saturated ring with carbon atoms and at least one heteroatom. Exemplary heteroatoms include N, O, Si, P, B, and S atoms. Heterocycloalkyl may include monocyclic and polycyclic rings such as 3- to 10-membered monocyclic rings, 6- to 12-membered bicyclic rings, 5- to 12-membered spiro bicycles, and 5- to 12-membered bridged rings. The heteroatoms in the heterocycloalkyl radical are optionally oxidized. One or more nitrogen atoms, if present, are optionally quaternized. The heterocycloalkyl is attached to the rest of the molecule through any atom of the heterocycloalkyl, valence permitting, such as any carbon or nitrogen atoms of the heterocycloalkyl. Examples of heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 2-oxa-6-azaspiro[3.3]heptane, and 1,1-dioxo-thiomorpholinyl.

The term "heterocycloalkenyl" refers to an unsaturated ring with carbon atoms and at least one heteroatom and there is at least one double bond between two ring carbons. Heterocycloalkenyl does not include heteroaryl rings. Exemplary heteroatoms include N, O, Si, P, B, and S atoms. Heterocycloalkenyl may include monocyclic and polycyclic rings such as 3- to 10-membered monocyclic rings, 6- to 12-membered bicyclic rings, and 5- to 12-membered bridged rings. In other embodiments, a heterocycloalkenyl comprises five to seven ring atoms. The heterocycloalkenyl may be attached to the rest of the molecule by a single bond. Examples of monocyclic cycloalkenyls include, e.g., pyrroline (dihydropyrrole), pyrazoline (dihydropyrazole), imidazoline (dihydroimidazole), triazoline (dihydrotriazole), dihydrofuran, dihydrothiophene, oxazoline (dihydrooxazole), isoxazoline (dihydroisoxazole), thiazoline (dihydrothiazole), isothiazoline (dihydroisothiazole), oxadiazoline (dihydrooxadiazole), thiadiazoline (dihydrothiadiazole), dihydropyridine, tetrahydropyridine, dihydropyridazine, tetrahydropyridazine, dihydropyrimidine, tetrahydropyrimidine, dihydropyrazine, tetrahydropyrazine, pyran, dihydropyran, thiopyran, dihydrothiopyran, dioxine, dihydrodioxine, oxazine, dihydrooxazine, thiazine, and dihydrothiazine.

The term "substituted" refers to moieties having substituents replacing a hydrogen on one or more carbons or substitutable heteroatoms, e.g., an NH or $NH_2$ of a compound. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

In some embodiments, substituents may include any substituents described herein, for example: halogen, hydroxy, oxo (=O), thioxo (=S), cyano (—CN), nitro (—$NO_2$), imino (=N—H), oximo (=N—OH), hydrazino (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2), and —$R^b$—S(O)$_t$N($R^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl, any of which may be optionally substituted by alkyl, alkenyl, alkynyl, halogen, haloalkyl, haloalkenyl, haloalkynyl, oxo (=O), thioxo (=S), cyano (—CN), nitro (—$NO_2$), imino (=N—H), oximo (=N—OH), hydrazine (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2); wherein each $R^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each $R^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—$NO_2$), imino (=N—H), oximo (=N—OH), hydrazine (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2); and wherein each $R^b$ is independently selected from a direct bond or a straight or branched alkylene, alkenylene, or alkynylene chain, and each Re is a straight or branched alkylene, alkenylene or alkynylene chain.

Double bonds to oxygen atoms, such as oxo groups, are represented herein as both "=O" and "(O)". Double bonds to nitrogen atoms are represented as both "=NR" and "(NR)". Double bonds to sulfur atoms are represented as both "=S" and "(S)".

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

As used herein, "treatment" or "treating" refers to an approach for obtaining beneficial or desired results with respect to a disease, disorder, or medical condition including but not limited to a therapeutic benefit and/or a prophylactic benefit. A therapeutic benefit can include, for example, the eradication or amelioration of the underlying disorder being treated. Also, a therapeutic benefit can include, for example, the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made. Treatment via administration of a compound described herein does not require the involvement of a medical professional.

Compounds

The following is a discussion of compounds and salts thereof that may be used in the methods of the disclosure. In certain embodiments, the compounds and salts are described in Formulas (I), (Ia), (Ib), (Ic), (Id), (Ie), (II), and (IIa).

In one aspect, disclosed herein is a compound represented by Formula (I):

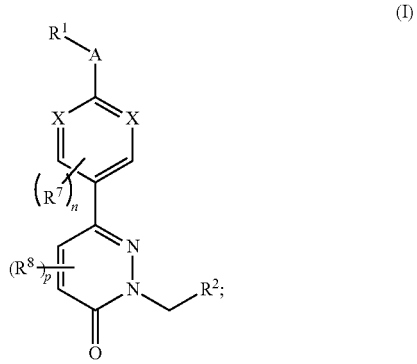

or a salt thereof, wherein:
each X is independently selected from $C(R^3)$, N, and $N^+(-O^-)$ wherein at least one X is N or $N^+(-O^-)$;
A is selected from —O—, —$NR^4$—, —$CR^5R^6$—, —C(O)—, —S—, —S(O)—, and —$S(O)_2$—;
$R^1$ is selected from:
$C_{1-6}$ alkyl, $C_{2-6}$ alkenyl, $C_{2-6}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)OR^{10}$, —$OC(O)R^{10}$, —$N(R^{10})C(O)N(R^{10})_2$, —$OC(O)N(R^{10})_2$, —$N(R^{10})C(O)OR^{10}$, —$S(O)R^{10}$, —$S(O)_2R^{10}$, —$NO_2$, =O, =S, =$N(R^{10})$, —CN, $C_{3-10}$ carbocycle and 3- to 10-membered heterocycle, wherein the $C_{3-10}$ carbocycle and 3- to 10-membered heterocycle are each optionally substituted with one or more $R^9$; and $C_{3-10}$ carbocycle and 3- to 10-membered heterocycle, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^9$; or $R^1$ together with $R^3$ form a 5- to 10-membered heterocycle or $C_{5-10}$ carbocycle, wherein the 5- to 10-membered heterocycle or $C_{5-10}$ carbocycle is optionally substituted with one or more $R^9$; $R^1$ together with $R^5$ form a 3- to 10-membered heterocycle or $C_{3-10}$ carbocycle, wherein the 3- to 10-membered heterocycle or $C_{3-10}$ carbocycle is optionally substituted with one or more $R^9$; or $R^1$ together with $R^4$ form a 3- to 10-membered heterocycle, wherein the 3- to 10-membered heterocycle is optionally substituted with one or more $R^9$;

$R^2$ is a heteroaryl optionally substituted with one or more substituents independently selected from:
halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN; and when $R^2$ is pyridyl or pyrimidyl, a substituent on a nitrogen atom of the pyridyl or pyrimidyl is optionally further selected from —$O^-$;

$C_{1-6}$ alkyl, $C_{2-6}$ alkenyl, $C_{2-6}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, —CN, $C_{3-10}$ carbocycle and 3- to 10-membered heterocycle, wherein the $C_{3-10}$ carbocycle and 3- to 10-membered heterocycle are each optionally substituted with one or more $R^9$; and $C_{3-10}$ carbocycle and 3- to 10-membered heterocycle, each of which is optionally substituted with one or more $R^9$;

each $R^3$, $R^5$, and $R^6$ is independently selected from:
hydrogen, halogen, —$OR^{10}$, —$SR^{10}$, —$N(R^{10})_2$, —$NO_2$, —CN, and $C_{1-6}$ alkyl optionally substituted with one or more substituents independently selected from halogen, —$OR^{10}$, —$SR^{10}$, —$N(R^{10})_2$, —$NO_2$, and —CN; or $R^3$ together with $R^1$ form a 5- to 10-membered heterocycle or $C_{5-10}$ carbocycle, wherein the 5- to 10-membered heterocycle or $C_{5-10}$ carbocycle is optionally substituted with one or more $R^9$; $R^5$ together with $R^1$ form a 3- to 10-membered heterocycle or $C_{3-10}$ carbocycle, wherein the 3- to 10-membered heterocycle or C$_{3-10}$ carbocycle is optionally substituted with one or more R$^9$;

R$^4$ is independently selected from:

hydrogen; and

C$_{1-6}$ alkyl optionally substituted with one or more substituents independently selected from halogen, —OR$^{10}$, —SR$^{10}$, —N(R$^{10}$)$_2$, —NO$_2$, and —CN; or R$^4$ together with R$^1$ form a 3- to 10-membered heterocycle, which is optionally substituted with one or more R$^9$;

R$^7$ and R$^8$ are independently selected from:

halogen, —OR$^{10}$, —SR$^{10}$, —N(R$^{10}$)$_2$, —NO$_2$, —CN, and C$_{1-6}$ alkyl optionally substituted with one or more substituents independently selected from halogen, —OR$^{10}$, —SR$^{10}$, —N(R$^{10}$)$_2$, —NO$_2$, and —CN;

each R$^9$ is independently selected from:

halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(C)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, =O, =S, =N(R$^{10}$), —CN; and C$_{1-3}$ alkyl, C$_{2-3}$ alkenyl, and C$_{2-3}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, =O, =S, =N(R$^{10}$), and —CN;

each R$^{10}$ is independently selected from:

hydrogen; and

C$_{1-6}$ alkyl, C$_{2-6}$ alkenyl, and C$_{2-6}$ alkynyl, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, 3- to 10-membered heterocycle; and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and C$_{1-6}$ haloalkyl;

n is 0, 1, or 2; and p is 0, 1, or 2.

In certain embodiments, for a compound or salt of Formula (I), each X is independently selected from C(R$^3$) and N wherein at least one X is N. In some embodiments, one X is N and one X is C(R$^3$). In some embodiments, one X is N$^+$(—O$^-$) and one X is C(R$^3$). In some embodiments, each X is N. In some embodiments, one X is N, and one X is N$^+$(—O$^-$).

In certain embodiments, for a compound or salt of Formula (I), each X is further selected from C(R$^3$).

In some embodiments, a compound or salt thereof of Formula (I) is represented by Formula (Ia):

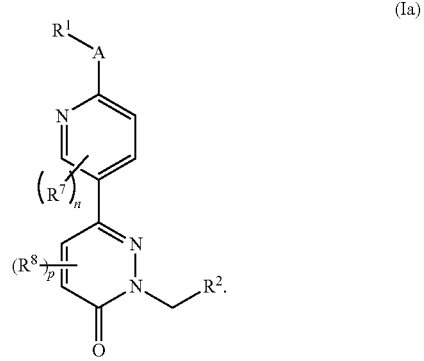

(Ia)

In some embodiments, a compound or salt thereof of Formula (I) is represented by Formula (Ib):

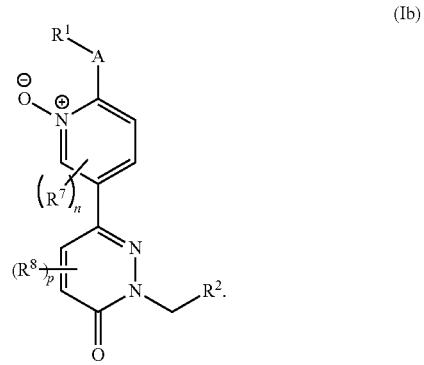

(Ib)

In some embodiments, a compound or salt thereof of Formula (I) is represented by Formula (Ic):

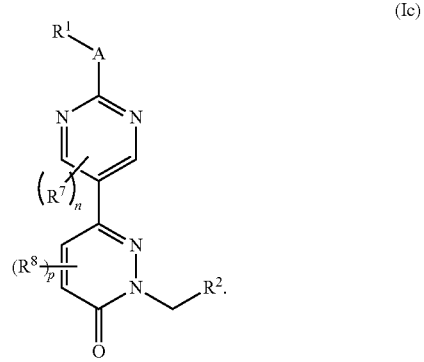

(Ic)

In some embodiments, a compound or salt thereof of Formula (I) is represented by Formula (Id):

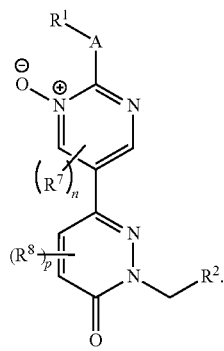
(Id)

In certain embodiments, a compound of Formula (I) is represented by Formula (Ia) or Formula (Ib):

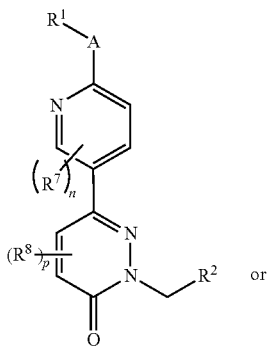
(Ia)
(Ib)

In certain embodiments, a compound of Formula (I) is represented by Formula (Ic) or Formula (Id):

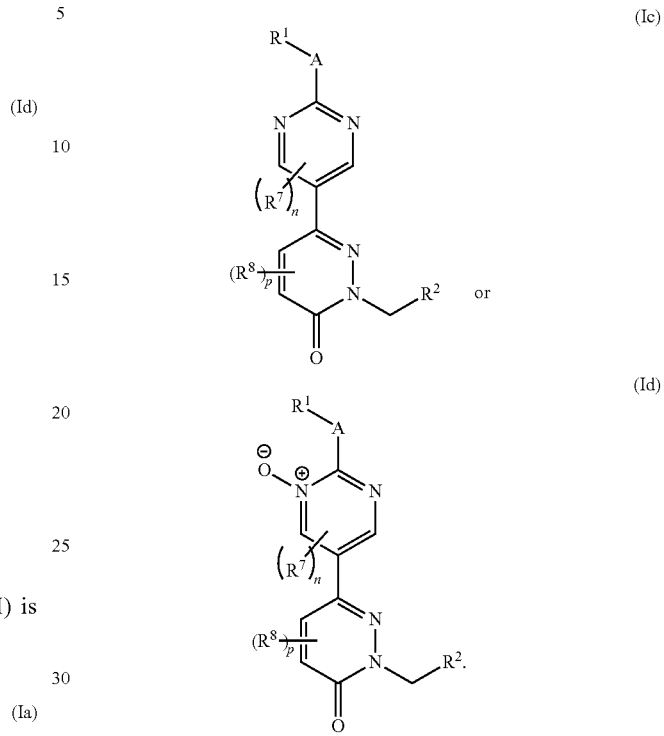
(Ic)
(Id)

In certain embodiments, the compound of Formula (I) is represented by Formula (Ia) or Formula (Ic):

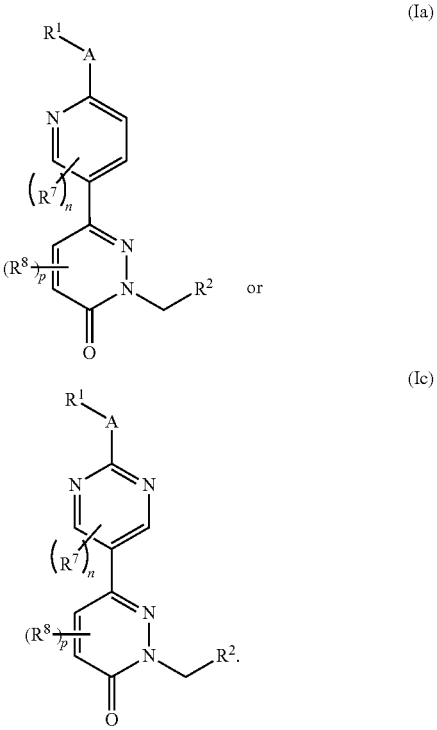
(Ia)
(Ic)

In certain embodiments, for a compound or salt of any one of Formula (I), (Ia), (Ib), (Ic), (Id), A is selected from —O—, —NR$^4$—, —CR$^5$R$^6$—, and —C(O)—. In some embodiments, A is selected from —O— and —NR$^4$. In some embodiments, A is —O—.

In certain embodiments, for a compound or salt of any one of Formula (I), (Ia), (Ib), (Ic), or (Id), R$^1$ is selected from:
- C$_{1-6}$ alkyl, C$_{2-6}$ alkenyl, and C$_{2-6}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —N(R$^{10}$)C(O)N(R$^{10}$)$_2$, —OC(O)N(R$^{10}$)$_2$, —N(R$^{10}$)C(O)OR$^{10}$, —S(O)R$^{10}$, —S(O)$_2$R$^{10}$, —NO$_2$, =O, =S, =N(R$^{10}$), —CN, C$_{3-10}$ carbocycle and 3- to 10-membered heterocycle, wherein the C$_{3-10}$ carbocycle and 3- to 10-membered heterocycle are each optionally substituted with one or more R$^9$; and
- C$_{3-10}$ carbocycle and 3- to 10-membered heterocycle, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, =O, =S, =N(R$^{10}$), and —CN; or
- R$^1$ together with R$^3$ form a 5- to 10-membered heterocycle or C$_{5-10}$ carbocycle, wherein the 5- to 10-membered heterocycle or C$_{5-10}$ carbocycle is optionally substituted with one or more R$^9$; or R$^1$ together with R$^5$ form a 3- to 10-membered heterocycle or C$_{3-10}$ carbocycle, wherein the 3- to 10-membered heterocycle or C$_{3-10}$ carbocycle is optionally substituted with one or more R$^9$; or R$^1$ together with R$^4$ form a 3- to 10-membered heterocycle, wherein the 3- to 10-membered heterocycle is optionally substituted with one or more R$^9$.

In certain embodiments, for a compound or salt of any one of Formula (I), (Ia), (Ib), (Ic), or (Id), R$^1$ is selected from:
- C$_{1-5}$ alkyl optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —CN, C$_{3-7}$ carbocycle and 3- to 7-membered heterocycle, wherein the C$_{3-7}$ carbocycle and 3- to 7-membered heterocycle are each optionally substituted with one or more R$^9$; and
- C$_{3-7}$ carbocycle optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —CN, C$_{1-6}$ alkyl, and C$_{1-6}$ haloalkyl; or
- or R$^1$ together with R$^4$ form a 3- to 6-membered heterocycle, wherein the 3- to 6-membered heterocycle is optionally substituted with one or more R$^9$.

In certain embodiments, for a compound or salt of any one of Formula (I), (Ia), (Ib), (Ic), or (Id), R$^1$ is selected from:
- C$_{1-5}$ alkyl optionally substituted with one or more substituents independently selected from halogen, —OR$^{10}$, —SR$^{10}$, C$_{3-5}$ carbocycle and 3- to 5-membered heterocycle, wherein the C$_{3-5}$ carbocycle and 3- to 5-membered heterocycle are each optionally substituted with one or more R$^9$;
- C$_4$-C$_6$ saturated carbocycle; or
- R$^1$ together with R$^4$ form a 5-membered saturated heterocycle optionally substituted with one or more R$^9$;
- wherein R$^9$ is independently selected from halogen, —OR$^{10}$, —N(R$^{10}$)$_2$, —NO$_2$, =O, —CN; and C$_{1-3}$ alkyl optionally substituted with one or more substituents independently selected from halogen, —OR$^{10}$, —N(R$^{10}$)$_2$, —NO$_2$, =O, and —CN.

In certain embodiments, for a compound or salt of any one of Formula (I), (Ia), (Ib), (Ic), (Id), R$^1$ is selected from —CHF$_2$, —CH(CH$_3$)$_2$, —CH$_2$CH(CH$_3$)$_2$, —CH$_2$CF(CH$_3$)$_2$, —CH$_2$CF$_3$, —CH$_2$CH$_2$CF$_3$, —CH$_2$CH$_2$OCH$_3$, —CH$_2$CH$_2$OCF$_3$, —CH$_2$C(CH$_3$)$_2$OCH$_3$, —CH$_2$SCH$_3$, —CH$_2$CH$_2$SCH$_3$, —CH$_2$CH(CH$_3$)SCH$_3$, —CH$_3$, —CH$_2$CH$_3$, —CH$_2$CH$_2$CH$_3$, —CH(CH$_3$)CH$_2$CH$_3$, —CH$_2$CF$_2$CH$_3$, —CH$_2$C(CH$_3$)$_3$, —CH$_2$CH(CH$_3$)$_2$

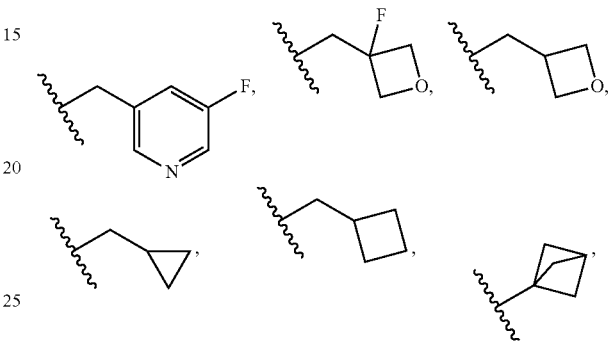

or R$^1$ together with R$^4$ form a 5-membered saturated heterocycle substituted with —CH$_3$, or —CF$_3$.

In some embodiments, R$^1$ is selected from C$_{1-5}$ alkyl optionally substituted with one or more substituents independently selected from halogen, —OR$^{10}$, —SR$^{10}$, C$_{3-5}$ carbocycle and 3- to 5-membered heterocycle, wherein the C$_{3-5}$ carbocycle and 3- to 5-membered heterocycle are each optionally substituted with one or more R$^9$.

In certain embodiments, for a compound or salt of any one of Formula (I), (Ia), (Ib), (Ic), (Id), R$^1$ is C$_{1-6}$ alkyl optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —N(R$^{10}$)C(O)N(R$^{10}$)$_2$, —OC(O)N(R$^{10}$)$_2$, —N(R$^{10}$)C(O)OR$^{10}$, —S(O)R$^{10}$, —S(O)$_2$R$^{10}$, —NO$_2$, =O, =S, =N(R$^{10}$), —CN, C$_{3-10}$ carbocycle and 3- to 10-membered heterocycle, wherein the C$_{3-10}$ carbocycle and 3- to 10-membered heterocycle are each optionally substituted with one or more R$^9$. In some embodiments, R$^1$ is C$_{1-6}$ alkyl substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —N(R$^{10}$)C(O)N(R$^{10}$)$_2$, —OC(O)N(R$^{10}$)$_2$, —N(R$^{10}$)C(O)OR$^{10}$, —S(O)R$^{10}$, —S(O)$_2$R$^{10}$, —NO$_2$, =O, =S, =N(R$^{10}$), —CN, C$_{3-10}$ carbocycle and 3- to 10-membered heterocycle, wherein the C$_{3-10}$ carbocycle and 3- to 10-membered heterocycle are each optionally substituted with one or more R$^9$. In some embodiments, R$^1$ is C$_{1-6}$ alkyl substituted with one or more substituents independently selected from halogen, —OR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —NO$_2$, =O, =N(R$^{10}$), —CN, C$_{3-10}$ carbocycle and 3- to 10-membered heterocycle, wherein the C$_{3-10}$ carbocycle and 3- to 10-membered heterocycle are each optionally substituted with one or more R$^9$. In some embodiments, R$^1$ is selected from C$_{1-3}$ alkyl optionally substituted with one or more substituents independently selected from halogen, —OR$^{10}$, —SR$^{10}$, —N(R$^{10}$)$_2$, —NO$_2$, =O, =S, =N(R$^{10}$), —CN, C$_{3-10}$ carbocycle and 3- to 10-membered heterocycle, wherein the $C_{3-10}$ carbocycle and 3- to 10-membered heterocycle are each optionally substituted with one or more $R^9$.

In certain embodiments, for a compound or salt of any one of Formula (I), (Ia), (Ib), (Ic), (Id), $R^1$ is $C_{1-3}$ alkyl substituted with one or more substituents independently selected from halogen, $-OR^{10}$, $-N(R^{10})_2$, $-NO_2$, $=O$, $-CN$, $C_{3-10}$ carbocycle and 3- to 10-membered heterocycle, wherein the $C_{3-10}$ carbocycle and 3- to 10-membered heterocycle are each optionally substituted with one or more $R^9$. In some embodiments, $R^1$ is $C_{1-3}$ alkyl substituted with one or more halogen substituents. In some embodiments, $R^1$ is a $C_{1-3}$ fluoroalkyl. In some embodiments, $R^1$ is selected from $-CHF_2$ and $-CH_2CF_3$. In some embodiments, $R^1$ is $C_{3-10}$ carbocycle optionally substituted with one or more substituents independently selected from halogen, $-CN$, $-OH$, $-SH$, $-NO_2$, $-NH_2$, $=O$, $=S$, $-O-C_{1-6}$ alkyl, $-S-C_{1-6}$ alkyl, $-N(C_{1-6}$ alkyl$)_2$, $-NH(C_{1-6}$ alkyl$)$, $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, $R^1$ is selected from $C_{1-3}$ alkyl optionally substituted with one or more substituents independently selected from halogen, $-OR^{10}$, $C_{3-10}$ carbocycle and 3- to 10-membered heterocycle, wherein the $C_{3-10}$ carbocycle and 3- to 10-membered heterocycle are each optionally substituted with one or more $R^9$. In some embodiments, $R^1$ is selected from $-CHF_2$, $-CH_2CF_3$, $-CH_2CH_2OCF_3$, $-CH_3$, $-CH_2CH_3$, $-CH_2CH_2CH_3$, and $-CH_2CH_2OCH_3$,

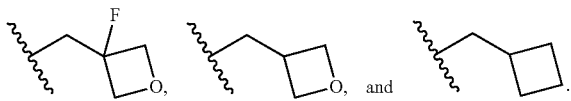 [SMILES: *CC1(F)COC1 ; *CC1COC1 ; *CC1CCC1]

In some embodiments, $R^1$ is selected from $-CHF_2$, $-CH(CH_3)_2$, $-CH_2CH(CH_3)_2$, $-CH_2CF(CH_3)_2$, $-CH_2CF_3$, $-CH_2CH_2CF_3$, $-CH_2CH_2OCH_3$, $-CH_2CH_2OCF_3$, $-CH_2C(CH_3)_2OCH_3$, $-CH_2SCH_3$, $-CH_2CH_2SCH_3$, $-CH_2CH(CH_3)SCH_3$, $-CH_3$, $-CH_2CH_3$, $-CH_2CH_2CH_3$, $-CH(CH_3)CH_2CH_3$, $-CH_2CF_2CH_3$, $-CH_2C(CH_3)_3$, $-CH_2CH(CH_3)_2$,

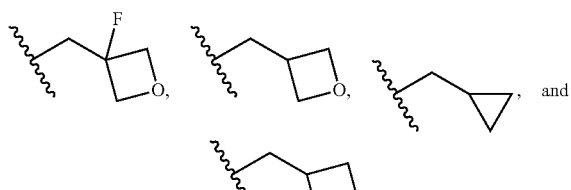

In some embodiments, $R^1$ is $-CH_2CF_3$.

In some embodiments, for a compound or salt of any one of Formula (I), (Ia), (Ib), (Ic), (Id), $R^1$ together with $R^4$ form a 3- to 6-membered heterocycle, wherein the 3- to 6-membered heterocycle is optionally substituted with one or more $R^9$. In some embodiments, $R^1$ together with $R^4$ form a 5-membered saturated heterocycle optionally substituted with one or more $R^9$. In some embodiments, $R^1$ together with $R^4$ form a 5-membered saturated heterocycle optionally substituted with one or more substituents selected from $C_{1-3}$ alkyl, and $C_{1-3}$ haloalkyl.

In certain embodiments, for a compound or salt of any one of Formula (I), (Ia), (Ib), (Ic), or (Id), $R^1$ is selected from optionally substituted $C_3$-$C_6$ cycloalkyl, such as cyclopropyl, cyclobutyl, cyclopentyl, bicyclopentyl, and spiropentyl, any of which is optionally substituted. In certain embodiments, $R^1$ is selected from alkyl, e.g., methyl, ethyl, propyl, iso-propyl, t-butyl, iso-butyl, sec-butyl, any of which may be optionally substituted. In some embodiments, $R^1$ is selected from optionally substituted saturated $C_4$-$C_6$ cycloalkyl. In certain embodiments, $R^1$ is selected from:

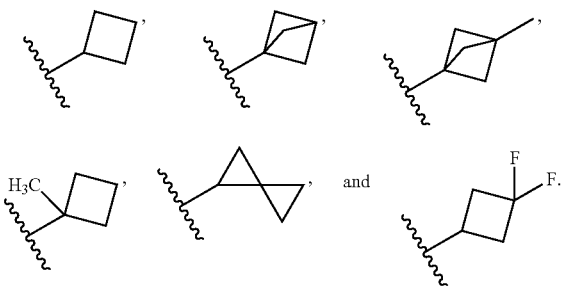

In certain embodiments, $R^1$ is selected from:

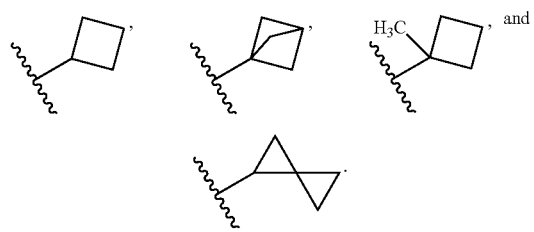

In certain embodiments, $R^1$ is selected from optionally substituted

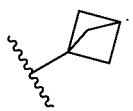 [SMILES: *C12CC(C1)C2]

In some embodiments, $R^1$ is

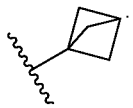 [SMILES: *C12CC(C1)C2]

In certain embodiments, for a compound or salt of any one of Formula (I), (Ia), (Ib), (Ic), (Id), $R^1$ together with $R^3$ form a 5- to 10-membered heterocycle or $C_{5-10}$ carbocycle, wherein the 5- to 10-membered heterocycle or $C_{5-10}$ carbocycle is optionally substituted with one or more $R^9$. In some embodiments, $R^1$ together with $R^3$ form a $C_{5-10}$ carbocycle or 5- to 10-membered heterocycle, such as a $C_{5-6}$ carbocycle or 5- to 6-membered heterocycle, for example:

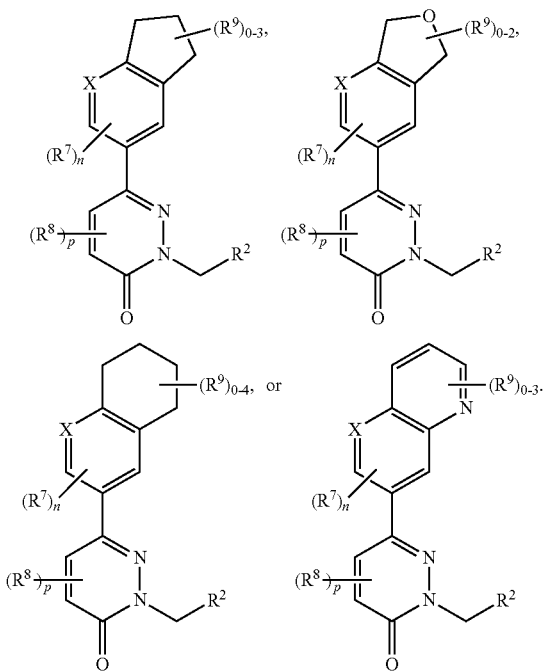

In certain embodiments, for a compound or salt of any one of Formula (I), (Ia), (Ib), (Ic), (Id), $R^1$ together with $R^5$ form a 3- to 10-membered heterocycle or $C_{3-10}$ carbocycle, wherein the 3- to 10-membered heterocycle or $C_{3-10}$ carbocycle is optionally substituted with one or more $R^9$. In some embodiments, $R^1$ together with $R^5$ form a 3- to 10-membered heterocycle or $C_{3-10}$ carbocycle, for example:

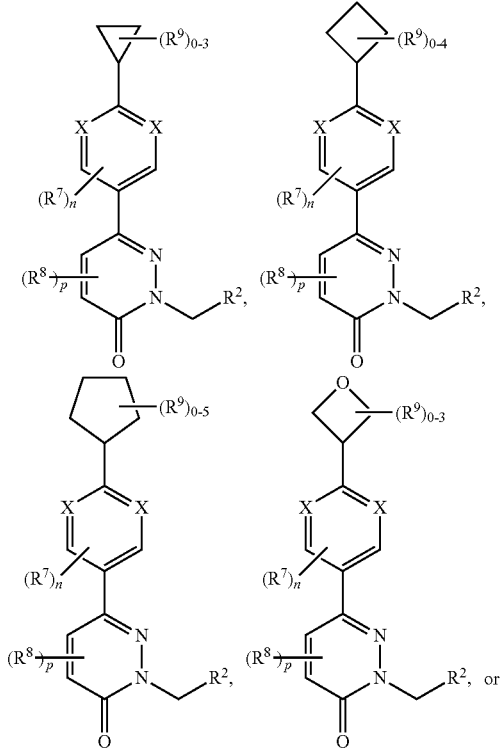

In certain embodiments, for a compound or salt of any one of Formula (I), (Ia), (Ib), (Ic), (Id), $R^1$ together with $R^4$ form a 3- to 10-membered heterocycle, wherein the 3- to 10-membered heterocycle is optionally substituted with one or more $R^9$. In some embodiments, $R^1$ together with $R^4$ form a 3- to 10-membered heterocycle, for example:

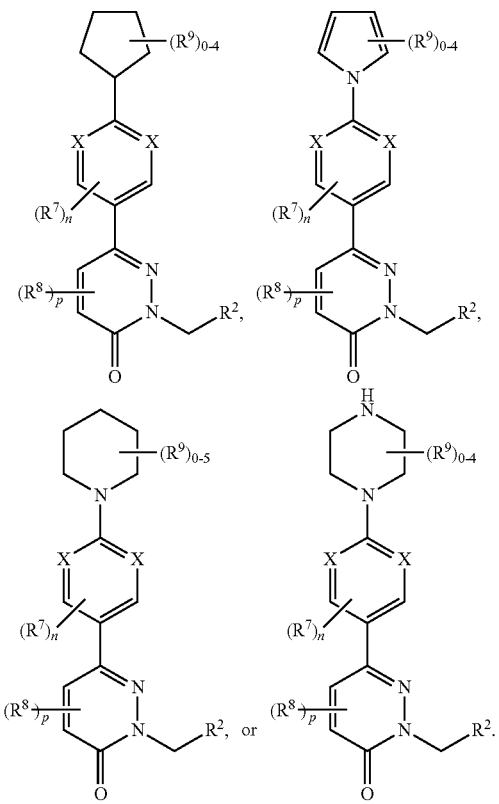

In some embodiments, for a compound or salt of any one of Formula (I), (Ia), (Ib), (Ic), (Id), each $R^9$ of $R^1$ is independently selected from halogen, —$OR^{10}$, —$N(R^{10})_2$, —$NO_2$, =O, —CN; and $C_{1-3}$ alkyl optionally substituted with one or more substituents independently selected from halogen, —$OR^{10}$, —$N(R^{10})_2$, —$NO_2$, =O, and —CN. In some embodiments, each $R^9$ of $R^1$ is independently selected from halogen and —$OR^{10}$; and $C_{1-3}$ alkyl optionally substituted with one or more substituents independently selected from halogen and —OR[10]. In some embodiments, each R[9] of R[1] is independently selected from —CH$_3$, —CF$_3$, and =O In some embodiments, for a compound or salt of any one of Formula (I), (Ia), (Ib), (Ic), (Id), R[2] is an optionally substituted 5-membered heteroaryl, 6-membered heteroaryl, or a 9-membered bicyclic heterocycle. In some embodiments, R[2] is an optionally substituted 5-membered heteroaryl. In certain embodiments, R[2] is an optionally substituted 5-membered heteroaryl with at least one endocyclic nitrogen or oxygen atom in the 5-membered heteroaryl, e.g., oxazole, isoxazole, thiazole, pyrrole, pyrazole, furan, diazole, triazole, imidazole, oxadiazole, thiadiazole, isoxazole, isothiazole, and tetrazole. In certain embodiments, for a compound or salt of any one of Formula (I), (Ia), (Ib), (Ic), (Id), R[2] is selected from:

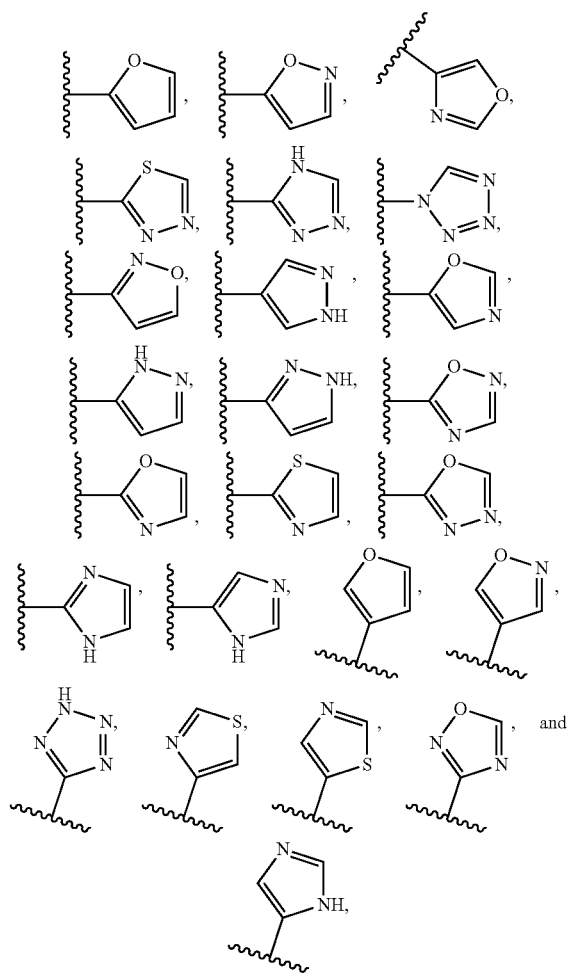

any one of which is optionally substituted. In some embodiments, R[2] is selected from:

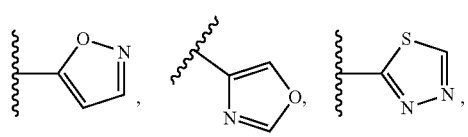

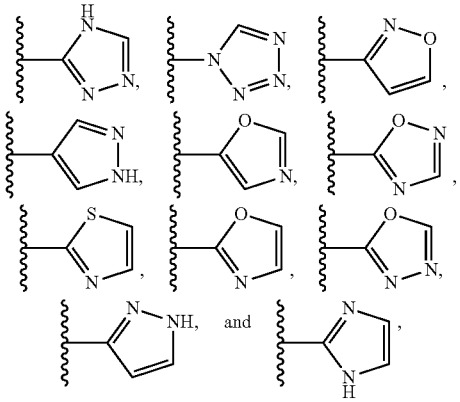

any one of which is optionally substituted. In some embodiments, R[2] is selected from:

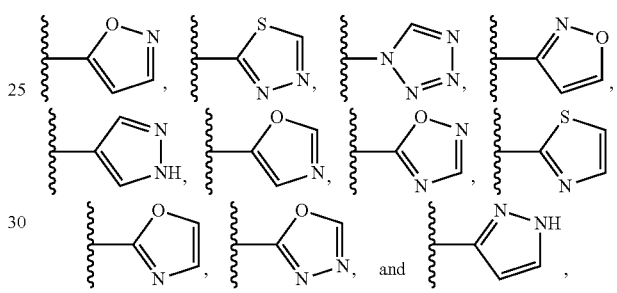

any one of which is optionally substituted. In some embodiments, R[2] is selected from:

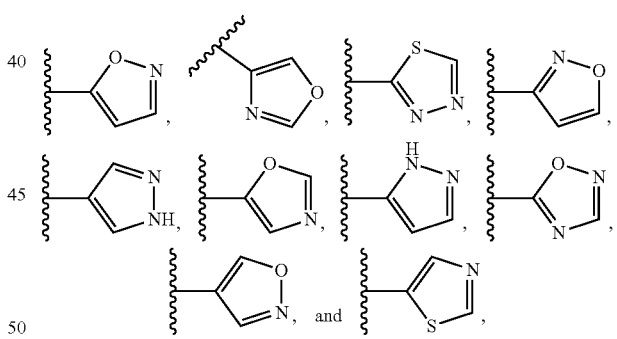

any one of which is optionally substituted.

In certain embodiments, for a compound or salt of any one of Formula (I), (Ia), (Ib), (Ic), (Id), R[2] is selected from optionally substituted 5- or 6-membered monocyclic heteroaryl and optionally substituted 9-membered bicyclic heteroaryl. In some embodiments, R[2] is selected from isoxazole, oxazole, thiadiazole, triazole, isothiazole, tetrazole, pyrazole, pyrrole, furan, imidazole, oxadiazole, thiazole, pyridine, pyridazine, pyrimidine, pyrazine, tetrazine, benzoxazole, benzothiazole, benzimidazole, indole, indazole, and imidazopyridine, any of which is optionally substituted. In some embodiments, R[2] is selected from isoxazole, oxazole, thiadiazole, triazole, tetrazole, pyrazole, oxadiazole, thiazole, pyridine, pyridazine, pyrazine, benzoxazole, indazole, and imidazopyridine, any of which is optionally substituted.

In some embodiments, R² is not substituted at either ortho position on R² relative to the point of connectivity to the rest of the molecule. In some embodiments, R² is not substituted at either ortho position on R² with a carbocycle or heterocycle. In some embodiments, R² is selected from isoxazole, oxazole, thiadiazole, triazole, tetrazole, pyrazole, oxadiazole, thiazole, isoxazole, thiadiazole any of which is optionally substituted. In some embodiments, R² is selected from isoxazole, oxazole, thiadiazole, pyrazole, oxadiazole, thiazole, isoxazole, thiadiazole any of which is optionally substituted.

In certain embodiments, for a compound or salt of any one of Formula (I), (Ia), (Ib), (Ic), (Id), substituents on R² are independently selected from halogen, —OR¹⁰, —SR¹⁰, —N(R¹⁰)₂, —NO₂, and —CN; C₁₋₆ alkyl optionally substituted with one or more substituents independently selected from halogen, —OR¹⁰, —N(R¹⁰)₂, —NO₂, and —CN; and optionally substituted C₃₋₁₀ carbocycle. In some embodiments, R² is a heteroaryl, e.g., 5-membered heteroaryl, optionally substituted with one or more substituents selected from halogen, —OR¹⁰, and —N(R¹⁰)₂; C₁₋₄ alkyl optionally substituted with one or more substituents independently selected from halogen; and optionally substituted C₃₋₁₀ carbocycle, e.g., optionally substituted phenyl or optionally substituted cycloalkyl such as cyclopropyl.

In certain embodiments, for a compound or salt of any one of Formula (I), (Ia), (Ib), (Ic), (Id), R² is selected from:

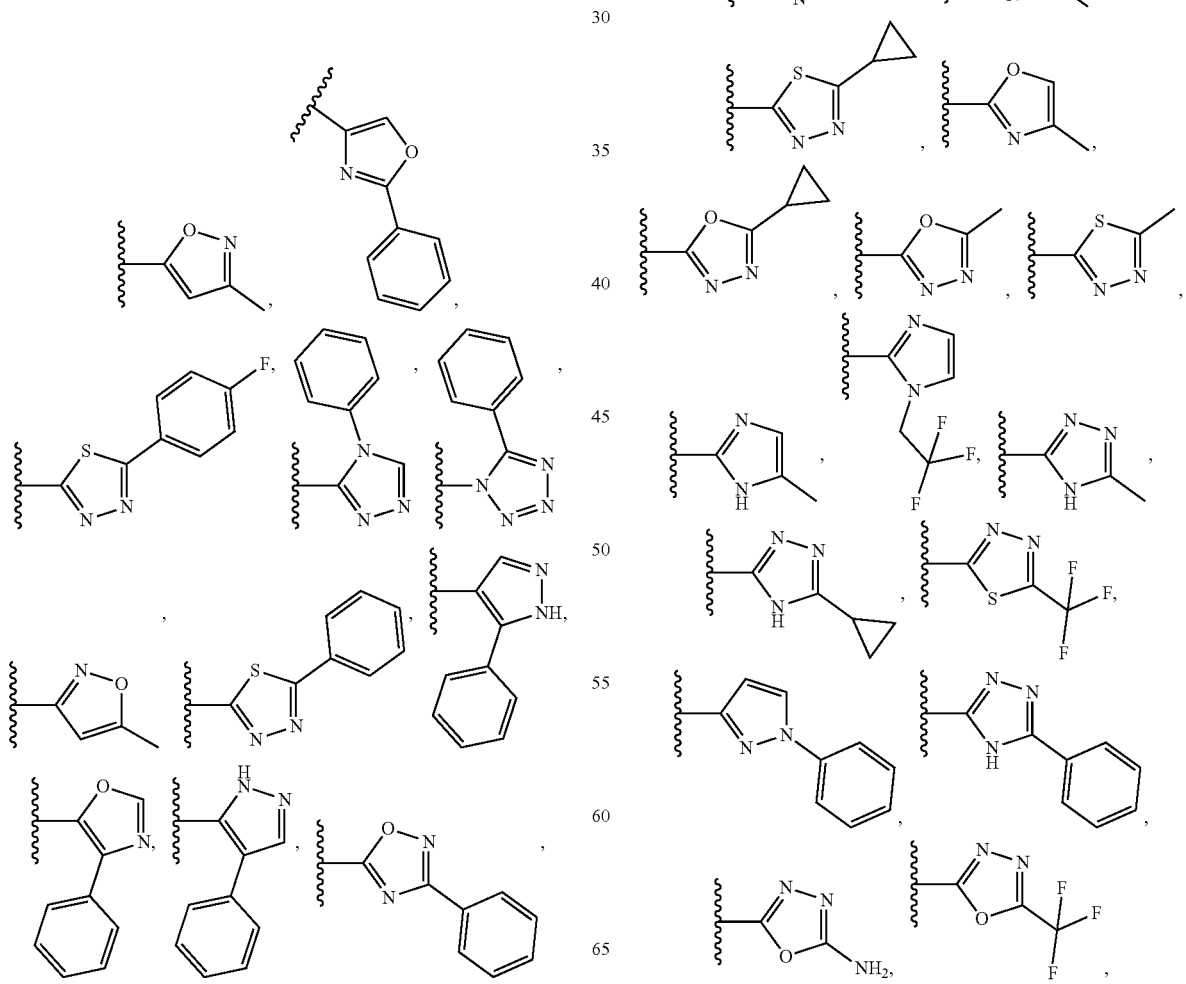

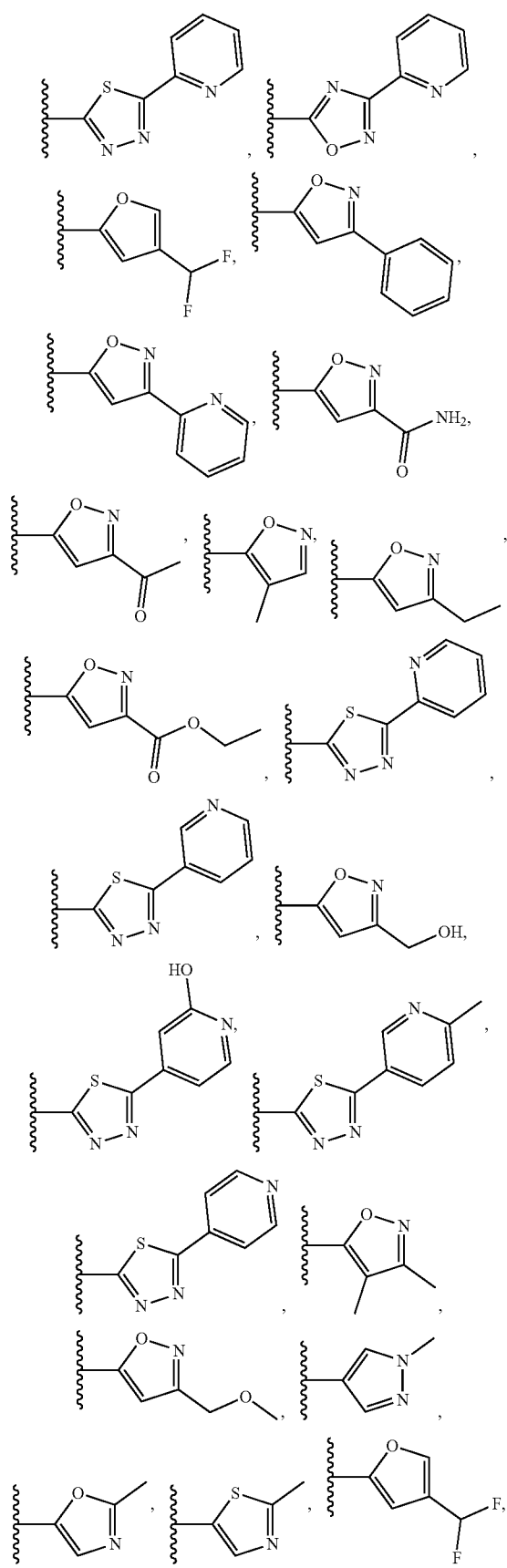
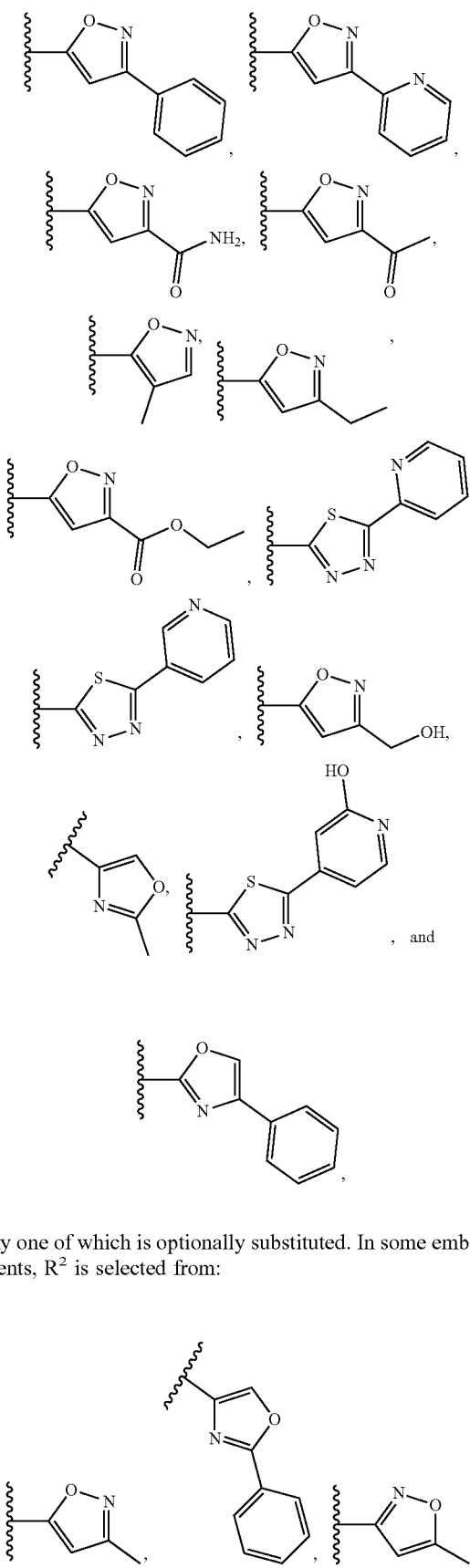
any one of which is optionally substituted. In some embodiments, $R^2$ is selected from:
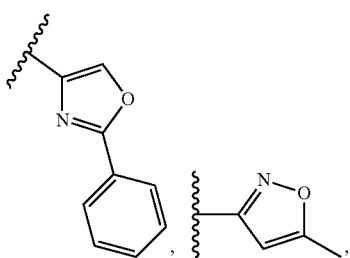

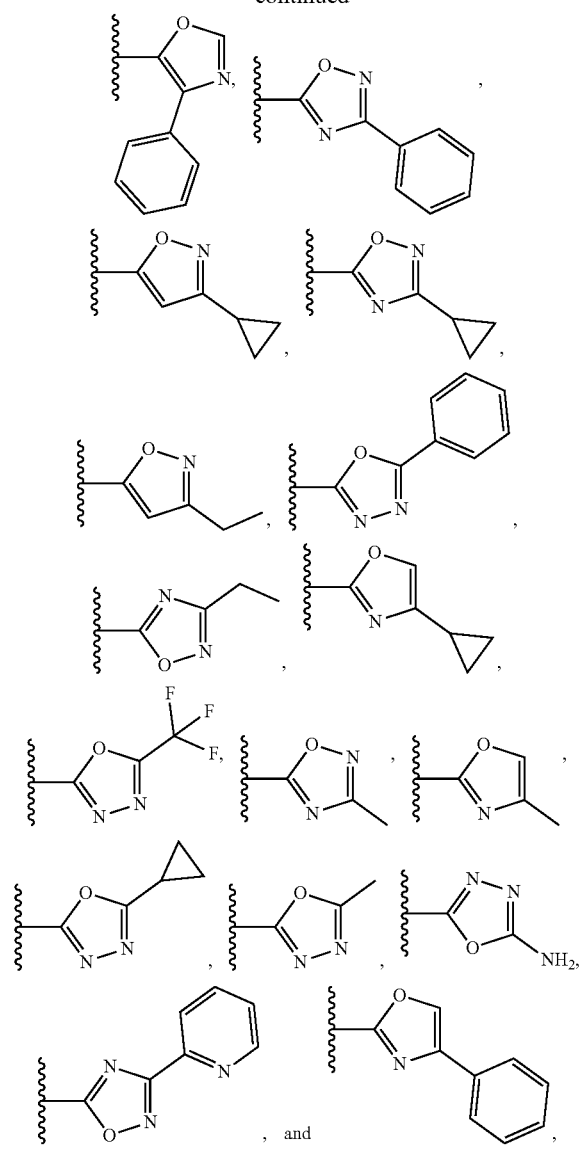
any one of which is optionally substituted. In some embodiments, R² is selected from:
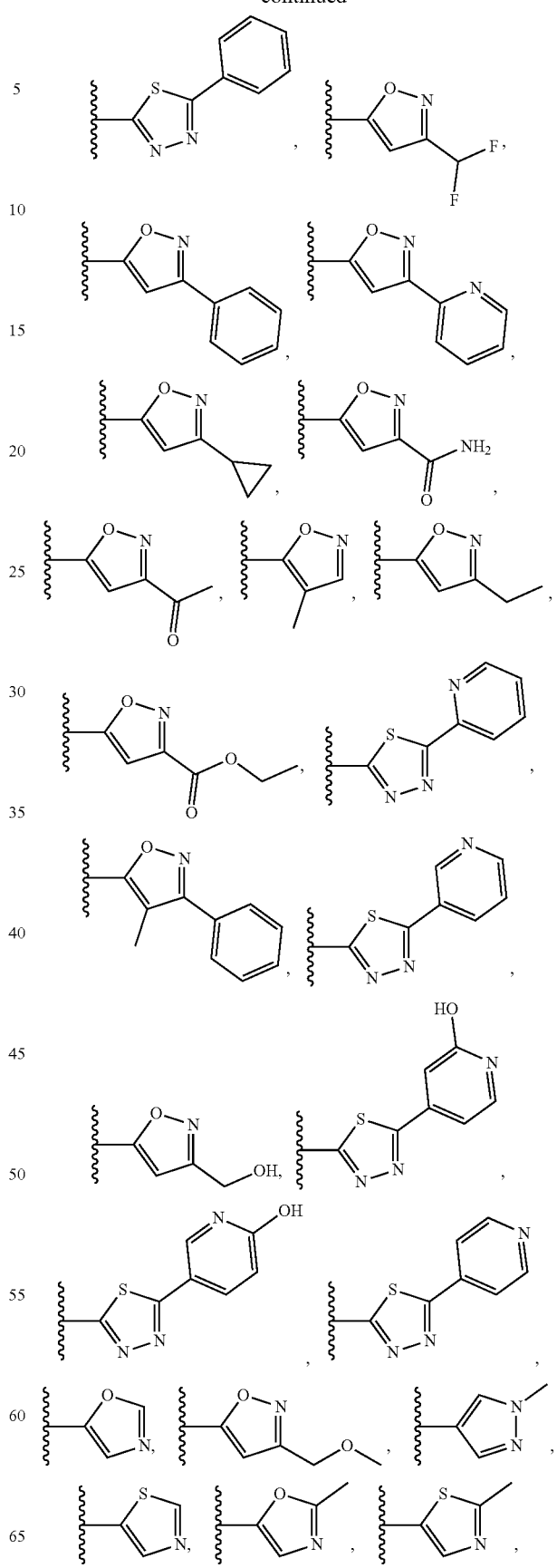

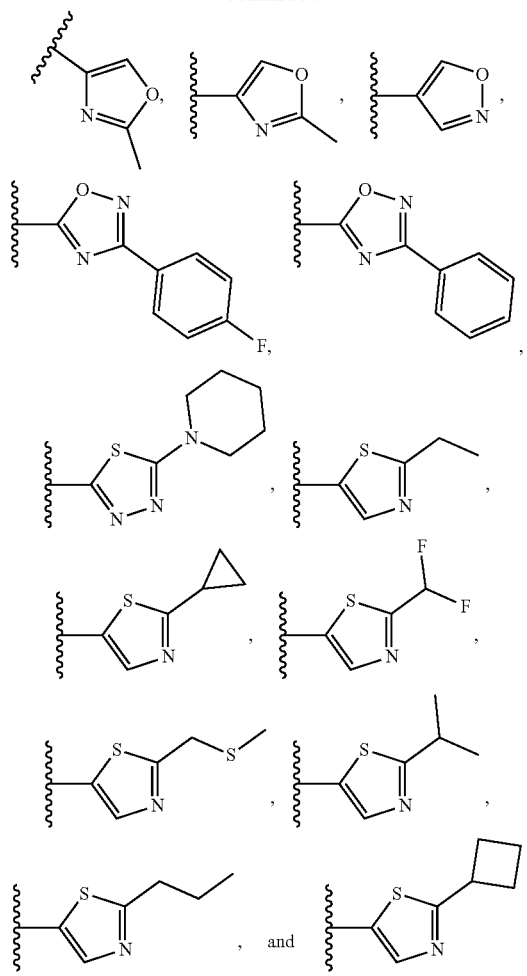

any one of which is optionally substituted.

In certain embodiments, for a compound or salt of any one of Formula (I), (Ia), (Ib), (Ic), (Id), $R^2$ is selected from optionally substituted 6-membered heteroaryl. In some embodiments, $R^2$ may be selected from 6-membered heteroaryls, such as pyridine, pyridazine, pyrimidine, pyrazine, triazene and N-oxides thereof. In some embodiments, $R^2$ is selected from optionally substituted pyridyl, optionally substituted pyrimidyl, optionally substituted pyridyl N-oxide, and optionally substituted pyrimidyl N-oxide. In some embodiments, $R^2$ is selected from optionally substituted pyridyl and optionally substituted pyrimidyl. In certain embodiments, for a compound or salt of any one of Formula (I), (Ia), (Ib), (Ic), (Id), $R^2$ is a 6-membered heteroaryl, e.g., pyridinyl or pyrimidinyl, optionally substituted with halogen, $-OR^{10}$, $-SR^{10}$, $-N(R^{10})_2$, $-NO_2$, and $-CN$; $C_{1-6}$ alkyl optionally substituted with one or more substituents independently selected from halogen, $-OR^{10}$, $-SR^{10}$, $-N(R^{10})_2$, $-NO_2$, and $-CN$; and optionally substituted $C_{3-10}$ carbocycle. In certain embodiments, for a compound or salt of any one of Formula (I), (Ia), (Ib), (Ic), (Id), $R^2$ is a 6-membered heteroaryl, e.g., pyridinyl or pyrimidinyl, optionally substituted with halogen, $-OR^{10}$, $-SR^{10}$, and $-N(R^{10})_2$; and $C_{1-4}$ alkyl optionally substituted with one or more substituents independently selected from halogen and $-OR^{10}$. In some embodiments, $R^2$ is selected from:

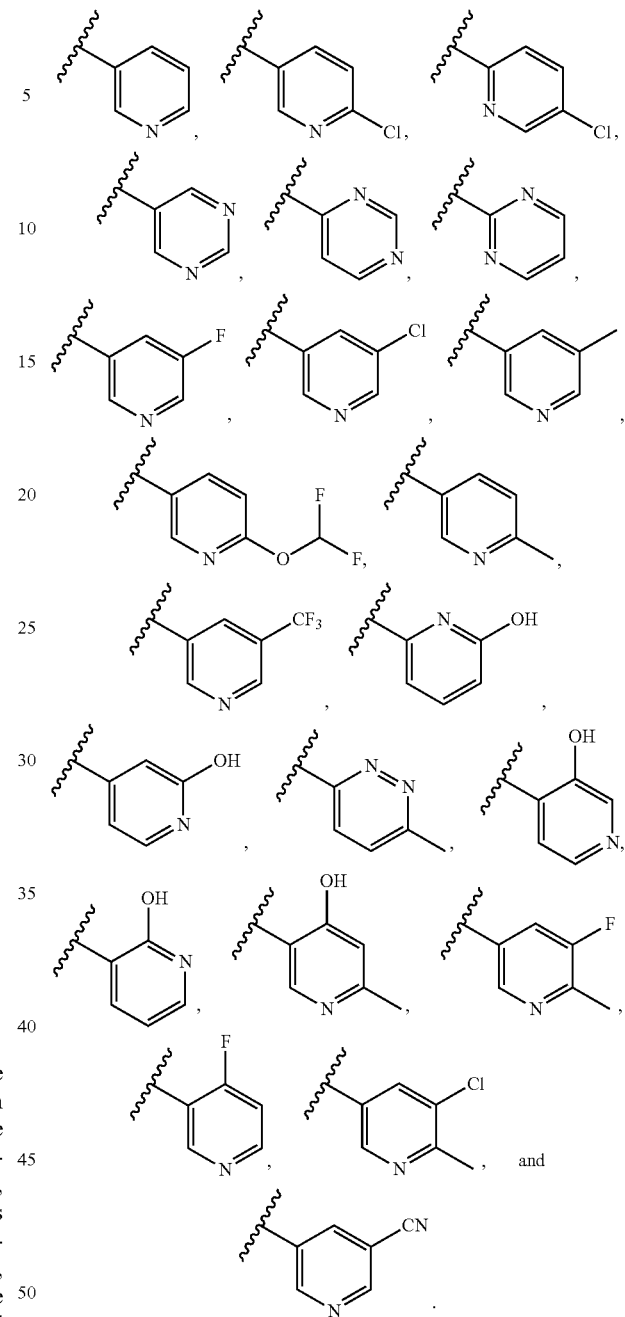

In certain embodiments, for a compound or salt of any one of Formula (I), (Ia), (Ib), (Ic), (Id), $R^2$ is selected from optionally substituted pyridine, optionally substituted pyrazine, optionally substituted pyridazine, and optionally substituted pyrimidine. In some embodiments, $R^2$ is selected from

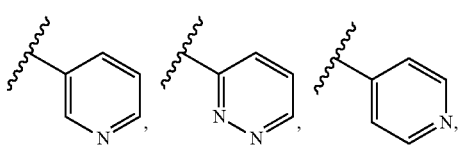

-continued

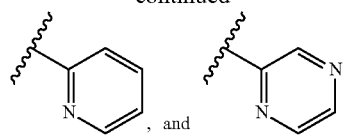, and any of which is optionally substituted with one or more substituents independently selected from: halogen, —OR$^{10}$, —SR$^{10}$, —CN, and a substituent on a nitrogen atom of the pyridyl is optionally selected from —O$^-$; and C$_{1-6}$ alkyl optionally substituted with one or more substituents independently selected from halogen and —OR$^{10}$. In some embodiments, R$^2$ is selected from:

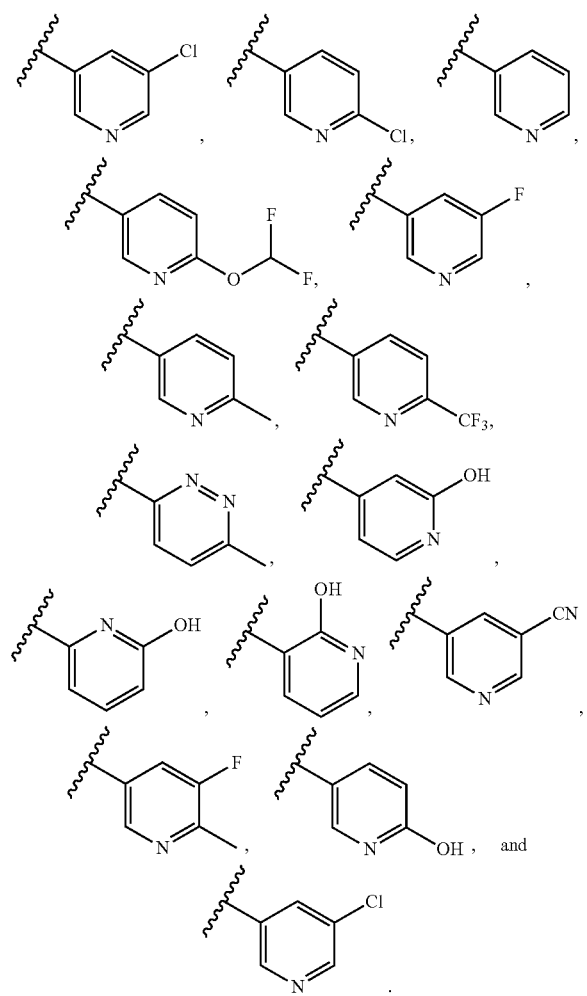

In certain embodiments, for a compound or salt of any one of Formula (I), (Ia), (Ib), (Ic), (Id), R$^2$ is selected from optionally substituted bicyclic heteroaryl. In some embodiments, R$^2$ is selected from optionally substituted 9-membered bicyclic heteroaryl, e.g., optionally substituted benzoxazole, benzothiazole, or benzimidazole. In certain embodiments, for a compound or salt of any one of Formula (I), (Ia), (Ib), (Ic), (Id), R$^2$ is a 9-membered bicyclic heteroaryl, e.g., benzoxazole, optionally substituted with halogen, —OR$^{10}$, —SR$^{10}$, —N(R$^{10}$)$_2$, —NO$_2$, and —CN; C$_{1-6}$ alkyl optionally substituted with one or more substituents independently selected from halogen, —OR$^{10}$, —SR$^{10}$, —N(R$^{10}$)$_2$, —NO$_2$, and —CN; and optionally substituted C$_{3-10}$ carbocycle. In some embodiments, R$^2$ is selected from optionally substituted benzoxazole. In some embodiments, R$^2$ is selected from:

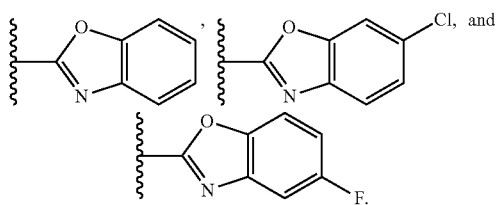

In certain embodiments, for a compound or salt of any one of Formula (I), (Ia), (Ib), (Ic), (Id), R$^2$ is selected optionally substituted 9-membered bicyclic heteroaryl. In some embodiments, R$^2$ is selected from benzoxazole, benzothiazole, benzimidazole, indole, indazole, and imidazopyridine, any of which is optionally substituted. In some embodiments, R$^2$ is selected from benzoxazole, benzothiazole, indole, indazole, and imidazopyridine, any of which is optionally substituted. In some embodiments, R$^2$ is selected from benzoxazole, indazole, and imidazopyridine, any of which is optionally substituted. In some embodiments, R$^2$ is selected from optionally substituted benzoxazole. In some embodiments, R$^2$ is selected from:

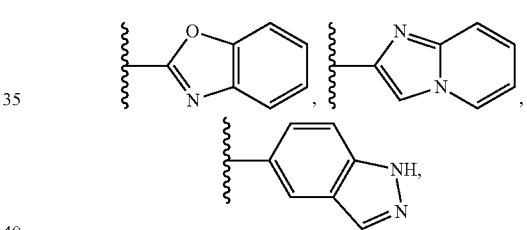

any of which is optionally substituted with one or more substituents independently selected from halogen, —OR$^{10}$, —SR$^{10}$, and —CN. In some embodiments, R$^2$ is selected from:

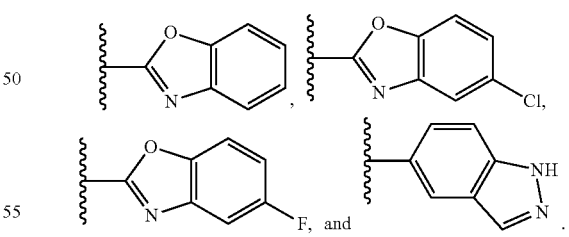

In some embodiments, for a compound or salt of any one of Formula (I), (Ia), (Ib), (Ic), (Id), when R$^2$ is substituted at either or both ortho positions of the heteroaryl ring relative to the point of connectivity to the rest of the molecule, each ortho substituent on R$^2$ is independently selected from halogen, —OR$^{10}$, —SR$^{10}$, —N(R$^{10}$)$_2$, —NO$_2$, —CN, and C$_{1-3}$ alkyl optionally substituted with one or more substituents independently selected from halogen, —OR$^{10}$, —SR$^{10}$, —N(R$^{10}$)$_2$, —NO$_2$, and —CN. In some embodiments, for a compound or salt of any one of Formula (I), (Ia), (Ib), (Ic), (Id), when R² is substituted at either or both ortho positions of the heteroaryl ring relative to the point of connectivity to the rest of the molecule, each ortho substituent on R² is independently selected from halogen, —OH, —OCH₃, —OCF₃, and C₁₋₃ alkyl optionally substituted with one or more substituents independently selected from halogen.

In some embodiments, for a compound or salt of any one of Formula (I), (Ia), (Ib), (Ic), (Id), R² is not substituted at either ortho position of the heteroaryl ring relative to the point of connectivity to the rest of the molecule. In some embodiments, for a compound or salt of any one of Formula (I), (Ia), (Ib), (Ic), (Id), R² is not substituted by a heterocycle or carbocycle at either ortho position of the heteroaryl ring relative to the point of connectivity to the rest of the molecule.

In certain embodiments, for a compound or salt of Formula (I), each R³ is selected from hydrogen, halogen, —OR¹⁰, —SR¹⁰, —N(R¹⁰)₂, —NO₂, —CN, and C₁₋₆ alkyl optionally substituted with one or more substituents independently selected from halogen, —OR¹⁰, —SR¹⁰, —N(R¹⁰)₂, —NO₂, and —CN. In some embodiments, R³ together with R¹ form a 5- to 6-membered heterocycle or C₅₋₆ carbocycle, wherein the 5- to 6-membered heterocycle or C₅₋₆ carbocycle is optionally substituted with one or more R⁹. In some embodiments, R³ is hydrogen.

In certain embodiments, for a compound or salt of any one of Formula (I), (Ia), (Ib), (Ic), (Id), R⁴ is independently selected from hydrogen; and C₁₋₆ alkyl optionally substituted with one or more substituents independently selected from halogen, —OR¹⁰, —SR¹⁰, —N(R¹⁰)₂, —NO₂, and —CN; or R⁴ together with R¹ form a 3- to 10-membered heterocycle, which is optionally substituted with one or more R⁹. In some embodiments, R⁴ is hydrogen.

In certain embodiments, for a compound or salt of any one of Formula (I), (Ia), (Ib), (Ic), (Id), each R⁵ and R⁶ is independently selected from hydrogen, halogen, —OR¹⁰, —SR¹⁰, —N(R¹⁰)₂, —NO₂, —CN, and C₁₋₆ alkyl optionally substituted with one or more substituents independently selected from halogen, —OR², —SR¹⁰, —N(R¹⁰)₂, —NO₂, and —CN.

In certain embodiments, for a compound or salt of any one of Formula (I), (Ia), (Ib), (Ic), (Id), each R⁷ and R⁸ is independently selected from halogen, —OR¹⁰, —SR¹⁰, —N(R¹⁰)₂, —NO₂, —CN, and C₁₋₆ alkyl optionally substituted with one or more substituents independently selected from halogen, —OR¹⁰, —SR¹⁰, —N(R¹⁰)₂, —NO₂, and —CN. In certain embodiments, for a compound or salt of any one of Formula (I), (Ia), (Ib), (Ic), (Id), each R⁷ and R⁸ is independently selected from halogen, —OR¹⁰, —SR¹⁰, —N(R¹⁰)₂, —NO₂, —CN, —CHF₂, —CF₃, —CH₂F, and C₂₋₆ alkyl optionally substituted with one or more substituents independently selected from halogen, —OR¹⁰, —SR¹⁰, —N(R¹⁰)₂, —NO₂, and —CN.

In certain embodiments, for a compound or salt of any one of Formula (I), (Ia), (Ib), (Ic), (Id), each R⁹ is independently selected from halogen, —OR¹⁰, —N(R¹⁰)₂, —NO₂, =O, =S, —CN; and C₁₋₃ alkyl, C₂₋₃ alkenyl, C₂₋₃ alkynyl, each of which is optionally substituted with one or more substituents independently selected from halogen, —OR¹⁰, —N(R¹⁰)₂, —NO₂, —CN. In some embodiments, R⁹ is a halogen. In some embodiments, R⁹ is an unsubstituted C₁₋₃ alkyl. In some embodiments, R⁹ is =O. In some embodiments, R⁹ is a haloalkyl. In some embodiments, R⁹ is a C₁₋₃ alkyl substituted with one or more fluorine substituents.

In certain embodiments, for a compound or salt of any one of Formula (I), (Ia), (Ib), (Ic), (Id), each R¹⁰ is independently selected from hydrogen; and C₁₋₆ alkyl optionally substituted with one or more substituents independently selected from halogen, —CN, —OH, —SH, —NO₂, —NH₂, =O, =S, —O—C₁₋₆ alkyl, —S—C₁₋₆ alkyl, —N(C₁₋₆ alkyl)₂, —NH(C₁₋₆ alkyl), C₃₋₁₀ carbocycle, 3- to 10-membered heterocycle; and C₃₋₁₀ carbocycle, and 3- to 10-membered heterocycle, each of which is optionally substituted with one or more substituents independently selected from halogen, —CN, —OH, —SH, —NO₂, —NH₂, =O, =S, —O—C₁₋₆ alkyl, —S—C₁₋₆ alkyl, —N(C₁₋₆ alkyl)₂, —NH(C₁₋₆ alkyl), C₁₋₆ alkyl, C₃₋₁₀ carbocycle, 3- to 10-membered heterocycle, and haloalkyl.

In certain embodiments, for a compound or salt of any one of Formula (I), (Ia), (Ib), (Ic), (Id), n is 0.

In certain embodiments, for a compound or salt of any one of Formula (I), (Ia), (Ib), (Ic), (Id), p is 0.

In one aspect, disclosed herein is a compound represented by Formula (Ie):

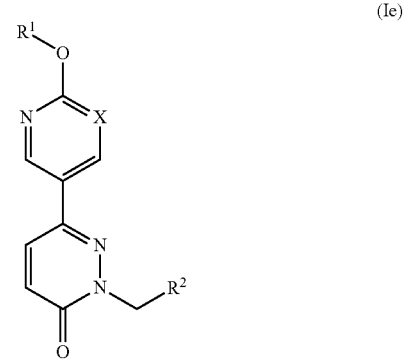

or a salt thereof, wherein:
X is independently selected from C(R³) and N;
R¹ is selected from
    C₁₋₆ alkyl optionally substituted with one or more substituents independently selected from halogen, —OH, —SH, —NH₂, —NO₂, —CN, C₃₋₁₀ carbocycle and 3- to 10-membered heterocycle, wherein the C₃₋₁₀ carbocycle and 3- to 10-membered heterocycle are each optionally substituted with one or more R⁹;
R² is a heteroaryl, e.g., a 5-, 6-, or 9-membered heteroaryl, optionally substituted with one or more substituents independently selected from
    halogen, —OR¹⁰, —SR¹⁰, —N(R¹⁰)₂, —NO₂, and —CN;
    C₁₋₆ alkyl optionally substituted with one or more substituents independently selected from halogen, —OR¹⁰, —SR¹⁰, —N(R¹⁰)₂, —NO₂, —CN; and
    C₃₋₁₀ carbocycle optionally substituted with one or more R⁹;
each R⁹ is independently selected from
    halogen, —OR¹⁰, —N(R¹⁰)₂, —NO₂, —CN; and
    C₁₋₃ alkyl optionally substituted with one or more substituents independently selected from halogen, —OR¹⁰, —N(R¹⁰)₂, —NO₂, and —CN; and
each R¹⁰ is independently selected from
    hydrogen; and
    C₁₋₆ alkyl optionally substituted with one or more substituents independently selected from halogen, —CN, —OH, —SH, —NO₂, —NH₂, —O—C₁₋₆ alkyl, —N(C₁₋₆ alkyl)₂, and —NH(C₁₋₆ alkyl).

In certain embodiments, for a compound or salt of any one of Formula (I), (Ia), (Ib), (Ic), or (Id), R¹-A is further selected from hydrogen. For example, a compound of the disclosure may be represented by:

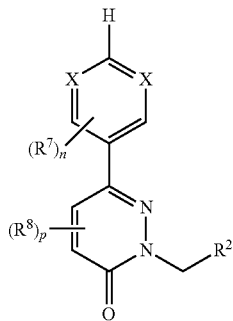

or a salt thereof.

In certain embodiments, for a compound or salt of Formula (I):
each X is N or N⁺(—O⁻), preferably each X is N;
A is selected from —O—, —NR⁴—, or —CR⁵R⁶—, preferably A is —O—;
$R^1$ is selected from $C_{1-5}$ alkyl optionally substituted with one or more substituents independently selected from halogen, —OR¹⁰, —SR¹⁰, $C_{3-5}$ carbocycle and 3- to 5-membered heterocycle, wherein the $C_{3-5}$ carbocycle and 3- to 5-membered heterocycle are each optionally substituted with one or more $R^9$, preferably $R^1$ is selected from $C_{1-3}$ alkyl optionally substituted with one or more substituents independently selected from halogen;
$R^2$ is selected from optionally substituted 5- or 6-membered monocyclic heteroaryl and optionally substituted 9-membered bicyclic heteroaryl, preferably $R^2$ is selected from optionally substituted 6-membered heteroaryl, wherein substituents on $R^2$ are independently selected from halogen, —OR¹⁰, —SR¹⁰, —CN, $C_{1-3}$ alkyl and $C_{1-3}$ haloalkyl;
$R^7$ and $R^8$ are independently selected from halogen, —OR¹⁰, —SR¹⁰, —N(R¹⁰)₂, —NO₂, —CN, and $C_{1-3}$ alkyl optionally substituted with one or more substituents independently selected from halogen;
n is 0 or 1; and
p is 0 or 1.

In certain embodiments, a compound of the disclosure is selected from a compound of Table 1 or a salt thereof.

In one aspect, disclosed herein is a compound represented by Formula (II):

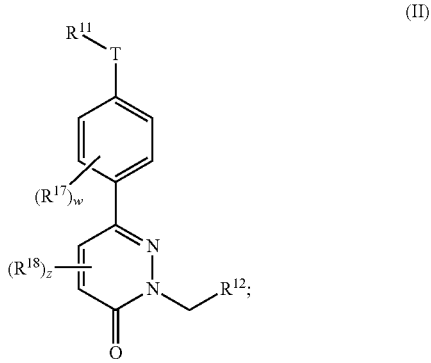

(II)

or a salt thereof, wherein:
T is selected from —O—, —NR¹⁴—, —CR¹⁵R¹⁶—, —C(O)—, —S—, —S(O)—, and —S(O)₂;
$R^{11}$ is selected from:
  $C_{1-5}$ haloalkyl optionally further substituted with one or more substituents independently selected from —OR²⁰, —SR²⁰, —N(R²⁰)₂, —NO₂, =O, =S, —CN, $C_{3-10}$ carbocycle and 3- to 10-membered heterocycle, wherein the $C_{3-10}$ carbocycle and 3- to 10-membered heterocycle are each optionally substituted with one or more $R^{19}$;
$R^{12}$ is a heteroaryl optionally substituted with one or more substituents independently selected from halogen, —OR²⁰, —SR²⁰, —N(R²⁰)₂, —C(O)R²⁰, —C(O)N(R²⁰)₂, —N(R²⁰)C(O)R²⁰, —N(R²⁰)C(O)N(R²⁰)₂, —OC(O)N(R²⁰)₂, —N(R²⁰)C(O)OR²⁰, —C(O)OR²⁰, —OC(O)R²⁰, —S(O)R²⁰, —S(O)₂R²⁰, —NO₂, =O, =S, =N(R²⁰), and —CN; and when $R^{12}$ is pyridyl or pyrimidyl, a substituent on a nitrogen atom of the pyridyl or pyrimidyl is optionally further selected from —O⁻;
$C_{1-6}$ alkyl, $C_{2-6}$ alkenyl, $C_{2-6}$ alkynyl, each of which is optionally substituted with one or more substituents independently selected from halogen, —OR²⁰, —SR²⁰, —N(R²⁰)₂, —C(O)R², —C(O)N(R²⁰)₂, —N(R²⁰)C(O)R²⁰, —N(R²⁰)C(O)N(R²⁰)₂, —OC(O)N(R²⁰)₂, —N(R²⁰)C(O)OR²⁰, —C(O)OR²⁰, —OC(O)R²⁰, —S(O)R²⁰, —S(O)₂R²⁰, —NO₂, =O, =S, =N(R²⁰), —CN, $C_{3-10}$ carbocycle and 3- to 10-membered heterocycle, wherein the $C_{3-10}$ carbocycle and 3- to 10-membered heterocycle are each optionally substituted with one or more $R^{19}$; and
$C_{3-10}$ carbocycle and 3- to 10-membered heterocycle, each of which is optionally substituted with one or more —$R^{19}$;
each $R^{15}$ and $R^{16}$ is independently selected from hydrogen, halogen, —OR²⁰, —SR²⁰, —N(R²⁰)₂, —NO₂, —CN, and $C_{1-6}$ alkyl optionally substituted with one or more substituents independently selected from halogen, —OR²⁰, —SR²⁰, —N(R²⁰)₂, —NO₂, and —CN;
$R^{14}$ is independently selected from hydrogen, and $C_{1-6}$ alkyl optionally substituted with one or more substituents independently selected from halogen, —OR²⁰, —SR²⁰, —N(R²⁰)₂, —NO₂, and —CN;
each $R^{17}$ and $R^{18}$ is independently selected from:
halogen, —OR²⁰, —SR²⁰, —N(R²⁰)₂, —NO₂, —CN, and $C_{1-6}$ alkyl optionally substituted with one or more substituents independently selected from halogen, —OR²⁰, —SR²⁰, —N(R²⁰)₂, —NO₂, and —CN;
each $R^{19}$ is independently selected from:
halogen, —OR²⁰, —SR²⁰, —N(R²⁰)₂, —C(O)R²⁰, —C(O)R²⁰, —C(O)N(R²⁰)₂, —N(R²⁰)C(O)R²⁰, —N(R²⁰)C(O)N(R²⁰)₂, —OC(O)N(R²⁰)₂, —N(R²⁰)C(O)OR²⁰, —C(O)OR²⁰, —OC(O)R²⁰, —S(O)R²⁰, —S(O)₂R²⁰, —NO₂, =O, =S, =N(R²⁰), —CN; and
$C_{1-3}$ alkyl, $C_{2-3}$ alkenyl, $C_{2-3}$ alkynyl, each of which is optionally substituted with one or more substituents independently selected from halogen, —OR²⁰, —SR²⁰, —N(R²⁰)₂, —C(O)R²⁰, —C(O)N(R²⁰)₂, —N(R²⁰)C(O)R²⁰, —N(R²⁰)C(O)N(R²⁰)₂, —OC(O)N(R²⁰)₂, —N(R²⁰)C(O)OR²⁰, —C(O)OR²⁰, —OC(O)R²⁰, —S(O)R²⁰, —S(O)₂R²⁰, —NO₂, =O, =S, =N(R²⁰), and —CN;
each $R^{20}$ is independently selected from:
hydrogen; and
$C_{1-6}$ alkyl, $C_{2-6}$ alkenyl, $C_{2-6}$ alkynyl, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, 3- to 10-membered heterocycle; and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and haloalkyl;

w is 0, 1, or 2; and z is 0, 1, or 2.

In certain embodiments, for a compound or salt of Formula (II), T is selected from —O—, —NR$^{14}$—, and —CR$^{15}$R$^{16}$—. In some embodiments, T is —O—.

In certain embodiments, for a compound or salt of Formula (II), R$^{11}$ is selected from C$_{1-5}$ haloalkyl optionally further substituted with one or more substituents independently selected from —OH, —SH, —NH$_2$, —NO$_2$, =O, =S, —CN, C$_{3-10}$ carbocycle and 3- to 10-membered heterocycle, wherein the C$_{3-10}$ carbocycle and 3- to 10-membered heterocycle are each optionally substituted with one or more R$^{19}$. In some embodiments, R$^{11}$ is selected from C$_{1-3}$ haloalkyl optionally further substituted with one or more substituents independently selected from —OR$^{20}$, —SR$^{20}$, —N(R$^{20}$)$_2$, =O, —CN, C$_{3-10}$ carbocycle and 3- to 10-membered heterocycle. In certain embodiments, R$^{11}$ is C$_{1-3}$ alkyl substituted with one or more halogen substituents. In some embodiments, R$^{11}$ is —CHF$_2$ or —CH$_2$CF$_3$.

In certain embodiments, for a compound or salt of any one of Formula (II), R$^{11}$ is selected from optionally substituted C$_3$-C$_6$ cycloalkyl, such as cyclopropyl, cyclobutyl, cyclopentyl, bicyclopentyl, and spiropentyl, any of which is optionally substituted. In certain embodiments, R$^{11}$ is selected from alkyl, e.g., methyl, ethyl, propyl, iso-propyl, t-butyl, iso-butyl, sec-butyl, any of which may be optionally substituted. In certain embodiments, R$^{11}$ is selected from:

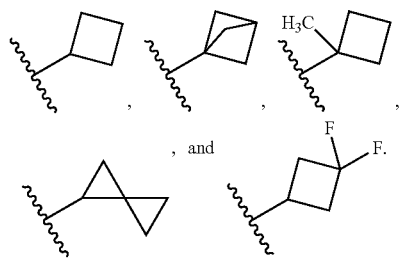

In certain embodiments, R$^{11}$ is selected from:

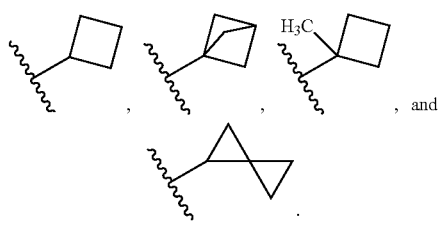

In certain embodiments, R$^{11}$ is selected from optionally substituted

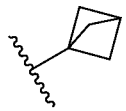

In some embodiments, for a compound of Formula (II), R$^{12}$ is an optionally substituted 5-membered heteroaryl, 6-membered heteroaryl, or a 9-membered bicyclic heterocycle. In some embodiments, R$^{12}$ is an optionally substituted 5-membered heteroaryl. In certain embodiments, R$^{12}$ is an optionally substituted 5-membered heteroaryl with at least one endocyclic nitrogen or oxygen atom in the 5-membered heteroaryl, e.g., oxazole, thiazole, pyrrole, pyrazole, furan, diazole, triazole, imidazole, oxadiazole, thiadiazole, isoxazole, isothiazole, and tetrazole. In certain embodiments, for a compound or salt of Formula (II), R$^{12}$ is selected from:

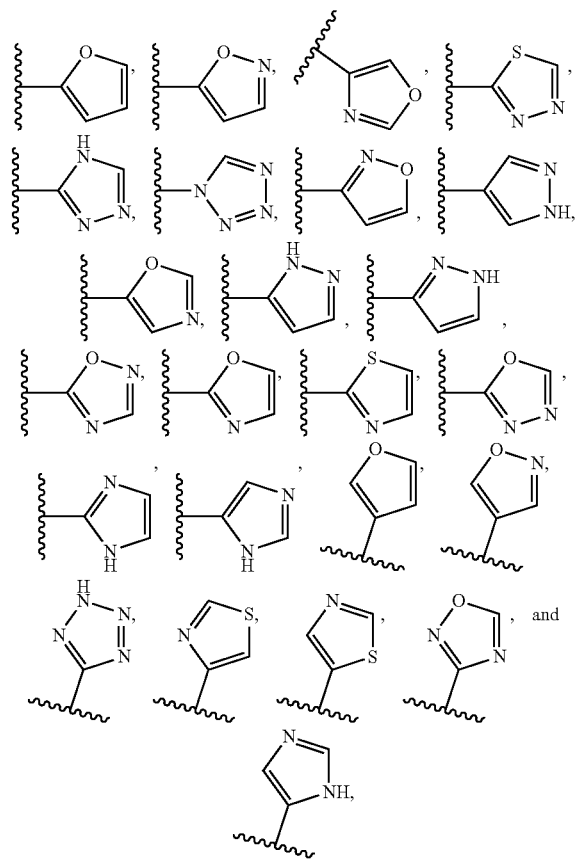

any one of which is optionally substituted. In some embodiments, R$^{12}$ is selected from:

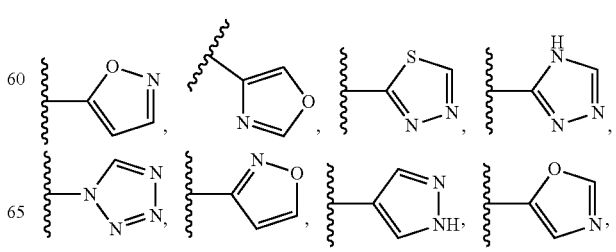

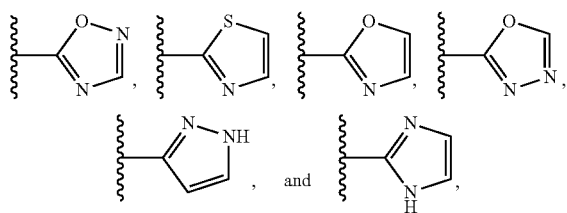

any one of which is optionally substituted. In some embodiments, $R^{12}$ is selected from:

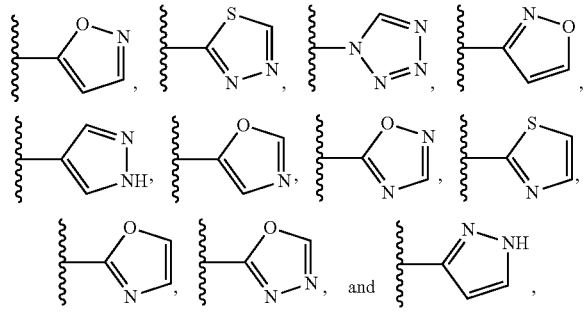

any one of which is optionally substituted. In some embodiments, $R^{12}$ is selected from:

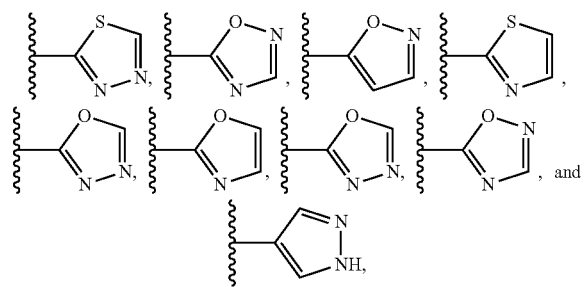

any of which is optionally substituted. In some embodiments, $R^{12}$ is selected from:

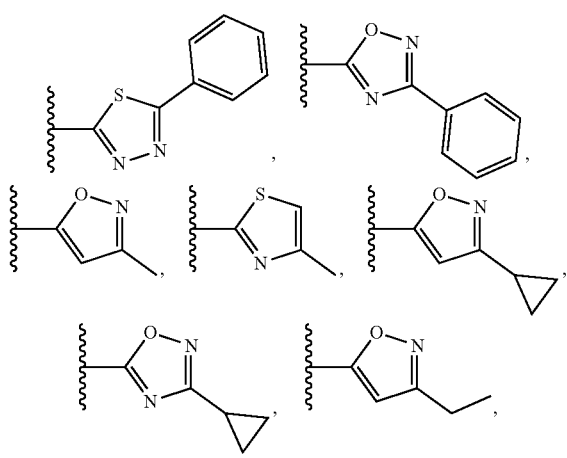

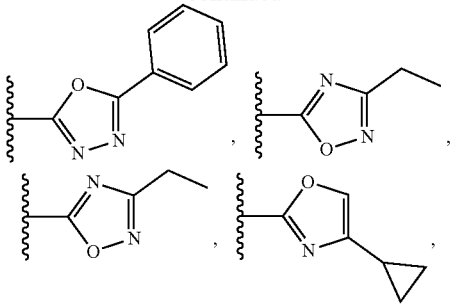

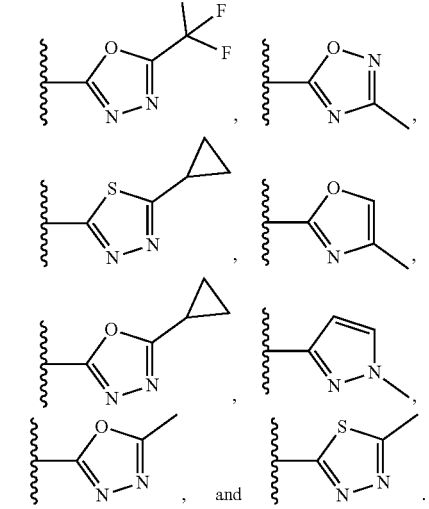

In some embodiments, $R^{12}$ is selected from optionally substituted 5- or 6-membered monocyclic heteroaryl and optionally substituted 9-membered bicyclic heteroaryl. In some embodiments, $R^{12}$ is selected from isoxazole, oxazole, thiadiazole, triazole, isothiazole, tetrazole, pyrazole, pyrrole, furan, imidazole, oxadiazole, thiazole, pyridine, pyridazine, pyrimidine, pyrazine, tetrazine, benzoxazole, benzothiazole, benzimidazole, indole, indazole, and imidazopyridine, any of which is optionally substituted. In some embodiments, $R^{12}$ is selected from isoxazole, oxazole, thiadiazole, triazole, pyrazole, imidazole, oxadiazole, thiazole, pyridine, pyrimidine, benzoxazole, benzimidazole, any of which is optionally substituted. In some embodiments, $R^{12}$ is selected from isoxazole, oxazole, thiadiazole, oxadiazole, pyrazole, tetrazole, thiazole, pyridine, benzoxazole, any of which is optionally substituted. In some embodiments, $R^{12}$ is not substituted at either ortho position on $R^{12}$ relative to the point of connectivity to the rest of the molecule. In some embodiments, $R^{12}$ is not substituted at either ortho position on $R^{12}$ with a carbocycle or heterocycle. In some embodiments, $R^{12}$ is selected from isoxazole, oxazole, thiadiazole, oxadiazole, pyrazole, tetrazole, and thiazole, any of which is optionally substituted.

In certain embodiments, for a compound of Formula (II), substituents on $R^{12}$ are independently selected from halogen, —$OR^{20}$, —$SR^{20}$, —$N(R^{20})_2$, —$NO_2$, and —CN; $C_{1-6}$ alkyl optionally substituted with one or more substituents independently selected from halogen, —$OR^{20}$, —$SR^{10}$, —$N(R^{20})_2$, —$NO_2$, and —CN; and optionally substituted $C_{3-10}$ carbocycle. In some embodiments, $R^2$ is a heteroaryl, e.g., 5-membered heteroaryl, optionally substituted with one or more substituents selected from halogen, —$OR^{10}$, and —$N(R^{20})_2$; $C_{1-4}$ alkyl optionally substituted with one or more substituents independently selected from halogen; and optionally substituted $C_{3-10}$ carbocycle, e.g., optionally substituted phenyl or optionally substituted cycloalkyl such as cyclopropyl.
In certain embodiments, for a compound or salt of Formula (II), $R^{12}$ is selected from:
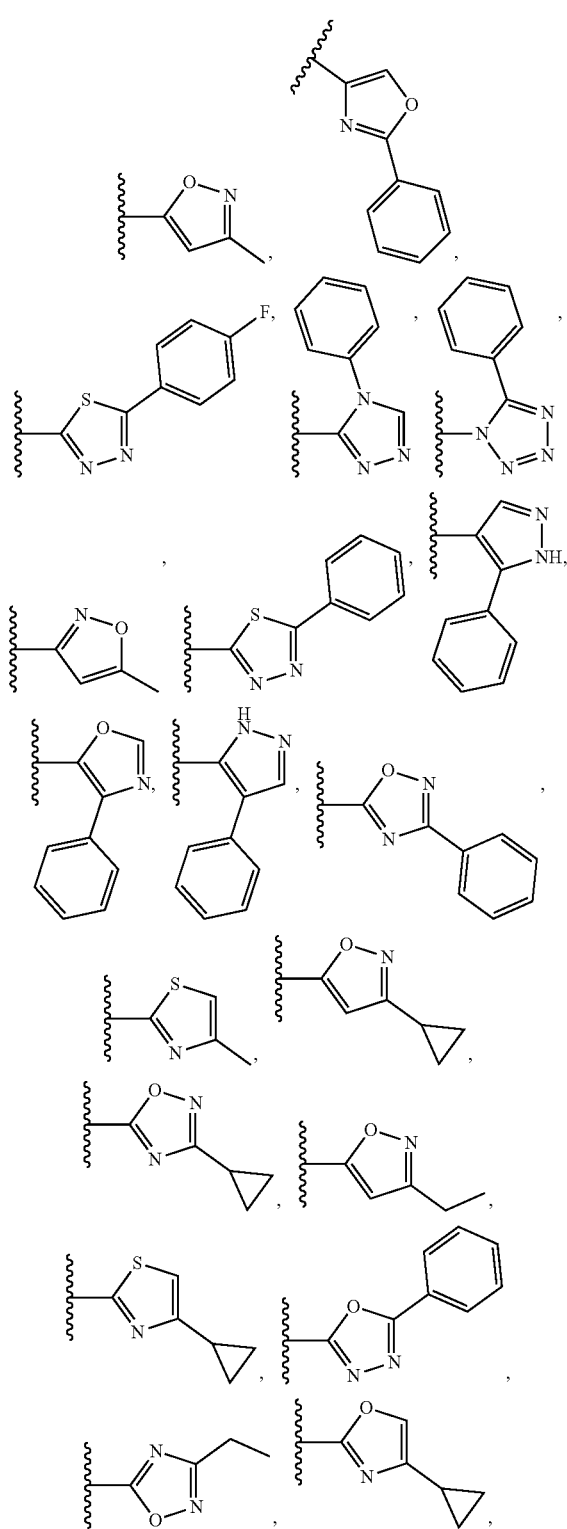
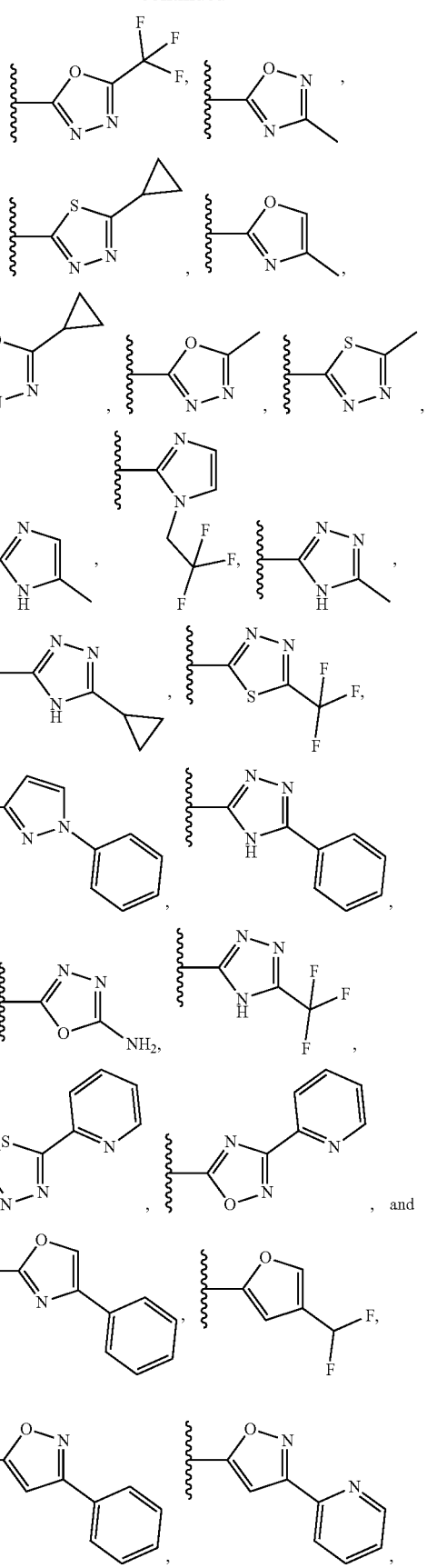

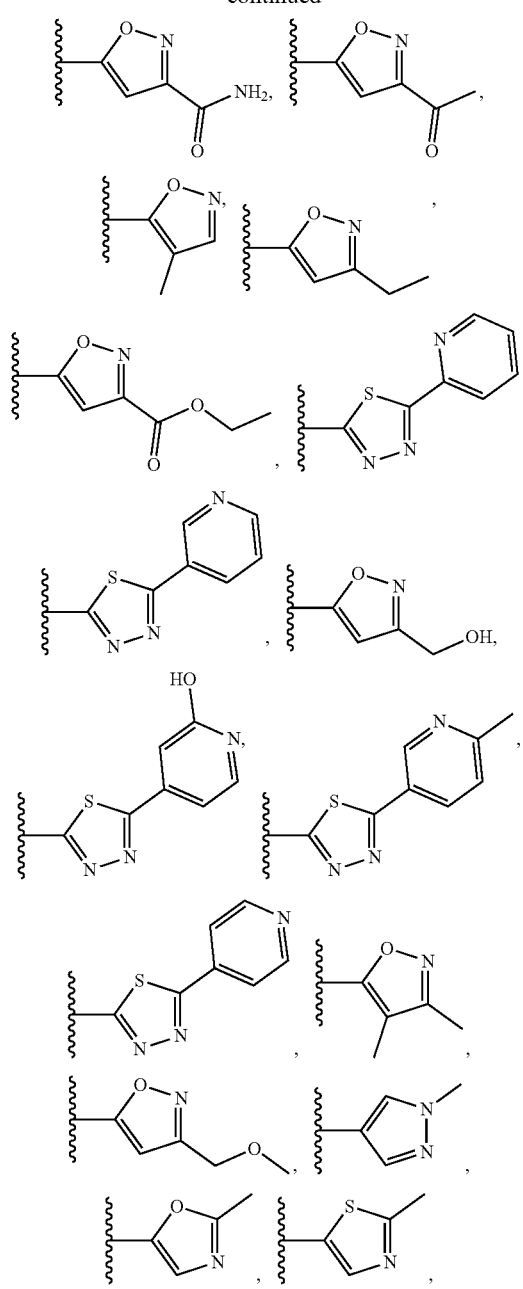
any one of which is optionally substituted. In some embodiments, $R^{12}$ is selected from:
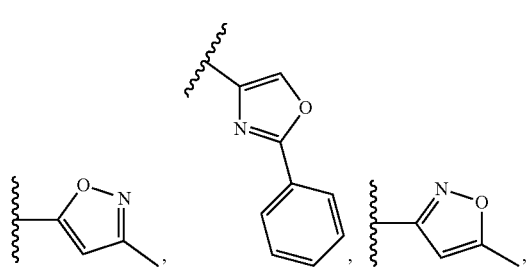
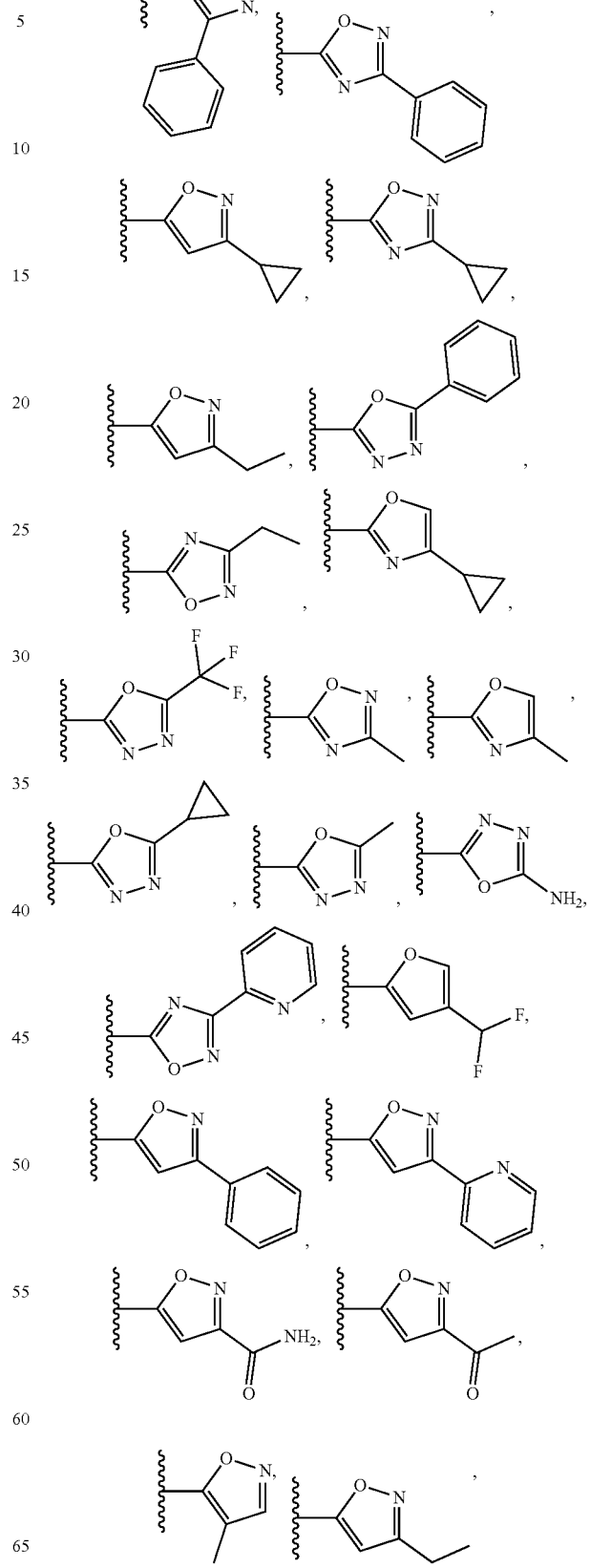

-continued

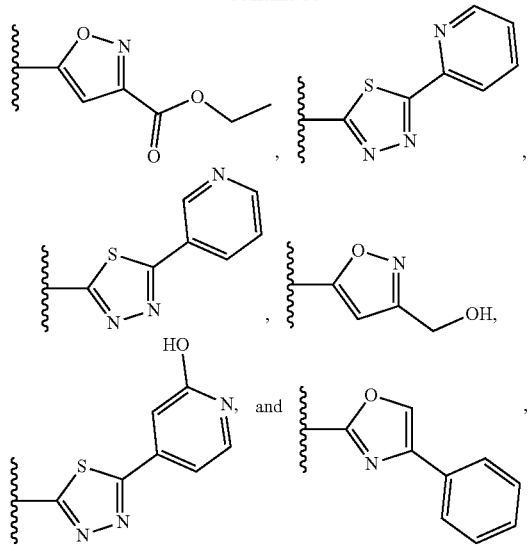

any one of which is optionally substituted.

In certain embodiments, for a compound or salt of Formula (II), $R^{12}$ is selected from optionally substituted 6-membered heteroaryl. In some embodiments, $R^{12}$ may be selected from 6-membered heteroaryls, such as pyridine, pyridazine, pyrimidine, pyrazine, triazene and N-oxides thereof. In some embodiments, $R^{12}$ is selected from optionally substituted pyridyl, optionally substituted pyrimidyl, optionally substituted pyridyl N-oxide, and optionally substituted pyrimidyl N-oxide. In some embodiments, $R^{12}$ is selected from optionally substituted pyridyl and optionally substituted pyrimidyl. In certain embodiments, for a compound or salt of Formula (II), $R^{12}$ is a 6-membered heteroaryl, e.g., pyridinyl or pyrimidinyl, optionally substituted with halogen, —$OR^{20}$, —$SR^{20}$, —$N(R^{20})_2$, —$NO_2$, and —CN; $C_{1-6}$ alkyl optionally substituted with one or more substituents independently selected from halogen, —$OR^{20}$, —$SR^{20}$, —$N(R^{20})_2$, —$NO_2$, and —CN; and optionally substituted $C_{3-10}$ carbocycle. In certain embodiments, for a compound or salt of Formula (II), $R^{12}$ is a 6-membered heteroaryl, e.g., pyridinyl or pyrimidinyl, optionally substituted with halogen, —$OR^{20}$, —$SR^{20}$, and —$N(R^{20})_2$; and $C_{1-4}$ alkyl optionally substituted with one or more substituents independently selected from halogen and —$OR^{20}$. In some embodiments, $R^{12}$ is selected from:

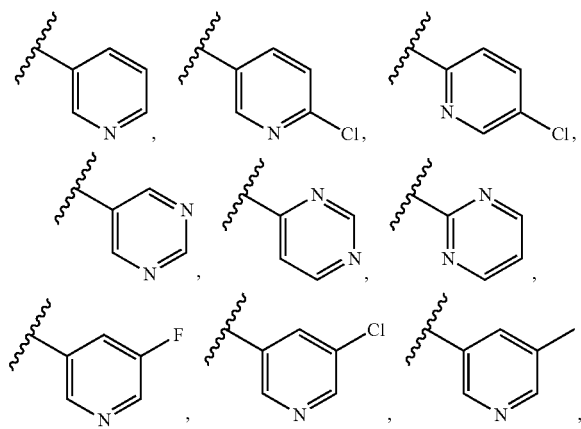

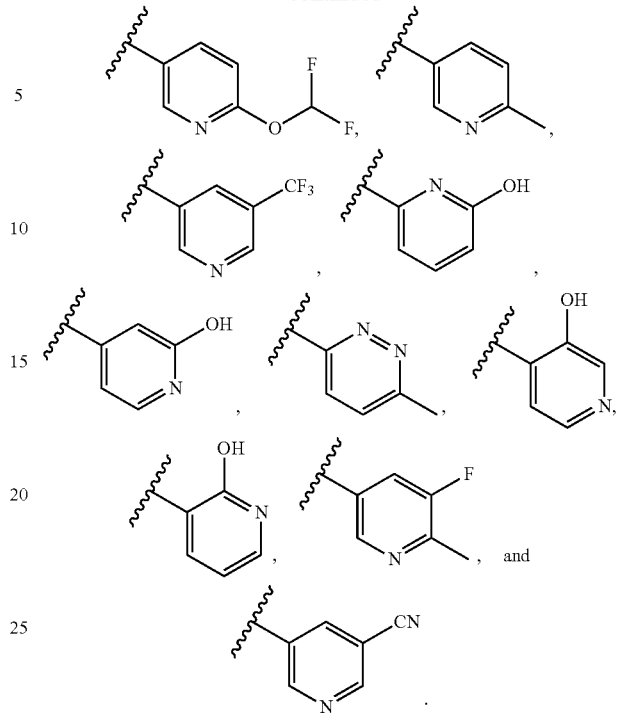

In some embodiments, $R^{12}$ is selected from pyridine and pyrimidine any of which is optionally substituted. In some embodiments, $R^{12}$ is selected from:

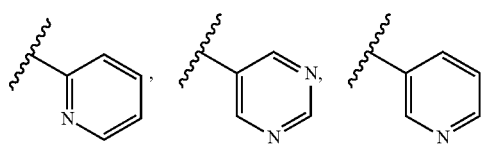 [SMILES: *c1ccccn1 ; *c1cncnc1 ; *c1cccnc1]

any of which is optionally substituted.

In some embodiments, $R^{12}$ is selected from optionally substituted benzoxazole. In some embodiments, $R^{12}$ is optionally substituted

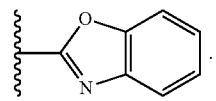

In certain embodiments, for a compound or salt of Formula (II), $R^{12}$ is selected from optionally substituted bicyclic heteroaryl. In some embodiments, $R^{12}$ is selected from optionally substituted 9-membered bicyclic heteroaryl, e.g., optionally substituted benzoxazole, benzothiazole, or benzimidazole. In certain embodiments, for a compound or salt of Formula (II), $R^{12}$ is a 9-membered bicyclic heteroaryl, e.g., benzoxazole, optionally substituted with halogen, —$OR^{20}$, —$SR^{20}$, —$N(R^{20})_2$, —$NO_2$, and —CN; $C_{1-6}$ alkyl optionally substituted with one or more substituents independently selected from halogen, —$OR^{20}$, —$SR^{20}$, —$N(R^{20})_2$, —$NO_2$, and —CN; and optionally substituted $C_{3-10}$ carbocycle. In some embodiments, $R^{12}$ is selected from optionally substituted benzoxazole. In some embodiments, $R^{12}$ is selected from

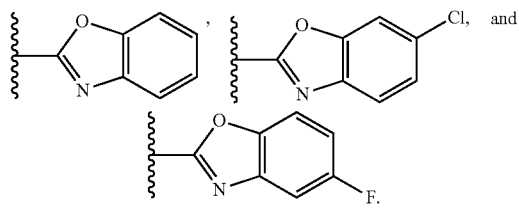

In some embodiments, for a compound or salt of Formula (II), when $R^{12}$ is substituted at either or both ortho positions of the heteroaryl ring relative to the point of connectivity to the rest of the molecule, each ortho substituent on $R^{12}$ is independently selected from halogen, —$OR^{20}$, —$SR^{20}$, —$N(R^{20})_2$, —$NO_2$, —CN, and $C_{1-3}$ alkyl optionally substituted with one or more substituents independently selected from halogen, —$OR^{20}$, —$SR^{20}$, —$N(R^{20})_2$, —$NO_2$, and —CN. In some embodiments, for a compound or salt of Formula (II), when $R^{12}$ is substituted at either or both ortho positions of the heteroaryl ring relative to the point of connectivity to the rest of the molecule, each ortho substituent on $R^{12}$ is independently selected from halogen, —OH, —$OCH_3$, —$OCF_3$, and $C_{1-3}$ alkyl optionally substituted with one or more substituents independently selected from halogen.

In some embodiments, for a compound or salt of Formula (II), $R^{12}$ is not substituted at either ortho position of the heteroaryl ring relative to the point of connectivity to the rest of the molecule. In some embodiments, for a compound or salt of Formula (II), $R^{12}$ is not substituted by a heterocycle or carbocycle at either ortho position of the heteroaryl ring relative to the point of connectivity to the rest of the molecule.

In certain embodiments, for a compound of Formula (II), $R^{14}$ is independently selected from hydrogen; and $C_{1-6}$ alkyl optionally substituted with one or more substituents independently selected from halogen, —$OR^{20}$, —$SR^{20}$, —$N(R^{20})_2$, —$NO_2$, and —CN. In some embodiments, $R^{14}$ is hydrogen.

In certain embodiments, for a compound of Formula (II), each $R^{15}$ and $R^{16}$ is independently selected from hydrogen, halogen, —$OR^{20}$, —$SR^{20}$, —$N(R^{20})_2$, —$NO_2$, —CN, and $C_{1-6}$ alkyl optionally substituted with one or more substituents independently selected from halogen, —$OR^{20}$, —$SR^{20}$, —$N(R^{20})_2$, —$NO_2$, and —CN.

In certain embodiments, for a compound of Formula (II), each $R^{17}$ and $R^{18}$ is independently selected from halogen, —$OR^{20}$, —$SR^{20}$, —$N(R^{20})_2$, —$NO_2$, —CN, —$CHF_2$, —$CF_3$, —$CH_2F$, and $C_{2-6}$ alkyl optionally substituted with one or more substituents independently selected from halogen, —$OR^{20}$, —$SR^{20}$, —$N(R^{20})_2$, —$NO_2$, and —CN. In certain embodiments, for a compound of Formula (II), each $R^{17}$ and $R^{18}$ is independently selected from halogen, —$OR^{20}$, —$SR^{20}$, —$N(R^{20})_2$, —$NO_2$, —CN, and $C_{1-6}$ alkyl optionally substituted with one or more substituents independently selected from halogen, —$OR^{20}$, —$SR^{20}$, —$N(R^{20})_2$, —$NO_2$, and —CN.

In certain embodiments, for a compound of Formula (II), each $R^{19}$ is independently selected from halogen, —$OR^{20}$, —$SR^{20}$, —$N(R^{20})_2$, —$NO_2$, =O, =S, —CN; and $C_{1-3}$ alkyl, $C_{2-3}$ alkenyl, $C_{2-3}$ alkynyl, each of which is optionally substituted with one or more substituents independently selected from halogen, —$OR^{20}$, —$SR^{20}$, —$N(R^{20})_2$, —$NO_2$, —CN. In some embodiments, $R^{19}$ is a halogen. In some embodiments, $R^{19}$ is an unsubstituted $C_{1-3}$ alkyl. In some embodiments, $R^{19}$ is =O. In some embodiments, $R^{19}$ is a haloalkyl. In some embodiments, $R^{19}$ is a $C_{1-3}$ alkyl substituted with one or more fluorine substituents.

In certain embodiments, for a compound of Formula (II), each $R^{20}$ is independently selected from hydrogen; and $C_{1-6}$ alkyl optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl)$_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl)$_2$, —$NH(C_{1-6}$ alkyl), $C_{1-6}$ alkyl, $C_{3-10}$ carbocycle, 3- to 10-membered heterocycle, and haloalkyl. In some embodiments, $R^{20}$ is a $C_{1-2}$ alkyl substituted with a 4- to 6-membered heterocycle. In some embodiments, $R^{20}$ is hydrogen.

In certain embodiments, for a compound of Formula (II), w is 0.

In certain embodiments, for a compound of Formula (II), z is 0.

In one aspect, disclosed herein is a compound represented by Formula (IIa)

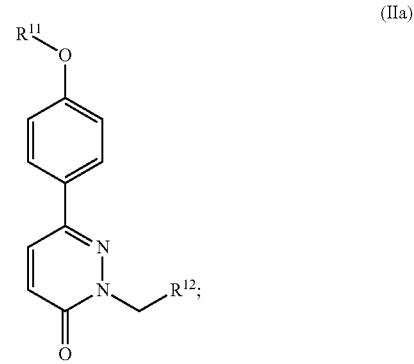

or a salt thereof, wherein,
$R^{11}$ is selected from:
   $C_{1-5}$ haloalkyl optionally further substituted with one or more substituents independently selected from —OH, —SH, —$NH_2$, —$NO_2$, —CN, $C_{3-10}$ carbocycle and 3- to 10-membered heterocycle, wherein the $C_{3-10}$ carbocycle and 3- to 10-membered heterocycle are each optionally substituted with one or more $R^{19}$;
$R^{12}$ is a heteroaryl, e.g., a 5-, 6-, or 9-membered heteroaryl, optionally substituted with one or more substituents independently selected from:
   halogen, —$OR^{20}$, —$SR^{20}$, —$N(R^{20})_2$, —$NO_2$, —CN; and
   $C_{3-10}$ carbocycle optionally substituted with one or more —$R^{19}$;
each $R^{19}$ is independently selected from:
   halogen, —$OR^{20}$, —$SR^{20}$, —$N(R^{20})_2$, —$NO_2$, —CN; and
   $C_{1-3}$ alkyl optionally substituted with one or more substituents independently selected from halogen, —$OR^{20}$, —$SR^{20}$, —$N(R^{20})_2$, —$NO_2$, and —CN; and
each $R^{20}$ is independently selected from:
   hydrogen; and
   $C_{1-6}$ alkyl optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, and —NH (C$_{1-6}$ alkyl).

In certain embodiments, for a compound or salt of any one of Formula (II) R$^{11}$-T is further selected from hydrogen. For example, a compound of the disclosure may be represented by:

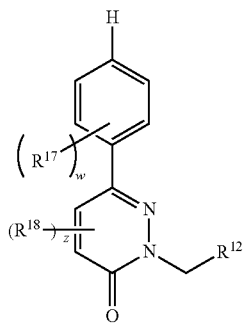

or a salt thereof.

In certain embodiments, a compound of the disclosure is selected from a compound of Table 2 or a salt thereof.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, compounds described herein are intended to include all Z-, E- and tautomeric forms as well.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

in the content of $^2$H, $^3$H, $^{11}$C, $^{13}$C and/or $^{14}$C. In one particular embodiment, the compound is deuterated in at least one position. Such deuterated forms can be made by the procedure described in U.S. Pat. Nos. 5,846,514 and 6,334, 997. As described in U.S. Pat. Nos. 5,846,514 and 6,334, 997, deuteration can improve the metabolic stability and or efficacy, thus increasing the duration of action of drugs.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, and $^{125}$I are all contemplated. All isotopic variations of the compounds of the present invention, whether radioactive or not, are encompassed within the scope of the present invention.

In certain embodiments, the compounds disclosed herein have some or all of the $^1$H atoms replaced with $^2$H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

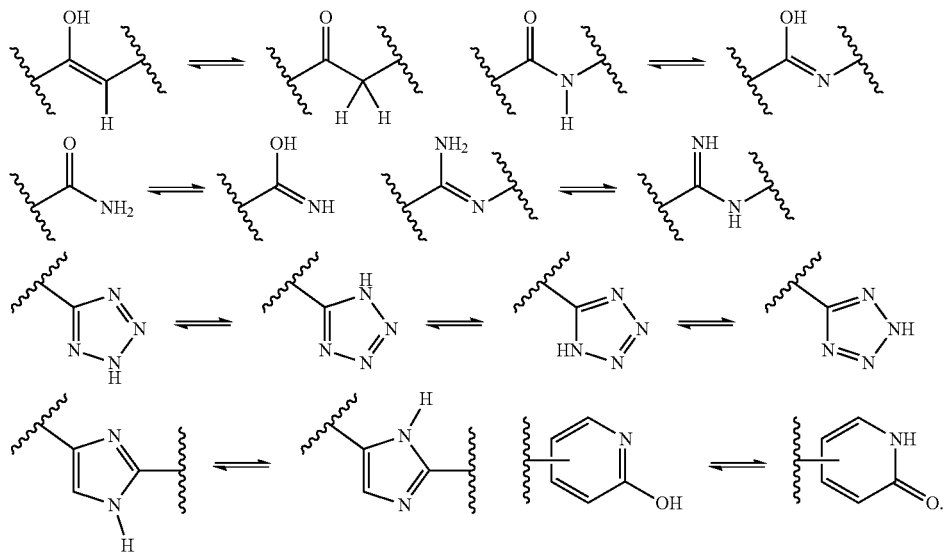

The compounds disclosed herein, in some embodiments, are used in different enriched isotopic forms, e.g., enriched Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

Included in the present disclosure are salts, particularly pharmaceutically acceptable salts, of the compounds described herein. The compounds of the present disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

The methods and compositions described herein include the use of amorphous forms as well as crystalline forms (also known as polymorphs). The compounds described herein may be in the form of pharmaceutically acceptable salts. As well, in some embodiments, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compounds or salts of the compounds may be prodrugs, e.g., wherein a hydroxyl in the parent compound is presented as an ester or a carbonate, or carboxylic acid present in the parent compound is presented as an ester. The term "prodrug" is intended to encompass compounds which, under physiologic conditions, are converted into pharmaceutical agents of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) are preferred prodrugs of the present disclosure.

Prodrug forms of the herein described compounds, wherein the prodrug is metabolized in vivo to produce a compound as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. Prodrugs may help enhance the cell permeability of a compound relative to the parent drug. The prodrug may also have improved solubility in pharmaceutical compositions over the parent drug. Prodrugs may be designed as reversible drug derivatives, for use as modifiers to enhance drug transport to site-specific tissues or to increase drug residence inside of a cell.

In some embodiments, the design of a prodrug increases the lipophilicity of the pharmaceutical agent. In some embodiments, the design of a prodrug increases the effective water solubility. See, e.g., Fedorak et al., *Am. J. Physiol.,* 269:G210-218 (1995); McLoed et al., *Gastroenterol,* 106: 405-413 (1994); Hochhaus et al., *Biomed. Chrom.,* 6:283-286 (1992); J. Larsen and H. Bundgaard, *Int. J. Pharmaceutics,* 37, 87 (1987); J. Larsen et al., *Int. J. Pharmaceutics,* 47, 103 (1988); Sinkula et al., *J. Pharm. Sci.,* 64:181-210 (1975); T. Higuchi and V. Stella, *Pro-drugs as Novel Delivery Systems,* Vol. 14 of the A.C.S. Symposium Series; and Edward B. Roche, *Bioreversible Carriers in Drug Design,* American Pharmaceutical Association and Pergamon Press, 1987, all incorporated herein for such disclosure). According to another embodiment, the present disclosure provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

Therapeutic Applications

Methods of administration of a compound or salt of Formula (I), (Ia), (Ib), (Ic), (Id), (Ie), (II), or (IIa) discussed herein may be used for the treatment of neuromuscular conditions and movement disorders. Examples of neuromuscular conditions include but are not limited to Duchenne Muscular Dystrophy, Becker muscular dystrophy, myotonic dystrophy 1, myotonic dystrophy 2, facioscapulohumeral muscular dystrophy, oculopharyngeal muscular dystrophy, limb girdle muscular dystrophies, tendinitis and carpal tunnel syndrome. Examples of movement disorders include but are not limited to muscle spasticity disorders, spasticity associated with multiple sclerosis, Parkinson's disease, Alzheimer's disease, or cerebral palsy, or injury or a traumatic event such as stroke, traumatic brain injury, spinal cord injury, hypoxia, meningitis, encephalitis, phenylketonuria, or amyotrophic lateral sclerosis. Also included are other conditions that may respond to the inhibition of skeletal myosin II, skeletal troponin C, skeletal troponin I, skeletal tropomyosin, skeletal troponin T, skeletal regulatory light chains, skeletal myosin binding protein C or skeletal actin.

In some embodiments, disclosed herein are methods to treat neuromuscular and movement disorders by the administration of a compound or salt of Formula (I), (Ia), (Ib), (Ic), (Id), (Ie), (II), or (IIa). In some embodiments, disclosed herein are methods to treat neuromuscular and movement disorders by the administration of a compound or salt of Formula (III);

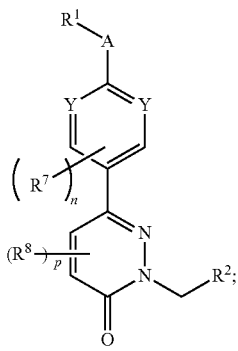

(III)

or a salt thereof, wherein:

each Y is independently selected from $C(R^3)$, N, and $N^+(-O^-)$;

A is selected from $-O-$, $-NR^4-$, $-CR^5R^6-$, $-C(O)-$, $-S-$, $-S(O)-$, and $-S(O)_2-$;

$R^1$ is selected from:

$C_{1-6}$ alkyl, $C_{2-6}$ alkenyl, $C_{2-6}$ alkynyl, each of which is optionally substituted with one or more substituents independently selected from halogen, $-OR^{10}$, $-SR^{10}$, $-N(R^{10})_2$, $-C(O)R^{10}$, $-C(O)N(R^{10})_2$, $-N(R^{10})C(O)R^{10}$, $-C(O)OR^{10}$, $-OC(O)R^{10}$, $-N(R^{10})C(O)N(R^{10})_2$, $-OC(O)N(R^{10})_2$, $-N(R^{10})C(O)OR^{10}$, $-S(O)R^{10}$, $-S(O)_2R^{10}$, $-NO_2$, $=O$, $=S$, $=N(R^{10})$, $-CN$, $C_{3-10}$ carbocycle and 3- to 10-membered heterocycle, wherein the $C_{3-10}$ carbocycle and 3- to 10-membered heterocycle are each optionally substituted with one or more $R^9$; and $C_{3-10}$ carbocycle and 3- to 10-membered heterocycle, each of which is optionally substituted with one or more substituents independently selected from halogen, $-OR^{10}$, $-N(R^{10})_2$, $-C(O)R^{10}$, $-C(O)N(R^{10})_2$, $-N(R^{10})C(O)R^{10}$, $-N(R^{10})C(O)N(R^{10})_2$, $-OC(O)N(R^{10})_2$, $-N(R^{10})C(O)OR^{10}$, $-C(O)OR^{10}$, $-OC(O)R^{10}$, $-S(O)R^{10}$, $-S(O)_2R^{10}$, $-NO_2$, $=O$, $=S$, $=N(R^{10})$, and $-CN$; or $R^1$ together with $R^3$ form a 5- to 10-membered heterocycle or $C_{5-10}$ carbocycle, wherein the 5- to 10-membered heterocycle or $C_{5-10}$ carbocycle is optionally substituted with one or more $R^9$; or $R^1$ together with $R^5$ form a 3- to 10-membered heterocycle or $C_{3-10}$ carbocycle, wherein the 3- to 10-membered heterocycle or $C_{3-10}$ carbocycle is optionally substituted with one or more $R^9$; or $R^1$ together with $R^4$ form a 3- to 10-membered heterocycle, wherein the 3- to 10-membered heterocycle is optionally substituted with one or more $R^9$;

$R^2$ is a heteroaryl optionally substituted with one or more substituents independently selected from halogen, $-OR^{10}$, $-N(R^{10})_2$, $-C(O)R^{10}$, $-C(O)N(R^{10})_2$, $-N(R^{10})C(O)R^{10}$, $-N(R^{10})C(O)N(R^{10})_2$, $-OC(O)N(R^{10})_2$, $-N(R^{10})C(O)OR^{10}$, $-C(O)OR^{10}$, $-OC(O)R^{10}$, $-S(O)R^{10}$, $-S(O)_2R^{10}$, $-NO_2$, $=O$, $=S$, $=N(R^{10})$, and $-CN$; and when $R^2$ is pyridyl or pyrimidyl, a substituent on a nitrogen atom of the pyridyl or pyrimidyl is optionally further selected from $-O^-$;

$C_{1-6}$ alkyl, $C_{2-6}$ alkenyl, $C_{2-6}$ alkynyl, each of which is optionally substituted with one or more substituents independently selected from halogen, $-OR^{10}$, $-SR^{10}$, $-N(R^{10})_2$, $-C(O)R^{10}$, $-C(O)N(R^{10})_2$, $-N(R^{10})C(O)R^{10}$, $-N(R^{10})C(O)N(R^{10})_2$, $-OC(O)N(R^{10})_2$, $-N(R^{10})C(O)OR^{10}$, $-C(O)OR^{10}$, $-OC(O)R^{10}$, $-S(O)R^{10}$, $-S(O)_2R^{10}$, $-NO_2$, $=O$, $=S$, $=N(R^{10})$, $-CN$, $C_{3-10}$ carbocycle and 3- to 10-membered heterocycle, wherein the $C_{3-10}$ carbocycle and 3- to 10-membered heterocycle are each optionally substituted with one or more $R^9$; and $C_{3-10}$ carbocycle and 3- to 10-membered heterocycle, each of which is optionally substituted with one or more $R^9$;

each $R^3$, $R^5$, and $R^6$ is independently selected from:

hydrogen, halogen, $-OR^{10}$, $-SR^{10}$, $-N(R^{10})_2$, $-NO_2$, $-CN$, and $C_{1-6}$ alkyl optionally substituted with one or more substituents independently selected from halogen, $-OR^{10}$, $-SR^{10}$, $-N(R^{10})_2$, $-NO_2$, and $-CN$; or $R^3$ together with $R^1$ form a 5- to 10-membered heterocycle or $C_{5-10}$ carbocycle, wherein the 5- to 10-membered heterocycle or $C_{5-10}$ carbocycle is optionally substituted with one or more $R^9$; $R^5$ together with $R^1$ form a 3- to 10-membered heterocycle or $C_{3-10}$ carbocycle, wherein the 3- to 10-membered heterocycle or $C_{3-10}$ carbocycle is optionally substituted with one or more $R^9$;

$R^4$ is independently selected from:

hydrogen; and $C_{1-6}$ alkyl optionally substituted with one or more substituents independently selected from halogen, $-OR^{10}$, $-SR^{10}$, $-N(R^{10})_2$, $-NO_2$, and $-CN$; or $R^4$ together with $R^1$ form a 3- to 10-membered heterocycle, which is optionally substituted with one or more $R^9$;

each $R^7$ and $R^8$ is independently selected from:

halogen, $-OR^{10}$, $-SR^{10}$, $-N(R^{10})_2$, $-NO_2$, $-CN$, and $C_{1-6}$ alkyl optionally substituted with one or more substituents independently selected from halogen, $-OR^{10}$, $-SR^{10}$, $-N(R^{10})_2$, $-NO_2$, and $-CN$;

each $R^9$ is independently selected from:

halogen, $-OR^{10}$, $-SR^{10}$, $-N(R^{10})_2$, $-C(O)R^{10}$, $-C(O)N(R^{10})_2$, $-N(R^{10})C(O)R^{10}$, $-N(R^{10})C(O)N(R^{10})_2$, $-OC(O)N(R^{10})_2$, $-N(R^{10})C(O)OR^{10}$, $-C(O)OR^{10}$, $-OC(O)R^{10}$, $-S(O)R^{10}$, $-S(O)_2R^{10}$, $-NO_2$, $=O$, $=S$, $=N(R^{10})$, $-CN$; and $C_{1-3}$ alkyl, $C_{2-3}$ alkenyl, $C_{2-3}$ alkynyl, each of which is optionally substituted with one or more substituents independently selected from halogen, $-OR^{10}$, $-SR^{10}$, $-N(R^{10})_2$, $-C(O)R^{10}$, $-C(O)N(R^{10})_2$, $-N(R^{10})C(O)R^{10}$, $-N(R^{10})C(O)N(R^{10})_2$, $-OC(O)N(R^{10})_2$, $-N(R^{10})C(O)OR^{10}$, $-C(O)OR^{10}$, $-OC(O)R^{10}$, $-S(O)R^{10}$, $-S(O)_2R^{10}$, $-NO_2$, $=O$, $=S$, $=N(R^{10})$, and $-CN$;

each $R^{10}$ is independently selected from:

hydrogen; and $C_{1-6}$ alkyl, $C_{2-6}$ alkenyl, $C_{2-6}$ alkynyl, each of which is optionally substituted with one or more substituents independently selected from halogen, $-CN$, $-OH$, $-SH$, $-NO_2$, $-NH_2$, $=O$, $=S$, $-O-C_{1-6}$ alkyl, $-S-C_{1-6}$ alkyl, $-N(C_{1-6}$ alkyl$)_2$, $-NH(C_{1-6}$ alkyl$)$, $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, $-CN$, $-OH$, $-SH$, $-NO_2$, $-NH_2$, $=O$, $=S$, $-O-C_{1-6}$ alkyl, $-S-C_{1-6}$ alkyl, $-N(C_{1-6}$ alkyl$)_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and haloalkyl;

n is 0, 1, or 2; and p is 0, 1, or 2.

In certain embodiments, the disclosure provides a method of treating activity-induced muscle damage, comprising administering to a subject in need thereof a compound or salt of Formula (III'):

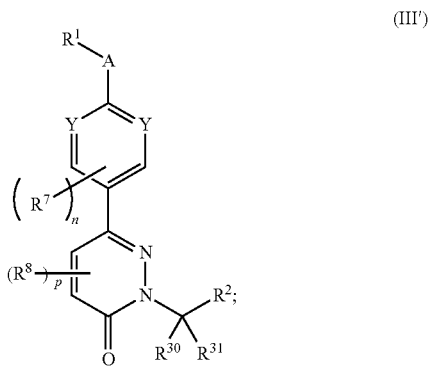

(III')

or a salt thereof, wherein:

each Y is independently selected from C(R$^3$), N, and N$^+$(—O$^-$);

A is absent or selected from —O—, —NR$^4$—, —CR$^5$R$^6$—, —C(O)—, —S—, —S(O)—, and —S(O)$_2$—;

R$^1$ is selected from:

C$_{1-6}$ alkyl, C$_{2-6}$ alkenyl, and C$_{2-6}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, =O, =S, =N(R$^{10}$), —CN, C$_{3-10}$ carbocycle, and 3- to 10-membered heterocycle, wherein the C$_{3-10}$ carbocycle and 3- to 10-membered heterocycle are each optionally substituted with one or more R$^9$; and C$_{3-10}$ carbocycle and 3- to 10-membered heterocycle, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, =O, =S, =N(R$^{10}$), and —CN; or R$^1$ together with R$^3$ form a 5- to 10-membered heterocycle or C$_{5-10}$ carbocycle, wherein the 5- to 10-membered heterocycle or C$_{5-10}$ carbocycle is optionally substituted with one or more R$^9$; or R$^1$ together with R$^5$ form a 3- to 10-membered heterocycle or saturated C$_{3-10}$ carbocycle, wherein the 3- to 10-membered heterocycle or saturated C$_{3-10}$ carbocycle is optionally substituted with one or more R$^9$; or R$^1$ together with R$^4$ form a 3- to 10-membered heterocycle, wherein the 3- to 10-membered heterocycle is optionally substituted with one or more R$^9$; and when A is —NR$^4$—, R$^1$ is additionally selected from hydrogen, and when A is —C(O)—, R$^1$ is additionally selected from —N(R$^{10}$)$_2$ and —OR$^{10}$;

when A is absent R$^1$ is further selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, and —CN;

R$^2$ is a heteroaryl optionally substituted with one or more substituents independently selected from:

halogen, —OR$^{10}$, —SR$^{10}$, —N(R$^{10}$), —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, =O, =S, =N(R$^{10}$), and —CN; and when R$^2$ is pyridyl or pyrimidyl, a substituent on a nitrogen atom of the pyridyl or pyrimidyl is optionally further selected from —O$^-$;

C$_{1-6}$ alkyl, C$_{2-6}$ alkenyl, and C$_{2-6}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, =O, =S, =N(R$^{10}$), —CN, C$_{3-10}$ carbocycle and 3- to 10-membered heterocycle, wherein the C$_{3-10}$ carbocycle and 3- to 10-membered heterocycle are each optionally substituted with one or more R$^9$; and C$_{3-10}$ carbocycle and 3- to 10-membered heterocycle, each of which is optionally substituted with one or more R$^9$;

each R$^3$, R$^5$, and R$^6$ is independently selected from:

hydrogen, halogen, —OR$^{10}$, —SR$^{10}$, —N(R$^{10}$)$_2$, —NO$_2$, —CN, and C$_{1-6}$ alkyl optionally substituted with one or more substituents independently selected from halogen, —OR$^{10}$, —SR$^{10}$, —N(R$^{10}$)$_2$, —NO$_2$, and —CN; or R$^3$ together with R$^1$ form a 5- to 10-membered heterocycle or C$_{5-10}$ carbocycle, wherein the 5- to 10-membered heterocycle or C$_{5-10}$ carbocycle is optionally substituted with one or more R$^9$; R$^5$ together with R$^1$ form a 3- to 10-membered heterocycle or C$_{3-10}$ carbocycle, wherein the 3- to 10-membered heterocycle or C$_{3-10}$ carbocycle is optionally substituted with one or more R$^9$;

R$^4$ is independently selected from:

hydrogen; and

C$_{1-6}$ alkyl optionally substituted with one or more substituents independently selected from halogen, —OR$^{10}$, —SR$^{10}$, —N(R$^{10}$)$_2$, —NO$_2$, and —CN; or R$^4$ together with R$^1$ form a 3- to 10-membered heterocycle, which is optionally substituted with one or more R$^9$;

each R$^7$ and R$^8$ is independently selected from halogen, —OR$^{10}$, —SR$^{10}$, —N(R$^{10}$)$_2$, —NO$_2$, —CN, and C$_{1-6}$ alkyl optionally substituted with one or more substituents independently selected from halogen, —OR$^{10}$, —SR$^{10}$, —N(R$^{10}$)$_2$, —NO$_2$, and —CN;

each R$^9$ is independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, =O, =S, =N(R$^{10}$), —CN; and C$_{1-3}$ alkyl, C$_{2-3}$ alkenyl, C$_{2-3}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$—, —S(O)R$^{10}$, —S(O)$_2$R$^{10}$, —NO$_2$, =O, =S, =N(R$^{10}$), and —CN;

each R$^{10}$ is independently selected from
hydrogen; and
C$_{1-6}$ alkyl, C$_{2-6}$ alkenyl, C$_{2-6}$ alkynyl, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, 3- to 10-membered heterocycle; and
C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —OC$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and haloalkyl;

R$^{30}$ and R$^{31}$ are independently selected from R$^{10}$ or R$^{30}$ and R$^{31}$ come together to form a C$_{3-7}$ carbocycle, wherein the 3- to 7-membered heterocycle, wherein C$_{3-7}$ carbocycle and 3- to 7-membered heterocycle are optionally substituted with R$^9$;

n is 0, 1, or 2; and
p is 0, 1, or 2.

In certain embodiments, for a compound or salt of Formula (III) or (III'), each Y is independently selected from C(R$^3$) and N wherein at least one Y is N. In some embodiments, one Y is N and one Y is C(R$^3$). In some embodiments, one Y is N$^+$(—O$^-$) and one Y is C(R$^3$). In some embodiments, each Y is N. In some embodiments, one Y is N, and one Y is N$^+$(—O$^-$). In certain embodiments, for a compound or salt of Formula (III) or (III'), each Y is further selected from C(R$^3$).

In certain embodiments, for a compound or salt of Formula (III) or (III'), A is selected from —O—, —CR$^5$R$^6$—, and —C(O)—. In some embodiments, A is selected from —O— and —NR$^4$. In some embodiments, A is —O—.

In certain embodiments, for a compound or salt of Formula (III) or (III'), R$^1$ is C$_{1-6}$ alkyl optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —N(R$^{10}$)C(O)N(R$^{10}$)$_2$, —OC(O)N(R$^{10}$)$_2$, —N(R$^{10}$)C(O)OR$^{10}$, —S(O)R$^{10}$, —S(O)$_2$R$^{10}$, —NO$_2$, =O, =S, =N(R$^{10}$), —CN, C$_{3-10}$ carbocycle and 3- to 10-membered heterocycle, wherein the C$_{3-10}$ carbocycle and 3- to 10-membered heterocycle are each optionally substituted with one or more R$^9$. In some embodiments, R$^1$ is C$_{1-6}$ alkyl substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —N(R$^{10}$)C(O)N(R$^{10}$)$_2$, —OC(O)N(R$^{10}$)$_2$, —N(R$^{10}$)C(O)OR$^{10}$, —S(O)R$^{10}$, —S(O)$_2$R$^{10}$, —NO$_2$, =O, =S, =N(R$^{10}$), —CN, C$_{3-10}$ carbocycle and 3- to 10-membered heterocycle, wherein the C$_{3-10}$ carbocycle and 3- to 10-membered heterocycle are each optionally substituted with one or more R$^9$. In some embodiments, R$^1$ is C$_{1-6}$ alkyl substituted with one or more substituents independently selected from halogen, —OR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —NO$_2$, =O, =N(R$^{10}$), —CN, C$_{3-10}$ carbocycle and 3- to 10-membered heterocycle, wherein the C$_{3-10}$ carbocycle and 3- to 10-membered heterocycle are each optionally substituted with one or more R$^9$. In some embodiments, R$^1$ is selected from C$_{1-3}$ alkyl optionally substituted with one or more substituents independently selected from halogen, —OR$^{10}$, —SR$^{10}$, —N(R$^{10}$)$_2$, —NO$_2$, =O, =S, =N(R$^{10}$), —CN, C$_{3-10}$ carbocycle and 3- to 10-membered heterocycle, wherein the C$_{3-10}$ carbocycle and 3- to 10-membered heterocycle are each optionally substituted with one or more R$^9$. In some embodiments, R$^1$ is C$_{1-3}$ alkyl substituted with one or more substituents independently selected from halogen, —OR$^{10}$, —N(R$^{10}$)$_2$, —NO$_2$, =O, —CN, C$_{3-10}$ carbocycle and 3- to 10-membered heterocycle, wherein the C$_{3-10}$ carbocycle and 3- to 10-membered heterocycle are each optionally substituted with one or more R$^9$. In some embodiments, R$^1$ is C$_{1-3}$ alkyl substituted with one or more halogen substituents. In some embodiments, R$^1$ is a C$_{1-3}$ fluoroalkyl. In some embodiments, R$^1$ is selected from —CHF$_2$ and —CH$_2$CF$_3$.

In certain embodiments, for a compound or salt of Formula (III) or (III'), R$^1$ is selected from optionally substituted C$_3$-C$_6$ cycloalkyl, such as cyclopropyl, cyclobutyl, cyclopentyl, bicyclopentyl, and spiropentyl, any of which is optionally substituted. In certain embodiments, R$^1$ is selected from alkyl, e.g., methyl, ethyl, propyl, iso-propyl, t-butyl, iso-butyl, sec-butyl, any of which may be optionally substituted. In certain embodiments, R$^1$ is selected from:

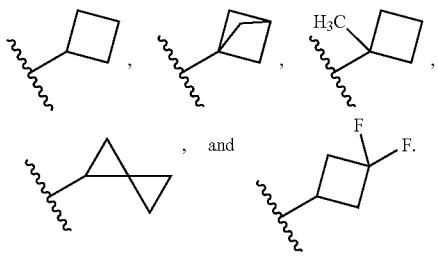

In certain embodiments, R$^1$ is selected from optionally substituted

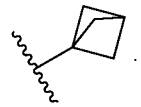 [SMILES: *C12CC(C1)C2]

In certain embodiments, for a compound or salt of Formula (III) or (III'), R$^1$ together with R$^3$ form a 5- to 10-membered heterocycle or C$_{5-10}$ carbocycle, wherein the 5- to 10-membered heterocycle or C$_{5-10}$ carbocycle is optionally substituted with one or more R$^9$. In some embodiments, R$^1$ together with R$^3$ form a C$_{5-10}$ carbocycle or 5- to 10-membered heterocycle, such as a C$_{5-6}$ carbocycle or 5- to 6-membered heterocycle, for example:

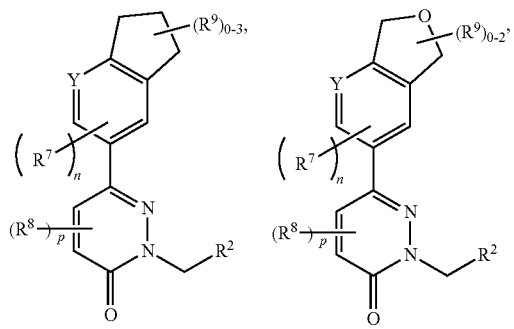

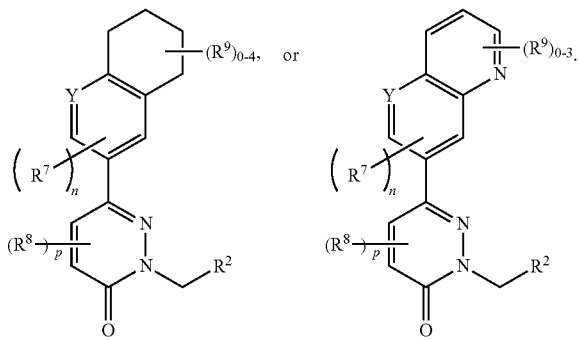

In certain embodiments, for a compound or salt of Formula (III) or (III'), $R^1$ together with $R^5$ form a 3- to 10-membered heterocycle or $C_{3-10}$ carbocycle, wherein the 3- to 10-membered heterocycle or $C_{3-10}$ carbocycle is optionally substituted with one or more $R^9$. In some embodiments, $R^1$ together with $R^5$ form a 3- to 10-membered heterocycle or $C_{3-10}$ carbocycle, for example:

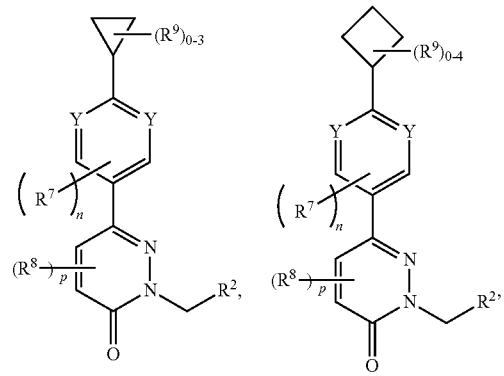

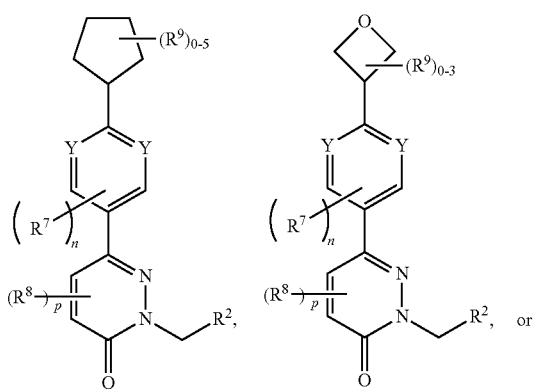

In certain embodiments, for a compound or salt of Formula (III) or (III'), $R^1$ together with $R^4$ form a 3- to 10-membered heterocycle, wherein the 3- to 10-membered heterocycle is optionally substituted with one or more $R^9$. In some embodiments, $R^1$ together with $R^4$ form a 3- to 10-membered heterocycle, for example:

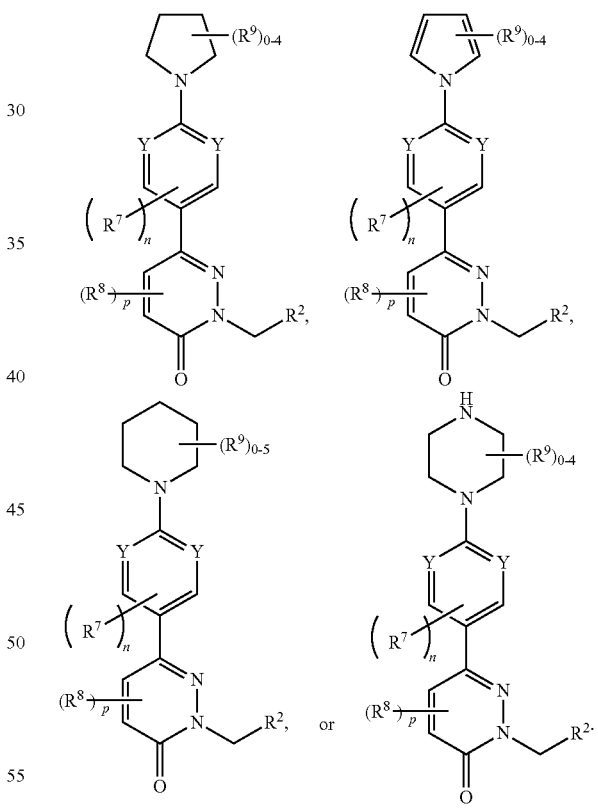

In some embodiments, for a compound or salt of Formula (III) or (III'), $R^2$ is an optionally substituted 5-membered heteroaryl, 6-membered heteroaryl, or a 9-membered bicyclic heterocycle. In some embodiments, $R^2$ is an optionally substituted 5-membered heteroaryl. In certain embodiments, $R^2$ is an optionally substituted 5-membered heteroaryl with at least one endocyclic nitrogen or oxygen atom in the 5-membered heteroaryl, e.g., oxazole, isoxazole, thiazole, pyrrole, pyrazole, furan, diazole, triazole, imidazole, oxadiazole, thiadiazole, isoxazole, isothiazole, and tetrazole. In certain embodiments, for a compound or salt Formula (III) or (III'), R² is selected from:

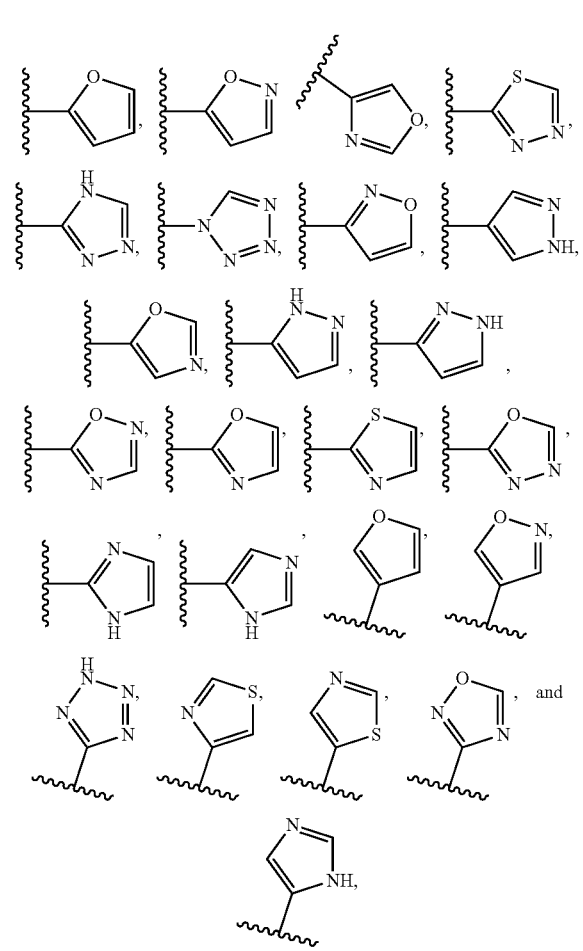

any one of which is optionally substituted. In some embodiments, R² is selected from:

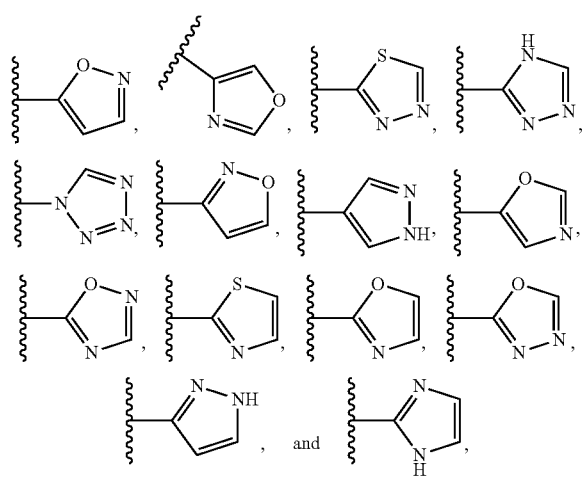

any one of which is optionally substituted. In some embodiments, R² is selected from:

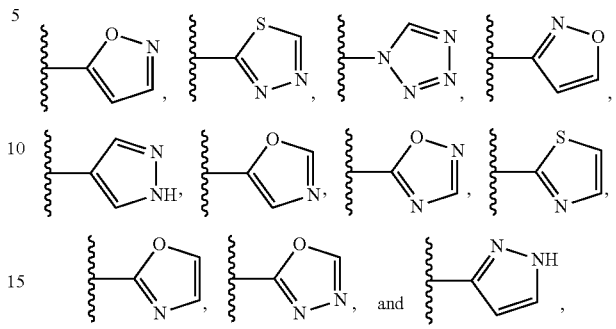

any one of which is optionally substituted.

In certain embodiments, for a compound or salt of Formula (III) or (III'), substituents on R² are independently selected from halogen, —OR¹⁰, —SR¹⁰, —N(R¹⁰)₂, —NO₂, and —CN; C₁₋₆ alkyl optionally substituted with one or more substituents independently selected from halogen, —OR¹⁰, —SR¹⁰, —N(R¹⁰)₂, —NO₂, and —CN; and optionally substituted C₃₋₁₀ carbocycle. In some embodiments, R² is a heteroaryl, e.g., 5-membered heteroaryl, optionally substituted with one or more substituents selected from halogen, —OR¹⁰, and —N(R¹⁰)₂; C₁₋₄ alkyl optionally substituted with one or more substituents independently selected from halogen; and optionally substituted C₃₋₁₀ carbocycle, e.g., optionally substituted phenyl or optionally substituted cycloalkyl such as cyclopropyl.

In certain embodiments, for a compound or salt of Formula (III) or (III'), R² is selected from:

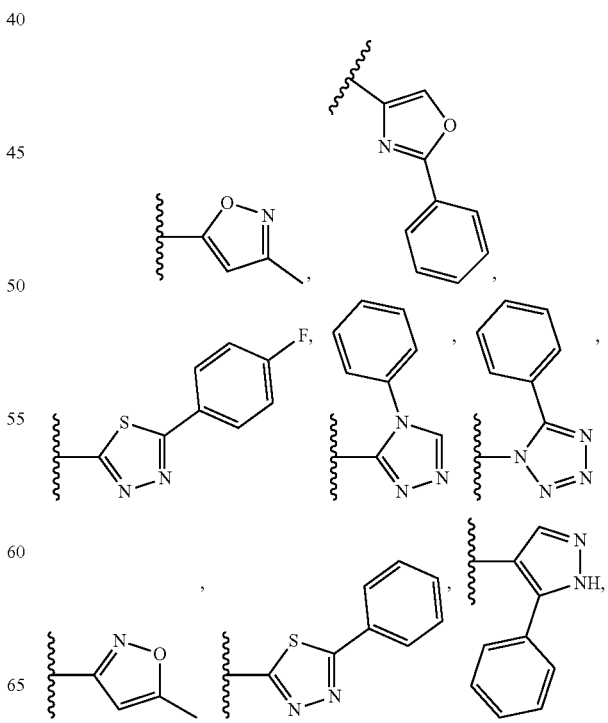

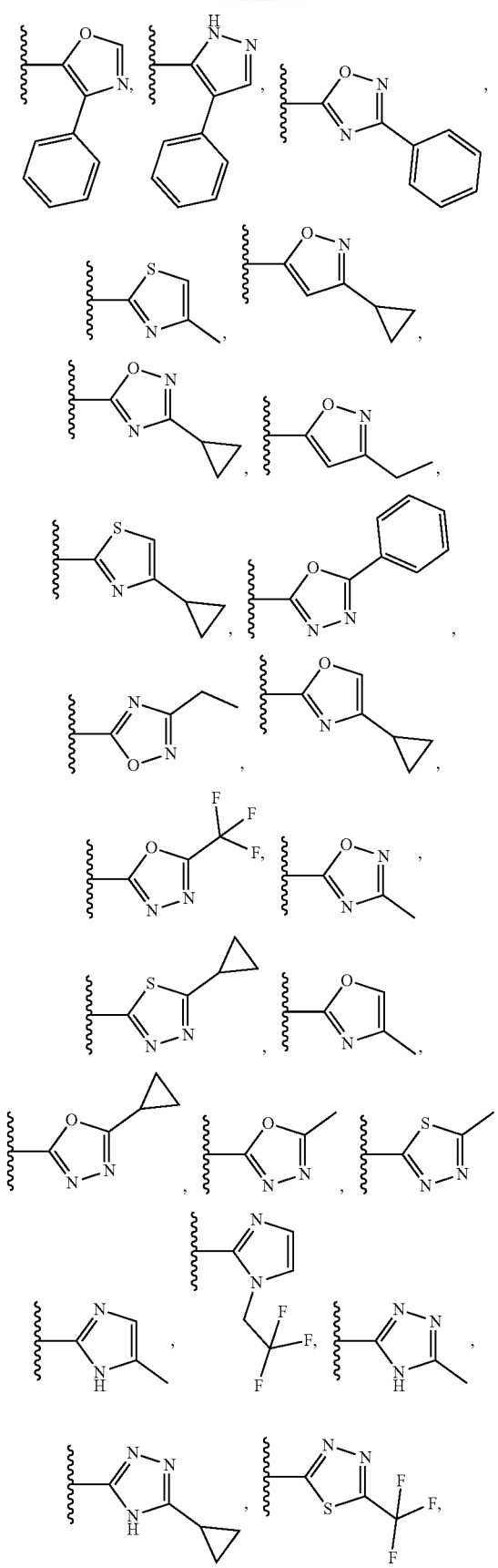
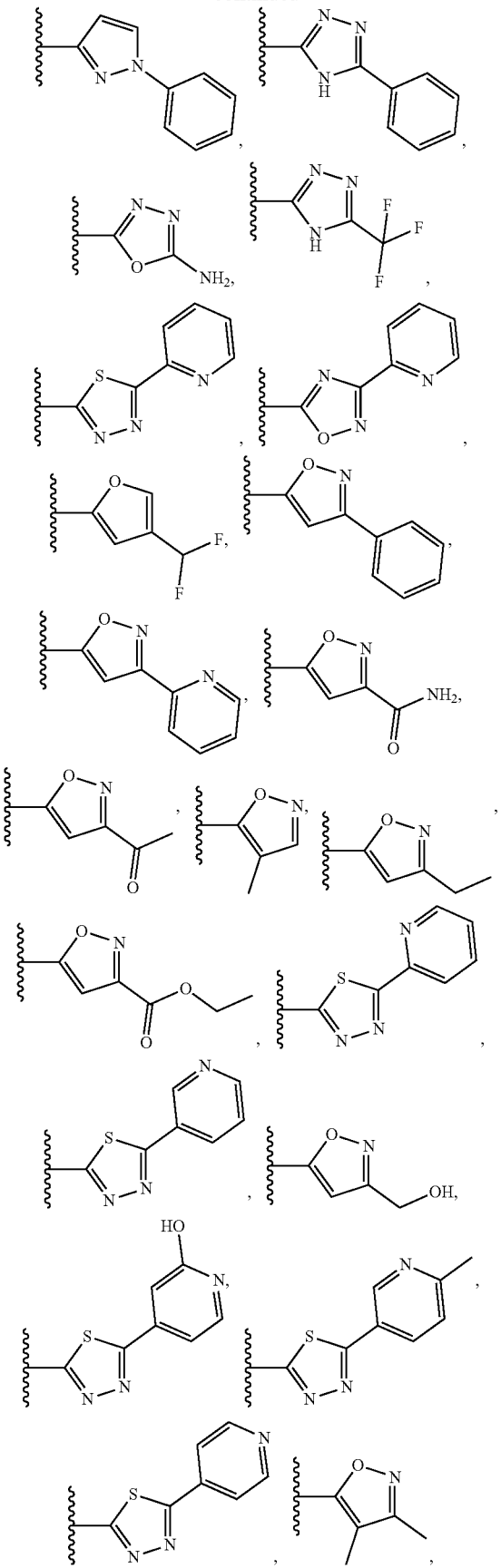

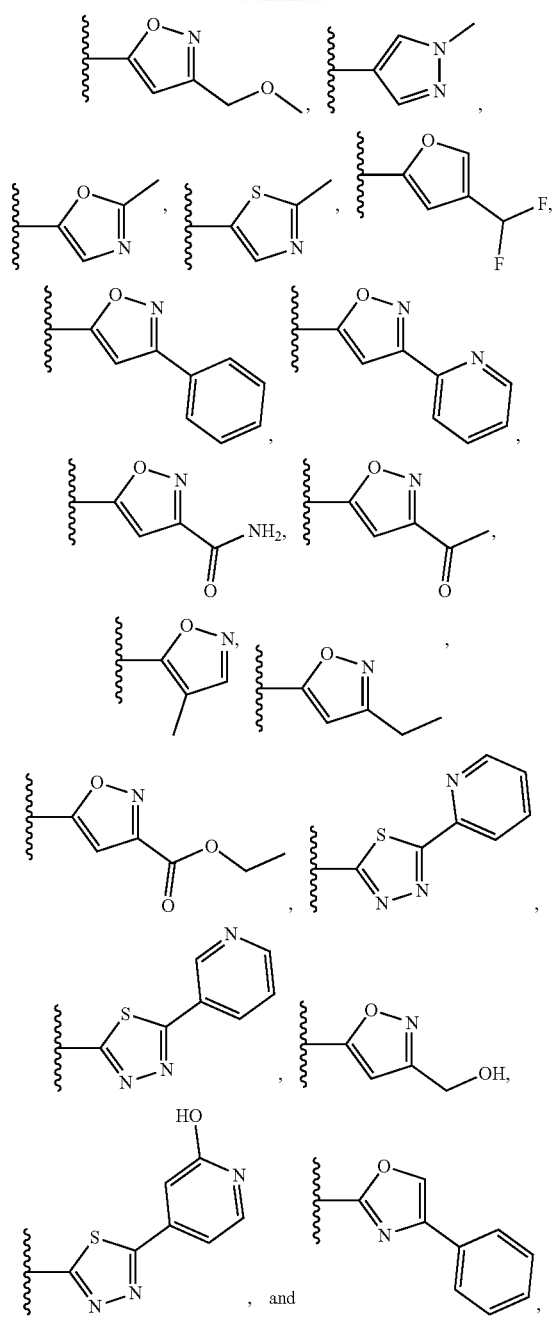

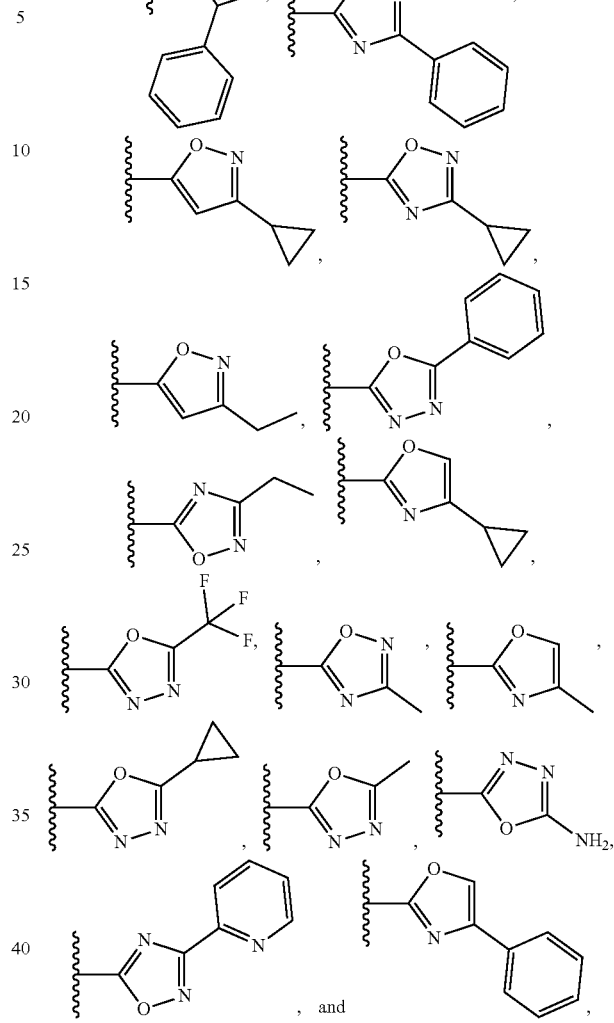

any one of which is optionally substituted. In some embodiments, $R^2$ is selected from:

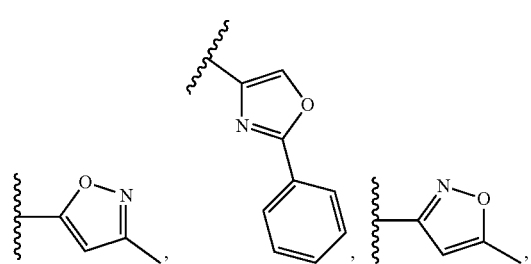

any one of which is optionally substituted.

In certain embodiments, for a compound or salt of Formula (III) or (III'), $R^2$ is selected from optionally substituted 6-membered heteroaryl. In some embodiments, $R^2$ may be selected from 6-membered heteroaryls, such as pyridine, pyridazine, pyrimidine, pyrazine, triazene and N-oxides thereof. In some embodiments, $R^2$ is selected from optionally substituted pyridyl, optionally substituted pyrimidyl, optionally substituted pyridyl N-oxide, and optionally substituted pyrimidyl N-oxide. In some embodiments, $R^2$ is selected from optionally substituted pyridyl and optionally substituted pyrimidyl. In certain embodiments, for a compound or salt of Formula (III) or (III'), $R^2$ is a 6-membered heteroaryl, e.g., pyridinyl or pyrimidinyl, optionally substituted with halogen, —$OR^{10}$, —$SR^{10}$, —$N(R^{10})_2$, —$NO_2$, and —CN; $C_{1-6}$ alkyl optionally substituted with one or more substituents independently selected from halogen, —$OR^{10}$, —$SR^{10}$, —$N(R^{10})_2$, —$NO_2$, and —CN; and optionally substituted $C_{3-10}$ carbocycle. In certain embodiments, for a compound or salt of Formula (III) or (III'), $R^2$ is a 6-membered heteroaryl, e.g., pyridinyl or pyrimidinyl, optionally substituted with halogen, —$OR^{10}$, —$SR^{10}$, and —$N(R^{10})_2$; and $C_{1-4}$ alkyl optionally substituted with one or more substituents independently selected from halogen and —OR$^{10}$. In some embodiments, R$^2$ is selected from:

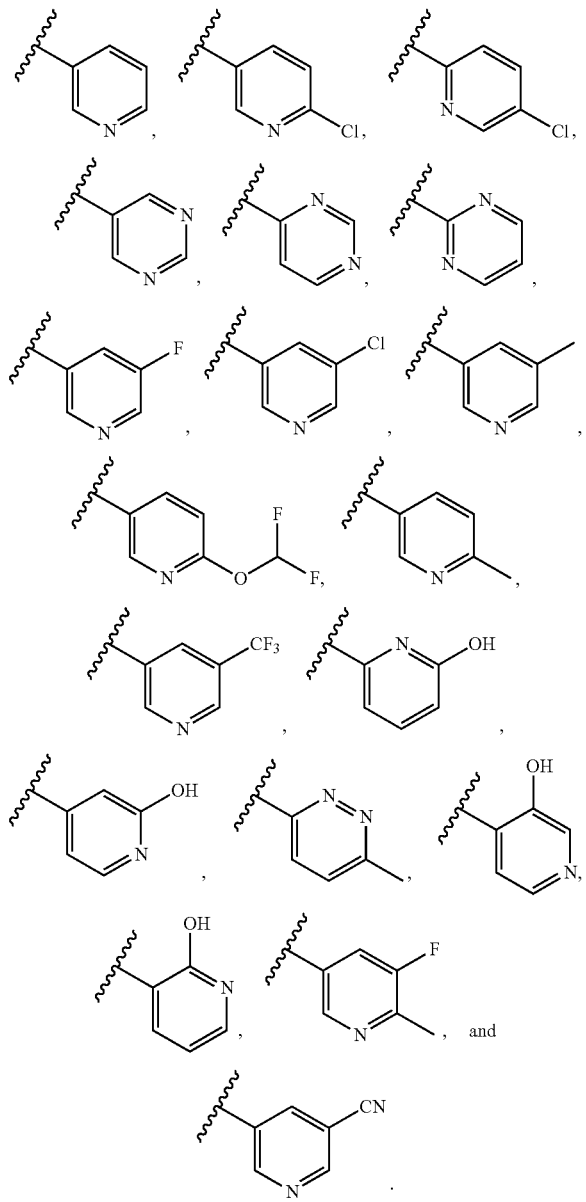

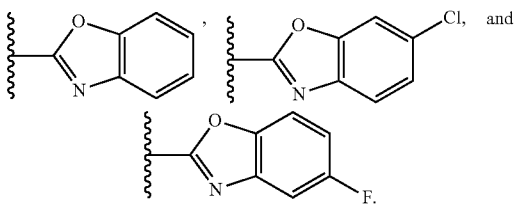

In certain embodiments, for a compound or salt of Formula (III) or (III'), R$^2$ is selected from optionally substituted bicyclic heteroaryl. In some embodiments, R$^2$ is selected from optionally substituted 9-membered bicyclic heteroaryl, e.g., optionally substituted benzoxazole, benzothiazole, or benzimidazole. In certain embodiments, for a compound or salt of Formula (III) or (III'), R$^2$ is a 9-membered bicyclic heteroaryl, e.g., benzoxazole, optionally substituted with halogen, —OR$^{10}$, —SR$^{10}$, —N(R$^{10}$)$_2$, —NO$_2$, and —CN; C$_{1-6}$ alkyl optionally substituted with one or more substituents independently selected from halogen, —OR$^{10}$, —SR$^{10}$, —N(R$^{10}$)$_2$, —NO$_2$, and —CN; and optionally substituted C$_{3-10}$ carbocycle. In some embodiments, R$^2$ is selected from optionally substituted benzoxazole. In some embodiments, R$^2$ is selected from:

In certain embodiments, for a compound or salt of Formula (III) or (III'), each R$^3$ is selected from hydrogen, halogen, —OR$^{10}$, —SR$^{10}$, —N(R$^{10}$)$_2$, —NO$_2$, —CN, and C$_{1-6}$ alkyl optionally substituted with one or more substituents independently selected from halogen, —OR$^{10}$, —SR$^{10}$, —N(R$^{10}$)$_2$, —NO$_2$, and —CN. In some embodiments, R$^3$ together with R$^1$ form a 5- to 6-membered heterocycle or C$_{5-6}$ carbocycle, wherein the 5- to 6-membered heterocycle or C$_{5-6}$ carbocycle is optionally substituted with one or more R$^9$. In some embodiments, R$^3$ is hydrogen.

In certain embodiments, for a compound or salt of Formula (III) or (III'), R$^4$ is independently selected from hydrogen; and C$_{1-6}$ alkyl optionally substituted with one or more substituents independently selected from halogen, —OR$^{10}$, —SR$^{10}$, —N(R$^{10}$)$_2$, —NO$_2$, and —CN; or R$^4$ together with R$^1$ form a 3- to 10-membered heterocycle, which is optionally substituted with one or more R$^9$. In some embodiments, R$^4$ is hydrogen.

In certain embodiments, for a compound or salt of Formula (III) or (III'), each R$^5$ and R$^6$ is independently selected from hydrogen, halogen, —OR$^{10}$, —SR$^{10}$, —N(R$^{10}$)$_2$, —NO$_2$, —CN, and C$_{1-6}$ alkyl optionally substituted with one or more substituents independently selected from halogen, —OR$^{10}$, —SR$^{10}$—N(R$^{10}$)$_2$, —NO$_2$, and —CN.

In certain embodiments, for a compound or salt of Formula (III) or (III') each R$^7$ and R$^8$ is independently selected from halogen, —OR$^{10}$, —SR$^{10}$, —N(R$^{10}$)$_2$, —NO$_2$, —CN, and C$_{1-6}$ alkyl optionally substituted with one or more substituents independently selected from halogen, —OR$^{10}$, —SR$^{10}$, —N(R$^{10}$)$_2$, —NO$_2$, and —CN. In certain embodiments, for a compound or salt of Formula (III) or (III') each R$^7$ and R$^8$ is independently selected from halogen, —OR$^{10}$, —SR$^{10}$, —N(R$^{10}$)$_2$, —NO$_2$, —CN, —CHF$_2$, —CF$_3$, —CH$_2$F, and C$_{2-6}$ alkyl optionally substituted with one or more substituents independently selected from halogen, —OR$^{10}$, —SR$^{10}$, —N(R$^{10}$)$_2$, —NO$_2$, and —CN.

In certain embodiments, for a compound or salt of Formula (III) or (III'), each R$^9$ is independently selected from halogen, —OR$^{10}$, —SR$^{10}$, —N(R$^{10}$)$_2$, —NO$_2$, =O, =S, —CN; and C$_{1-3}$ alkyl, C$_{2-3}$ alkenyl, C$_{2-3}$ alkynyl, each of which is optionally substituted with one or more substituents independently selected from halogen, —OR$^{10}$, —SR$^{10}$, —N(R$^{10}$)$_2$, —NO$_2$, —CN. In some embodiments, R$^9$ is a halogen. In some embodiments, R$^9$ is an unsubstituted C$_{1-3}$ alkyl. In some embodiments, R$^9$ is =O. In some embodiments, R$^9$ is a haloalkyl. In some embodiments, R$^9$ is a C$_{1-3}$ alkyl substituted with one or more fluorine substituents.

In certain embodiments, for a compound or salt of Formula (III) or (III'), each R$^{10}$ is independently selected from hydrogen; and C$_{1-6}$ alkyl optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, 3- to 10-membered heterocycle; and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{3-10}$ carbocycle, 3- to 10-membered heterocycle, and haloalkyl.

In certain embodiments, for a compound or salt of Formula (III) or (III'), n is 0.

In certain embodiments, for a compound or salt of Formula (III) or (III'), p is 0.

In certain embodiments, for a compound or salt of Formula (III) or (III'), R$^1$-A is further selected from hydrogen. For example, a compound of the disclosure is represented by:

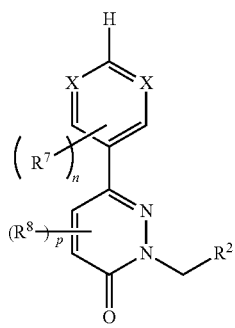

or a salt thereof.

Presented herein are methods to treat neuromuscular and movement disorders by reduction of skeletal muscle contraction. Treatment of subjects with neuromuscular and movement disorders with a selective fast skeletal muscle (type II) myosin inhibitor of a compound or salt of Formula (I), (Ia), (Ib), (Ic), (Id), (Ie), (II), (IIa), (III), or (III') may reduce muscle breakdown by preventing excessive uncoordinated muscle contractures resulting in less muscle damage. Furthermore, methods of the disclosure may reduce muscle damage while minimizing the impact on physical function in subjects. Preservation of function may occur both by limiting damaging levels of force generation in type II fibers and by increasing reliance on healthier type I fibers. Reduction of skeletal muscle contraction or uncoordinated muscle contractures can be reduced by the inhibition of skeletal myosin II. In certain embodiments, the inhibitor of skeletal myosin II is a compound or salt of Formula (I), (Ia), (Ib), (Ic), (Id), (Ie), (II), (IIa), (III), or (III') as disclosed herein.

In some embodiments, disclosed herein is a method of inhibiting muscle myosin II, comprising administering a compound or salt of Formula (I), (Ia), (Ib), (Ic), (Id), (Ie), (II), (IIa), (III), or (III') to a subject in need thereof. In some embodiments, the compound or salt does not appreciably inhibit cardiac muscle contraction. In some embodiments, wherein the compound or salt does not appreciably inhibit cardiac muscle contraction. In some embodiments, the compound or salt reduces cardiac muscle force by less than 10%.

In some aspects, methods of treating neuromuscular conditions or movement disorders may comprise administering a compound or salt of Formula (I), (Ia), (Ib), (Ic), (Id), (Ie), (II), (IIa), (III), or (III') to inhibit skeletal muscle contraction. In some embodiments, the compound or salt of Formula (I), (Ia), (Ib), (Ic), (Id), (Ie), (II), (IIa), (III), or (III') does not significantly inhibit cardiac muscle contraction. In some embodiments, cardiac muscle contraction is inhibited by 20% or less. In some embodiments, cardiac muscle contraction is inhibited by 15% or less. In some embodiments, cardiac muscle contraction is inhibited by 10% or less. In some embodiments, cardiac muscle contraction is inhibited by 9% or less. In some embodiments, cardiac muscle contraction is inhibited by 8% or less. In some embodiments, cardiac muscle contraction is inhibited by 7% or less. In some embodiments, cardiac muscle contraction is inhibited by 6% or less. In some embodiments, cardiac muscle contraction is inhibited by 5% or less. In some embodiments, cardiac muscle contraction is inhibited by 4% or less. In some embodiments, cardiac muscle contraction is inhibited by 3% or less. In some embodiments, cardiac muscle contraction is inhibited by 2% or less. In some embodiments, cardiac muscle contraction is inhibited by 1% or less.

A subject's activities of daily life (ADL) or habitual physical activity may be monitored prior to and following the treatment with a compound or salt of Formula (I), (Ia), (Ib), (Ic), (Id), (Ie), (II), (IIa), (III), or (III'). ADL or habitual physical activity is subject-dependent and may range from simple walking to extensive exercise depending on the subject's ability and routine. Treatment options and dosages of the skeletal muscle contraction inhibitors discussed herein may be personalized to a subject such that the ADL and habitual physical activity remains unchanged.

In some aspects, methods of treating neuromuscular conditions or movement disorders may comprise administering a compound or salt of Formula (I), (Ia), (Ib), (Ic), (Id), (Ie), (II), (IIa), (III), or (III') to inhibit skeletal muscle contraction. A compound or salt of Formula (I), (Ia), (Ib), (Ic), (Id), (Ie), (II), (IIa), (III), or (III') may be given in an amount relative to the amount needed to reduce skeletal muscle contraction by 50%. The compound or salt of Formula (I), (Ia), (Ib), (Ic), (Id), (Ie), (II), (IIa), (III), or (III') may be administered in an amount less than the amount needed to reduce skeletal muscle contraction by 50% relative to pre-treatment skeletal muscle contraction capacity of the subject. The compound or salt of Formula (I), (Ia), (Ib), (Ic), (Id), (Ie), (II), (IIa), (III), or (III') may be administered in an amount that reduces skeletal muscle contraction by 5% to 45% relative to pre-treatment skeletal muscle contraction capacity of said subject. In some cases, the compound or salt of Formula (I), (Ia), (Ib), (Ic), (Id), (Ie), (II), (IIa), (III), or (III') may be administered in an amount that reduces skeletal muscle contraction by less than 10%, less than 15%, less than 20%, less than 25%, less than 30%, less than 35%, less than 40%, less than 45% or even less than 50% relative to pre-treatment skeletal muscle contraction capacity of said subject. In certain embodiments, the compound or salt of Formula (I), (Ia), (Ib), (Ic), (Id), (Ie), (II), (IIa), (III), or (III') may be administered in an amount that reduces skeletal muscle contraction from 1% to 50% relative to pre-treatment skeletal muscle contraction capacity of said subject.

In some aspects, methods of treating neuromuscular conditions or movement disorders may comprise administering a compound or salt of Formula (I), (Ia), (Ib), (Ic), (Id), (Ie), (II), (IIa), (III), or (III') to inhibit type I skeletal muscle contraction. The inhibitor of type I skeletal muscle contraction may be given in an amount relative to the amount needed to reduce type I skeletal muscle contraction by 20%. The inhibitor of type I skeletal muscle contraction may be administered in an amount less than the amount needed to reduce type I skeletal muscle contraction by 20% relative to pre-treatment type I skeletal muscle contraction capacity of the subject. The inhibitor of type I skeletal muscle contraction may be administered in an amount that reduces type I skeletal muscle contraction by 0.01% to 20% relative to pre-treatment type I skeletal muscle contraction capacity of said subject. In some cases, the inhibitor may be administered in an amount that reduces type I skeletal muscle contraction by less than 0.01%, less than 0.1%, less than 0.5%, less than 1%, less than 5%, less than 10%, less than 15% or less than 20% relative to pre-treatment type I skeletal muscle contraction capacity of said subject. In certain embodiments, the inhibitor may be administered in an amount that reduces type I skeletal muscle contraction from 0.01% to 20% relative to pre-treatment type I skeletal muscle contraction capacity of said subject.

In some aspects, methods of treating neuromuscular conditions or movement disorders may comprise administering a compound or salt of Formula (I), (Ia), (Ib), (Ic), (Id), (Ie), (II), (IIa), (III), or (III') to inhibit type II skeletal muscle contraction. The inhibitor of type II skeletal muscle contraction may be given in an amount relative to the amount needed to reduce type II skeletal muscle contraction by 90%. The inhibitor of type II skeletal muscle contraction may be administered in an amount less than the amount needed to reduce type II skeletal muscle contraction by 90% relative to pre-treatment type II skeletal muscle contraction capacity of the subject. The inhibitor of type II skeletal muscle contraction may be administered in an amount that reduces type II skeletal muscle contraction by 5% to 75% relative to pre-treatment type II skeletal muscle contraction capacity of said subject. In some cases, the inhibitor may be administered in an amount that reduces type II skeletal muscle contraction by less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85% or even less than 90% relative to pre-treatment type II skeletal muscle contraction capacity of said subject. In certain embodiments, the inhibitor may be administered in an amount that reduces type II skeletal muscle contraction by from 1% to 50% relative to pre-treatment type II skeletal muscle contraction capacity of said subject.

In some aspects, methods of treating contraction-induced injury in skeletal muscle fiber may comprise administering a compound or salt of Formula (I), (Ia), (Ib), (Ic), (Id), (Ie), (II), (IIa), (III), or (III') to inhibit skeletal muscle contraction and/or skeletal muscle myosin II. In certain embodiments, the inhibitor does not appreciably inhibit cardiac muscle contraction.

In some aspects, methods of treating metabolic myopathies, e.g. McArdle's syndrome, may comprise administering a compound or salt of Formula (I), (Ia), (Ib), (Ic), (Id), (Ie), (II), (IIa), (III), or (III').

In certain embodiments, the contraction-induced injury in skeletal muscle fiber is from involuntary skeletal muscle contraction. The involuntary skeletal muscle contraction may be associated with a neuromuscular condition or spasticity-associated condition. In certain embodiments, the contraction-induced injury in skeletal muscle fiber may be from voluntary skeletal muscle contraction, e.g., physical exercise.

In certain embodiments, the administration of a compound or salt of Formula (I), (Ia), (Ib), (Ic), (Id), (Ie), (II), (IIa), (III), or (III') to a subject modulates one or more biomarkers associated with muscle contraction. Examples of biomarkers include but are not limited to creatinine kinase (CK), Troponin T (TnT), Troponin C (TnC), Troponin I (TnI), pyruvate kinase (PK), lactate dehydrogenase (LDH), myoglobin, isoforms of TnI (such as cardiac, slow skeletal, fast skeletal muscles) and inflammatory markers (IL-1, IL-6, IL-4, TNF-α). Biomarkers may also include measures of muscle inflammation for example, edema. The level of biomarkers described herein may increase after the administration of the inhibitor relative to pre-treatment level of the biomarkers. Alternatively, the level of biomarkers may decrease after the administration of the inhibitor relative to pre-treatment level of the biomarkers. The modulation of one or more biomarkers with an inhibitor described herein may indicate treatment of a neuromuscular condition such as those described herein.

Levels of CK in a subject increase when the subject is active as compared to when the subject is inactive (e.g., sleeping) and therefore CK is a potential metric for evaluating skeletal muscle breakdown caused by skeletal muscle contraction. In certain embodiments, a compound or salt of Formula (I), (Ia), (Ib), (Ic), (Id), (Ie), (II), (IIa), (III), or (III') may be administered to a subject prior to mild, moderate or strenuous activity to reduce or prevent skeletal muscle breakdown from the activity. Moderate to strenuous activity may be dependent on a subject's abilities and may include physical exercise that increases the heart rate by at least 20% or more, such as about 50% or more relative to the subject's resting heart rate. Examples of moderate to strenuous activity include walking, running, weight lifting, biking, swimming, hiking, etc.

In certain embodiments, a compound or salt of Formula (I), (Ia), (Ib), (Ic), (Id), (Ie), (II), (IIa), (III), or (III') is administered prior to, during, or after moderate or strenuous activity to reduce or prevent skeletal muscle breakdown from the activity. The compound or salt of Formula (I), (Ia), (Ib), (Ic), (Id), (Ie), (II), (IIa), (III), or (III') may reduce the subject's level of CK relative to the untreated subject performing the same activity. The level of CK may be measured in the peripheral blood of the subject during or after the activity. The administration of an inhibitor described herein may reduce the level of CK by 5% to 90% in an active subject relative to the untreated subject performing the same activity, thereby reducing or preventing skeletal muscle breakdown from the activity. The administration of an inhibitor described herein may modulate the level of CK by about 5% to about 90% relative to the untreated subject performing the same activity, thereby reducing or preventing skeletal muscle breakdown from the activity. The administration of an inhibitor described herein may reduce the level of CK by at least about 5% relative to the untreated subject performing the same activity thereby reducing or preventing skeletal muscle breakdown from the activity. The administration of an inhibitor described herein may modulate the level of CK by at most about 90% relative to the untreated subject performing the same activity. The administration of an inhibitor described herein may reduce the level of CK by about 5% to about 15%, about 5% to about 25%, about 5% to about 35%, about 5% to about 45%, about 5% to about 55%, about 5% to about 65%, about 5% to about 75%, about 5% to about 85%, about 5% to about 90%, about 15% to about 25%, about 15% to about 35%, about 15% to about 45%, about 15% to about 55%, about 15% to about 65%, about 15% to about 75%, about 15% to about 85%, about 15% to about 90%, about 25% to about 35%, about 25% to about 45%, about 25% to about 55%, about 25% to about 65%, about 25% to about 75%, about 25% to about 85%, about 25% to about 90%, about 35% to about 45%, about 35% to about 55%, about 35% to about 65%, about 35% to about 75%, about 35% to about 85%, about 35% to about 90%, about 45% to about 55%, about 45% to about 65%, about 45% to about 75%, about 45% to about 85%, about 45% to about 90%, about 55% to about 65%, about 55% to about 75%, about 55% to about 85%, about 55% to about 90%, about 65% to about 75%, about 65% to about 85%, about 65% to about 90%, about 75% to about 85%, about 75% to about 90%, or about 85% to about 90% relative to the untreated subject performing the same activity, thereby reducing or preventing skeletal muscle breakdown from the activity. The administration of an inhibitor described herein may modulate the level of CK by about 5%, about 15%, about 25%, about 35%, about 45%, about 55%, about 65%, about 75%, about 85%, or about 90% relative to the untreated subject performing the same activity, thereby reducing or preventing skeletal muscle breakdown from the activity.

The administration of a compound or salt of Formula (I), (Ia), (Ib), (Ic), (Id), (Ie), (II), (IIa), (III), or (III') to a subject may modulate the levels of inflammatory markers, e.g., reduce the level of one or more inflammatory markers relative to the untreated subject or the subject prior to treatment. The level of inflammatory markers may be measured in the peripheral blood of the subject. Examples of inflammatory markers may include but are not limited to IL-1, IL-6 and TNF-α. Inflammatory markers may also be in the form of conditions such as edema which may be measured using magnetic resonance imaging. The level of inflammatory markers in the peripheral blood may increase after the administration of the inhibitor relative to pre-treatment level of inflammatory marker for the subject. Alternatively, the level of inflammatory markers in the peripheral blood may decrease after the administration of the inhibitor relative to pre-treatment level of inflammatory marker for the subject. The administration of an inhibitor described herein may modulate the level of inflammatory markers by 5% to 90% relative to pre-treatment level of inflammatory marker for the subject. In some cases, the level of inflammatory markers may be modulated by about 5% to about 90% relative to pre-treatment level of inflammatory markers of the subject. In some cases, the level of inflammatory markers may be modulated by at least about 5% relative to pre-treatment level of inflammatory markers of the subject. In some cases, the level of inflammatory markers may be modulated by at most about 90% relative to pre-treatment level of inflammatory markers of the subject. In some cases, the level of inflammatory markers may be modulated by about 5% to about 15%, about 5% to about 25%, about 5% to about 35%, about 5% to about 45%, about 5% to about 55%, about 5% to about 65%, about 5% to about 75%, about 5% to about 85%, about 5% to about 90%, about 15% to about 25%, about 15% to about 35%, about 15% to about 45%, about 15% to about 55%, about 15% to about 65%, about 15% to about 75%, about 15% to about 85%, about 15% to about 90%, about 25% to about 35%, about 25% to about 45%, about 25% to about 55%, about 25% to about 65%, about 25% to about 75%, about 25% to about 85%, about 25% to about 90%, about 35% to about 45%, about 35% to about 55%, about 35% to about 65%, about 35% to about 75%, about 35% to about 85%, about 35% to about 90%, about 45% to about 55%, about 45% to about 65%, about 45% to about 75%, about 45% to about 85%, about 45% to about 90%, about 55% to about 65%, about 55% to about 75%, about 55% to about 85%, about 55% to about 90%, about 65% to about 75%, about 65% to about 85%, about 65% to about 90%, about 75% to about 85%, about 75% to about 90%, or about 85% to about 90% relative to pre-treatment level of inflammatory markers of the subject. In some cases, the level of inflammatory markers may be modulated by about 5%, about 15%, about 25%, about 35%, about 45%, about 55%, about 65%, about 75%, about 85%, or about 90% relative to pre-treatment level of inflammatory markers of the subject.

The administration of a compound or salt of Formula (I), (Ia), (Ib), (Ic), (Id), (Ie), (II), (IIa), (III), or (III') to a subject may modulate the levels of circulating fast skeletal muscle Troponin I (fS-TnI). The level of fS-TnI may be measured in the peripheral blood. The level of fS-TnI in the peripheral blood may increase after the administration of the inhibitor relative to pre-treatment level of fS-TnI for the subject. Alternatively, the level of fS-TnI in the peripheral blood may decrease after the administration of the inhibitor relative to pre-treatment level of fS-TnI for the subject. The administration of an inhibitor described herein may modulate the level of fS-TnI by 5% to 90% relative to pre-treatment level of fS-TnI for the subject. In some cases, the level of fS-TnI may be modulated by at least about 5% relative to pre-treatment level of fS-TnI of the subject. In some cases, the level of fS-TnI may be modulated by at most about 90% relative to pre-treatment level of fS-TnI of the subject. In some cases, the level of fS-TnI may be modulated by about 5% to about 15%, about 5% to about 25%, about 5% to about 35%, about 5% to about 45%, about 5% to about 55%, about 5% to about 65%, about 5% to about 75%, about 5% to about 85%, about 5% to about 90%, about 15% to about 25%, about 15% to about 35%, about 15% to about 45%, about 15% to about 55%, about 15% to about 65%, about 15% to about 75%, about 15% to about 85%, about 15% to about 90%, about 25% to about 35%, about 25% to about 45%, about 25% to about 55%, about 25% to about 65%, about 25% to about 75%, about 25% to about 85%, about 25% to about 90%, about 35% to about 45%, about 35% to about 55%, about 35% to about 65%, about 35% to about 75%, about 35% to about 85%, about 35% to about 90%, about 45% to about 55%, about 45% to about 65%, about 45% to about 75%, about 45% to about 85%, about 45% to about 90%, about 55% to about 65%, about 55% to about 75%, about 55% to about 85%, about 55% to about 90%, about 65% to about 75%, about 65% to about 85%, about 65% to about 90%, about 75% to about 85%, about 75% to about 90%, or about 85% to about 90% relative to pre-treatment level of fS-TnI of the subject. In some cases, the level of fS-TnI may be modulated by about 5%, about 15%, about 25%, about 35%, about 45%, about 55%, about 65%, about 75%, about 85%, or about 90% relative to pre-treatment level of fS-TnI of the subject.

Isoforms of troponin may be measured in a subject prior to and following the administration a compound or salt of Formula (I), (Ia), (Ib), (Ic), (Id), (Ie), (II), (IIa), (III), or (III'). Inhibition of skeletal muscle contraction may not inhibit some isoforms of troponin, such as cardiac troponin I (cTnI) or slow skeletal troponin I (ssTnI). In some cases, the inhibition of skeletal muscle contraction may not appreciably inhibit cTnI or ssTnI. As used herein with regard to cTnI or ssTnI, the phrase not appreciably refers to the cTnI or ssTnI reduced by less than 10%, less than 8%, less than 6%, less than 4%, less than 2%, less than 1%, less than 0.5% or even less than 0.1% relative to the cTnI or ssTnI prior to the administration of the inhibitor.

The administration of a compound or salt of Formula (I), (Ia), (Ib), (Ic), (Id), (Ie), (II), (IIa), (III), or (III') may reduce involuntary muscle contractions. Involuntary muscle contractions may be reduced by 20% to 90% relative to involuntary muscle contractions prior to the administration of the inhibitor. In some cases, involuntary muscle contractions may be reduced by at least about 20% relative to pre-treatment involuntary muscle contractions. In some cases, involuntary muscle contractions may be reduced by at most about 90% relative to pre-treatment involuntary muscle contractions. In some cases, involuntary muscle contractions may be reduced by about 20% to about 25%, about 20% to about 30%, about 20% to about 40%, about 20% to about 50%, about 20% to about 70%, about 20% to about 75%, about 20% to about 80%, about 20% to about 85%, about 20% to about 90%, about 25% to about 30%, about 25% to about 40%, about 25% to about 50%, about 25% to about 70%, about 25% to about 75%, about 25% to about 80%, about 25% to about 85%, about 25% to about 90%, about 30% to about 40%, about 30% to about 50%, about 30% to about 70%, about 30% to about 75%, about 30% to about 80%, about 30% to about 85%, about 30% to about 90%, about 40% to about 50%, about 40% to about 70%, about 40% to about 75%, about 40% to about 80%, about 40% to about 85%, about 40% to about 90%, about 50% to about 70%, about 50% to about 75%, about 50% to about 80%, about 50% to about 85%, about 50% to about 90%, about 70% to about 75%, about 70% to about 80%, about 70% to about 85%, about 70% to about 90%, about 75% to about 80%, about 75% to about 85%, about 75% to about 90%, about 80% to about 85%, about 80% to about 90%, or about 85% to about 90% relative to pre-treatment involuntary muscle contractions. In some cases, involuntary muscle contractions may be reduced by about 20%, about 25%, about 30%, about 40%, about 50%, about 70%, about 75%, about 80%, about 85%, or about 90% relative to pre-treatment involuntary muscle contractions.

A compound or salt of Formula (I), (Ia), (Ib), (Ic), (Id), (Ie), (II), (IIa), (III), or (III') may be used to improve activities of daily living (ADL) or habitual physical activity in a subject as mature, functional undamaged muscle may be restored. Examples of ADL or habitual activities include but are not limited to stair climb, time to get up, timed chair rise, habitual walk speed, North Star Ambulatory assessment, incremental/endurance shuttle walk and 6 minute walk distance tests. ADL or habitual physical activity levels or capacity may be measured prior to and following the administration of a skeletal muscle inhibitor. Inhibition of skeletal muscle contraction may not affect ADL or habitual physical activity. In some cases, the inhibition of skeletal muscle contraction may not appreciably affect ADL or habitual physical activity. As used herein with regard to ADL or habitual physical activity, the phrase not appreciably refers to the level of ADL or habitual activity reduced by less than 20%, less than 15%, less than 10%, less than 8%, less than 6%, less than 4%, less than 2%, less than 1%, less than 0.5% or even less than 0.1% relative to the ADL or habitual activity prior to the administration of the inhibitor. Skeletal muscle contraction or force in a subject may be measured prior to and following the administration of the compound or salt of Formula (I), (Ia), (Ib), (Ic), (Id), (Ie), (II), (IIa), (III), or (III'). Such measurements may be performed to generate a dose response curve for the compound or salt of Formula (I), (Ia), (Ib), (Ic), (Id), (Ie), (II), (IIa), (III), or (III'). Dosage of the compound or salt of Formula (I), (Ia), (Ib), (Ic), (Id), (Ie), (II), (IIa), (III), or (III') may be adjusted by about 5% to 50% relative to a dose that reduces type II skeletal muscle contraction by 90%. In some cases, dosage of the skeletal muscle contraction inhibitor may be adjusted by at least about 5% relative to a dose that reduces type II skeletal muscle contraction by 90%. In some cases, dosage of the skeletal muscle contraction inhibitor may be adjusted by at most about 50% relative to a dose that reduces type II skeletal muscle contraction by 90%. In some cases, dosage of the skeletal muscle contraction inhibitor may be adjusted by about 5% to about 10%, about 5% to about 15%, about 5% to about 20%, about 5% to about 25%, about 5% to about 30%, about 5% to about 35%, about 5% to about 40%, about 5% to about 50%, about 10% to about 15%, about 10% to about 20%, about 10% to about 25%, about 10% to about 30%, about 10% to about 35%, about 10% to about 40%, about 10% to about 50%, about 15% to about 20%, about 15% to about 25%, about 15% to about 30%, about 15% to about 35%, about 15% to about 40%, about 15% to about 50%, about 20% to about 25%, about 20% to about 30%, about 20% to about 35%, about 20% to about 40%, about 20% to about 50%, about 25% to about 30%, about 25% to about 35%, about 25% to about 40%, about 25% to about 50%, about 30% to about 35%, about 30% to about 40%, about 30% to about 50%, about 35% to about 40%, about 35% to about 50%, or about 40% to about 50% relative to a dose that reduces type II skeletal muscle contraction by 90%. In some cases, dosage of the skeletal muscle contraction inhibitor may be adjusted by about 10%, about 12%, about 15%, about 18%, about 20%, about 25%, about 30%, about 35%, about 40%, about 45% or about 50% relative to a dose that reduces type II skeletal muscle contraction by 90%. Skeletal muscle contraction may be measured by a muscle force test after nerve stimulation using surface electrodes (e.g., foot plantar flexion after peroneal nerve stimulation in the leg), isolated limb assay, heart rate monitor or an activity monitor or equivalents thereof prior to and following the administration of a skeletal muscle contraction inhibitor.

Cardiac muscle force or cardiac muscle contraction of a subject may be measured prior to and following the administration of a compound or salt of Formula (I), (Ia), (Ib), (Ic), (Id), (Ie), (II), (IIa), (III), or (III'). Inhibition of skeletal muscle contraction may not inhibit cardiac muscle contraction or cardiac muscle force. In some embodiments, the inhibition of skeletal muscle contraction may not appreciably inhibit cardiac muscle contraction. In certain embodiments with regard to cardiac muscle contraction, the phrase not appreciably refers to cardiac muscle force reduced by less than 10%, less than 8%, less than 6%, less than 4%, less than 2%, less than 1%, less than 0.5% or even less than 0.1% relative to the cardiac muscle force prior to the administration of the inhibitor. Cardiac muscle force or cardiac muscle contraction of a subject following the administration of a compound or salt of Formula (I), (Ia), (Ib), (Ic), (Id), (Ie), (II), (IIa), (III), or (III') may be within 0.1% to 10% of the cardiac muscle contraction or cardiac muscle force prior to the administration of the inhibitor. In some embodiments, administration of a compound or salt of Formula (I), (Ia), (Ib), (Ic), (Id), (Ie), (II), (IIa), (III), or (III') may inhibit skeletal muscle contraction and cardiac muscle contraction or cardiac muscle force. In some embodiments, cardiac muscle force reduced by more than 0.1%, more than 0.5%, more than 1%, more than 2%, more than 4%, more than 6%, more than 8%, or more than 10%. In some embodiments, a reduction of skeletal muscle contraction and cardiac muscle contraction are described by a ratio to one another. For example, in some embodiments, the ratio of the reduction in skeletal muscle contraction to reduction in cardiac muscle contraction is from about 1:1 to about 100:1, about 2:1 to about 50:1, about 3:1 to about 40:1, about 4:1 to about 30:1, about 5:1 to about 20:1, about 7:1 to about 15:1, or about 8:1 to about 12:1. Cardiac muscle force or cardiac muscle contraction may be measured using an echocardiogram (fractional shortening) or other equivalent tests.

Tidal volume in lung in a subject may be measured prior to and following the administration of a compound or salt of Formula (I), (Ia), (Ib), (Ic), (Id), (Ie), (II), (IIa), (III), or (III'). Administration may not inhibit tidal volume in a lung. In some cases, administration may not appreciably inhibit tidal volume in a lung. In certain embodiments with regard to tidal lung volume in a lung, the phrase not appreciably refers to the tidal volume in a lung reduced by less than 10%, less than 8%, less than 6%, less than 4%, less than 2%, less than 1%, less than 0.5% or less than 0.1% relative to the tidal volume in a lung prior to the administration of the inhibitor. Tidal volume in a lung in a subject may be measured using forced volume in one second test (FEV1) or forced vital capacity test (FVC) or equivalent tests thereof.

Smooth muscle contraction in a subject may be measured prior to and following the administration of a skeletal muscle contraction inhibitor. Inhibition of skeletal muscle contraction may not inhibit smooth muscle contraction. In some cases, the inhibition of skeletal muscle contraction may not appreciably inhibit smooth muscle contraction. As used herein with regard to smooth muscle contraction, the phrase not appreciably refers to the smooth muscle contraction reduced by less than 10%, less than 8%, less than 6%, less than 4%, less than 2%, less than 1%, less than 0.5% or even less than 0.1% relative to the smooth muscle contraction prior to the administration of the inhibitor. Smooth muscle contraction in a subject may be evaluated by measuring a subject's blood pressure.

Neuromuscular coupling in a subject may be measured prior to and following the administration of a compound or salt of Formula (I), (Ia), (Ib), (Ic), (Id), (Ie), (II), (IIa), (III), or (III'). Inhibition of skeletal muscle contraction, with an inhibitor described herein, may not impair nerve conduction, neurotransmitter release or electrical depolarization of skeletal muscle in a subject. In some cases, the inhibition of skeletal muscle contraction may not appreciably impair neuromuscular coupling in a subject. As used herein with regard to neuromuscular coupling, the phrase not appreciably refers to a level of neuromuscular coupling in the subject reduced by less than 10%, less than 8%, less than 6%, less than 4%, less than 2%, less than 1%, less than 0.5% or less than 0.1% relative to the level of neuromuscular coupling in the subject prior to the administration of the inhibitor. Neuromuscular coupling in a subject may be evaluated by measuring nerve induced electrical depolarization of skeletal muscle by the recording of electrical activity produced by skeletal muscles after electrical or voluntary stimulation with electromyography (EMG) using surface or needle electrodes.

In some aspects, the method of treating a neuromuscular condition or movement disorder can comprise administering a compound or salt of Formula (I), (Ia), (Ib), (Ic), (Id), (Ie), (II), (IIa), (III), or (III') wherein the compound or salt of Formula (I), (Ia), (Ib), (Ic), (Id), (Ie), (II), (IIa), (III), or (III') may inhibit myosin ATPase activity, native skeletal muscle myofibril ATPase (calcium regulated) or a reconstituted S1 with actin, tropomyosin and troponin. In vitro assays may be used to test the effect of the test compound or inhibitor on the myosin ATPase activity. Test compounds can be screened for assessing their inhibitory activity of muscle contraction. Inhibitory activity can be measured using an absorbance assay to determine actin-activated ATPase activity. Rabbit muscle myosin sub-fragment 1 (S1) can be mixed with polymerized actin and distributed into wells of assay plates without nucleotides. Test compounds can then be added into the wells with a pin array. The reaction can be initiated with MgATP. The amount of ATP consumption over a defined time period in the test vessel may be compared to the amount of ATP consumption in a control vessel. The defined period of time may be 5 minutes to 20 minutes. The ATP consumption can be determined by direct or indirect assays. The test compounds that reproducibly and strongly inhibited the myosin S1 ATPase activity can be evaluated further in dose response assay to determine IC50 for the compound ex vivo on dissected muscles. The assay may measure ATPase activity indirectly by coupling the myosin to pyruvate kinase and lactate dehydrogenase to provide an absorbance detection method at 340 nm based upon the conversion of NADH to NAD+ driven by ADP accumulation. In some cases, wherein ATP consumption is decreased by at least 20% in said test vessel than said control vessel, said test compound may be selected as a compound or salt of Formula (I), (Ia), (Ib), (Ic), (Id), (Ie), (II), (IIa), (III), or (III'). A test compound may be selected when there is at least 20% greater inhibition of NAD+ generation in a kinetic assay.

The inhibitor or test compound selected may not inhibit cardiac muscle myosin S1 ATPase in in vitro assays. In some cases, the cardiac muscle myosin S1 ATPase or cardiac myofibrils or reconstituted system may be inhibited by less than 10%, less than 8%, less than 5%, less than 3%, less than 2%, less than 1% or less than 0.5% when a test compound or compound or salt of Formula (I), (Ia), (Ib), (Ic), (Id), (Ie), (II), (IIa), (III), or (III') is tested in an in-vitro assay.

Test compounds of skeletal muscle contraction may be tested on skinned fibers. Single skeletal muscle fibers, treated so as to remove membranes and allow for a direct activation of contraction after calcium administration may be used. An inhibitor compound or salt of Formula (I), (Ia), (Ib), (Ic), (Id), (Ie), (II), (IIa), (III), or (III') may inhibit contraction of a single skeletal muscle fiber by about 5% to about 90% relative to pre-treatment value or an untreated control single skeletal muscle fiber. An inhibitor may inhibit contraction of a single skeletal muscle fiber by at least about 5% relative to pre-treatment value or an untreated control single skeletal muscle fiber. An inhibitor may inhibit contraction of a single skeletal muscle fiber by at most about 90% relative to pre-treatment value or an untreated control single skeletal muscle fiber. An inhibitor may inhibit contraction of a single skeletal muscle fiber by about 5% to about 10%, about 5% to about 20%, about 5% to about 30%, about 5% to about 40%, about 5% to about 50%, about 5% to about 60%, about 5% to about 70%, about 5% to about 80%, about 5% to about 90%, about 10% to about 20%, about 10% to about 30%, about 10% to about 40%, about 10% to about 50%, about 10% to about 60%, about 10% to about 70%, about 10% to about 80%, about 10% to about 90%, about 20% to about 30%, about 20% to about 40%, about 20% to about 50%, about 20% to about 60%, about 20% to about 70%, about 20% to about 80%, about 20% to about 90%, about 30% to about 40%, about 30% to about 50%, about 30% to about 60%, about 30% to about 70%, about 30% to about 80%, about 30% to about 90%, about 40% to about 50%, about 40% to about 60%, about 40% to about 70%, about 40% to about 80%, about 40% to about 90%, about 50% to about 60%, about 50% to about 70%, about 50% to about 80%, about 50% to about 90%, about 60% to about 70%, about 60% to about 80%, about 60% to about 90%, about 70% to about 80%, about 70% to about 90%, or about 80% to about 90% relative to pre-treatment capacity or an untreated control single skeletal muscle fiber. An inhibitor may inhibit contraction of a single skeletal muscle fiber by about 5%, about 10%, about 20%, about 30%, about 40%, about 50%, about 60%, about 70%, about 80%, or about 90% relative to pre-treatment capacity or an untreated control single skeletal muscle fiber.

An inhibitor compound or salt of Formula (I), (Ia), (Ib), (Ic), (Id), (Ie), (II), (IIa), (III), or (III') may inhibit contraction of a single skeletal muscle by about 5% to about 90% relative to pre-treatment value or an untreated control single skeletal muscle. An inhibitor may inhibit contraction of a single skeletal muscle by at least about 5% relative to pre-treatment value or an untreated control single skeletal muscle. An inhibitor may inhibit contraction of a single skeletal muscle by at most about 90% relative to pre-treatment value or an untreated control single skeletal muscle. An inhibitor may inhibit contraction of a single skeletal muscle by about 5% to about 10%, about 5% to about 20%, about 5% to about 30%, about 5% to about 40%, about 5% to about 50%, about 5% to about 60%, about 5% to about 70%, about 5% to about 80%, about 5% to about 90%, about 10% to about 20%, about 10% to about 30%, about 10% to about 40%, about 10% to about 50%, about 10% to about 60%, about 10% to about 70%, about 10% to about 80%, about 10% to about 90%, about 20% to about 30%, about 20% to about 40%, about 20% to about 50%, about 20% to about 60%, about 20% to about 70%, about 20% to about 80%, about 20% to about 90%, about 30% to about 40%, about 30% to about 50%, about 30% to about 60%, about 30% to about 70%, about 30% to about 80%, about 30% to about 90%, about 40% to about 50%, about 40% to about 60%, about 40% to about 70%, about 40% to about 80%, about 40% to about 90%, about 50% to about 60%, about 50% to about 70%, about 50% to about 80%, about 50% to about 90%, about 60% to about 70%, about 60% to about 80%, about 60% to about 90%, about 70% to about 80%, about 70% to about 90%, or about 80% to about 90% relative to pre-treatment capacity or an untreated control single skeletal muscle. An inhibitor may inhibit contraction of a single skeletal muscle by about 5%, about 10%, about 20%, about 30%, about 40%, about 50%, about 60%, about 70%, about 80%, or about 90% relative to pre-treatment capacity or an untreated control single skeletal muscle.

The effect of a test compound on slow type I skeletal muscle fibers, cardiac muscle bundles or lung muscle fibers, may be evaluated. A test compound or inhibitor compound or salt of Formula (I), (Ia), (Ib), (Ic), (Id), (Ie), (II), (IIa), (III), or (III') may be selected so as not to appreciably modulate the function of slow type I skeletal muscle fibers, cardiac muscle bundles or lung muscle fibers and be specific for type II skeletal muscles. As used herein, the term "appreciably modulate" can refer to the contraction capacity of muscles following the inhibitor administration to be reduced less than 10%, less than 8%, less than 6%, less than 4%, less than 2%, less than 1%, less than 0.5% or even less than 0.1% relative to the muscle force/contraction prior to the administration of the inhibitor.

In some aspects, a method of treating a neuromuscular condition or a movement disorder may comprise administering to a subject in need thereof a compound or salt of Formula (I), (Ia), (Ib), (Ic), (Id), (Ie), (II), (IIa), (III), or (III') wherein the compound or salt of Formula (I), (Ia), (Ib), (Ic), (Id), (Ie), (II), (IIa), (III), or (III') reduces skeletal muscle contraction by 5% to 90% in an ex vivo assay. The ex vivo assays used may be mouse models. The mouse models used may be dystrophy mouse models such as an mdx mouse. The mdx mouse has a point mutation in its dystrophin gene, changing the amino acid coding for a glutamine to a threonine producing a nonfunctional dystrophin protein resulting in DMD where there is increased muscle damage and weakness. Extensor digitorum longus muscles may be dissected from mdx mice and mounted on a lever arm. The muscles may be bathed in an oxygenated Krebs solution to maintain muscle function. A test compound or compound or salt of Formula (I), (Ia), (Ib), (Ic), (Id), (Ie), (II), (IIa), (III), or (III') may be applied to the muscles. An isometric (fixed length) contraction step may then be performed wherein the muscles are stimulated with a series of electrical pulses. An eccentric (lengthening) contraction step may be performed wherein the muscles are stretched to 10%, 15%, 20%, 25%, or 30% greater than its rested length, while relaxed or while stimulated with an electrical pulse. In some embodiments, the eccentric contraction step is repeated from 2 to 50 times. In some embodiments, the eccentric contraction step is repeated from 2 to 40 times. In some embodiments, the eccentric contraction step is repeated from 2 to 30 times. In some embodiments, the eccentric contraction step is repeated from 2 to 20 times. In some embodiments, the eccentric contraction step is repeated from 2 to 10 times. In some embodiments, the eccentric contraction step is repeated 4, 5, 6, 7, 8, 9, 10, 11, 12, 13, 14, or 15 times to cause muscle fiber injury. In some embodiments, the electric pulses may have a frequency of about 1 Hz to about 500 Hz. In some embodiments, the electric pulses may have a frequency of about 1 Hz to about 400 Hz. In some embodiments, the electric pulses may have a frequency of about 1 Hz to about 300 Hz. In some embodiments, the electric pulses may have a frequency of about 1 Hz to about 200 Hz. In some embodiments, the electric pulses may have a frequency of about 1 Hz to about 100 Hz. The electric pulse may have a frequency of about 50, 55, 60, 65, 70, 75, 80, 85, 90, 95, 100, 105, 110, 115, 120, 125, 130, 135, 140, 145 or 150 Hz. A series of electric pulses may comprise of individual pulses of different frequencies. The time period of each pulse in the series of electric pulses may be between 0.1 second to 0.5 seconds for each pulse. The time for each pulse may be 0.1, 0.2, 0.3, 0.35, 0.4 or 0.5 seconds. Muscle membrane damage may also be measured by incubating muscles in procion orange after the isometric or eccentric contraction. Procion orange is a fluorescent dye that is taken up by muscle fibers with injured membranes. The number or proportion of dye-positive fibers may then quantified by histology. When the test force drop and/or proportion of dye-positive fibers may be at least 20% less than the control force drop and/or dye uptake, the test compound may be selected as a compound or salt of Formula (I), (Ia), (Ib), (Ic), (Id), (Ie), (II), (IIa), (III), or (III').

Using an isometric or eccentric set of contractions, the force generated by the muscle may be measured. The change in force generated by the muscle before and after an isometric or eccentric set of contractions may be calculated as the test force drop. The calculations may be compared to the change in force generated by the muscle contraction from the first pulse to the last pulse in a control sample without exposure to the test compound (control force drop). Force drop can be used as a surrogate of muscle injury and a test compound or inhibitor compound or salt of Formula (I), (Ia), (Ib), (Ic), (Id), (Ie), (II), (IIa), (III), or (III') may be selected when the test force drop is at least 20% less than the control force drop.

Pharmaceutical Formulations

The compositions and methods described herein may be considered useful as pharmaceutical compositions for administration to a subject in need thereof. Pharmaceutical compositions may comprise at least the a compound or salt of Formula (I), (Ia), (Ib), (Ic), (Id), (Ie), (II), (IIa), (III), or (III') described herein and one or more pharmaceutically acceptable carriers, diluents, excipients, stabilizers, dispersing agents, suspending agents, and/or thickening agents.

Pharmaceutical compositions comprising a compound or salt of Formula (I), (Ia), (Ib), (Ic), (Id), (Ie), (II), (IIa), (III), or (III') may be formulated using one or more physiologically-acceptable carriers comprising excipients and auxiliaries. Formulation may be modified depending upon the route of administration chosen. Pharmaceutical compositions comprising a compound, salt or conjugate may be manufactured, for example, by lyophilizing the compound, salt or conjugate, mixing, dissolving, emulsifying, encapsulating or entrapping the conjugate. The pharmaceutical compositions may also include the compounds, salts or conjugates in a free-base form or pharmaceutically-acceptable salt form.

Methods for formulation of a compound or salt of Formula (I), (Ia), (Ib), (Ic), (Id), (Ie), (II), (IIa), (III), or (III') may include formulating any of the compounds, salts or conjugates with one or more inert, pharmaceutically-acceptable excipients or carriers to form a solid, semi-solid, or liquid composition. Solid compositions may include, for example, powders, tablets, dispersible granules and capsules, and in some aspects, the solid compositions further contain nontoxic, auxiliary substances, for example wetting or emulsifying agents, pH buffering agents, and other pharmaceutically-acceptable additives. Alternatively, the compounds, salts or conjugates may be lyophilized or in powder form for re-constitution with a suitable vehicle, e.g., sterile pyrogen-free water, before use.

Pharmaceutical compositions comprising a compound or salt of Formula (I), (Ia), (Ib), (Ic), (Id), (Ie), (II), (IIa), (III), or (III') may comprise at least one active ingredient (e.g., a compound, salt or conjugate and other agents). The active ingredients may be entrapped in microcapsules prepared, for example, by coacervation techniques or by interfacial polymerization (e.g., hydroxymethylcellulose or gelatin microcapsules and poly-(methylmethacylate) microcapsules, respectively), in colloidal drug-delivery systems (e.g., liposomes, albumin microspheres, microemulsions, nanoparticles and nanocapsules) or in macroemulsions.

The compositions and formulations may be sterilized. Sterilization may be accomplished by filtration through sterile filtration.

The compositions comprising a compound or salt of Formula (I), (Ia), (Ib), (Ic), (Id), (Ie), (II), (IIa), (III), or (III') may be formulated for administration as an injection. Non-limiting examples of formulations for injection may include a sterile suspension, solution or emulsion in oily or aqueous vehicles. Suitable oily vehicles may include, but are not limited to, lipophilic solvents or vehicles such as fatty oils or synthetic fatty acid esters, or liposomes. Aqueous injection suspensions may contain substances which increase the viscosity of the suspension. The suspension may also contain suitable stabilizers. Injections may be formulated for bolus injection or continuous infusion. Alternatively, the compositions may be lyophilized or in powder form for reconstitution with a suitable vehicle, e.g., sterile pyrogen-free water, before use.

For parenteral administration, a compound or salt of Formula (I), (Ia), (Ib), (Ic), (Id), (Ie), (II), (IIa), (III), or (III') may be formulated in a unit dosage injectable form (e.g., solution, suspension, emulsion) in association with a pharmaceutically acceptable parenteral vehicle. Such vehicles may be inherently non-toxic, and non-therapeutic. Vehicles may be water, saline, Ringer's solution, dextrose solution, and 5% human serum albumin. Non-aqueous vehicles such as fixed oils and ethyl oleate may also be used. Liposomes may be used as carriers. The vehicle may contain minor amounts of additives such as substances that enhance isotonicity and chemical stability (e.g., buffers and preservatives).

In one embodiment the invention relates to methods and compositions of Formula (I), (Ia), (Ib), (Ic), (Id), (Ie), (II), (IIa), (III), or (III') formulated for oral delivery to a subject in need. In one embodiment a composition is formulated so as to deliver one or more pharmaceutically active agents to a subject through a mucosa layer in the mouth or esophagus. In another embodiment the composition is formulated to deliver one or more pharmaceutically active agents to a subject through a mucosa layer in the stomach and/or intestines.

In one embodiment compositions of Formula (I), (Ia), (Ib), (Ic), (Id), (Ie), (II), (IIa), (III), or (III') are provided in modified release dosage forms. Suitable modified release dosage vehicles include, but are not limited to, hydrophilic or hydrophobic matrix devices, water-soluble separating layer coatings, enteric coatings, osmotic devices, multi-particulate devices, and combinations thereof. The compositions may also comprise non-release controlling excipients.

In another embodiment compositions of Formula (I), (Ia), (Ib), (Ic), (Id), (Ie), (II), (IIa), (III), or (III') are provided in enteric coated dosage forms. These enteric coated dosage forms can also comprise non-release controlling excipients. In one embodiment the compositions are in the form of enteric-coated granules, as controlled-release capsules for oral administration. The compositions can further comprise cellulose, disodium hydrogen phosphate, hydroxypropyl cellulose, pyridazine, lactose, mannitol, or sodium lauryl sulfate. In another embodiment the compositions are in the form of enteric-coated pellets, as controlled-release capsules for oral administration. The compositions can further comprise glycerol monostearate 40-50, hydroxypropyl cellulose, pyridazine, magnesium stearate, methacrylic acid copolymer type C, polysorbate 80, sugar spheres, talc, or triethyl citrate.

In another embodiment the compositions of Formula (I), (Ia), (Ib), (Ic), (Id), (Ie), (II), (IIa), (III), or (III') are enteric-coated controlled-release tablets for oral administration. The compositions can further comprise carnauba wax, crospovidone, diacetylated monoglycerides, ethylcellulose, hydroxypropyl cellulose, pyridazine phthalate, magnesium stearate, mannitol, sodium hydroxide, sodium stearyl fumarate, talc, titanium dioxide, or yellow ferric oxide.

Sustained-release preparations comprising a compound or salt of Formula (I), (Ia), (Ib), (Ic), (Id), (Ie), (II), (IIa), (III), or (III') may be also be prepared. Examples of sustained-release preparations may include semipermeable matrices of solid hydrophobic polymers that may contain the compound, salt or conjugate, and these matrices may be in the form of shaped articles (e.g., films or microcapsules). Examples of sustained-release matrices may include polyesters, hydrogels (e.g., poly(2-hydroxyethyl-methacrylate), or poly(vinyl alcohol)), polylactides, copolymers of L-glutamic acid and y ethyl-L-glutamate, non-degradable ethylene-vinyl acetate, degradable lactic acid-glycolic acid copolymers such as the LUPRON DEPO™ (i.e., injectable microspheres composed of lactic acid-glycolic acid copolymer and leuprolide acetate), and poly-D-(−)-3-hydroxybutyric acid.

Pharmaceutical formulations comprising a compound or salt of Formula (I), (Ia), (Ib), (Ic), (Id), (Ie), (II), (IIa), (III), or (III') may be prepared for storage by mixing a compound, salt or conjugate with a pharmaceutically acceptable carrier, excipient, and/or a stabilizer. This formulation may be a lyophilized formulation or an aqueous solution. Acceptable carriers, excipients, and/or stabilizers may be nontoxic to recipients at the dosages and concentrations used. Acceptable carriers, excipients, and/or stabilizers may include buffers such as phosphate, citrate, and other organic acids; antioxidants including ascorbic acid and methionine; preservatives, polypeptides; proteins, such as serum albumin or gelatin; hydrophilic polymers; amino acids; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes; and/or non-ionic surfactants or polyethylene glycol.

In another embodiment the compositions of Formula (I), (Ia), (Ib), (Ic), (Id), (Ie), (II), (IIa), (III), or (III') can further comprise calcium stearate, crospovidone, hydroxypropyl methylcellulose, iron oxide, mannitol, methacrylic acid copolymer, polysorbate 80, povidone, propylene glycol, sodium carbonate, sodium lauryl sulfate, titanium dioxide, and triethyl citrate.

In another embodiment compositions of Formula (I), (Ia), (Ib), (Ic), (Id), (Ie), (II), (IIa), (III), or (III') are provided in effervescent dosage forms. These effervescent dosage forms can also comprise non-release controlling excipients.

In another embodiment compositions of Formula (I), (Ia), (Ib), (Ic), (Id), (Ie), (II), (IIa), (III), or (III') can be provided in a dosage form that has at least one component that can facilitate the immediate release of an active agent, and at least one component that can facilitate the controlled release of an active agent. In a further embodiment the dosage form can be capable of giving a discontinuous release of the compound in the form of at least two consecutive pulses separated in time from 0.1 up to 24 hours. The compositions can comprise one or more release controlling and non-release controlling excipients, such as those excipients suitable for a disruptable semi-permeable membrane and as swellable substances.

In another embodiment compositions of Formula (I), (Ia), (Ib), (Ic), (Id), (Ie), (II), (IIa), (III), or (III') are provided in a dosage form for oral administration to a subject, which comprise one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

In some embodiments, the compositions of Formula (I), (Ia), (Ib), (Ic), (Id), (Ie), (II), (IIa), (III), or (III') provided herein can be in unit-dosage forms or multiple-dosage forms. Unit-dosage forms, as used herein, refer to physically discrete units suitable for administration to human or non-human animal subjects and packaged individually. Each unit-dose can contain a predetermined quantity of an active ingredient(s) sufficient to produce the desired therapeutic effect, in association with the required pharmaceutical carriers or excipients. Examples of unit-dosage forms include, but are not limited to, ampoules, syringes, and individually packaged tablets and capsules. In some embodiments, unit-dosage forms may be administered in fractions or multiples thereof. A multiple-dosage form is a plurality of identical unit-dosage forms packaged in a single container, which can be administered in segregated unit-dosage form. Examples of multiple-dosage forms include, but are not limited to, vials, bottles of tablets or capsules, or bottles of pints or gallons. In another embodiment the multiple dosage forms comprise different pharmaceutically active agents.

In some embodiments, the compositions of Formula (I), (Ia), (Ib), (Ic), (Id), (Ie), (II), (IIa), (III), or (III') may also be formulated as a modified release dosage form, including immediate-, delayed-, extended-, prolonged-, sustained-, pulsatile-, controlled-, extended, accelerated- and fast-, targeted-, programmed-release, and gastric retention dosage forms. These dosage forms can be prepared according to known methods and techniques (see, Remington: The Science and Practice of Pharmacy, supra; Modified-Release Drug Delivery Technology, Rathbone et al., Eds., Drugs and the Pharmaceutical Science, Marcel Dekker, Inc.: New York, N.Y., 2002; Vol. 126, which are herein incorporated by reference in their entirety).

Combination Therapies

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually hours, days, weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

In certain embodiments, a compound or salt of the disclosure may be administered in combination with an oral corticosteroid. In certain embodiments, a compound or salt of the disclosure is administered in combination with deflazacort. In certain embodiments, a compound or salt of the disclosure is administered in combination with prednisone. In certain embodiments, a compound or salt of the disclosure is administered in combination with a morpholino antisense oligomer. In certain embodiments, a compound or salt of the disclosure is administered in combination with and exon skipping therapy. In certain embodiments, the additional therapeutic agent is eteplirsen or ataluren.

In certain embodiments, a compound or salt of the disclosure is used in combination with a gene therapy. In certain embodiments, the compound or salt of the disclosure is used in combination with adeno-associated virus (AAV) containing genes encoding replacement proteins, e.g., dystrophin, or truncated version thereof, e.g., microdystrophin.

In certain embodiments, a compound or salt of the disclosure is administered in combination with vamorolone.

EXAMPLES

The invention now being generally described, it will be more readily understood by reference to the following examples which are included merely for purposes of illustration of certain aspects and embodiments of the present invention, and are not intended to limit the invention in any way.

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

Example 1. General Scheme—Synthesis of 2-((3-ethylisoxazol-5-yl)methyl)-6-(2-(2,2,2-trifluoroethoxy)pyrimidin-5-yl)pyridazine-3(2H)-one (Compound 36)

Example 2. Exemplary Scheme—Synthesis of 2-((3-ethylisoxazol-5-yl)methyl)-6-(2-(2,2,2-trifluoroethoxy)pyrimidin-5-yl)pyridazine-3(2H)-one (Compound 36)

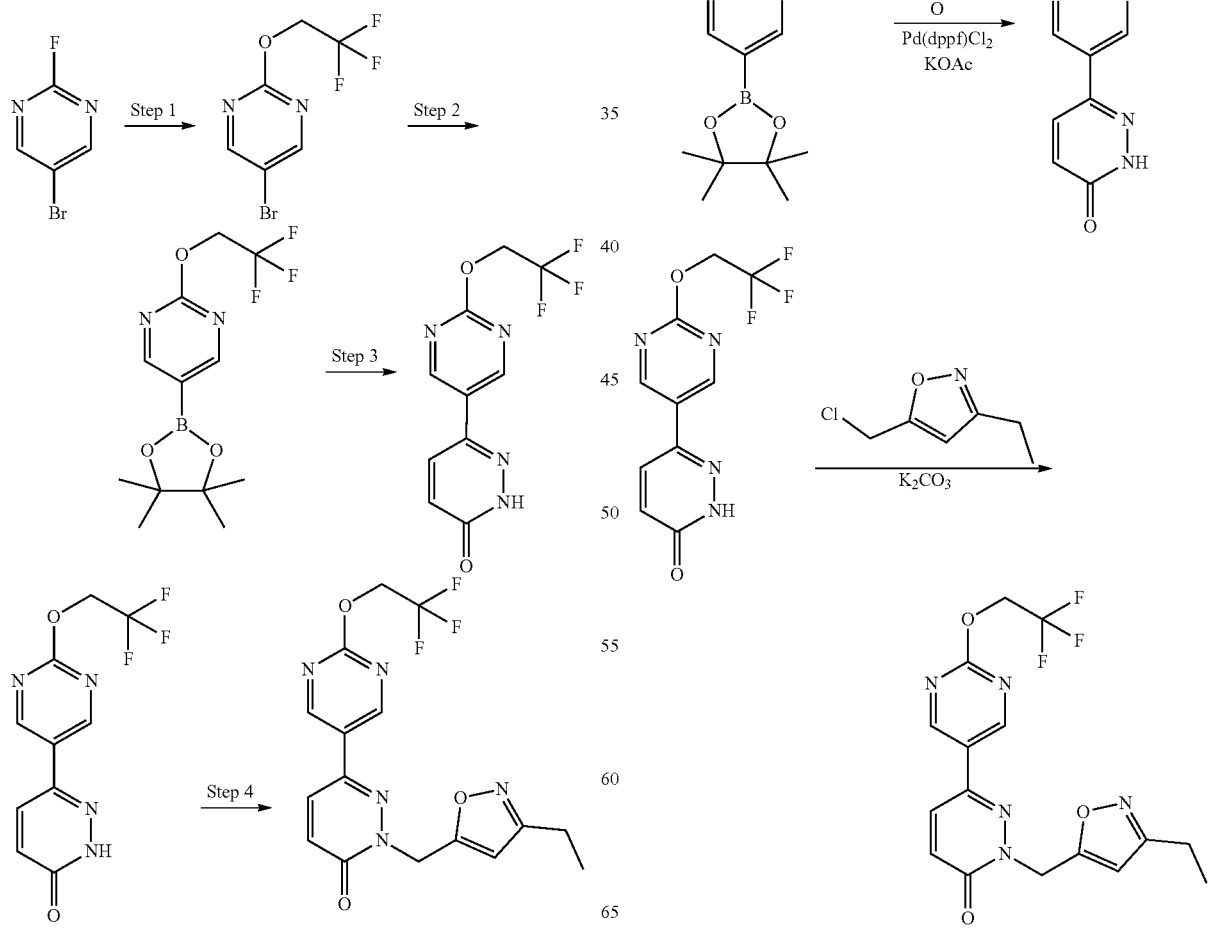

Step 1: Substitution of Pyridine, Pyrimidine, or Phenyl Groups

Bromofluoropyrimidine was combined with an alcohol (e.g. 2,2,2-trifluoroethanol), cesium carbonate and a non-protic solvent (e.g. DMF). The mixture was heated gently if necessary to increase the rate of fluoro displacement. Isolation of the major product provided the corresponding 2-substituted pyrimidines.

Steps 2-3: Cross Coupling of Pyridine, Pyrimidine, or Phenyl Groups with Pyrizidinones A Suzuki reaction at the C-4 bromo position using a palladium catalyst (e.g. [1,1-bis(diphenylphosphino)ferrocene]dichloropalladium (II)) and a mild base (e.g. potassium acetate) in dioxane/water produced the bi-aryl cores in good yield.

Step 4: Alkylation of Compounds

The nitrogen was cleanly alkylated using a wide variety of heteroarylmethylbromides or heteroarylmethylchlorides (e.g. 5-(chloromethyl)-3-ethylisoxazole) and inorganic base in polar aprotic solvents (e.g. DMF). Alternatively, the nitrogen of the pyridizinone could be functionalized using Mitsunobu methodology. This required a hydroxymethyl-heteroaryl compound, triphenylphosphine and a carbodiimide reagent (e.g. DEAD). Both alternatives were utilized in preparation of desired products depending on the availability of the appropriate coupling partners. Examples 1 and 2 may be modified as appropriate to prepare compounds described in Tables 1 and 2 herein.

Example 3: 6-[2-[(3-fluorooxetan-3-yl)methoxy]pyrimidin-5-yl]-2-[(5-phenyl-1,3,4-thiadiazol-2-yl)methyl]-2,3-dihydropyridazin-3-one (Compound 36)

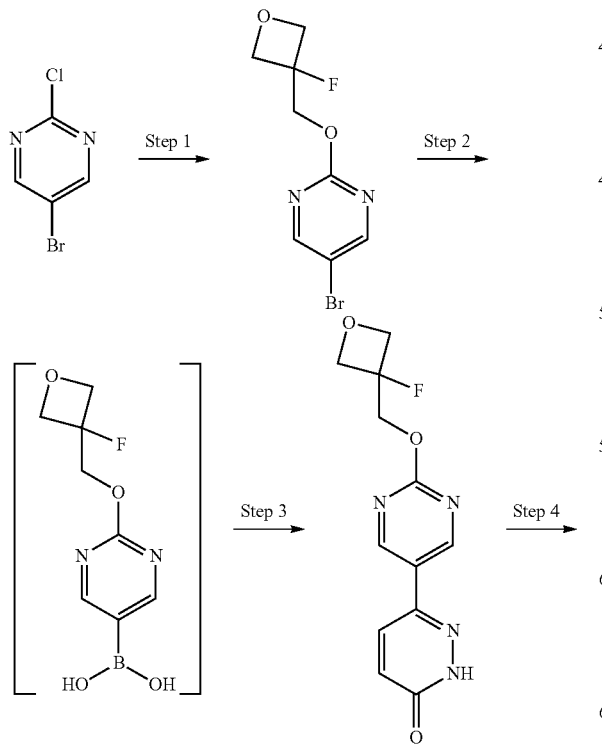

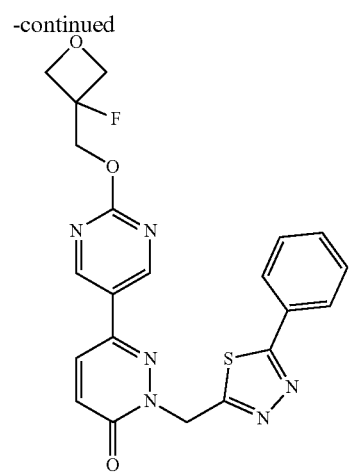

Step 1: 5-bromo-2-((3-fluorooxetan-3-yl)methoxy)pyrimidine

Following step 1 in example 2 gave the title as a solid 160 mg (58.8%). LC/MS (ESI): 263 [M+H]$^+$.

Step 2/3: 6-(2-((3-fluorooxetan-3-yl)methoxy)pyrimidin-5-yl)pyridazine-3(2H)-one Following step 2 in example 2 afforded the title compound as a white solid (500 mg, 32.8%). LC/MS (ESI): 279 [M+H]$^+$.

Step 4: 6-[2-[(3-fluorooxetan-3-yl)methoxy]pyrimidin-5-yl]-2-[(5-phenyl-1,3,4-thiadiazol-2-yl)methyl]-2,3-dihydropyridazin-3-one To a stirred solution of 6-[2-[(3-fluorooxetan-3-yl)methoxy]pyrimidin-5-yl]-2,3-dihydropyridazin-3-one (100 mg, 0.36 mmol) and (5-phenyl-1,3,4-thiadiazol-2-yl)methanol (69.0 mg, 0.36 mmol) in THF (1.5 mL) were added PPh$_3$ (188 mg, 0.72 mmol) and DEAD (94.0 mg, 0.54 mmol). The reaction was stirred at 25° C. for 2 h. The mixture was concentrated under vacuum to give a residue, which was purified by Prep-HPLC to afford the title compound as a white solid (24 mg, 14.8%). $^1$H NMR (DMSO-d6, 300 MHz): δ 9.14 (s, 2H), 8.20 (d, J=9.6 Hz, 1H), 8.00-7.97 (m, 2H), 7.59-7.53 (m, 3H), 7.26 (d, J=9.9 Hz, 1H), 5.83 (s, 2H), 4.88-4.71 (m, 6H); LC/MS (ESI): 453 [M+H]$^+$.

Example 4: 6-[2-[(3-fluorooxetan-3-yl)methoxy]pyrimidin-5-yl]-2-[[3-(4-fluorophenyl)-1,2,4-oxadiazol-5-yl]methyl]-2,3-dihydropyridazin-3-one (Compound 90)

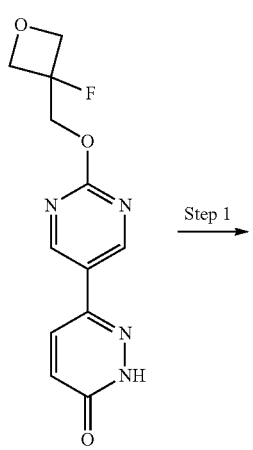

→ Step 1

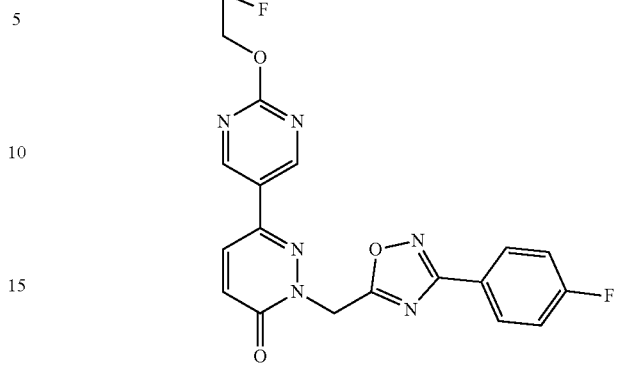

Step 1: 6-[2-[(3-fluorooxetan-3-yl)methoxy]pyrimidin-5-yl]-2-[[3-(4-fluorophenyl)-1,2,4-oxadiazol-5-yl]methyl]-2,3-dihydropyridazin-3-one To a solution of 6-[2-[(3-fluorooxetan-3-yl)methoxy]pyrimidin-5-yl]-2,3-dihydropyridazin-3-one (100 mg, 0.036 mmol) in DMF (1 mL) were added $Cs_2CO_3$ (351 mg, 0.11 mmol) and 5-(chloromethyl)-3-(4-fluorophenyl)-1,2,4-oxadiazole (76.4 mg, 0.036 mmol). The resulting mixture was stirred for 1 hr at 0° C. The resulting mixture was purified by Prep-HPLC to afford the title compound as a white solid (10 mg, 6.1%). $^1$H NMR (CD$_3$OD, 300 MHz): δ 9.13 (s, 2H), 8.17-8.05 (m, 3H), 7.30-7.21 (m, 3H), 5.80 (s, 2H), 5.03-4.75 (m, 6H); LC/MS (ESI): 456 [M+H]$^+$.

The following compound was synthesized following Example 4:

| Cmpd No. | Structure | Name | NMR/ MS |
|---|---|---|---|
| 91 | 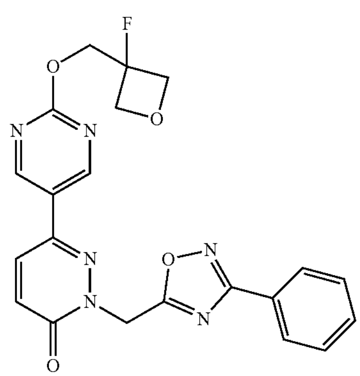 [SMILES: O=c1ccc(-c2cnc(OCC3(F)COC3)nc2)nn1Cc1nc(-c2ccccc2)no1] | 6-(2-((3-fluorooxetan-3-yl)methoxy)pyrimidin-5-yl)-2-(3-phenyl-1,2,4-oxadiazol-5-yl)methyl)pyridazine-3(2H)-one | $^1$H NMR (DMSO-d6, 300 MHz): δ 9.13 (s, 2H), 8.24 (d, J = 9.6 Hz, 1H), 8.00-7.97 (m, 2H), 7.60-7.56 (m, 3H), 7.27 (d, J = 9.6 Hz, 1H), 5.80 (s, 2H), 4.88-4.71 (m, 6H); LC/MS (ESI): 437 [M + H]+ |

Example 5: 6-(6-(difluoromethoxy)pyridazi-3-yl)-2-((5-phenyl-1,3,4-thiadiazol-2-yl)methyl)pyridazine-3(2H)-one (Compound 22)

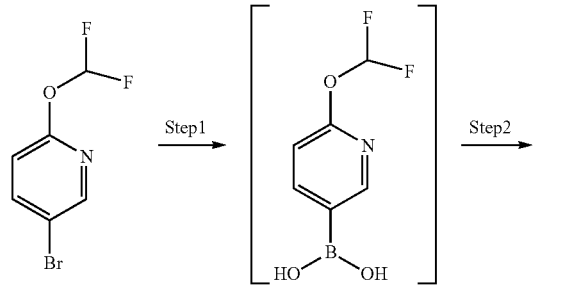

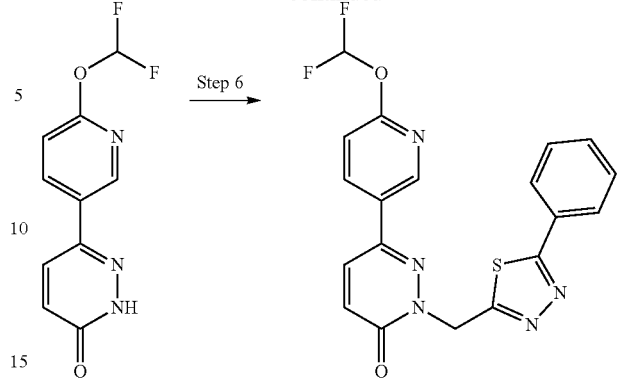

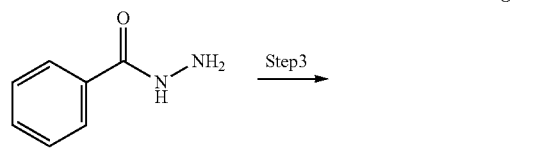

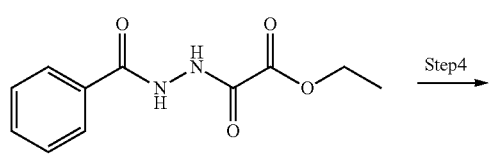

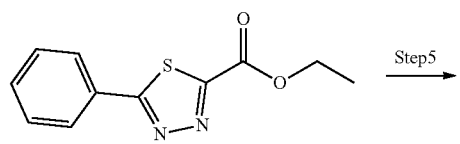

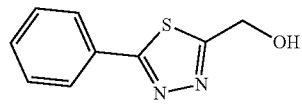

Step 1/2: 6-(6-(difluoromethoxy)pyridazi-3-yl)pyridazine-3(2H)-one

Following steps 1 and 2 in example 2 afforded the title compound as a white solid (3.5 g, 72.1%). LC/MS (ESI): 240 [M+H]$^+$.

Step 3: ethyl 2-(2-benzoylhydrazineyl)-2-oxoacetate

To a solution of benzohydrazide (1.00 g, 7.35 mmol) in DCM (5.0 mL) were added ethyl oxalochloridate (1.00 g, 7.32 mmol). The resulting mixture was stirred for 1 hr at 25° C. The reaction was concentrated to give a residue, which was purified by chromatography on silica gel (Flash 40 g, 30-80% EA:PE) to give the title compound as a white solid (0.5 g, 28.8%). LC/MS (ESI): 237 [M+H]$^+$.

Step 4: ethyl 5-phenyl-1,3,4-thiadiazole-2-carboxylate

A mixture of ethyl ethyl 2-(2-benzoylhydrazineyl)-2-oxoacetate (480 mg, 2.03 mmol), Lawesson reagent (1.49 g, 4.06 mmol) in Toluene (5.0 mL) was stirred for 2 hr at 80° C. The resulting mixture was concentrated under vacuum to give a residue, which was purified by chromatography on silica gel (Flash 40 g, 20-50% EA:PE) to give the title compound as a white solid (390 mg, 81.9%). LC/MS (ESI): 235 [M+H]$^+$.

Step 5: (5-phenyl-1,3,4-thiadiazol-2-yl)methanol

To a solution of ethyl 5-phenyl-1,3,4-thiadiazole-2-carboxylate (440 mg, 1.888 mmol) in MeOH (5.0 mL) was added NaBH$_4$ (142 mg, 3.76 mmol). The resulting solution was stirred for 1 hr at 25° C. The resulting mixture was concentrated to give a residue, which was purified by chromatography on silica gel (Flash 40 g, 50-80% EA:PE) to give the title compound as a white solid (300 mg, 83.1%). LC/MS (ESI): 193 [M+H]$^+$.

Step 6: 6-[2-[(3-fluorooxetan-3-yl)methoxy]pyrimidin-5-yl]-2-[(5-phenyl-1,3,4-thiadiazol-2-yl)methyl]-2,3-dihydropyridazin-3-one Following step 4 in example 8 afford the title compound as a white solid (38.8 mg, 22.5%). $^1$H NMR (DMSO-d6, 400 MHz): δ 8.81 (d, J$_1$=2.4 Hz, 1H), 8.42 (dd, J$_1$=8.4 Hz, J$_2$=2.4 Hz, 1H), 8.21 (d, J$_1$=10.0 Hz, 1H), 7.99-7.97 (m, 2H), 7.79 (t, J=73.2 Hz, 1H), 7.59-7.53 (m, 3H), 7.27-7.24 (m, 2H), 5.83 (s, 2H); LC/MS (ESI): 414 [M+H]$^+$.

The following compounds were synthesized following Example 5 (via Mitsunobo or Substitution):

| Compound No. | Structure | Name | NMR/MS |
|---|---|---|---|
| 17 | 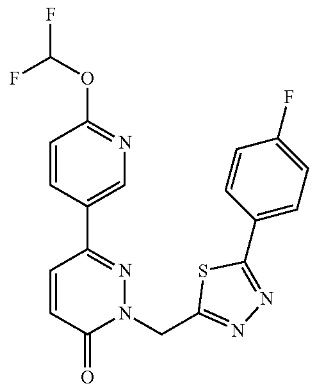 [SMILES: O=c1ccc(-c2ccc(OC(F)F)nc2)nn1Cc1nnc(-c2ccc(F)cc2)s1] | 6-(6-(difluoromethoxy)pyridazi-3-yl)-2-((5-(4-fluorophenyl)-1,3,4-thiadiazol-2-yl)methyl)pyridazine-3(2H)-one | $^1$H NMR (DMSO-d6, 300 MHz): δ 8.81 (d, J₁ = 2.4 Hz, 1H), 8.42 (dd, J₁ = 8.7 Hz, J₂ = 2.7 Hz, 1H), 8.20 (d, J₁ = 9.9 Hz, 1H), 8.07-8.04 (m, 2H), 7.78 (t, J = 72.6 Hz, 1H), 7.39-7.37 (m, 2H), 7.27-7.23 (m, 2H), 5.82 (s, 2H); LC/MS (ESI): 432 [M + H]⁺ |
| 10 | 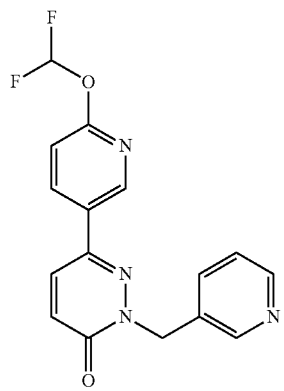 | 6-(6-(difluoromethoxy)pyridazi-3-yl)-2-(pyridazi-3-ylmethyl)pyridazine-3(2H)-one | $^1$H NMR (DMSO-d6, 300 MHz): δ 8.78 (d, J₁ = 2.1 Hz, 1H), 8.65 (s, 1H), 8.52 (d, J = 3.9 Hz, 1H), 8.40 (dd, J₁ = 8.7 Hz, J₂ = 2.4 Hz, 1H), 8.13 (d, J₁ = 9.6 Hz, 1H), 7.83-7.80 (m, 1H), 7.77 (t, J = 72.3 Hz, 1H), 7.41-7.37 (m, 1H), 7.24-7.17 (m, 2H), 5.38 (s, 2H); LC/MS (ESI): 331 [M + H]+ |
| 9 | 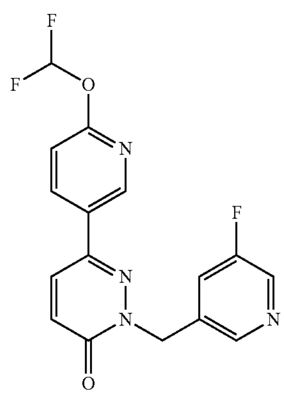 | 6-(6-(difluoromethoxy)pyridazi-3-yl)-2-((5-fluoropyridin-3-yl)methyl)pyridazine-3(2H)-one | $^1$H NMR (DMSO-d6, 300 MHz): δ 8.79 (d, J₁ = 2.1 Hz, 1H), 8.54-8.53 (m, 2H), 8.40 (dd, J₁ = 8.7 Hz, J₂ = 2.4 Hz, 1H), 8.14 (d, J₁ = 9.9 Hz, 1H), 7.78 (t, J = 72.3 Hz, 1H), 7.77-7.33 (m, 1H), 7.25-7.14 (m, 2H), 5.42 (s, 2H); LC/MS (ESI): 349 [M + H]+ |
| 2 | 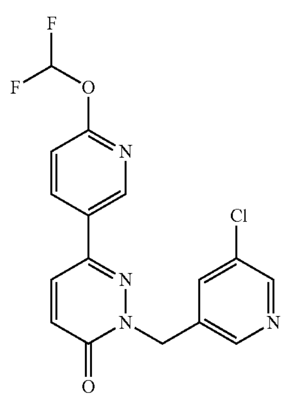 | 2-((5-chloropyridin-3-yl)methyl)-6-(6-(difluoromethoxy)pyridazi-3-yl)pyridazine-3(2H)-one | $^1$H NMR (DMSO-d6, 300 MHz): δ 8.78 (s, 1H), 8.61-8.59 (s, 2H), 8.40 (dd, J1 = 8.7 Hz, J2 = 2.4 Hz, 1H), 8.15 (d, J₁ = 9.9 Hz, 1H), 7.96-7.95 (m, 1H), 7.77 (t, J = 72.6 Hz, 1H), 7.25-7.14 (m, 2H), 5.40 (s, 2H); LC/MS (ESI): 365 [M + H]+ |

Example 6: 2-[(4-chlorophenyl)methyl]-6-[2-(2,2,2-trifluoroethoxy)pyrimidin-5-yl]-2,3-dihydro-pyridazin-3-one (Compound 1)

Step 1: 5-bromo-2-(2,2,2-trifluoroethoxy)pyrimidine

To a mixture of 5-bromo-2-chloropyrimidine (10 g, 0.021 mol, 1.0 equiv) in DMSO (10 mL) were added 2,2,2-trifluoroethan-1-ol (6.21 g, 0.025 mol, 1.20 equiv) and $Cs_2CO_3$ (25.27 g, 0.062 mol, 3.0 equiv) at room temperature. The reaction mixture was stirred for 2 h at 70° C. The solution was diluted with water and extracted with EtOAc (30 mL×3). The combined organic layers were washed with brine, dried over $Na_2SO_4$ and the solvent removed in vacuo. Purification by chromatography on silica gel (Flash 300 g, 0-40% EtOAc:cyclohexane) afforded the title compound as yellow oil (10.0 g, 94.08%). LC/MS (ESI): 257 [M+H]$^+$.

Step 2: [2-(2,2,2-trifluoroethoxy)pyrimidin-5-yl] boronic acid

To a mixture of 5-bromo-2-(2,2,2-trifluoroethoxy)pyrimidine (5.0 g, 19.45 mmol, 1.0 equiv) in dioxane (40 mL) were added 4,4,5,5-tetramethyl-2-(4,4,5,5-tetramethyl-1,3,2-dioxaborolan-2-yl)-1,3,2-dioxaborolane (7.41 g, 29.18 mmol, 1.5 equiv), KOAc (5.73 g, 58.36 mmol, 3.0 equiv) and Pd(dppf)Cl$_2$ (1.42 g, 1.94 mmol, 0.1 equiv). Into the flask purged and maintained with an inert atmosphere of nitrogen. The reaction mixture was stirred for 4 h at 80° C. and confirmed by LCMS. The reaction was used directly in the next step without workup.

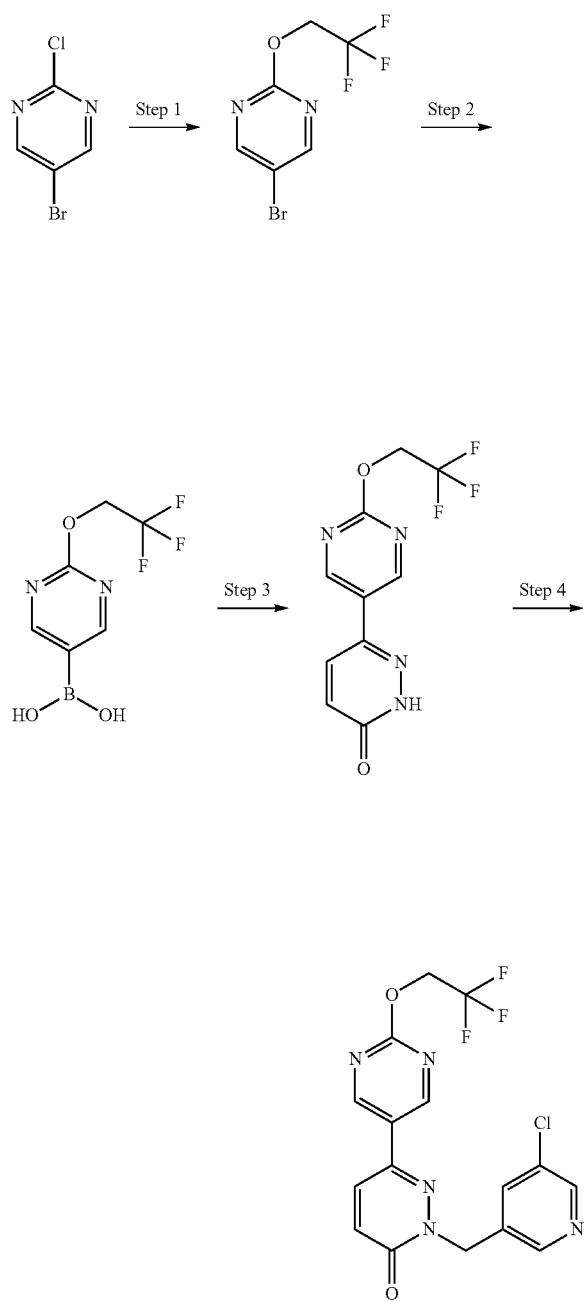

Step 3: 6-[2-(2,2,2-trifluoroethoxy)pyrimidin-5-yl]-2,3-dihydropyridazin-3-one

To a mixture of [2-(2,2,2-trifluoroethoxy)pyrimidin-5-yl] boronic acid (4.2 g, 18.93 mmol, 1.0 equiv) in dioxane (40 mL) were added 6-bromo-2,3-dihydropyridazin-3-one (3.31 g, 18.916 mmol, 1.00 equiv), Pd(dppf)Cl$_2$ (0.69 g, 0.943 mmol, 0.05 equiv), $K_2CO_3$ (3.92 g, 28.387 mmol, 1.5 equiv) and H$_2$O (4 mL). Into the flask purged and maintained with an inert atmosphere of nitrogen. The resulting solution was stirred for 2 h at 90° C. The solution was diluted with water and extracted with EtOAc (30 mL×3). The combined organics were washed with brine, dried over $Na_2SO_4$ and the solvent removed in vacuo. Purification by chromatography on silica gel (Flash 300 g, 50-100% EtOAc:cyclohexane) afforded the title compound as brown solid (3.0 g, 58.24%). LC/MS (ESI): 273 [M+H]$^+$.

Step 4: 2-[(5-chloropyridin-3-yl)methyl]-6-[2-(2,2,2-trifluoroethoxy)pyrimidin-5-yl]-2,3-dihydro-pyridazin-3-one To a mixture of 6-[2-(2,2,2-trifluoroethoxy)pyrimidin-5-yl]-2,3-dihydropyridazin-3-one (1.0 g, 3.67 mmol, 1.0 equiv) in DMF (10 mL) were added 3-(bromomethyl)-5-chloropyridine (0.82 g, 0.004 mmol, 1.0 equiv) and Cs$_2$CO$_3$ (2.39 g, 0.007 mmol, 2.0 equiv) at room temperature. The resulting solution was stirred for 2 h at room temperature.

The following compounds were synthesized following Example 6:

| Cmpd No. | Structure | Name | NMR/MS |
|---|---|---|---|
| 88 | 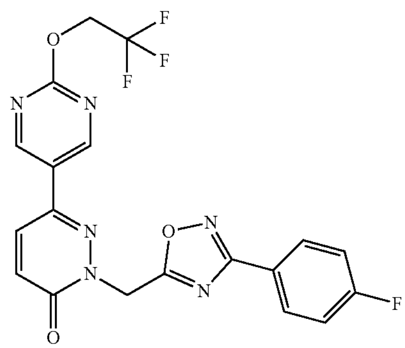 [SMILES: O=c1ccc(-c2cnc(OCC(F)(F)F)nc2)nn1Cc1nc(-c2ccc(F)cc2)no1] | 2-((3-(4-fluorophenyl)-1,2,4-oxadiazol-5-yl)methyl)-6-(2-(2,2,2-trifluoroethoxy)pyrimidin-5-yl)pyridazine-3(2H)-one | $^1$H NMR (300 MHz, DMSO-d6): δ 9.15 (s, 2H), 8.13 (d, J = 6.3 Hz, 1H), 8.11-8.05 (m, 2H), 7.30-7.21 (m, 3H), 5.81 (s, 2H), 5.03 (q, J = 8.7 Hz, 2H); LC/MS (ESI): 449 [M + H]+ |
| 89 | 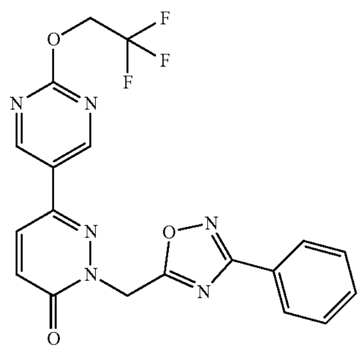 [SMILES: O=c1ccc(-c2cnc(OCC(F)(F)F)nc2)nn1Cc1nc(-c2ccccc2)no1] | 2-((3-phenyl-1,2,4-oxadiazol-5-yl)methyl)-6-(2-(2,2,2-trifluoroethoxy)pyrimidin-5-yl)pyridazine-3(2H)-one | $^1$H NMR (300 MHz, DMSO-d6): δ 9.16 (s, 2H), 8.15 (d, J = 9.9 Hz, 1H), 8.06-8.02 (m, 2H), 7.59-7.48 (m, 3H), 7.23 (d, J = 9.9 Hz, 1H), 5.81 (s, 2H), 5.03 (q, J = 8.4 Hz, 2H); LC/MS (ESI): 432 [M + H]+ |
| 1 | 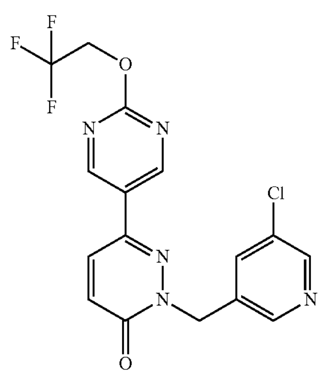 | 2-((5-chloropyridin-3-yl)methyl)-6-(2-(2,2,2-trifluoroethoxy)pyrimidin-5-yl)pyridazine-3(2H)-one | $^1$H NMR (300 MHz, DMSO-$d_6$): δ 9.18 (s, 2H), 8.61 (dd, J = 8.7, 1.5 Hz, 2H), 8.15 (d, J = 9.9 Hz, 1H), 7.99 (s, 1H), 7.18 (d, J = 9.6 Hz, 1H), 5.39 (s, 2H), 5.12 (q, J = 9.0 Hz, 2H); LC/MS (ESI): 398 [M + H]$^+$ |
| 6 | 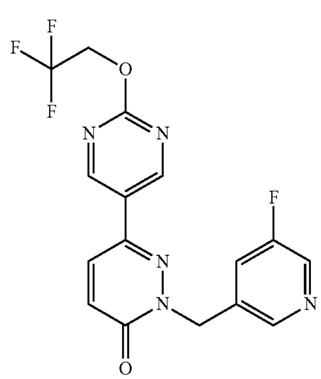 | 2-((5-fluoropyridin-3-yl)methyl)-6-(2-(2,2,2-trifluoroethoxy)pyrimidin-5-yl)pyridazine-3(2H)-one | $^1$H NMR (300 MHz, DMSO-$d_6$): δ 9.18 (s, 2H), 8.55-8.54 (m, 2H), 8.15 (d, J = 9.6 Hz, 1H), 7.81-7.77 (m, 1H), 7.19 (d, J = 9.9 Hz, 1H), 5.41 (s, 2H), 5.12 (q, J = 9.0 Hz, 2H); LC/MS (ESI): 382 [M + H]$^+$ |

Example 7: 6-[4-(difluoromethoxy)phenyl]-2-[(3-methyl-1,2-oxazol-5-yl)methyl]-2,3-dihydro-pyridazin-3-one (Compound 204)

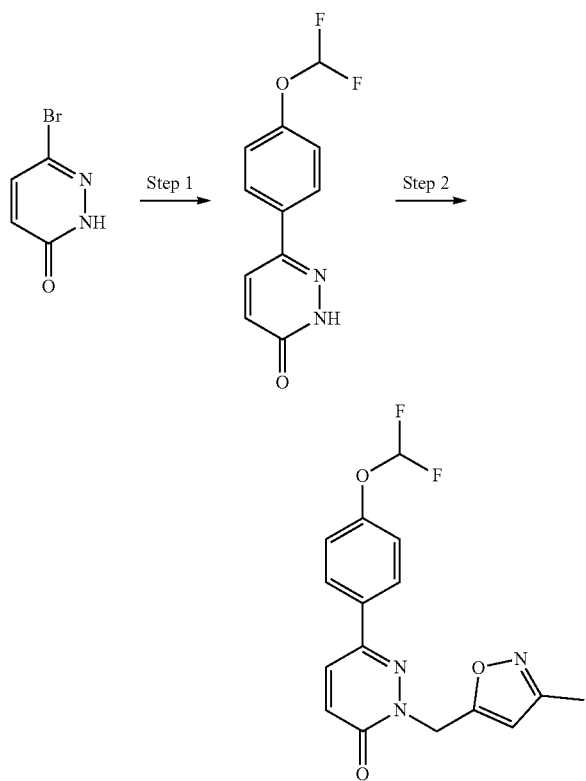

Step 1: 6-[4-(difluoromethoxy)phenyl]-2,3-dihydro-pyridazin-3-one

To a mixture of 6-bromo-2,3-dihydropyridazin-3-one (1.69 g, 9.67 mmol, 1.0 equiv) in in Dioxane (20 mL) were added [4-(difluoromethoxy)phenyl]boronic acid (2.0 g, 10.64 mmol, 1.1 equiv), $K_2CO_3$ (4.0 g, 29.0 mmol, 3.0 equiv), Pd(dppf)Cl$_2$ (707.51 mg, 0.97 mmol, 0.1 equiv) and H$_2$O (2 mL). The reaction mixture was stirred for 4 h at 90° C. under Argon atmosphere. The solution was diluted with water and extracted with EtOAc (30 mL×3). The combined organics were washed with brine, dried over Na$_2$SO$_4$ and the solvent removed in vacuo. Purification by chromatography on silica gel (Flash 300 g, 50-90% EtOAc:cyclohexane) afforded the title compound as an off-white solid (1.55 g, 67.30%). LC/MS (ESI): 239 [M+H]$^+$.

Step 2: 6-[4-(difluoromethoxy)phenyl]-2-[(3-methyl-1,2-oxazol-5-yl)methyl]-2,3-dihydro-pyridazine-3-one To a mixture of 6-[4-(difluoromethoxy)phenyl]-2,3-dihydropyridazin-3-one (100 mg, 0.42 mmol, 1.0 equiv) in DMF (2 mL) were added 5-(bromomethyl)-3-methyl-1,2-oxazole (81.28 mg, 0.462 mmol, 1.1 equiv) and Cs$_2$CO$_3$ (411.63 mg, 1.259 mmol, 3.0 equiv). The reaction mixture was stirred for 4 h at room temperature. The reaction was quenched by the addition of saturated aqueous sodium bicarbonate solution. The solution was diluted with water and extracted with EtOAc (30 mL×3). The combined organics were washed with brine, dried over Na$_2$SO$_4$ and the solvent removed in vacuo. The residue was purified by Prep-HPLC to afford a white solid (76 mg, 54.31%). $^1$H NMR (400 MHz, DMSO-d$_6$): δ 8.11 (d, J=10.0 Hz, 1H), 7.94 (d, J=8.0 Hz, 2H), 7.52-7.12 (m, 4H), 6.34 (s, 1H), 5.46 (s, 2H), 2.21 (s, 3H); LC/MS (ESI): 334 [M+H]$^+$ The following compounds were synthesized following Example 7:

| Cmpd No. | Structure | Name | NMR/MS |
|---|---|---|---|
| 204 | 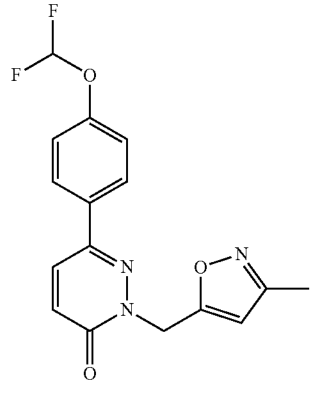 [SMILES: Cc1cc(Cn2nc(-c3ccc(OC(F)F)cc3)ccc2=O)on1] | 6-(4-(difluoromethoxy)phenyl)-2-((3-methylisoxazol-5-yl)methyl)pyridazine-3(2H)-one | $^1$H NMR (400 MHz, DMSO-d$_6$): δ 8.11 (d, J = 10.0 Hz, 1H), 7.94 (d, J = 8.0 Hz, 2H), 7.52-7.12 (m, 4H), 6.34 (s, 1H), 5.46 (s, 2H), 2.21 (s, 3H); LC/MS (ESI): 334 [M + H]$^+$ |

| Cmpd No. | Structure | Name | NMR/MS |
|---|---|---|---|
| 205 | 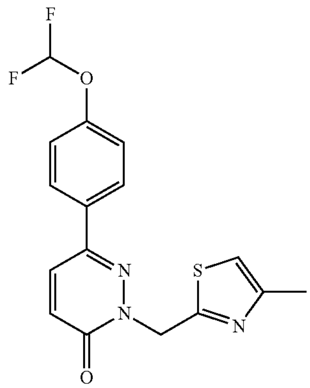 [SMILES: Cc1csc(Cn2nc(-c3ccc(OC(F)F)cc3)ccc2=O)n1] | 6-(4-(difluoromethoxy)phenyl)-2-((4-methylthiazol-2-yl)methyl)pyridazine-3(2H)-one | ¹H NMR (300 MHz, DMSO-d₆): δ 8.14-7.95 (d, J = 9.9 Hz, 1H), 7.98-7.95 (m, 2H), 7.58-7.09 (m, 5H), 5.58 (s, 2H), 2.34 (s, 3H); LC/MS (ESI): 350 [M + H]⁺ |
| 206 | 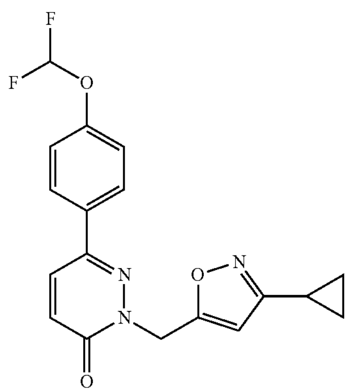 [SMILES: O=c1ccc(-c2ccc(OC(F)F)cc2)nn1Cc1cc(C2CC2)no1] | 2-((3-cyclopropylisoxazol-5-yl)methyl)-6-(4-(difluoromethoxy)phenyl)pyridazine-3(2H)-one | ¹H NMR (300 MHz, DMSO-d₆): δ 8.11 (d, J = 9.6 Hz, 1H), 7.97-7.92 (m, 2H), 7.58-7.09 (m, 4H), 6.24 (s, 1H), 5.42 (s, 2H), 2.02-1.93 (m, 1H), 1.01-0.95 (m, 2H), 0.77-0.74 (m, 2H); LC/MS (ESI): 360 [M + H]⁺ |
| 203 | 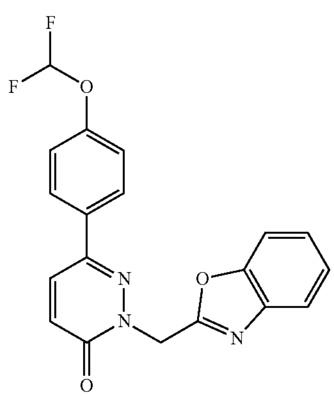 [SMILES: O=c1ccc(-c2ccc(OC(F)F)cc2)nn1Cc1nc2ccccc2o1] | 2-(benzo[d]oxazol-2-ylmethyl)-6-(4-(difluoromethoxy)phenyl)pyridazine-3(2H)-one | ¹H NMR (300 MHz, DMSO-d₆): δ 8.17 (d, J = 9.9 Hz, 1H), 7.97-7.94 (m, 2H), 7.75-7.71 (m, 2H), 7.58-7.09 (m, 6H), 5.69 (s, 2H); LC/MS (ESI): 370 [M + H]⁺ |
| 208 | 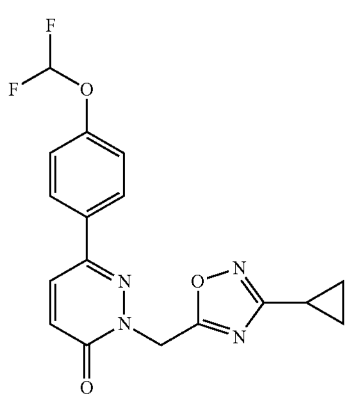 [SMILES: O=c1ccc(-c2ccc(OC(F)F)cc2)nn1Cc1nc(C2CC2)no1] | 2((3-cyclopropyl-1,2,4-oxadiazol-5-yl)methyl)-6-(4-(difluoromethoxy)phenyl)pyridazine-3(2H)-one | ¹H NMR (300 MHz, DMSO-d₆): δ 8.15 (d, J = 9.9 Hz, 1H), 7.96-7.93 (m, 2H), 7.58-7.09 (m, 4H), 5.62 (s, 2H), 2.16-2.07 (m, 1H), 1.09-1.00 (m, 2H), 0.88-0.86 (m, 2H); LC/MS (ESI): 361 [M + H]⁺ |

| Cmpd No. | Structure | Name | NMR/MS |
|---|---|---|---|
| 210 | 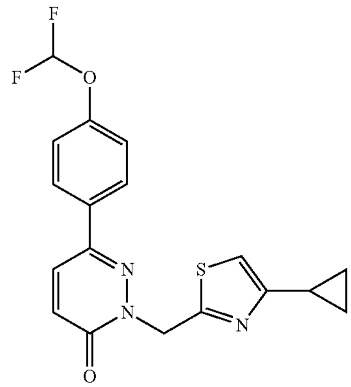 [SMILES: O=c1ccc(-c2ccc(OC(F)F)cc2)nn1Cc1nc(C2CC2)cs1] | 2-((4-cyclopropylthiazol-2-yl)methyl)-6-(4-(difluoromethoxy)phenyl)pyridazine-3(2H)-one | $^1$H NMR (300 MHz, DMSO-$d_6$): δ 8.13 (d, J = 9.9 Hz, 1H), 7.96 (d, J = 8.7 Hz, 2H), 7.60-7.05 (m, 5H), 5.55 (s, 2H), 2.10-2.01 (m, 1H), 0.91-0.76 (m, 4H); LC/MS (ESI): 376 [M + H]$^+$ |
| 202 | 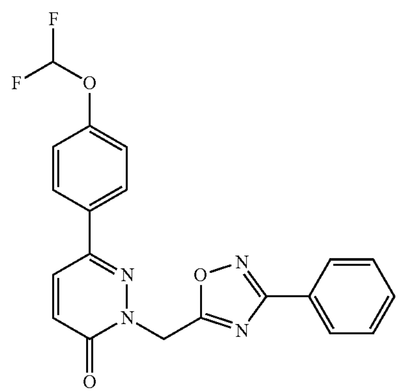 [SMILES: O=c1ccc(-c2ccc(OC(F)F)cc2)nn1Cc1nc(-c2ccccc2)no1] | 6-(4-(difluoromethoxy)phenyl)-2-((3-phenyl-1,2,4-oxadiazol-5-yl)methyl)pyridazine-3(2H)-one | $^1$H NMR (300 MHz, DMSO-$d_6$): δ 8.20 (d, J = 9.6 Hz, 1H), 7.98 (d, J = 7.6 Hz, 4H), 7.60-7.53 (m, 3H), 7.46-7.16 (m, 4H), 5.79 (s, 3H); LC/MS (ESI): 397 [M + H]$^+$ |

Example 8: 6'-(bicyclo[1.1.1]pentan-1-ylamino)-1-(pyridazi-3-ylmethyl)-[3,3'-bipyridin]-6(1H)-one (Compound 71)

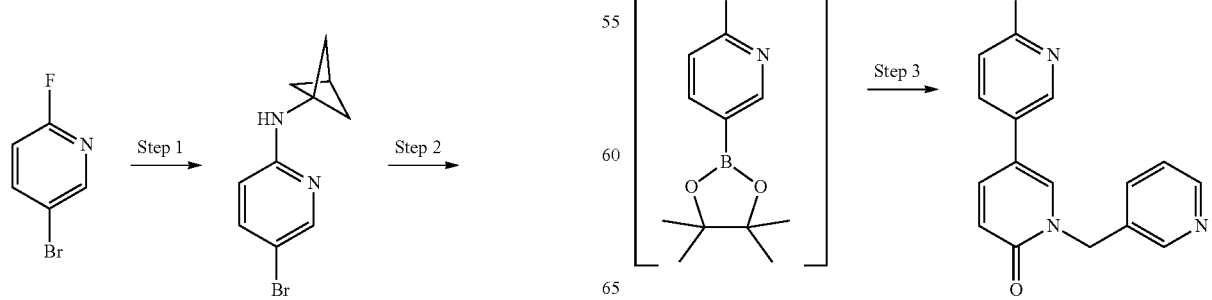

Step 1: N-(bicyclo[1.1.1]pentan-1-yl)-5-bromopyridin-2-amine

A mixture of 5-bromo-2-fluoropyridine (200 mg, 1.136 mmol), bicyclo[1.1.1]pentan-1-amine (141.72 mg, 1.705 mmol), Cs$_2$CO$_3$ (1.11 g, 3.409 mmol) in DMSO (3 mL) was stirred for 2 hr at 120° C. The residue was applied onto a silica gel column eluted with ethyl acetate/petroleum ether (1:2). This resulted in the title compound as a solid 110 mg (40.48%). MS m/z: 239 [M+H]$^+$

Step 2: N-(bicyclo[1.1.1]pentan-1-yl)-5-(4,4,5,5-tetramethyl-1,3,2-dioxaborolan-2-yl)pyridazi-2-amine To a mixture of N-(bicyclo[1.1.1]pentan-1-yl)-5-bromopyridin-2-amine (110 mg, 0.46 mmol, 1.0 equiv) in dioxane (1.1 mL) were added 4,4,5,5-tetramethyl-2-(4,4,5,5-tetramethyl-1,3,2-dioxaborolan-2-yl)-1,3,2-dioxaborolane (175 mg, 0.69 mmol, 1.5 equiv), KOAc (135 mg, 1.38 mmol, 3.0 equiv) and Pd(dppf)Cl$_2$ (37 mg, 0.05 mmol, 0.1 equiv). Into the flask purged and maintained with an inert atmosphere of nitrogen. The reaction mixture was stirred for 4 h at 80° C. and confirmed by LCMS. The reaction was used in next step directly without workup.

Step 3: 2-[3-[6-([bicyclo[1.1.1]pentan-1-yl]amino) pyridazi-3-yl]-6-oxo-1,6-dihydropyridazin-1-yl]-N-ethylacetamide To a mixture of N-(bicyclo[1.1.1]pentan-1-yl)-5-(4,4,5,5-tetramethyl-1,3,2-dioxaborolan-2-yl)pyridazi-2-amine (131 mg, 0.46 mmol, 1.0 equiv) in dioxane (1.1 mL) were added 6-bromo-2-(pyridazi-3-ylmethyl)pyridazine-3(2H)-one (122 mg, 0.46 mmol, 1.00 equiv), Pd(dppf)Cl$_2$ (23 mg, 0.03 mmol, 0.05 equiv), K$_2$CO$_3$ (95 mg, 0.69 mmol, 1.5 equiv) and H$_2$O (0.1 mL). Into the flask purged and maintained with an inert atmosphere of nitrogen. The resulting solution was stirred for 2 h at 90° C. The solution was diluted with water and extracted with EtOAc (×3). The combined organics were washed with brine, dried over Na$_2$SO$_4$ and the solvent removed in vacuo. Purification by chromatography on silica gel (Flash 300 g, 50-100% EtOAc:cyclohexane) afforded crude product. The crude product was purified by RP-HPLC to afford a white solid. $^1$H NMR (DMSO-d6, 300 MHz): δ 8.54 (d, J=2.1 Hz, 1H), 8.10 (t, J=5.1 Hz, 1H), 8.00 (d, J=9.9 Hz, 1H), 7.88 (dd, J$_1$=8.7 Hz, J$_1$=2.4 Hz 1H), 7.59 (s, 1H), 7.04 (d, J=9.9 Hz, 1H), 6.59 (d, J=8.7 Hz, 1H), 4.67 (s, 2H), 3.16-3.07 (m, 2H), 2.47 (s, 1H), 2.10 (s, 6H), 1.04 (t, J=7.2 Hz, 3H); LC/MS R$_t$=0.848 min; MS m/z: 340 [M+H]$^+$ The following compounds were synthesized following Example 8:

| Cmpd No. | Structure | Name | NMR/MS |
|---|---|---|---|
| 71 | 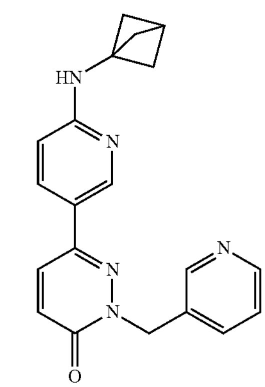 [SMILES: O=c1ccc(-c2ccc(NC34CC(C3)C4)nc2)nn1Cc1cccnc1] | 6-(6-(bicyclo[1.1.1]pentan-1-ylamino)pyridazi-3-yl)-2-(pyridazi-3-ylmethyl)pyridazine-3(2H)-one | $^1$H NMR (300 MHz, Methanol-d$_4$) δ 8.68 (s, 1H), 8.51-8.49 (m, 2H), 8.02-7.94 (m, 3H), 7.47-7.43 (m, 1H), 7.07 (d, J = 9.9 Hz, 1H), 6.73 (d, J = 9.0 Hz, 1H), 5.46 (s, 2H), 2.50 (s, 1H), 2.18 (s, 6H); LC/MS Rt = 0.732 min; MS m/z: 346 [M + H]$^+$ |
| 64 | 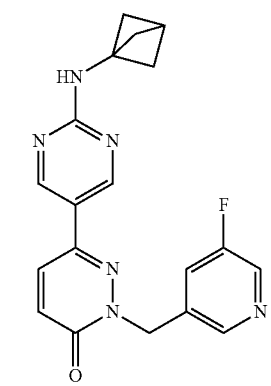 [SMILES: O=c1ccc(-c2cnc(NC34CC(C3)C4)nc2)nn1Cc1cncc(F)c1] | 6-(2-(bicyclo[1.1.1]pentan-1-ylamino)pyrimidin-5-yl)-2-((5-fluoropyridin-3-yl)methyl)pyridazine-3(2H)-one | $^1$H NMR (300 MHz, DMSO-d6) δ 8.81 (s, 2H), 8.54-8.52 (m, 2H), 8.30 (s, 1H), 8.02 (d, J = 9.9 Hz, 1H), 7.77-7.72 (m, 1H), 7.08 (d, J = 9.9 Hz, 1H), 5.36 (s, 2H), 2.46 (s, 1H), 2.09 (s, 6H); LC/MS Rt = 1.556 min; MS m/z: 365 [M + H]$^+$ |

| Cmpd No. | Structure | Name | NMR/MS |
|---|---|---|---|
| 97 | 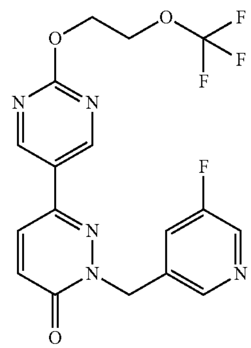 [SMILES: O=c1ccc(-c2cnc(OCCOC(F)(F)F)nc2)nn1Cc1cncc(F)c1] | 2-((5-fluoropyridin-3-yl)methyl)-6-(2-(2-(trifluoromethoxy)ethoxy)pyrimidin-5-yl)pyridazine-3(2H)-one | $^1$H NMR (300 MHz, DMSO-d6) δ 9.12 (s, 2H), 8.54 (d, J = 2.4 Hz, 2H), 8.13 (d, J = 9.9 Hz, 1H), 7.83-7.73 (m, 1H), 7.17 (d, J = 9.9 Hz, 1H), 5.40 (s, 2H), 4.63 (t, J = 3.9 Hz, 2H), 4.52-4.43 (m, 2H); LC/MS Rt = 1.677 min; MS m/z: 412 [M+ H]$^+$ |
| 351 | 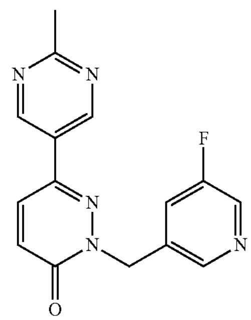 [SMILES: Cc1ncc(-c2ccc(=O)n(Cc3cncc(F)c3)n2)cn1] | 2-((5-((5 -3-yl)methyl)-6-(2-methylpyrimidin-5-yl)pyridazine-3(2H)-one | $^1$H NMR (400 MHz, DMSO-d6) δ 9.18 (s, 2H), 8.55-8.53 (m, 2H), 8.17 (d, J = 10.0 Hz, 1H), 7.79-7.76 (m, 1H), 7.18 (d, J = 9.8 Hz, 1H), 5.42 (s, 2H), 2.68 (s, 3H); LC/MS Rt = 1.082 min; MS m/z: 298 [M + H]$^+$ |
| 102 | 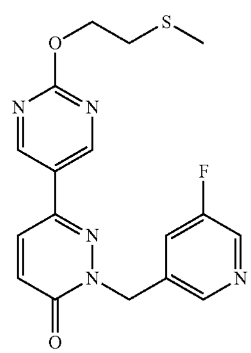 [SMILES: CSCCOc1ncc(-c2ccc(=O)n(Cc3cncc(F)c3)n2)cn1] | 2-(5-((5-fluoropyridin-3-yl)methyl)-6-(2-(2-(methylthio)ethoxy)pyrimidin-5-yl)pyridazine-3(2H)-one | $^1$H NMR (400 MHz, DMSO-d6) δ 9.11 (s, 2H), 8.54 (d, J = 3.2 Hz, 2H), 8.12 (d, J = 10.0 Hz, 1H), 7.98-7.76 (m, 1H), 7.17 (d, J = 9.6 Hz, 1H), 5.40 (s, 2H), 4.54 (t, J = 6.4 Hz 2H), 2.90 (t, J = 6.8 Hz, 2H), 2.16 (s, 3H); LC/MS Rt = 1.424 min; MS m/z: 374 [M + H]$^+$ |
| 103 | 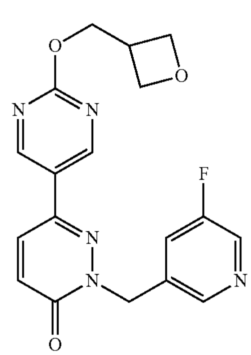 [SMILES: O=c1ccc(-c2cnc(OCC3COC3)nc2)nn1Cc1cncc(F)c1] | 2((5-fluoropyridin-3-yl)methyl)-6-(2-(oxetan-3-ylmethoxy)pyrimidin-5-yl)pyridazine-3(2H)-one | $^1$H NMR (300 MHz, DMSO-d6) δ 9.11 (s, 2H), 8.54 (d, J = 3.0 Hz, 2H), 8.13 (d, J = 9.9 Hz, 1H), 7.78 (dt, J = 9.4, 2.3 Hz, 1H), 7.17 (d, J = 9.9 Hz, 1H), 5.40 (s, 2H), 4.72 (dd, J = 7.8, 6.1 Hz, 2H), 4.60 (d, J = 6.9 Hz, 2H), 4.45 (t, J = 6.0 Hz, 2H), 3.49-3.39 (m, 1H); LC/MS Rt = 1.021 min; MS m/z: 370.3 [M + H]$^+$ |

-continued

| Cmpd No. | Structure | Name | NMR/MS |
|---|---|---|---|
| 104 | 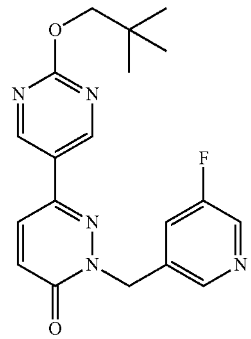 [SMILES: CC(C)(C)COc1ncc(-c2ccc(=O)n(Cc3cncc(F)c3)n2)cn1] | 2((5-fluoropyridin-3-yl)methyl)-6-(2-(neopentyloxy)pyrimidin-5-yl)pyridazine-3(2H)-one | ¹H NMR (400 MHz, DMSO-d6) δ 9.08 (s, 2H), 8.57-8.50 (m, 2H), 8.13 (d, J = 9.7 Hz, 1H), 7.79-7.75 (m, 1H), 7.17 (d, J = 9.6 Hz, 1H), 5.41 (s, H), 4.08 (s, 2H), 1.02 (s, 9H); LC/MS Rt = 1.721 min; MS m/z: 370 [M + H]⁺ |
| 121 | 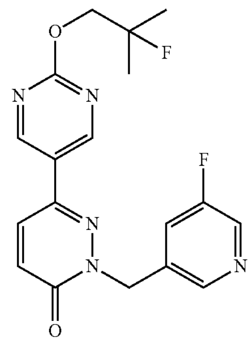 | 6-(2-(2-fluoro-2-methylpropoxy)pyrimidin-5-yl)-2-((5-fluoropyridin-3-yl)methyl)pyridazine-3(2H)-one | ¹H NMR (300 MHz, DMSO-d6) δ 9.11 (s, 2H), 8.54 (d, J = 3.0 Hz, 2H), 8.13 (d, J = 6.6 Hz, 1H), 7.80-7.76 (m, 1H), 7.17 (d, J = 6.6 Hz, 1H), 5.41 (s, 2H), 4.47, 4.40 (d, J = 41.4 Hz, 2H), 1.48 (s, 3H), 1.41 (s, 3H); LC/MS Rt = 0.985 min; MS m/z: 374 [M + H]⁺ |

Example 9: 2-((5-fluoropyridin-3-yl)methyl)-6-(2-(2-methoxyethoxy)pyrimidin-5-yl)pyridazine-3(2H)-one (Compound 70)

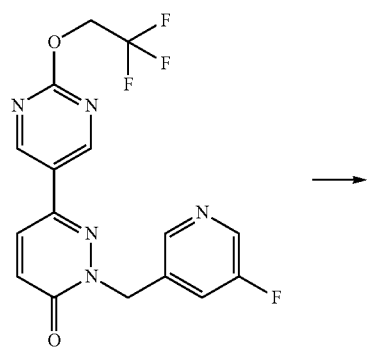

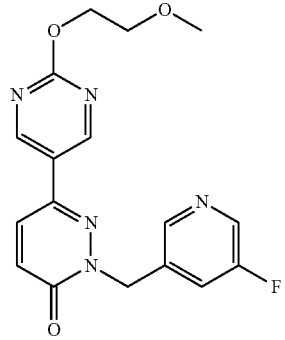

Step 1: 2-((5-fluoropyridin-3-yl)methyl)-6-(2-(2-methoxyethoxy)pyrimidin-5-yl)pyridazin-3(2H)-one To a stirred mixture of 2-((5-fluoropyridin-3-yl)methyl)-6-(2-(2,2,2-trifluoroethoxy)pyrimidin-5-yl)pyridazine-3 (2H)-one (100.00 mg, 0.272 mmol, 1.00 equiv) in 2-methoxy-ethanol (1 mL) was added K₂CO₃ (112.89 mg, 0.817 mmol, 3 equiv) in portions, the solution was stirred at 70° C. for 2 h. The resulting mixture was concentrated under reduced pressure. The crude product (120 mg) was purified by Prep-HPLC to afford the title compound as a white solid (35 mg, 35.97%). ¹H NMR (DMSO-d₆, 400 MHz) δ 9.10 (s, 2H), 8.54 (d, J=2.4 Hz, 2H), 8.12 (d, J=10.0 Hz, 1H), 7.82-7.74 (m, 1H), 7.16 (d, J=9.6 Hz, 1H), 5.40 (s, 2H), 4.52-4.45 (m, 2H), 3.73-3.66 (m, 2H), 3.31 (s, 3H). LC/MS: Rt=0.810 min, MS m/z: 358 [M+H]⁺.

The following compounds were synthesized following Example 9:

| Cmpd No. | Structure | Name | NMR/MS |
|---|---|---|---|
| 67 | 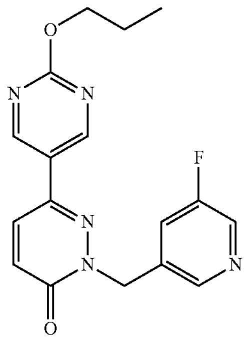 | 2-((5-fluoropyridin-3-yl)methyl)-6-(2-propoxypyrimidin-5-yl)pyridazine-3(2H)-one | $^1$H NMR (400 MHz, DMSO-d6) δ 9.09 (s, 2H), 8.55-8.54 (m, 2H), 8.12 (d, J = 10 Hz, 1H), 7.79-7.76 (m, 1H), 7.17 (d, J = 9.6 Hz, 1H), 5.40 (s, 2H), 4.33 (t, J = 6.4 Hz, 2H), 1.80-1.75 (m, 2H), 0.99 (t, J = 7.2 Hz, 3H); MS m/z: 328 [M + H]$^+$ |
| 68 | 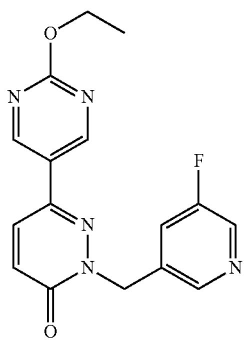 [SMILES: CCOc1ncc(-c2ccc(=O)n(Cc3cncc(F)c3)n2)cn1] | 6-(2-ethoxypyrimidin-5-yl)-2-((5-fluoropyridin-3-yl)methyl)pyridazine-3(2H)-one | $^1$H NMR (300 MHz, DMSO-d$_6$) δ 9.09 (s, 2H), 8.54 (d, J = 2.4 Hz, 2H), 8.11 (d, J = 9.9 Hz, 1H), 7.80-7.75 (m, 1H), 7.16 (d, J = 9.9 Hz, 1H), 5.40 (s, 2H), 4.42 (q, J = 6.9, 7.2 Hz, 2H), 1.36 (t, J = 6.9 Hz, 3H); LC/MS Rt = 0.850 min; MS m/z: 328 [M + H]$^+$ |
| 69 | 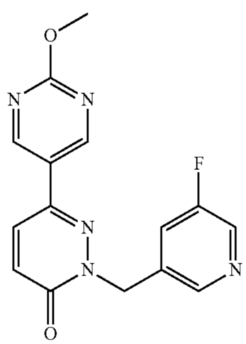 [SMILES: COc1ncc(-c2ccc(=O)n(Cc3cncc(F)c3)n2)cn1] | 2-((5-fluoropyridin-3-yl)methyl)-6-(2-methoxypyrimidin-5-yl)pyridazine-3(2H)-one | $^1$HNMR (400 MHz, DMSO-d$_6$) δ 9.05 (s, 2H), 8.49 (d, J = 2.8 Hz, 2H), 8.05 (d, J = 9.6 Hz, 1H), 7.75-7.71 (m, 1H), 7.12 (d, J = 9.6 Hz, 1H), 5.39 (s, 2H), 3.97 (s, 3H); LC/MS Rt = 2.684 min; MS m/z: 314 [M + H]$^+$ |
| 106 | 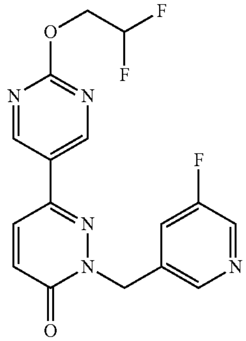 [SMILES: O=c1ccc(-c2cnc(OCC(F)F)nc2)nn1Cc1cncc(F)c1] | 6-(2-(2,2-difluoroethoxy)pyrimidin-5-yl)-2-((5-fluoropyridin-3-yl)methyl)pyridazine-3(2H)-one | $^1$H NMR (DMSO-d6, 400 MHz) δ 9.15 (s, 2H), 8.54 (d, J = 2.4 Hz, 2H), 8.14 (d, J = 9.6 Hz, 1H), 7.83-7.75 (m, 1H), 7.18 (d, J = 9.6 Hz, 1H), 6.45 (t, J = 3.2 Hz, 0H), 5.41 (s, 2H), 4.70 (td, J = 15.2, 3.6 Hz, 2H); LC/MS Rt = 1.228 min; MS m/z: 364 [M + H]+ |

| Cmpd No. | Structure | Name | NMR/MS |
|---|---|---|---|
| 108 | 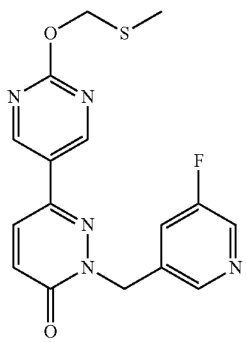 [SMILES: CSCOc1ncc(-c2ccc(=O)n(Cc3cncc(F)c3)n2)cn1] | 2-((5-fluoropyridin-3-yl)methyl)-6-(2-((methylthio)methoxy)pyrimidin-5-yl)pyridazine-3(2H)-one | ¹H NMR (300 MHz, DMSO-d6) δ 9.14 (s, 2H), 8.54 (d, J = 2.7 Hz, 2H), 8.13 (d, J = 9.9 Hz, 1H), 7.79 (d, J = 9.6 Hz, 1H), 7.17 (d, J = 9.6 Hz, 1H), 5.58 (s, 2H), 5.40 (s, 2H), 2.27 (s, 3H); LC/MS Rt = 5.971 min; MS m/z: 360 [M + H]+ |
| 110 | 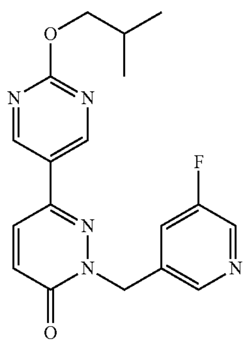 [SMILES: CC(C)COc1ncc(-c2ccc(=O)n(Cc3cncc(F)c3)n2)cn1] | 2-((5-fluoropyridin-3-yl)methyl)-6-(2-isobutoxypyrimidin-5-yl)pyridazine-3(2H)-one | ¹H NMR (300 MHz, DMSO-d6) δ 9.09 (s, 2H), 8.55-8.53 (m, 2H), 8.12 (d, J = 9.9 Hz, 1H), 7.80-7.76 (m, 1H), 7.17 (d, J = 9.6 Hz, 1H), 5.40 (s, 2H), 4.16 (d, J = 6.9 Hz, 2H), 2.12-2.03 (m, 1H), 0.99 (d, J = 6.6 Hz, 6H); LC/MS Rt = 1.317 min; MS m/z: 356 [M + H]+ |
| 113 | 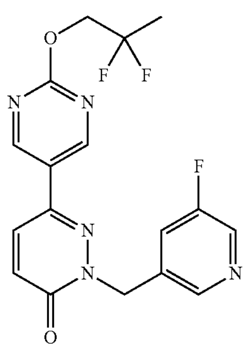 [SMILES: CC(F)(F)COc1ncc(-c2ccc(=O)n(Cc3cncc(F)c3)n2)cn1] | 6-(2-(2,2-difluoropropoxy)pyrimidin-5-yl)-2-((5-fluoropyridin-3-yl)methyl)pyridazine-3(2H)-one | ¹H NMR (DMSO-d6, 300 MHz) δ 9.15 (s, 2H), 8.54 (d, J = 2.4 Hz, 2H), 8.15 (d, J = 9.9 Hz, 1H), 7.84-7.73 (m, 1H), 7.18 (d, J = 9.9 Hz, 1H), 5.41 (s, 2H), 4.69 (t, J = 13.2Hz, 2H), 1.83-1.70 (t, J = 19.5 Hz, 3H); LC/MS Rt = 1.271 min; MS m/z: 378 [M +H]+ |
| 115 | 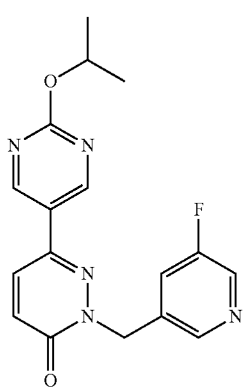 [SMILES: CC(C)Oc1ncc(-c2ccc(=O)n(Cc3cncc(F)c3)n2)cn1] | 2-((5-fluoropyridin-3-yl)methyl)-6-(2-isopropoxypyrimidin-5-yl)pyridazine-3(2H)-one | ¹H NMR (DMSO-d6, 300 MHz) δ 9.08 (s, 2H), 8.54 (d, J = 3.3 Hz, 2H), 8.11 (d, J = 9.9 Hz, 1H), 7.78 (m, 1H), 7.16 (d, J = 9.6 Hz, 1H), 5.40 (s, 2H), 5.27 (m, 1H), 1.36 (s, 3H), 1.34 (s, 3H); LC/MS Rt = 1.318 min; MS m/z: 342 [M + H]+ |

-continued

| Cmpd No. | Structure | Name | NMR/MS |
|---|---|---|---|
| 117 | 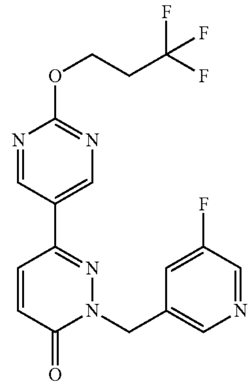 [SMILES: O=c1ccc(-c2cnc(OCCC(F)(F)F)nc2)nn1Cc1cncc(F)c1] | 2-((5-fluoropyridin-3-yl)methyl)-6-(2-(3,3,3-trifluoropropoxy)pyrimidin-5-yl)pyridazine-3(2H)-one | 1H NMR (300 MHz, DMSO-d6) δ 9.13 (s, 2H), 8.54 (d, J = 3.0 Hz, 2H), 8.13 (d, J = 9.6 Hz, 1H), 7.81-7.76 (m, 1H), 7.17 (d, J = 9.9 Hz, 1H), 5.40 (s, 2H), 4.60 (t, J = 6.0 Hz, 2H), 2.95-2.73 (m, 2H); LC/MS Rt = 1.315 min; MS m/z: 396 [M + H]+ |
| 119 | 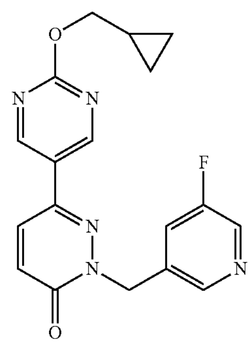 [SMILES: O=c1ccc(-c2cnc(OCC3CC3)nc2)nn1Cc1cncc(F)c1] | 6-(2-(cyclopropylmethoxy)pyrimidin-5-yl)-2-((5-fluoropyridin-3-yl)methyl)pyridazine-3(2H)-one | 1H NMR (300 MHz, DMSO-d6) δ 9.09 (s, 2H), 8.54 (d, J = 2.7 Hz, 2H), 8.12 (d, J = 9.6 Hz, 1H), 7.80-7.77 (m, 1H), 7.17 (d, J = 9.9 Hz, 1H), 5.40 (s, 2H), 4.21 (d, J = 7.5 Hz, 2H), 1.34-1.25 (m, 1H), 0.64-0.52 (m, 2H), 0.43-0.32 (m, 2H); LC/MS Rt = 1.280 min; MS m/z: 354 [M + H]+ |
| 120 | 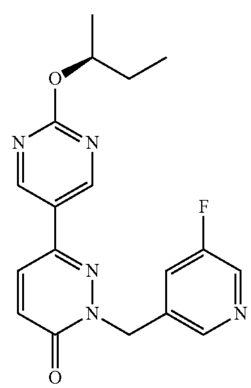 [SMILES: CC[C@H](C)Oc1ncc(-c2ccc(=O)n(Cc3cncc(F)c3)n2)cn1] | (S)-6-(2-(sec-butoxy)pyrimidin-5-yl)-2-((5-fluropyridin-3-yl)methyl)pyridazine-3(2H)-one | 1H NMR (400 MHz, DMSO-d6) δ 9.07 (s, 2H), 8.11 (d, J = 10.0 Hz, 1H), 2H), 8.54 (d, J = 2.8 Hz, 7.77 (d, J = 9.6 Hz, 1H), 7.16 (d, J = 9.6 Hz, 1H), 5.39 (s, 2H), 5.15-5.07 (m, 1H), 1.77-1.62 (m, 2H), 1.31 (d, J = 6.0 Hz, 3H), 0.92 (t, J = 7.2 Hz, 3H); LC/MS Rt = 1.674 min; MS m/z: 356 [M + H]+ |

Example 10: 2-((5-(methylthio)pyridazi-3-yl)methyl)-6-(2-(2,2,2-trifluoroethoxy)pyrimidin-5-yl)pyridazine-3(2H)-one (Compound 111)

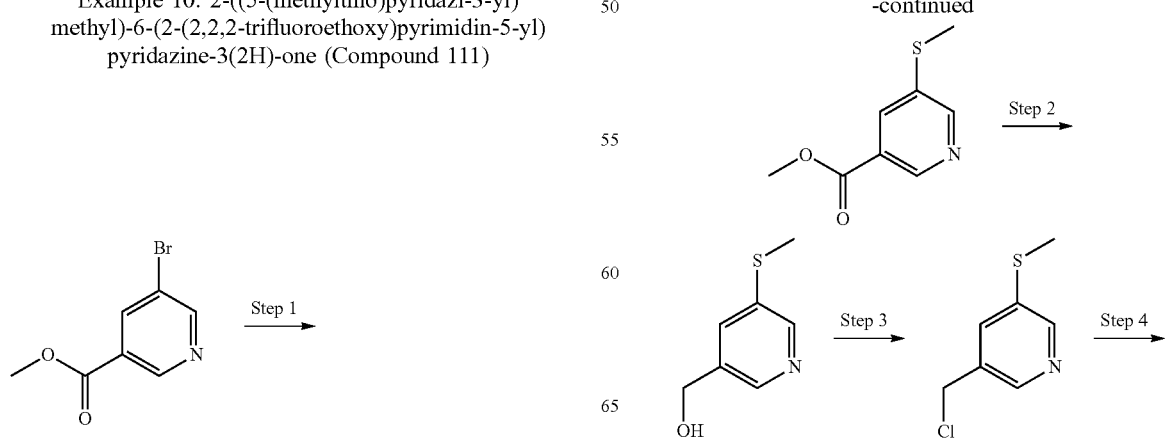

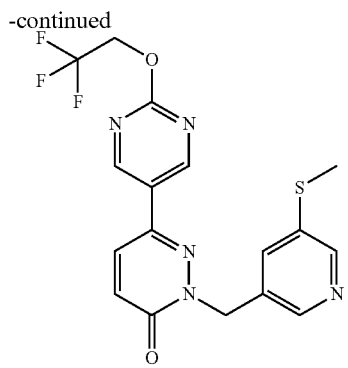

Step 1: methyl 5-(methylthio)nicotinate

A solution/mixture of methyl 5-bromopyridine-3-carboxylate (216.00 mg, 1.000 mmol, 1.00 equiv) and sodium thiomethoxide (70.08 mg, 1.000 mmol, 1.00 equiv) in DMF was stirred for overnight at 80 degrees C. under nitrogen atmosphere. The reaction was monitored by LCMS. The mixture was allowed to cool down to room temperature. The reaction was quenched with Water at 0 degrees C. The resulting mixture was extracted with EtOAc. The combined organic layers were washed with water, dried over anhydrous Na₂SO₄. After filtration, the filtrate was concentrated under reduced pressure. The residue was purified by silica gel column chromatography, eluted with PE/EtOAc to afford methyl 5-(methylthio)nicotinate (150 mg, 81.88%) as a solid.

Step 2: (5-(methylthio)pyridazi-3-yl)methanol

Under N₂ atmosphere, to a solution of methyl 5-(methylthio)nicotinate (150 mg, 0.82 mmol) in THF (3 mL) was added LAH (63 mg, 1.64 mmol) in several batches at 0° C. The resulting mixture was stirred for 1.5 h at 25° C. The reaction was then quenched by the addition of 4 mL of water and 10 mL of EA was added to mixture. The organic phase was separated, dried over Na₂SO₄, filtered and concentrated to give a residue, which was purified by silica gel chromatography to give the title compound as a solid (100 mg, 78.7%).

Step 3: 3-(chloromethyl)-5-(methylthio)pyridine

A solution of (5-(methylthio)pyridazi-3-yl)methanol (100 mg, 0.64 mmol) and SOCl₂ (152 mg, 1.29 mmol, 2.00 equiv) in DCM was stirred for overnight at room temperature under nitrogen atmosphere. The reaction was monitored by LCMS. Desired product could be detected by LCMS. The mixture was concentrated under vacuum and the crude product was used in next step without further purification.

Step 4: 2-((5-(methylthio)pyridazi-3-yl)methyl)-6-(2-(2,2,2-trifluoroethoxy)pyrimidin-5-yl)pyridazine-3(2H)-one To a stirred solution of 6-[2-[(3-fluorooxetan-3-yl)methoxy]pyrimidin-5-yl]-2,3-dihydro-pyridazin-3-one (174 mg, 0.64 mmol) and 3-(chloromethyl)-5-(methylthio)pyridine (111 mg, 0.64 mmol) in DMF (2 mL) were added K₂CO₃ (177 mg, 1.28 mmol, 2 equiv.) in portions. The reaction was stirred at 25° C. for 2 h. The resulting mixture was extracted with EtOAc and water. The combined organic layers were washed with brine, dried over anhydrous Na₂SO₄. After filtration, the filtrate was concentrated under reduced pressure. The residue was purified by Prep-HPLC to afford the title compound as a white solid (45 mg, 17.2%). ¹HNMR (300 MHz, Methanol-d₄) δ 9.14 (s, 2H), 8.41 (dd, J=12.9, 2.1 Hz, 2H), 8.06 (d, J=9.6 Hz, 1H), 7.87 (t, J=2.1 Hz, 1H), 7.16 (d, J=9.9 Hz, 1H), 5.47 (s, 2H), 5.04 (q, J=8.7 Hz, 2H), 2.55 (s, 3H). LC/MS Rt=2.406 min; MS m/z: 410 [M+H]⁺.

Example 11: 2-((3-methylisoxazol-5-yl)methyl)-6-(2-(methylthio)pyrimidin-5-yl)pyridazine-3(2H)-one (Compound 65)

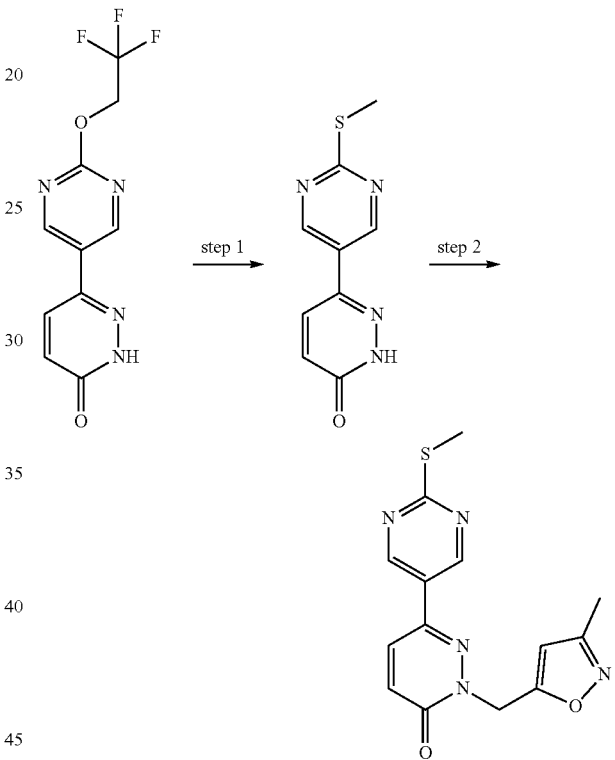

Step 1: 6-(2-(methylthio)pyrimidin-5-yl)pyridazine-3(2H)-one

A solution/mixture of 6-[2-(2,2,2-trifluoroethoxy)pyrimidin-5-yl]-2H-pyridazin-3-one (300.00 mg, 1.102 mmol, 1.00 equiv) and (methylsulfanyl)sodium (231.72 mg, 3.307 mmol, 3.00 equiv) in DMF (3.00 mL) was stirred for 1 h at 70° C. The reaction was quenched with sat. NH₄Cl (aq.) at 25° C. The resulting mixture was diluted with EtOAc (50 mL). The resulting mixture was washed with 5×10 mL of water. The residue was purified by reverse flash chromatography with the following conditions: column, C18 silica gel; mobile phase, MeOH in water, 10% to 50% gradient in 10 min; detector, UV 254 nm. The residue was purified by silica gel column chromatography, eluted with PE/EtOAc (1:1) to afford 6-[2-(methylsulfanyl)pyrimidin-5-yl]-2H-pyridazin-3-one (280 mg, 115.34%) as a white solid. MS m/z: 221 [M+H]⁺

Step 2: 2-((3-methylisoxazol-5-yl)methyl)-6-(2-(methylthio)pyrimidin-5-yl)pyridazine-3(2H)-one A mixture of 6-[2-(methylsulfanyl)pyrimidin-5-yl]-2H-pyridazin-3-one (200.00 mg, 0.908 mmol, 1.00 equiv), 5-(bromomethyl)-3-methyl-1,2-oxazole (191.80 mg, 1.090 mmol, 1.20 equiv) and K$_2$CO$_3$ (376.50 mg, 2.724 mmol, 3.00 equiv) in DMF (2.00 mL) was stirred for 2 h at 25° C. The resulting mixture was diluted with EtOAc (50 mL) and washed with 2×10 mL of water. The residue was purified by reverse flash chromatography with the following conditions: column, C18 silica gel; mobile phase, MeOH in water, 10% to 50% gradient in 10 min; detector, UV 254 nm. To afford 2-[(3-methyl-1,2-oxazol-5-yl)methyl]-6-[2-(methylsulfanyl)pyrimidin-5-yl]pyridazine-3-one (52.3 mg, 17.70%) as a white solid. $^1$H NMR (400 MHz, DMSO-d$_6$) δ 9.09 (s, 2H), 8.15 (d, J=9.6 Hz, 1H), 7.21-7.19 (m, 1H), 6.39 (s, 1H), 5.46 (s, 2H), 2.58 (s, 3H), 2.21 (s, 3H). LC/MS Rt=1.219 min; MS m/z: 316 [M+H]$^+$.

The following compounds were synthesized following Example 11:

| Cmpd No. | Structure | Name | NMR/MS |
|---|---|---|---|
| 66 | 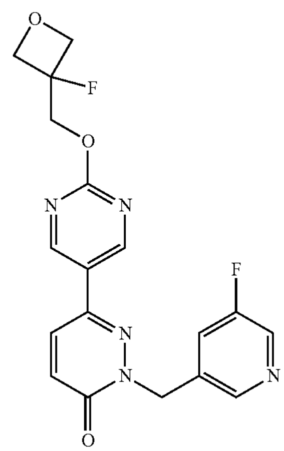 [SMILES: O=c1ccc(-c2cnc(OCC3(F)COC3)nc2)nn1Cc1cncc(F)c1] | 6-(2-((3-fluorooxetan-3-yl)methoxy)pyrimidin-5-yl)-2-((5-fluoropyridin-3-yl)methyl)pyridazine-3(2H)-one | $^1$H NMR (DMSO-d$_6$, 400 MHz,) δ 9.13 (s, 2H), 8.54 (d, J = 2.8 Hz, 2H), 8.14 (d, J = 9.6 Hz, 1H), 7.78 (dd, J = 9.6, 2.8Hz, 1H), 7.17 (d, J = 9.6 Hz, 1H), 5.41 (s, 2H), 4.87 (s, 1H), 4.81 (s, 1H), 4.77 (s, 2H).,4.72 (s, 2H); LC/MS R = 0.929 min, MS m/z: 388 [M + H]$^+$ |
| 101 | 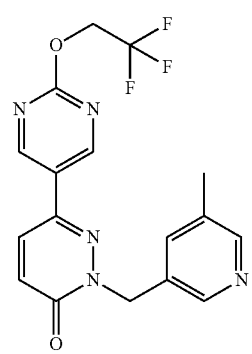 [SMILES: Cc1cncc(Cn2nc(-c3cnc(OCC(F)(F)F)nc3)ccc2=O)c1] | 2-((5-methylpyridin-3-yl)methyl)-6-(2-(2,2,2-trifluoroethoxy)pyrimidin-5-yl)pyridazine-3(2H)-one | $^1$H NMR (DMSO-d$_6$, 300 MHz) δ 9.17 (s, 2H), 8.46 (d, J = 3.0 Hz, 1H), 8.35 (d, J = 3.0 Hz, 1H), 8.14 (d, J = 9.6 Hz, 1H), 7.63 (t, J = 2.4 Hz, 1H), 7.17 (d, J = 9.6 Hz, 1H), 5.33 (s, 2H), 5.12 (m, 2H), 2.28 (s, 3H); LC/MS Rt = 0.734 min; MS m/z: 378 [M + H]$^+$ |

Example 12: 2-((2-ethylthiazol-5-yl)methyl)-6-(2-(2,2,2-trifluoroethoxy)pyrimidin-5-yl)pyridazine-3(2H)-one (Compound 99) and 2-((2-ethylthiazol-5-yl)methyl)-6-(2-propoxypyrimidin-5-yl)pyridazine-3(2H)-one (Compound 112)

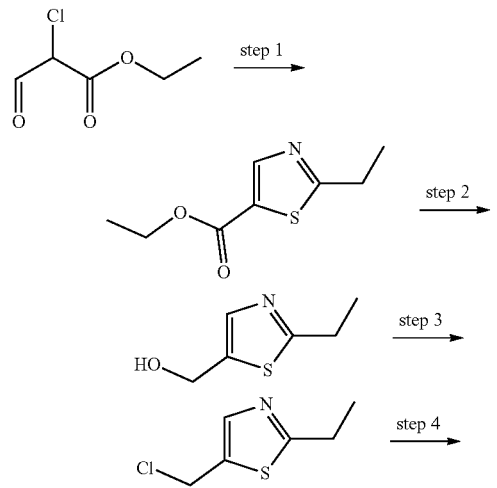

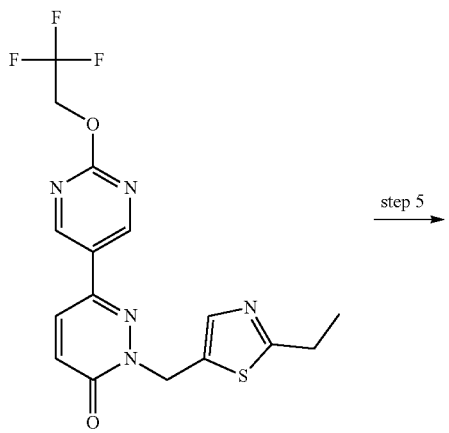

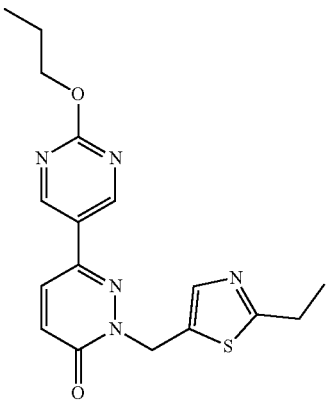

Step 1: ethyl 2-ethylthiazole-5-carboxylate

Into a 100-mL round-bottom flask, were placed ethyl 2-chloro-3-oxopropanoate (2.00 g, 13.284 mmol, 1.00 equiv), EtOH (20.00 mL), propanethioamide (1184.38 mg, 13.284 mmol, 1.00 equiv) and $MgSO_4$ (7994.69 mg, 66.419 mmol, 5.00 equiv). The resulting solution was stirred for 16 hr at 80° C. The mixture was cooled to 25° C. and filtered over celite, the filtrate was concentrated under vacuum, the residue was applied onto a silica gel column with ethyl acetate/petroleum ether (1:1) to afford 1 g (40.64%) of ethyl 2-ethyl-1,3-thiazole-5-carboxylate as a light yellow oil. MS m/z: 186 $[M+H]^+$

Step 2: (2-ethylthiazol-5-yl)methanol

To a solution of ethyl 2-ethyl-1,3-thiazole-5-carboxylate (20.00 g, 107.968 mmol, 1.00 equiv) in THF (300.00 mL) at 0° C. was added $LiAlH_4$ (4.10 g, 107.968 mmol, 1.00 equiv) partwise, the mixture was stirred at 0° C. for 1 h, 4 g of $Na_2SO_4 10H_2O$ was added partwise and then 2 g of $Na_2SO_4$ was added, the mixture was stirred for 30 mins and filtered through celite, the filtrate was concentrated under vacuum to get crude product 15 g (97.02%) as light yellow oil. MS m/z: 144 $[M+H]^+$

Step 3: 5-(chloromethyl)-2-ethylthiazole

To a solution of (2-ethyl-1,3-thiazol-5-yl)methanol (10.00 g, 69.832 mmol, 1.00 equiv) in DCM (100.00 mL) was added dropwise $SOCl_2$ (10.13 mL, 85.161 mmol, 2.00 equiv) at 0° C., the mixture was stirred for 1 h. The mixture was concentrated under vacuum and the residue was dissolved in 100 mL water and adjust PH=8 with saturated $Na_2CO_3$ solution, then extracted with 3×100 mL of EA, the organic layer was dried over $Na_2SO_4$ and concentrated under vacuum to get crude product which was purified by silica gel column to get light yellow oil 6 g (53.15%). MS m/z: 162 $[M+H]^+$

Step 4: 2-((2-ethylthiazol-5-yl)methyl)-6-(2-(2,2,2-trifluoroethoxy)pyrimidin-5-yl)pyridazine-3(2H)-one Into a 250-mL round-bottom flask, was placed 6-[2-(2,2,2-trifluoroethoxy)pyrimidin-5-yl]-2H-pyridazin-3-one (10.00 g, 36.739 mmol, 1.00 equiv), DMF (100.00 mL), 5-(chloromethyl)-2-ethyl-1,3-thiazole (7126.72 mg, 44.087 mmol, 1.20 equiv), $K_2CO_3$ (15232.78 mg, 110.218 mmol, 3.00 equiv). The resulting solution was stirred for 1 hr at 50° C. The residue was applied onto a silica gel column with ethyl acetate/petroleum ether (1:1). The collected fractions were combined and concentrated under vacuum to get product which was purified by Combiflash (Reversed phase: 0.05% ammonia/I) to afford 5.1 g (34.93%) of 2-[(2-ethyl-1,3-thiazol-5-yl)methyl]-6-[2-(2,2,2-trifluoroethoxy)pyrimidin-5-yl]pyridazine-3-one as a white solid. $^1H$ NMR (400 MHz, DMSO-$d_6$): δ 9.16 (s, 2H), 8.12 (d, J=9.6 Hz, 1H), 7.75 (s, 1H), 7.17 (d, J=9.6 Hz, 1H), 5.48 (s, 2H), 5.12 (q, J=8.8 Hz, 2H), 2.92 (q, J=7.6 Hz, 2H), 1.24 (t, J=7.6 Hz, 3H). LC/MS Rt=1.873 min; MS m/z: 398 $[M+H]^+$.

Step 5: 2-((2-ethylthiazol-5-yl)methyl)-6-(2-propoxypyrimidin-5-yl)pyridazine-3(2H)-one To a stirred solution of 2-[(2-ethyl-1,3-thiazol-5-yl)methyl]-6-[2-(2,2,2-trifluoroethoxy)pyrimidin-5-yl]pyridazine-3-one (100.00 mg, 0.252 mmol, 1.00 equiv) in DMF was added K₂CO₃ (104.34 mg, 0.755 mmol, 3.00 equiv) in portions at 25° C. under nitrogen atmosphere. To the above mixture was added propanol (302.46 mg, 5.033 mmol, 20.00 equiv) in portions at 25° C. The resulting mixture was stirred for additional 4 h at 25° C. The resulting mixture was concentrated under vacuum. The residue was purified by silica gel column chromatography, eluted with hexane/EtOAc (1:1) to afford 2-[(2-ethyl-1,3-thiazol-5-yl)methyl]-6-(2-propoxypyrimidin-5-yl)pyridazine-3-one (13.2 mg, 14.46%) as a light yellow solid. ¹H NMR (DMSO-d₆, 300 MHz) δ 9.08 (s, 2H), 8.10 (d, J=9.6 Hz, 1H), 7.75 (s, 1H), 7.16 (d, J=9.6 Hz, 1H), 5.48 (s, 2H), 4.33 (t, J=6.9 Hz, 2H), 2.93 (q, J=7.5 Hz, 2H), 1.812-1.742 (m, 2H), 1.25 (t, J=7.5 Hz, 3H), 0.99 (t, J=7.5 Hz, 3H). LC/MS Rt=1.349 min; MS m/z: 358 [M+H]⁺.

The following compounds were synthesized following Example 12:

| Cmpd No. | Structure | Name | NMR |
|---|---|---|---|
| 105 | 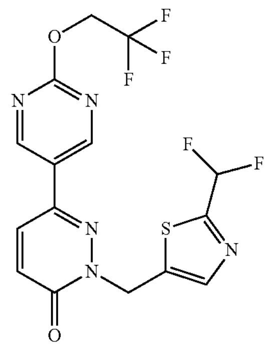 [SMILES: O=c1ccc(-c2cnc(OCC(F)(F)F)nc2)nn1Cc1cnc(C(F)F)s1] | 2-((2-(difluoromethyphthiazol-5-yl)methyl)-6-(2-(2,2,2-trifluoroethoxy)pyrimidin-5-yl)pyridazine-3(2H)-one | ¹H NMR (DMSO-d₆, 400 MHz) δ 9.18 (s, 2H), 8.16 (d, J = 9.6 Hz, 2H), 7.21 (d, J = 10.0 Hz, 1H), 7.44, 7.30, 7.17 (t, J = 54 Hz, 1H), 5.62 (s, 2H), 5.13 (q, J = 8.8 Hz, 2H); LC/MS Rt = 1.653 min; MS m/z: 420 [M + H]⁺] |
| 100 | 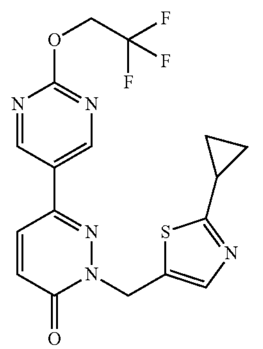 [SMILES: O=c1ccc(-c2cnc(OCC(F)(F)F)nc2)nn1Cc1cnc(C2CC2)s1] | 2-((2-cyclopropylthiazol-5-yl)methyl)-6-(2-(2,2,2-trifluoroethoxy)pyrimidin-5-yl)pyridazine-3(2H)-one | ¹H NMR (DMSO-d₆, 300 MHz) δ 9.17 (s, 2H), 8.13 (d, J = 9.9 Hz, 1H), 7.68 (s, 1H), 7.18 (d, J = 9.9 Hz, 1H), 5.45 (s, 2H), 5.13 (q, J = 9.0 Hz, 2H), 2.39-2.30 (m, 1H), 1.10-1.01 (m, 2H), 0.94-0.89 (m, 2H); LC/MS Rt = 1.370 min; MS m/z: 410 [M + H]⁺ |
| 116 | 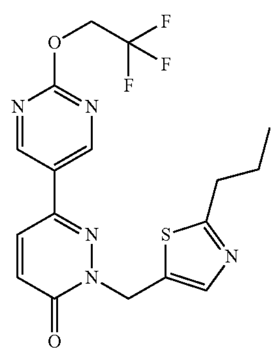 [SMILES: CCCc1ncc(Cn2nc(-c3cnc(OCC(F)(F)F)nc3)ccc2=O)s1] | 2-((2-propylthiazol-5-yl)methyl)-6-(2-(2,2,2-trifluoroethoxy)pyrimidin-5-yl)pyridazine-3(2H)-one | ¹H NMR (DMSO-d₆, 300 MHz) δ 9.17 (s, 2H), 8.13 (d, J = 9.6 Hz, 1H), 7.76 (s, 1H), 7.18 (d, J = 9.9 Hz, 1H), 5.49 (s, 2H), 5.13 (q, J = 9.0 Hz, 2H), 2.88 (t, J = 7.5 Hz, 2H), 1.76-1.63 (m, 2H), 0.92 (t, J = 7.2 Hz, 3H); LC/MS Rt = 1.432 min; MS m/z: 412 [M + H]⁺ |
| 114 | 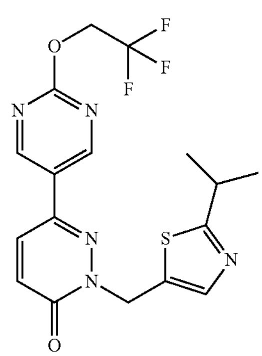 [SMILES: CC(C)c1ncc(Cn2nc(-c3cnc(OCC(F)(F)F)nc3)ccc2=O)s1] | 2-((2-isopropylthiazol-5-yl)methyl)-6-(2-(2,2,2-trifluoroethoxy)pyrimidin-5-yl)pyridazine-3(2H)-one | ¹H NMR (DMSO-d₆, 300 MHz) δ 9.17 (s, 2H), 8.13 (d, J = 9.9 Hz 1H), 7.77 (s, 1H), 7.18 (d, J = 9.6 Hz, 1H), 5.49 (s, 2H), 5.13 (q, J = 9.0 Hz, 2H), 3.29-3.15 (m, 1H), 1.28 (d, J = 6.9 Hz, 6H); LC/MS Rt = 2.462 min; MS m/z 412 [M + H]⁺ |

| Cmpd No. | Structure | Name | NMR |
|---|---|---|---|
| 109 | 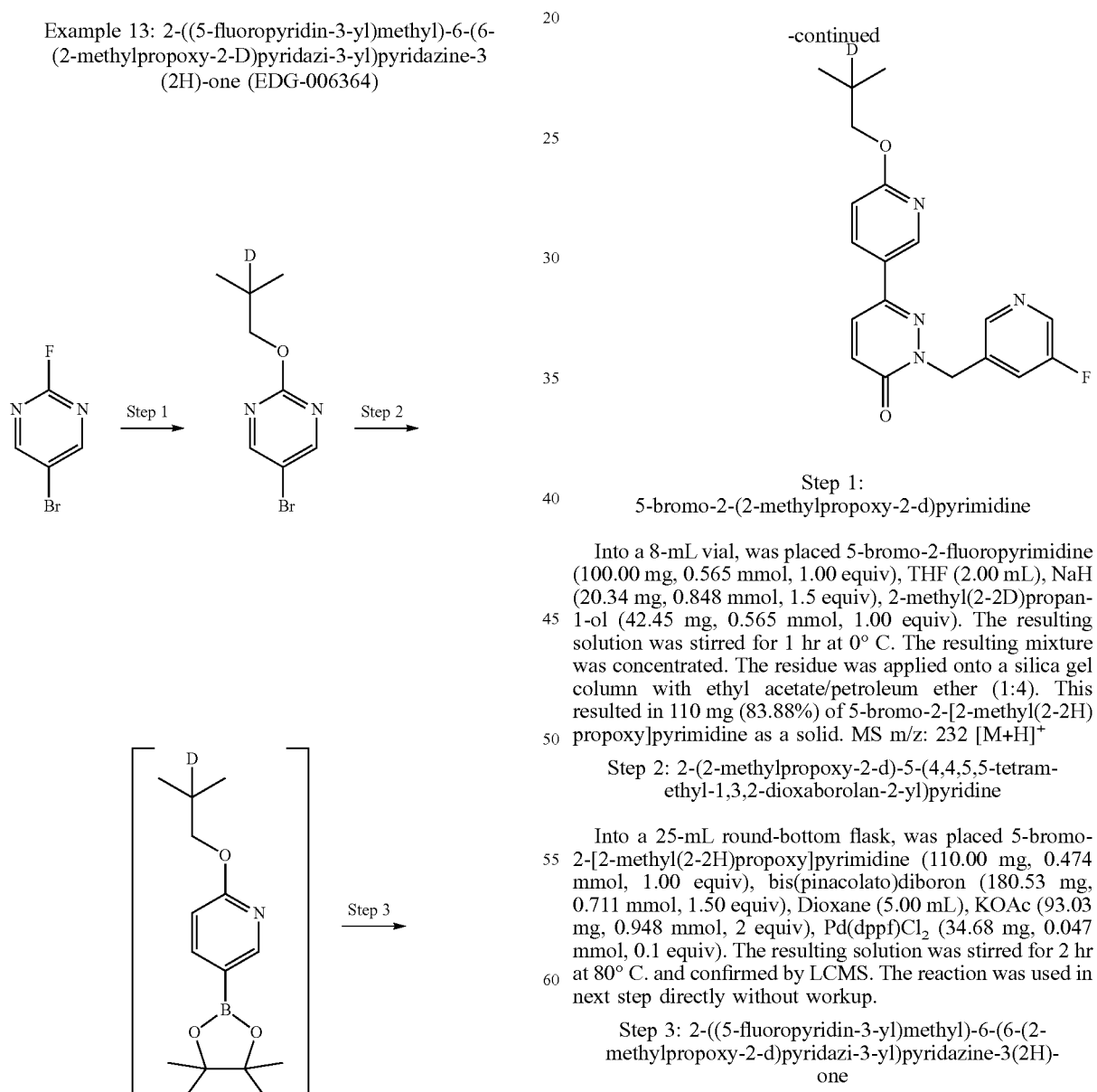 | 2-((2-((methylthio)methyl)thiazol-5-yl)methyl)-6-(2-(2,2,2-trifluoroethoxy)pyrimidin-5-yl)pyridazine-3(2H)-one | $^1$H NMR (DMSO-d$_6$, 300 MHz) δ 9.17 (s, 2H), 8.14 (d, J = 9.6 Hz, 1H), 7.79 (s, 1H), 7.19 (d, J = 9.6 Hz, 1H), 5.51 (s, 2H), 5.13 (q, J = 9.0 Hz, 2H), 4.00 (s, 2H), 2.08 (s, 3H); Rt = 1.458 min; MS m/z: 430 [M + H]$^+$ |

Example 13: 2-((5-fluoropyridin-3-yl)methyl)-6-(6-(2-methylpropoxy-2-D)pyridazi-3-yl)pyridazine-3(2H)-one (EDG-006364)

Step 1: 5-bromo-2-(2-methylpropoxy-2-d)pyrimidine

Into a 8-mL vial, was placed 5-bromo-2-fluoropyrimidine (100.00 mg, 0.565 mmol, 1.00 equiv), THF (2.00 mL), NaH (20.34 mg, 0.848 mmol, 1.5 equiv), 2-methyl(2-2D)propan-1-ol (42.45 mg, 0.565 mmol, 1.00 equiv). The resulting solution was stirred for 1 hr at 0° C. The resulting mixture was concentrated. The residue was applied onto a silica gel column with ethyl acetate/petroleum ether (1:4). This resulted in 110 mg (83.88%) of 5-bromo-2-[2-methyl(2-2H)propoxy]pyrimidine as a solid. MS m/z: 232 [M+H]$^+$

Step 2: 2-(2-methylpropoxy-2-d)-5-(4,4,5,5-tetramethyl-1,3,2-dioxaborolan-2-yl)pyridine Into a 25-mL round-bottom flask, was placed 5-bromo-2-[2-methyl(2-2H)propoxy]pyrimidine (110.00 mg, 0.474 mmol, 1.00 equiv), bis(pinacolato)diboron (180.53 mg, 0.711 mmol, 1.50 equiv), Dioxane (5.00 mL), KOAc (93.03 mg, 0.948 mmol, 2 equiv), Pd(dppf)Cl$_2$ (34.68 mg, 0.047 mmol, 0.1 equiv). The resulting solution was stirred for 2 hr at 80° C. and confirmed by LCMS. The reaction was used in next step directly without workup.

Step 3: 2-((5-fluoropyridin-3-yl)methyl)-6-(6-(2-methylpropoxy-2-d)pyridazi-3-yl)pyridazine-3(2H)-one Into a 8-mL vial, was placed 2-[2-methyl(2-2H)propoxy]pyrimidin-5-ylboronic acid (110.00 mg, 0.558 mmol, 1.00 equiv), 6-chloro-2-[(5-fluoropyridin-3-yl)methyl]pyridazine-3-one (133.79 mg, 0.558 mmol, 1.00 equiv), $K_2CO_3$ (154.33 mg, 1.117 mmol, 2 equiv), Dioxane (3.00 mL), $H_2O$ (0.50 mg), Pd(dppf)Cl$_2$ (40.85 mg, 0.056 mmol, 0.1 equiv). The resulting solution was stirred for 2 hr at 90° C. The resulting mixture was concentrated. The residue was applied onto a silica gel column with dichloromethane/methanol (20:1). This resulted in 100 mg (50.26%) of 2-[(5-fluoropyridin-3-yl)methyl]-6-[2-[2-methyl(2-2H)propoxy]pyrimidin-5-yl]pyridazine-3-one as a white solid. $^1$H NMR (400 MHz, DMSO-d$_6$) δ 9.09 (s, 2H), 8.55-8.53 (m, 2H), 8.12 (d, J=10.0 Hz, 1H), 7.77 (d, J=9.6 Hz, 1H), 7.16 (d, J=10.0 Hz, 1H), 5.40 (s, 2H), 4.15 (s, 2H), 0.98 (s, 6H). LC/MS Rt=1.676 min; MS m/z: 357 [M+H]$^+$ Example 14: 2-((5-fluoropyridin-3-yl)methyl)-6-(2-propoxypyrimidin-5-yl)pyridazine-3(2H)-one (Compound 125)

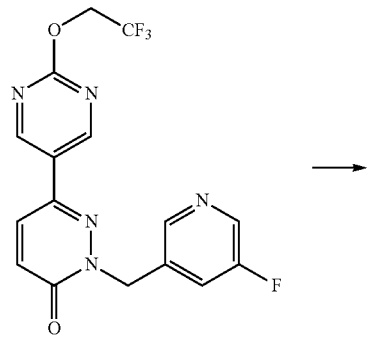

→

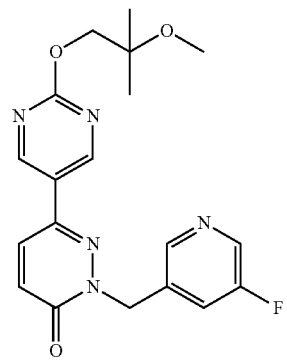

Step 1: N-cyclobutyl-2-[3-[2-(2-methylpropoxy)pyrimidin-5-yl]-6-oxopyridazin-1-yl]acet-amide To a stirred mixture of 2-((5-fluoropyridin-3-yl)methyl)-6-(2-(2,2,2-trifluoroethoxy)pyrimidin-5-yl)pyridazine-3(2H)-one (1.98 g, 5.217 mmol, 1.00 equiv) in 2-methoxy-2-methylpropan-1-ol (20 mL) was added $K_2CO_3$ (1.422 g, 10.435 mmol, 2.00 equiv) in portions, the solution was stirred at 80° C. for 4 h. The resulting mixture was concentrated under reduced pressure. The crude product was purified by Prep-HPLC to afford the title compound as a white solid.

The following compound was synthesized following Example 14:

| Compound No. | Structure | Name | NMR |
| --- | --- | --- | --- |
| 125 | 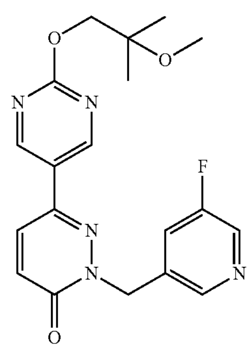 [SMILES: COC(C)(C)COc1ncc(-c2ccc(=O)n(Cc3cncc(F)c3)n2)cn1] | 2-((5-fluoropyridin-3-yl)methyl)-6-(2-(2-methoxy-2-methylpropoxy)pyrimidin-5-yl)pyridazine-3(2H)-one | 1H NMR (400 MHz, DMSO-d6) δ 9.09 (s, 2H), 8.55-8.53 (m, 2H), 8.14 (d, J = 10.0 Hz, 1H), 7.78-7.76 (m, 1H), 7.17 (d, J = 9.6 Hz, 1H), 5.40 (s, 2H), 4.28 (s, 2H), 3.16 (s, 3H), 1.22 (s, 6H); LC/MS Rt = 1.151 min; MS m/z: 386 [M + H]$^+$ |
| 123 | 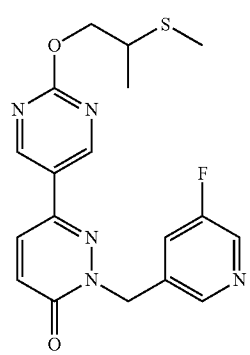 [SMILES: CSC(C)COc1ncc(-c2ccc(=O)n(Cc3cncc(F)c3)n2)cn1] | 2((5-fluoropyridin-3-yl)methyl)-6-(2-(2-(methylthio)propoxy)pyrimidin-5-yl)pyridazine-3(2H)-one | 1H NMR (300 MHz, DMSO-d6) δ 9.08 (s, 2H), 8.56 (s, 1H), 8.45 (d, J = 2.7 Hz, 1H), 8.05 (d, J = 9.9 Hz, 1H), 7.80-7.75 (m, 1H), 7.15 (d, J = 9.6 Hz, 1H), 5.52 (s 2H), 4.65 (dd, J1 = 10.8 Hz, J2 = 5.4 Hz, 1H), 4.37 (dd, J1 = 10.8 Hz, J2 = 7.8 Hz, 1H), 3.13 (m, 2H), 2.2 (s, 3H), 1.38 (d, J = 6.9 Hz, 3H); LC/MS Rt = 1.137 min; MS m/z: 388 [M + H]$^+$ |

| Compound No. | Structure | Name | NMR |
|---|---|---|---|
| 126 | 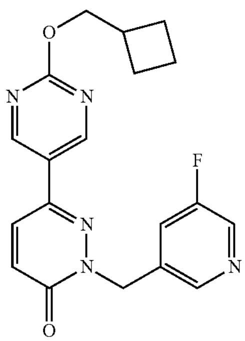 [SMILES: O=c1ccc(-c2cnc(OCC3CCC3)nc2)nn1Cc1cncc(F)c1] | 6-(2-(cyclobutylmethoxy)pyrimidin-5-yl)-2-((5-fluoropyridin-3-yl)methyl)pyridazine-3(2H)-one | 1H NMR (300 MHz, DMSO-d6) δ 9.08 (s, 2H), 8.54-8.53 (m, 2H), 8.15 (d, J = 9.9 Hz, 1H), 7.80-7.76 (m, 1H), 7.16 (d, J = 9.6 Hz, 1H), 5.40 (s, 2H), 4.35 (d, J = 6.9 Hz, 2H), 2.81-2.75 (m, 1H), 2.09-2.04 (m, 2H), 2.03-1.85 (m, 2H); LC/MS Rt = 1.484 min; MS m/z: 368 [M + H]+ |
| 127 | 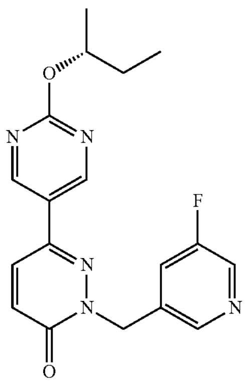 [SMILES: CC[C@@H](C)Oc1ncc(-c2ccc(=O)n(Cc3cncc(F)c3)n2)cn1] | I-6-(2-(sec-butoxy)pyrimidin-5-yl)-2-45-fluoropyridin-3-yl)methyl)pyridazine-3(2H)-one | 1H NMR (300 MHz, DMSO-d6) δ 9.07 (s, 2H), 8.54 (t, J = 3.0 Hz, 2H), 8.11 (d, J = 9.9 Hz, 1H), 7.79-7.76 (m, 1H), 7.16 (d, J = 9.9 Hz, 1H), 5.40 (s, 2H), 5.10-5.06 (m,1H), 1.78-1.58 (m, 2H), 1.31 (d, J = 6.3 Hz, 3H), 0.93 (t, J = 7.5 Hz, 3H); LC/MS Rt = 2.219 min; MS m/z: 356 [M + H]+ |
| 138 | 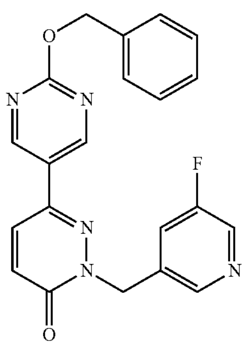 [SMILES: O=c1ccc(-c2cnc(OCc3ccccc3)nc2)nn1Cc1cncc(F)c1] | 6-(2-(benzyloxy)pyrimidin-5-yl)-2-45-fluoropyridin-3-yl)methyl)pyridazine-3(2H)-one | 1H NMR (300 MHz, DMSO-d6) δ 9.13 (s, 2H), 8.55-8.53 (m, 2H), 8.13 (d, J = 9.8 Hz, 1H), 7.86-7.71 (m, 1H), 7.52-7.45 (m, 2H), 7.44-7.31 (m, 3H), 7.17 (d, J = 9.8 Hz, 1H), 5.47 (s, 2H), 5.40 (s, 2H); LC/MS Rt = 1.944 min; MS m/z: 390 [M + H]+ |

Example 15: 2-((5-methoxypyridin-3-yl)methyl)-6-(2-(2,2,2-trifluoroethoxy)pyrimidin-5-yl)pyridazine-3(2H)-one (Compound 128)

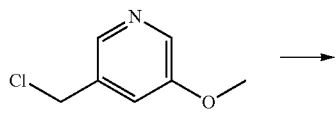

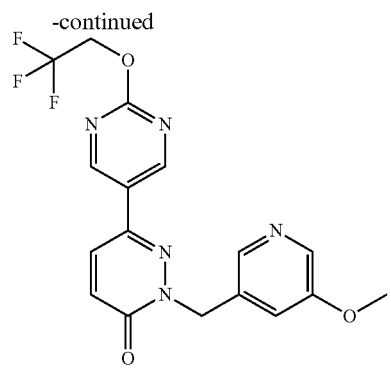

Step 1: 2-((5-methoxypyridin-3-yl)methyl)-6-(2-(2,2,2-trifluoroethoxy)pyrimidin-5-yl)pyridazine-3(2H)-one A mixture of 6-(2-(2,2,2-trifluoroethoxy)pyrimidin-5-yl)pyridazine-3(2H)-one (2.00 g, 7.348 mmol, 1.00 equiv), 3-(chloromethyl)-5-methoxypyridine (1.43 g, 7.348 mmol, 1.00 equiv), potassium carbonate (2.54 g, 18.370 mmol, 2.5 equiv) in dimethylformamide (20.00 mL) was added into a 40-mL flask and stirred for 48 h at 60° C. The mixture was purified by Pre-HPLC (0.05% $NH_3H_2O$—$H_2O$/I, 5% to 55% gradient, 30 min) to give 2-((5-methoxy-pyridin-3-yl)methyl)-6-(2-(2,2,2-trifluoroethoxy)pyrimidin-5-yl)pyridazine-3(2H)-one (1.3 g, 45.02%) as an off-white solid. $^1$H NMR (300 MHz, DMSO-$d_6$) δ 9.17 (s, 2H), 8.25-8.23 (m, 2H), 8.15 (d, J=9.6 Hz, 1H), 7.42-7.41 (m, 1H), 7.18 (d, J=9.6 Hz, 1H), 5.36 (s, 2H), 5.12 (q, J=9.0 Hz, 2H), 3.82 (s, 3H). LC/MS Rt=1.301 min; MS m/z: 394 [M+H]$^+$.

The following compounds were synthesized following Example 15:

| Cmpd No. | Structure | Name | NMR/MS |
|---|---|---|---|
| 132 | 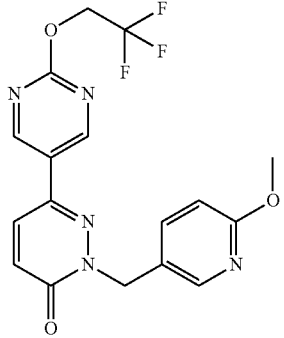 [SMILES: COc1ccc(Cn2nc(-c3cnc(OCC(F)(F)F)nc3)ccc2=O)cn1] | 2-((6-methoxypyridin-3-yl)methyl)-6-(2-(2,2,2-trifluoroethoxy)pyrimidin-5-yl)pyridazine-3(2H)-one | 1H NMR (300 MHz, DMSO-d6) δ 9.17 (d, J = 6.0 Hz, 2H), 8.28 (d, J = 1.8 Hz, 1H), 8.12 (d, J = 9.6 Hz, 1H), 7.82-7.78 (m, 1H), 7.15 (d, J = 9.9 Hz, 1H), 6.81 (d, J = 8.7 Hz, 1H), 5.27 (s, 2H), 5.12 (q, J = 9.0 Hz, 2H), 3.82 (s, 3H); LC/MS Rt = 1.460 min; MS m/z: 394 [M + H]+ |
| 133 | 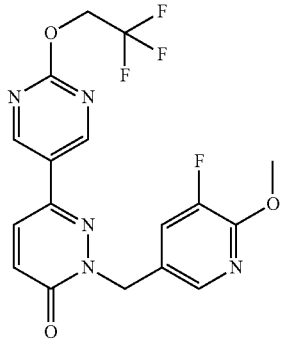 [SMILES: COc1ncc(Cn2nc(-c3cnc(OCC(F)(F)F)nc3)ccc2=O)cc1F] | 2-((5-fluoro-6-methoxypyridin-3-yl)methyl)-6-(2-(2,2,2-trifluoroethoxy)pyrimidin-5-yl)pyridazine-3(2H)-one | 1H NMR (400 MHz, DMSO-d6) δ 9.18 (s, 2H), 8.16-8.08 (m, 2H), 7.78 (dd, J = 11.2, 2.0 Hz, 1H), 7.16 (d, J = 9.6 Hz, 1H), 5.30 (s, 2H), 5.12 (q, J = 8.8 Hz, 2H), 3.93 (s, 3H); LC/MS Rt = 1.298 min; MS m/z: 412 [M + H]+ |
| 134 | 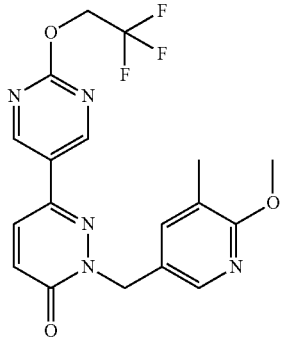 [SMILES: COc1ncc(Cn2nc(-c3cnc(OCC(F)(F)F)nc3)ccc2=O)cc1C] | 2-((6-methoxy-5-methylpyridin-3-yl)methyl)-6-(2-(2,2,2-trifluoroethoxy)pyrimidin-5-yl)pyridazine-3(2H)-one | 1H NMR (400 MHz, DMSO-d6) δ 9.17 (s, 2H), 8.11 (d, J = 9.6 Hz, 2H), 7.64-7.59 (m, 1H), 7.14 (d, J = 9.6 Hz, 1H), 5.24 (s, 2H), 5.12 (q, J = 8.8 Hz, 2H), 3.85 (s, 3H), 2.12 (s, 3H); LC/MS Rt = 1.961 min; MS m/z: 408 [M + H]+ |

| Cmpd No. | Structure | Name | NMR/MS |
|---|---|---|---|
| 135 | 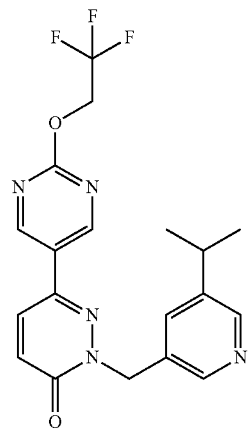 [SMILES: CC(C)c1cncc(Cn2nc(-c3cnc(OCC(F)(F)F)nc3)ccc2=O)c1] | 2-((5-isopropylpyridin-3-yl)methyl)-6-(2-(2,2,2-trifluoroethoxy)pyrimidin-5-yl)pyridazine-3(2H)-one | 1H NMR (300 MHz, DMSO-d6) δ 9.17 (s, 2H), 8.47-8.45 (m, 2H), 8.14 (d, J = 9.7 Hz, 1H), 7.76 (d, J = 2.2 Hz, 1H), 7.18 (d, J = 9.7 Hz, 1H), 5.36 (s, 2H), 5.12 (q, J = 8.9 Hz, 2H), 3.00-2.91 (m, 1H), 1.21 (d, J = 6.9 Hz, 6H); LC/MS Rt = 2.011 min; MS m/z: 406 [M + H]+ |
| 136 | 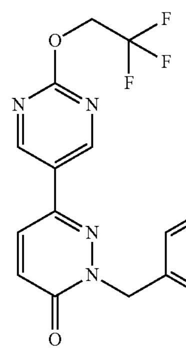 | 2-((5-fluoro-2-methylpyridin-3-yl)methyl)-6-(2-(2,2,2-trifluoroethoxy)pyrimidin-5-yl)pyridazine-3(2H)-one | 1H NMR (400 MHz, DMSO-d6) δ 9.12 (s, 2H), 8.39 (d, J = 2.8 Hz, 1H), 8.17 (d, J = 9.6 Hz, 1H), 7.51 (dd, J = 9.6, 2.9 Hz, 1H), 7.20 (d, J = 9.6 Hz, 1H), 5.38 (s, 2H), 5.12 (q, J = 8.8 Hz, 2H), 2.57 (s, 3H); LC/MS Rt = 1.524 min; MS m/z: 396 [M + H]+ |
| 137 | 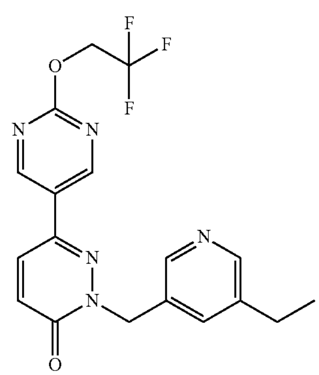 [SMILES: CCc1cncc(Cn2nc(-c3cnc(OCC(F)(F)F)nc3)ccc2=O)c1] | 2-((5-ethylpyridin-3-yl)methyl)-6-(2-(2,2,2-trifluoroethoxy)pyrimidin-5-yl)pyridazine-3(2H)-one | 1H NMR (300 MHz, DMSO-d6) δ 9.17-9.16 (m, 2H), 8.47 (d, J = 2.1 Hz, 1H), 8.39 (d, J = 2.1 Hz, 1H), 8.14 (d, J = 9.9 Hz, 1H), 7.69 (t, J = 2.1 Hz, 1H), 7.17 (d, J = 9.9 Hz, 1H), 5.35 (s, 2H), 5.16-5.08 (m, 2H), 2.61 (q, J = 7.5 Hz, 2H), 1.17 (td, J = 7.2 Hz, 3H); LC/MS Rt = 0.704 min; MS m/z: 392 [M + H]+ |
| 139 | 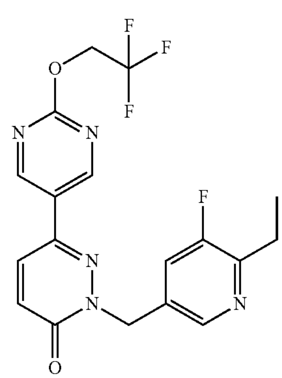 [SMILES: CCc1ncc(Cn2nc(-c3cnc(OCC(F)(F)F)nc3)ccc2=O)cc1F] | 2-((6-ethyl-5-fluoropyridin-3-yl)methyl)-6-(2-(2,2,2-trifluoroethoxy)pyrimidin-5-yl)pyridazine-3(2H)-one | 1H NMR (300 MHz, DMSO-d6) 69.18 (s, 2H), 8.44 (s, 1H), 8.14 (d, J = 9.6 Hz, 1H), 7.74-7.64 (m, 1H), 7.17 (d, J = 9.9 Hz, 1H), 5.36 (s, 2H), 5.12 (q, J = 9.0 Hz, 2H), 2.82-2.74 (m, 2H), 1.20 (t, J = 7.5 Hz, 3H); LC/MS Rt = 1.626 min; MS m/z: 410 [M + H]+ |

-continued

| Cmpd No. | Structure | Name | NMR/MS |
|---|---|---|---|
| 140 | 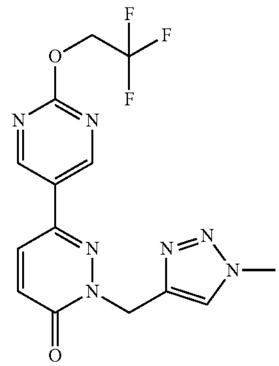 [SMILES: Cn1cc(Cn2nc(-c3cnc(OCC(F)(F)F)nc3)ccc2=O)nn1] | 2-((1-methyl-1H-1,2,3-triazol-4-yl)methyl)-6-(2-(2,2,2-trifluoroethoxy)pyrimidin-5-yl)pyridazine-3(2H)-one | 1H NMR (300 MHz, DMSO-d6) δ 9.15 (s, 2H), 8.13-8.10 (m, 2H), 7.16 (d, J = 9.6Hz, 1H), 5.39 (s, 2H), 5.16-5.07 (m, 2H), 4.01 (s, 3H); LC/MS Rt = 0.904 min; MS m/z: 368 [M + H]+ |

Example 16: 2-((2-ethylthiazol-5-yl)methyl)-6-(2-(2,2,2-trifluoroethoxy)pyrimidin-5-yl)pyridazine-3(2H)-one (Compound 99) and 2-((2-ethylthiazol-5-yl)methyl)-6-(2-isobutoxypyrimidin-5-yl)pyridazine-3(2H)-one (Compound 124)

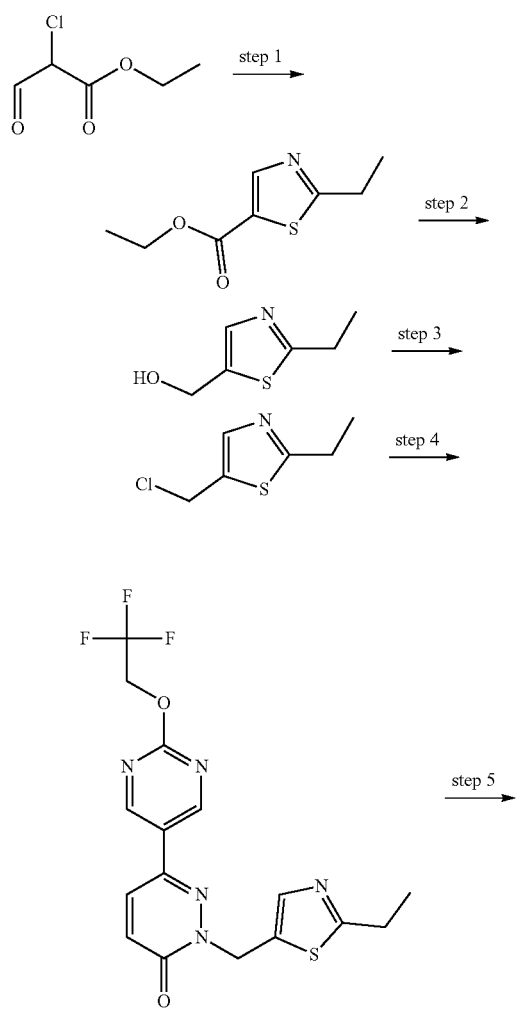

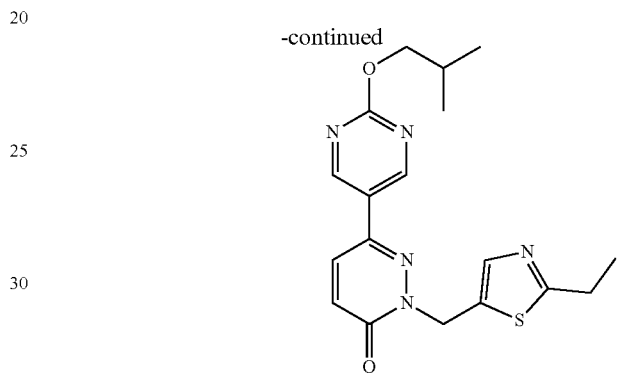

Step 1: ethyl 2-ethylthiazole-5-carboxylate

Into a 100-mL round-bottom flask, were placed ethyl 2-chloro-3-oxopropanoate (80.00 g, 0.531 mol, 1.00 equiv), EtOH (600.00 mL), propanethioamide (49.74 mg, 0.558 mol, 1.05 equiv), MgSO$_4$ (128.00 g, 1.062 mol, 2.00 equiv). The resulting solution was stirred for 16 hr at 80° C. The mixture was cooled to 25° C. and filtered over celite, the filtrate was concentrated under vacuum, the residue was applied onto a silica gel column with ethyl acetate/petroleum ether (1:1) to afford 60.00 g (60.96%) of ethyl 2-ethyl-1,3-thiazole-5-carboxylate as a light yellow oil. MS m/z: 186 [M+H][30]

Step 2: (2-ethylthiazol-5-yl)methanol

To a solution of ethyl 2-ethyl-1,3-thiazole-5-carboxylate (20.00 g, 107.968 mmol, 1.00 equiv) in THF (300.00 mL) at 0° C. was added LiAlH$_4$ (4.10 g, 107.968 mmol, 1.00 equiv) partwise, the mixture was stirred at 0° C. for 1 h, 4 g of Na$_2$SO$_4$10H$_2$O was added partwise and then 2 g of Na$_2$SO$_4$ was added, the mixture was stirred for 30 mins and filtered through celite, the filtrate was concentrated under vacuum to get crude product 15 g (97.02%) as light yellow oil. MS m/z: 144 [M+H]+

Step 3: 5-(chloromethyl)-2-ethylthiazole

To a solution of (2-ethyl-1,3-thiazol-5-yl)methanol (10.00 g, 69.832 mmol, 1.00 equiv) in DCM (100.00 mL) was added dropwise SOCl$_2$ (10.13 mL, 85.161 mmol, 2.00 equiv) at 0° C., the mixture was stirred for 1 h. The mixture was concentrated under vacuum and the residue was dissolved in 100 mL water and adjust PH=8 with saturated Na$_2$CO$_3$ solution, then extracted with 3×100 mL of EA, the organic layer was dried over Na$_2$SO$_4$ and concentrated under vacuum to get crude product which was purified by silica gel column to get light yellow oil 6 g (53.15%). MS m/z: 162 [M+H]$^+$ Step 4: 2-((2-ethylthiazol-5-yl)methyl)-6-(2-(2,2,2-trifluoroethoxy)pyrimidin-5-yl)pyridazine-3(2H)-one Into a 250-mL round-bottom flask, was placed 6-[2-(2,2-trifluoroethoxy)pyrimidin-5-yl]-2H-pyridazin-3-one (10.00 g, 36.739 mmol, 1.00 equiv), DMF (100.00 mL), 5-(chloromethyl)-2-ethyl-1,3-thiazole (7126.72 mg, 44.087 mmol, 1.20 equiv), K$_2$CO$_3$ (15232.78 mg, 110.218 mmol, 3.00 equiv). The resulting solution was stirred for 1 hr at 50° C. The residue was applied onto a silica gel column with ethyl acetate/petroleum ether (1:1). The collected fractions were combined and concentrated under vacuum to get product which was purified by Combiflash (Reversed phase: 0.05% ammonia/I) to afford 5.1 g (34.93%) of 2-[(2-ethyl-1,3-thiazol-5-yl)methyl]-6-[2-(2,2,2-trifluoroethoxy)pyrimidin-5-yl]pyridazine-3-one as a white solid. $^1$H NMR (400 MHz, DMSO-d$_6$): δ 9.16 (s, 2H), 8.12 (d, J=9.6 Hz, 1H), 7.75 (s, 1H), 7.17 (d, J=9.6 Hz, 1H), 5.48 (s, 2H), 5.12 (q, J=8.8 Hz, 2H), 2.92 (q, J=7.6 Hz, 2H), 1.24 (t, J=7.6 Hz, 3H). LC/MS Rt=1.873 min; MS m/z: 398 [M+H]$^+$.

Step 5: 2-((2-ethylthiazol-5-yl)methyl)-6-(2-isobutoxypyrimidin-5-yl)pyridazine-3(2H)-one To a stirred solution of 2-[(2-ethyl-1,3-thiazol-5-yl)methyl]-6-[2-(2,2,2-trifluoroethoxy)pyrimidin-5-yl]pyridazine-3-one (1.00 g, 2.516 mmol, 1.00 equiv) in 2-methylpropan-1-ol (10 mL) was added K$_2$CO$_3$ (0.70 mg, 5.033 mmol, 2.00 equiv) in portions at 25° C. under nitrogen atmosphere. The resulting mixture was slowly warmed to 70° C. and stirred for additional 6 h. The resulting mixture was concentrated under vacuum. The residue was purified by reverse flash chromatography with the following conditions: column, C18 silica gel; mobile phase, MeOH in water, 10% to 90% gradient in 40 min; detector, UV 254 nm. To afford 2-((2-ethyl-thiazol-5-yl)methyl)-6-(2-isobutoxypyrimidin-5-yl)pyridazine-3(2H)-one (800 mg, 85.58%) as a grey solid. $^1$H NMR (300 MHz, DMSO-d$_6$) δ 9.08 (s, 2H), 8.10 (d, J=9.9 Hz, 1H), 7.75 (s, 1H), 7.16 (d, J=9.9 Hz, 1H), 5.48 (s, 2H), 4.16 (d, J=6.6 Hz, 2H), 2.93 (q, J=7.5 Hz, 2H), 2.13-2.02 (m, 1H), 1.25 (t, J=7.5 Hz, 3H), 0.99 (d, J=6.7 Hz, 6H). LC/MS Rt=1.462 min; MS m/z: 372 [M+H]$^+$.

The following compounds were synthesized following Example 16:

| Cmpd No. | Structure | Name | NMR/MS |
| --- | --- | --- | --- |
| 122 | 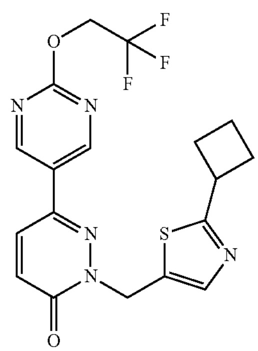 [SMILES: O=c1ccc(-c2cnc(OCC(F)(F)F)nc2)nn1Cc1cnc(C2CCC2)s1] | 2-((2-cyclobutylthiazol-5-yl)methyl)-6-(2-(2,2,2-trifluoroethoxy)pyrimidin-5-yl)pyridazine-3(2H)-one | $^1$H NMR (300 MHz, DMSO-d$_6$) δ 9.17 (s, 2H), 8.13 (d, J = 9.9 Hz, 1H), 7.78 (s, 1H), 7.18 (d, J = 9.6 Hz, 1H), 5.49 (s, 2H), 5.13 (q, J = 9.0 Hz, 2H), 3.86-3.74 (m, 1H), 2.40-1.80 (m, 6H); LC/MS Rt = 1.581 min; MS m/z: 424 [M + H]$^+$ |
| 129 | 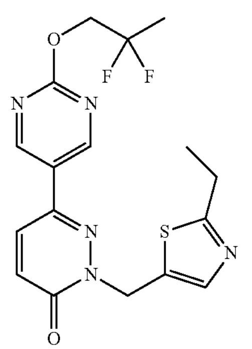 [SMILES: CCc1ncc(Cn2nc(-c3cnc(OCC(C)(F)F)nc3)ccc2=O)s1] | 6-(2-(2,2-difluoropropoxy)pyrimidin-5-yl)-2((2-ethylthiazol-5-yl)methyl)pyridazine-3(2H)-one | $^1$H NMR (300 MHz, DMSO-d$_6$) δ 9.14 (s, 2H), 8.12 (d, J = 9.9 Hz, 1H), 7.76 (s, 1H), 7.17 (d, J = 9.9 Hz, 1H), 5.49 (s, 2H), 4.70 (t, J = 13.2 Hz, 2H), 2.93 (q, J = 7.5 Hz, 2H), 1.77 (t, J = 19.5 Hz, 3H), 1.25 (t, J = 7.5 Hz, 3H); LC/MS Rt = 1.803 min; MS m/z: 394 [M + H]+ |

| Cmpd No. | Structure | Name | NMR/MS |
|---|---|---|---|
| 130 | (structure shown) | 6-(2-isobutoxypyrimidin-5-yl)-2-((2-methylthiazol-5-yl)methyl)pyridazine-3(2H)-one | $^1$H NMR (300 MHz, DMSO-$d_6$) δ 9.08 (s, 2H), 8.10 (d, J = 9.9 Hz, 1H), 7.72 (s, 1H), 7.16 (d, J = 9.9 Hz, 1H), 5.47 (s, 2H), 4.16 (d, J = 6.6 Hz, 2H), 2.60 (s, 3H), 2.27-2.04 (m, 1H), 1.00 (d, J = 6.6 Hz, 6H); LC/MS Rt = 1.817 min; MS m/z: 358 [M + H]+ |

Example 17: 5: 6-(2,4-dihydroxypyrimidin-5-yl)-2-((5-fluoropyridin-3-yl)methyl)pyridazine-3(2H)-one (Compound 353)

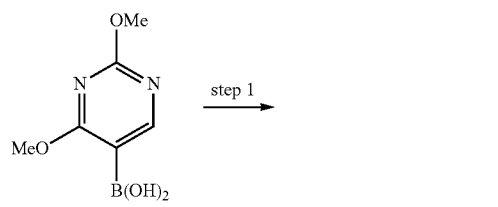

Step 1: 6-(2,4-dimethoxypyrimidin-5-yl)-2-((5-fluoropyridin-3-yl)methyl)pyridazine-3(2H)-one To a mixture of (2,4-dimethoxypyrimidin-5-yl)boronic acid (552 mg, 3 mmol, 1.0 equiv) in dioxane (5 mL) were added 6-chloro-2-((5-fluoropyridin-3-yl)methyl)pyridazine-3(2H)-one (717 mg, 3 mmol, 1.00 equiv), Pd(dppf)Cl$_2$ (110 mg, 0.15 mmol, 0.05 equiv), K$_2$CO$_3$ (621 mg, 4.5 mmol, 1.5 equiv) and H$_2$O (0.5 mL). Into the flask purged and maintained with an inert atmosphere of nitrogen. The resulting solution was stirred for 2 h at 90° C. The solution was diluted with water and extracted with EtOAc (×3). The combined organics were washed with brine, dried over Na$_2$SO$_4$ and the solvent removed in vacuo. Purification by chromatography on silica gel to afforded 6-(2,4-dimethoxy-pyrimidin-5-yl)-2-((5-fluoro-pyridin-3-yl)methyl) pyridazine-3(2H)-one as a solid (610 mg, 59.3%).

Step 2: 6-(2,4-dihydroxypyrimidin-5-yl)-2-((5-fluoropyridin-3-yl)methyl)pyridazine-3(2H)-one To a mixture of 6-(2,4-dimethoxypyrimidin-5-yl)-2-((5-fluoro-pyridin-3-yl)methyl)pyridazine-3(2H)-one (172 mg, 0.5 mmol, 1.0 equiv) in MeOH (6 mL) were added 4M HCl (8 mL). The resulting solution was stirred for 2 h at 90° C. The mixture was concentrated under reduced pressure. The crude product was purified by RP-HPLC to afford a white solid (28 mg, 17.8%). $^1$H NMR (300 MHz, DMSO-d6) δ 11.46 (s, 2H), 8.91-8.23 (m, 2H), 8.05-7.80 (m, 2H), 7.74-7.69 (m, 1H), 7.00 (d, J=9.8 Hz, 1H), 5.34 (s, 2H). LC/MS Rt=0.721 min; MS m/z: 316 [M+H]$^+$.

Example 18. Skeletal Myofibril ATPase Assay

Overview: Myosin ATPase activity is assessed by using a coupled reaction system, in which ADP generated by the myosin ATPase function is coupled to the disappearance of NADH through the pyruvate kinase/lactate dehydrogenase (PK-LDH) system. Myosin ATPase activity produces ADP, which is used as a substrate for PK to produce pyruvate and regenerate ATP. The pyruvate is then used as a substrate by LDH to oxidize NADH to NAD+. The rate of the reaction is monitored through the time-dependent disappearance of NADH using absorbance at 340 nm. Inhibition of ATPase activity by the assayed compounds is indicated by a reduced rate of NADH loss, relative to vehicle-treated controls, over the experimental time window. To assess the selectivity of the assayed compounds for skeletal myofibrils, the compounds are counter-screened in cardiac myofibrils.

Materials: The following stock solutions and reagents were used in the Skeletal Myofibril ATPase Assay:

| Stock Solutions |
| --- |
| PIPES, 200 mM in $H_2O$, pH 7.0 |
| $MgCl_2$ in $H_2O$, 200 mM |
| PM12 Buffer, 10X: 12 mM PIPES (from 200 mM stock), 20 mM $MgCl_2$ (from 200 mM stock) |
| EGTA in $H_2O$, 500 mM |
| CaCl2 in $H_2O$, 500 mM |
| DTT in $H_2O$, 1M |
| BSA in $H_2O$, 20 mg/mL |
| KCl in $H_2O$, 600 mM |
| ATP in 1X PM12, 100 mM |
| NADH in 1X PM12, 30 mM |
| PEP in 1X PM12, 100 mM, pH 7.0 |
| Antifoam 204, 1% in $H_2O$ |

Stock Solutions of pCa buffer. Combine PIPES, $CaCl_2$, and EGTA solutions with 70 mL of water. Adjust pH to 7.0 and bring final volume to 100 mL.

PREPARATION OF STOCKS SOLUTIONS FOR 100 ML OF PCA BUFFER

| pCA | 200 mM PIPES (mL) | Approx. Water (mL) | $CaCl_2$ | EGTA |
| --- | --- | --- | --- | --- |
| 4.0 | 6 | 74 | 10.025 | 9.975 |
| 4.5 | 6 | 74 | 9.800 | 10.200 |
| 5.0 | 6 | 74 | 9.325 | 10.675 |
| 5.5 | 6 | 74 | 8.100 | 11.900 |
| 5.75 | 6 | 74 | 7.200 | 12.800 |
| 6.0 | 6 | 74 | 6.000 | 14.000 |
| 6.25 | 6 | 74 | 4.500 | 15.500 |
| 6.5 | 6 | 74 | 3.025 | 16.975 |
| 6.75 | 6 | 74 | 1.975 | 18.025 |
| 7.0 | 6 | 74 | 1.165 | 18.835 |
| 8.0 | 6 | 74 | 0.126 | 19.874 |
| 10.0 | 6 | 74 | 0.001 | 19.999 |

Skeletal Myofibril ATPase Assay Procedure: BSA, ATP, NADH, PEP, and DTT solutions were thawed at room temperature, then transferred to ice. Pellet-frozen myofibrils (approximately twice the required volume) were transferred into a sufficiently large tube and capped. Myofibrils were thawed by rolling in a water bath for approximately 15 min at room temperature and cooled on ice. Buffers A and B were prepared by adjusting volumes as necessary for required number of wells and stored on ice. 0.5 µL of the compounds to be assayed were added into wells of a 384-well plate. Buffers A and B were mixed by inversion immediately prior to use, then 25 µL of each was dispensed using a Multidrop dispenser (Buffer A first, then Buffer B). The absorbance within the wells was measured at 340 nm, using a kinetic protocol in which the wells are read every 1.5-2 min for 1 h. The reaction rate was qualitatively assessed by subtracting the minimum absorbance value from the maximum value for each well, using either the SoftMax Pro plate reader software or a spreadsheet program such as Excel. Using GraphPad Prism 8.0, the data was normalized, with 100% activity defined as the absorbance change in the 1% DMSO vehicle wells and 0% assigned to no change in absorbance over the course of the experiment. The normalized data were fit to a variable-slope four-parameter logistic model, constraining the bottom to be 0 or greater. Compounds of Table 1 to 4 were tested and results of the assay appear in Table 5 herein. A=$IC_{50}$ is less than or equal to 10 µM; B=$IC_{50}$ is greater than 10 µM and less than 100 µM; C=$IC_{50}$ is greater than 100 µM; D=$IC_{50}$ is greater than 60 µM.II.

Example 19. Cardiac Myofibril ATPase Assay

Following example 15, the counter screen was done using frozen myofibril pellets obtained from cardiac tissue. The assay was done in the same manner as above, with the following notable exceptions: the final well concentration of myofibrils was 1.0 mg/mL and KCl was omitted from the recipe.

Compounds of Table 1 to 4 were tested and results of the assay appear in Table 6 herein. A=$IC_{50}$ is less than or equal to 10 µM; B=$IC_{50}$ is greater than 10 µM and less than 100 µM; C=$IC_{50}$ is greater than 100 µM; and D=$IC_{50}$ is greater than 60 µM.

Example 20. Tibialis Anterior Muscle Assay

Skeletal muscles of patients with Duchenne muscular dystrophy (DMD) and mdx mice lack dystrophin and are more susceptible to contraction-induced injury than control muscles. Two stretches of maximally activated tibialis anterior (TA) muscles in situ were used to evaluate the susceptibility to injury of limb muscles in mdx mice following the administration of a compound disclosed herein. stretches of 20% strain relative to muscle fiber length were initiated from the plateau of isometric contractions. The magnitude of damage was assessed one minute later by the deficit in isometric force.

Animals

Mice aged 2-19 months were tested. Specific pathogen free (SPF) C57BL control and mdx mice were either purchased or bred in-house with mating pairs purchased from the Jackson Laboratories. All control mice were of C57BL/10J strain with the exception of the 19-month old mice that were C57BL/6. The use of C57BL/6 mice for the oldest group was necessary, since unlike C57BL/10J mice, C57BL/6 mice may be purchased at advanced ages from the colonies of aging rodents maintained by the National Institute on Aging.

In Situ Preparation

Mice were anesthetized with an initial intraperitoneal injection of Avertin (tribromoethanol; 13-17 ll/g). Anesthesia was supplemented until no responses to tactile stimuli were detected. This level of anesthesia was maintained throughout the experiment with additional doses of Avertin. The tendon of the TA was exposed by an incision at the ankle. The tendon was cut several millimeters distal to the end of the muscle. The tendon was tied with 4.0 nylon suture as close to the muscle attachment as possible, and the tendon was folded back onto itself and tied again. The tendon and exposed muscle were kept moist by periodic applications of isotonic saline. The mouse was placed on a heated platform maintained at 37° C. The foot of the mouse was secured to the platform with cloth tape and the knee was immobilized in a clamp between sharpened screws. The tendon of the muscle was tied securely to the lever arm of a servomotor. The servomotor controlled the position of the muscle and monitored the force developed by the muscle. All data were displayed on a digital oscilloscope and stored on a computer.

The TA muscle was stimulated with 0.2-ms pulses via two needle electrodes that penetrated the skin on either side of the peroneal nerve near the knee. Stimulation voltage and subsequently muscle length (Lo) were adjusted for maximum isometric twitch force (Pt). While held at Lo, the muscle was stimulated at increasing frequencies, stepwise from 150 Hz by 50 Hz, until a maximum force (Po) was reached, typically at 250 Hz. A one- to two-minute rest period was allowed between each tetanic contraction. Muscle length was measured with calipers, based on well-defined anatomical landmarks near the knee and the ankle. Optimum fiber length was determined by multiplying Lo by the TA Lf/Lo ratio of 0.6.

Lengthening Contraction Protocol

Each muscle was exposed to two stretches in situ, with the muscle stimulated at 250 Hz, the frequency that most often resulted in Po. A protocol consisting of only two contractions was used to avoid fatigue. Stretches were initiated from the plateau of an isometric contraction at Lo. At time 0, stimulation was initiated and the muscle was held with no movement for 100 ms to allow maximum activation. From the plate au of the maximum isometric contraction, a length change of 20% Lf at a velocity of 1 Lf/s was imposed (LC1). Stimulation ceased at the end of the stretch ramp. The muscle was held at the stretched length for 100 ms and then returned to Lo at the same velocity. A second lengthening contraction identical to the first was administered 10 min later (LC2). Maximum isometric force was measured after 1 min (b1 min) and then again each 5 min for 15 min. Force deficits were calculated as the difference between the isometric force during LC1 and the maximum isometric force measured at any given time and expressed as a percentage of the isometric force during LC1. The recovery during the 15 min following the two-lengthening-contraction protocol was quantified as the difference between the isometric force measured at 15 min and the isometric force after the second lengthening contraction and expressed as a percentage of initial Po.

The experimental protocol consisted of two muscle stretches during maximal activation, followed by maximal activation to measure the decrease in maximum isometric force (Po). Panel A shows the length change of the muscle of 20% strain relative to fiber length (Lf), where 100% corresponds to optimum muscle length (Lo) for force development. The muscle was stretched at a velocity of 2 Lf/s. Panel B demonstrates the decrease in Po after the two-stretch protocol in a representative mdx mouse. Each lengthening contraction was initiated from the plateau of a maximum isometric contraction. Ten minutes after the first lengthening contraction (LC1), a second lengthening contraction occurred (LC2). Maximum force during an isometric contraction was measured 10 min after LC2 (þ 1 min). The force deficit was calculated by dividing the difference between the Po during LC1 and the Po measured at any time after LC1 by the Po during LC1 and multiplying by 100%. suture were trimmed from the muscle, and the muscle was weighed. After removal of TA muscles, deeply anesthetized mice were euthanized by the induction of a pneumothorax. Total muscle fiber cross-sectional area (CSA) of TA muscles was calculated by dividing muscle mass by the product of Lf and 1.06 mg/mm3, the density of mammalian skeletal muscle. Specific Po was calculated by dividing Po by CSA. The results of the assays are seen in FIGS. 3-6.

Figure 3:
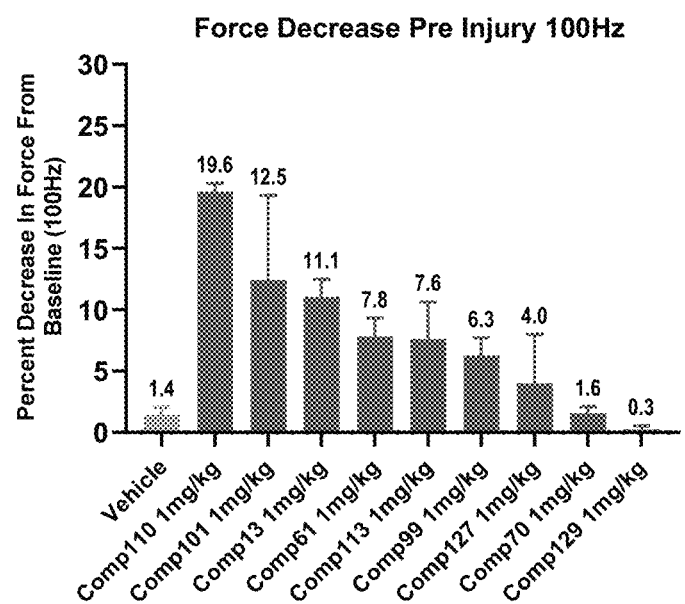
FIG. 3 depicts the force decrease pre injury at 100 Hz for various compounds of the disclosure.

FIG. 3 shows the force decrease pre injury at 100 Hz for compounds of the disclosure. Force was measured in the TA muscle of the mdx mouse in situ at 100 Hz before and after oral administration of the compound. A 100 Hz stimulus was applied every 10 minutes and the change in force, before starting the eccentric injury protocol was recorded. This metric gives an indication of the relative ability of the compound to decrease force in a target tissue.

Figure 4:
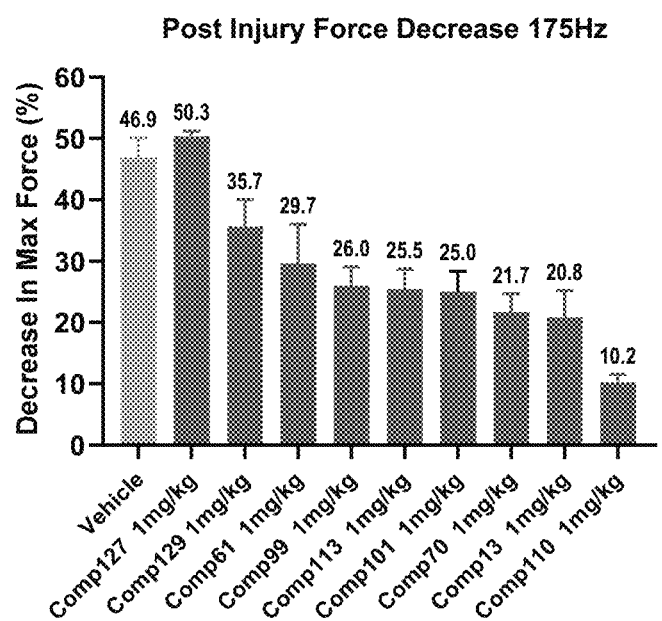
FIG. 4 depicts the post injury force decrease at 175 Hz for various compounds of the disclosure.
Figure 5:
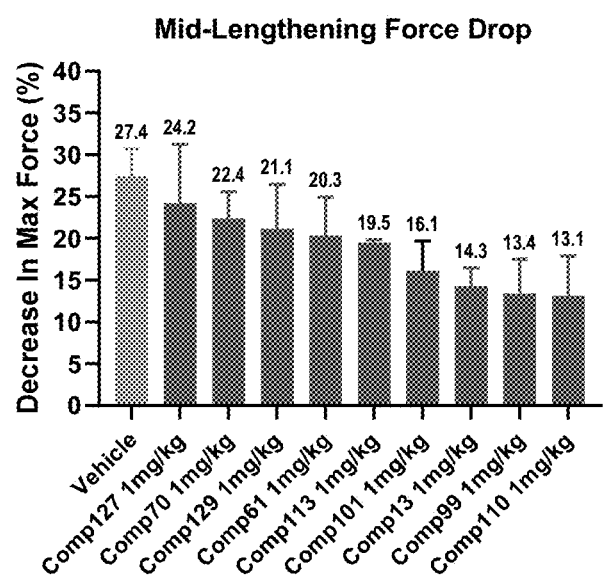
FIG. 5 depicts mid lengthening force drop for various compounds of the disclosure.

FIG. 4 shows the post injury force decrease at 175 Hz for compounds of the disclosure. Maximal force was measured at 175 Hz in the TA muscle in situ before and 10 minutes after two rounds of eccentric (lengthening) contraction. In mdx mice, lengthening contraction yields an exaggerated force drop. This measurement gives an indication of the ability of the compound to reduce the relative drop in force after eccentric contraction. FIG. 5 shows mid lengthening force drop for compounds of the disclosure. Injury to the TA muscle in situ was elicited via two maximal eccentric contractions with 20% lengthening, 10 minutes apart. This metric measures the relative drop in pre-lengthening force between the first and the second contraction.

Figure 6:
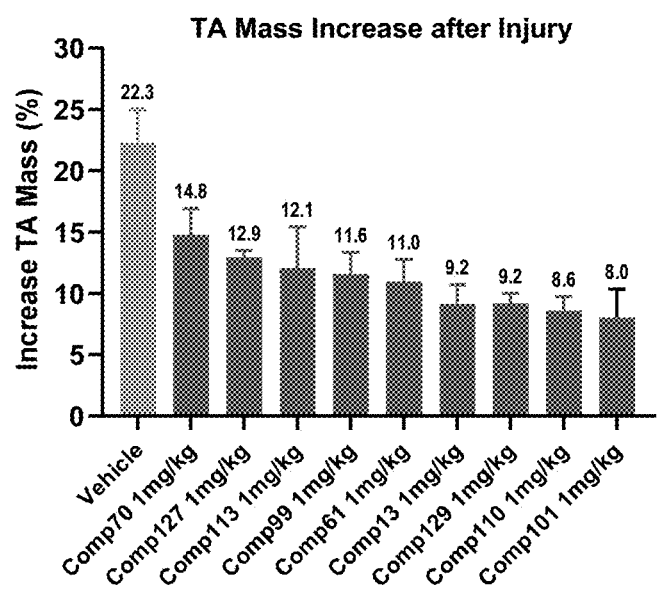
FIG. 6 depicts the TA mass increase after injury for various compounds of the disclosure.

FIG. 6 shows the TA mass increase after injury for compounds of the disclosure. Lengthening injury of the TA muscle in mdx mice causes a delayed increase in muscle weight post-injury. This is presumably due to fluid accumulation in the form of edema. Muscles (both injured and contralateral) were removed from the mouse 1 hour after injury and weighed. The relative increase in weight of injured to contralateral was recorded. Reduction in this relative change is indicative of reduced edema post-injury.

In some embodiments, compounds of the disclosure are below in Table 1.

TABLE 1

| Cmpd No. | Structure | Name | NMR/MS |
|---|---|---|---|
| 1 | 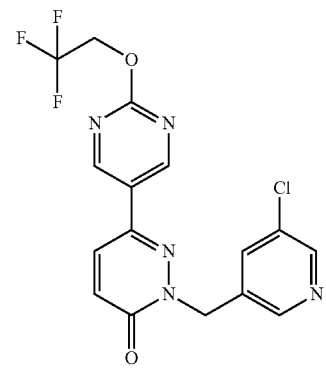 [SMILES: O=c1ccc(-c2cnc(OCC(F)(F)F)nc2)nn1Cc1cncc(Cl)c1] | 2-((5-chloropyridin-3-yl)methyl)-6-(2-(2,2,2-trifluoroethoxy)pyrimidin-5-yl)pyridazin-3(2H)-one | $^1$H NMR (300 MHz, DMSO-$d_6$) δ 9.18 (s, 2H), 8.61 (dd, J = 8.7, 1.5 Hz, 2H), 8.15 (d, J = 9.9 Hz, 1H), 7.99 (s, 1H), 7.18 (d, J = 9.6 Hz, 1H), 5.39 (s, 2H), 5.12 (q, J = 9.0 Hz, 2H) |

TABLE 1-continued

| Cmpd No. | Structure | Name | NMR/MS |
|---|---|---|---|
| 2 | 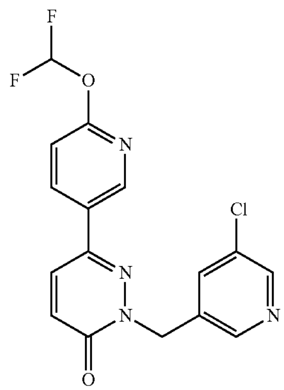 [SMILES: O=c1ccc(-c2ccc(OC(F)F)nc2)nn1Cc1cncc(Cl)c1] | 2-((5-chloropyridin-3-yl)methyl)-6-(6-(difluoromethoxy)pyridin-3-yl)pyridazin-3(2H)- | 1H NMR (DMSO-d6, 300 MHz): δ 8.78 (s, 1H), 8.61-8.59 (s, 2H), 8.40 (dd, $J_1$ = 8.7 Hz, $J_2$ = 2.4 Hz, 1H), 8.15 (d, $J_\backslash$ = 9.9 Hz, 1H), 7.96-7.95 (m, 1H), 7.77 (t, J = 72.6 Hz, 1H), 7.25-7.14 (m, 2H), 5.40 (s, 2H); LC/MS (ESI): 398 $[M + H]^+$ |
| 3 | 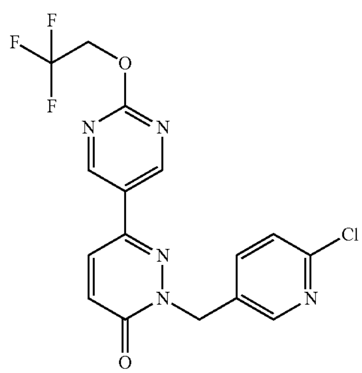 [SMILES: O=c1ccc(-c2cnc(OCC(F)(F)F)nc2)nn1Cc1ccc(Cl)nc1] | 2-((6-chloropyridin-3-yl)methyl)-6-(2-(2,2,2-trifluoroethoxy)pyrimidin-5-yl)pyridazin-3(2H)-one | LC/MS (ESI): 365 $[M + H]^+$ |
| 4 | 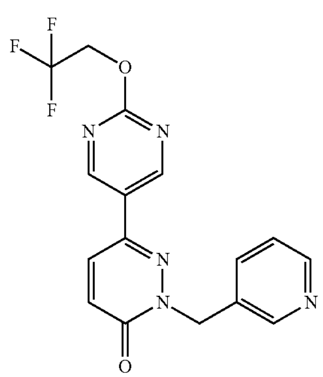 [SMILES: O=c1ccc(-c2cnc(OCC(F)(F)F)nc2)nn1Cc1cccnc1] | 2-(pyridin-3-ylmethyl)-6-(2-(2,2,2-trifluoroethoxy)pyrimidin-5-yl)pyridazin-3(2H)-one | 398.1 |
| 5 | 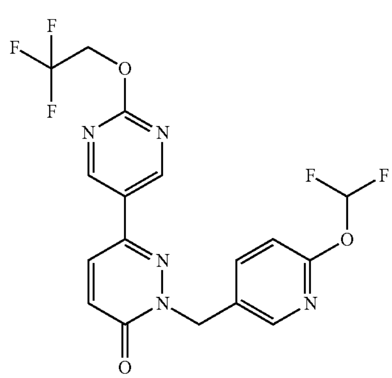 [SMILES: O=c1ccc(-c2cnc(OCC(F)(F)F)nc2)nn1Cc1ccc(OC(F)F)nc1] | 2-((6-(difluoromethoxy)pyridin-3-yl)methyl)-6-(2-(2,2,2-trifluoroethoxy)pyrimidin-5-yl)pyridazin-3(2H)-one | m/z = 364.3 (M + H) |

TABLE 1-continued

| Cmpd No. | Structure | Name | NMR/MS |
|---|---|---|---|
| 6 | 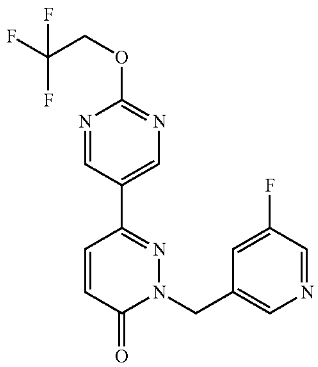 [SMILES: O=c1ccc(-c2cnc(OCC(F)(F)F)nc2)nn1Cc1cncc(F)c1] | 2-((5-fluoropyridin-3-yl)methyl)-6-(2-(2,2,2-trifluoroethoxy)pyrimidin-5-yl)pyridazin-3(2H)-one | 1H NMR (300 MHz, DMSO-$d_6$): δ 9.18 (s, 2H), 8.55-8.54 (m, 2H), 8.15 (d, J = 9.6 Hz, 1H), 7.81-7.77 (m, 1H), 7.19 (d, J = 9.9 Hz, 1H), 5.41 (s, 2H), 5.12 (q, J = 9.0 Hz, 2H); m/z = 430.3 (M + H) |
| 7 | 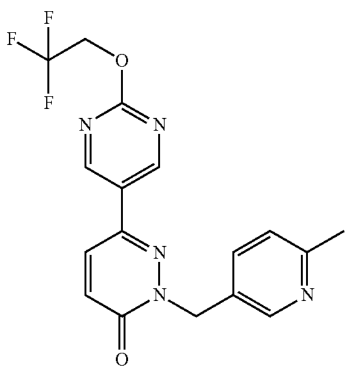 | 2-((6-methylpyridin-3-yl)methyl)-6-(2-(2,2,2-trifluoroethoxy)pyrimidin-5-yl)pyridazin-3(2H)-one | LC/MS (ESI): 382 [M + H]$^+$ |
| 8 | 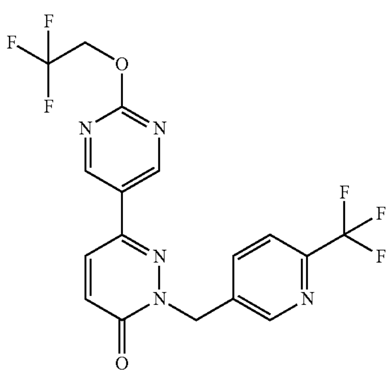 [SMILES: O=c1ccc(-c2cnc(OCC(F)(F)F)nc2)nn1Cc1ccc(C(F)(F)F)nc1] | 6-(2-(2,2,2-trifluoroethoxy)pyrimidin-5-yl)-2-((6-(trifluoromethyl)pyridin-3-yl)methyl)pyridazin-3(2H)-one | [M + H]+ 378.2 |
| 9 | 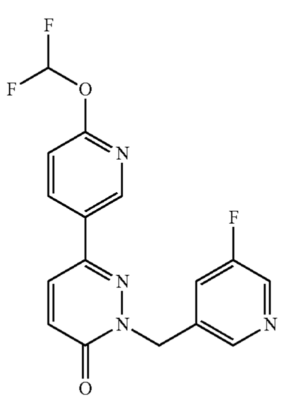 [SMILES: O=c1ccc(-c2ccc(OC(F)F)nc2)nn1Cc1cncc(F)c1] | 6-(6-(difluoromethoxy)pyridin-3-yl)-2-((5-fluoropyridin-3-yl)methyl)pyridazin-3(2H)-one | $^1$H NMR (DMSO-d6, 300 MHz): δ 8.79 (d, J$_1$ = 2.1 Hz, 1H), 8.54-8.53 (m, 2H), 8.40 (dd, J$_1$ = 8.7 Hz, J$_2$ = 2.4 Hz, 1H), 8.14 (d, J$_1$ = 9.9 Hz, 1H), 7.78 (t, J = 72.3 Hz, 1H), 7.77-7.33 (m, 1H), 7.25-7.14 (m, 2H), 5.42 (s, 2H); m/z = 432.3 (M + H) |

TABLE 1-continued

| Cmpd No. | Structure | Name | NMR/MS |
|---|---|---|---|
| 10 | 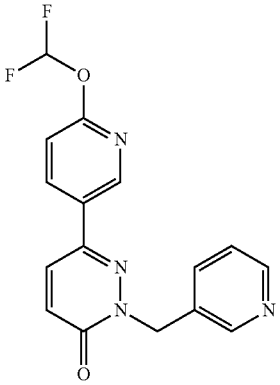 [SMILES: O=c1ccc(-c2ccc(OC(F)F)nc2)nn1Cc1cccnc1] | 6-(6-(difluoromethoxy)pyridin-3-yl)-2-(pyridin-3-ylmethyl)pyridazin-3(2H)-one | $^1$HNMR (DMSO-d6, 300 MHz): δ8.78 (d, $J_1$ = 2.1 Hz, 1H), 8.65 (s, 1H), 8.52 (d, J = 3.9 Hz, 1H), 8.40 (dd, $J_1$ = 8.7 Hz, $J_2$ = 2.4 Hz, 1H), 8.13 (d, $J_1$ = 9.6 Hz, 1H), 7.83-7.80 (m, 1H), 7.77 (t, J = 72.3 Hz, 1H), 7.41-7.371H), 7.24-7.17 (m, 2H), 5.38 (s, 2H); LC/MS (ESI): 349 [M + H]$^+$ |
| 11 | 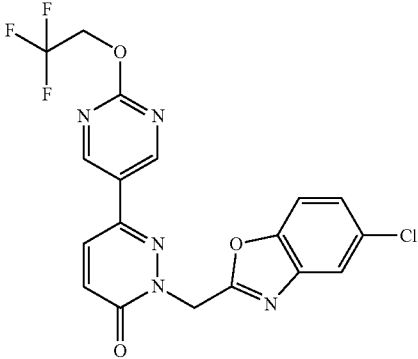 [SMILES: O=c1ccc(-c2cnc(OCC(F)(F)F)nc2)nn1Cc1nc2cc(Cl)ccc2o1] | 2-((5-chlorobenzo[d]oxazol-2-yl)methyl)-6-(2-(2,2,2-trifluoroethoxy)pyrimidin-5-yl)pyridazin-3(2H)-one | LC/MS (ESI): 331 [M + H]$^+$ |
| 12 | 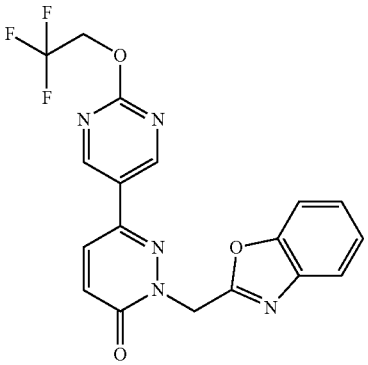 [SMILES: O=c1ccc(-c2cnc(OCC(F)(F)F)nc2)nn1Cc1nc2ccccc2o1] | 2-(benzo[d]oxazol-2-ylmethyl)-6-(2-(2,2,2-trifluoroethoxy)pyrimidin-5-yl)pyridazin-3(2H)-one | m/z = 438.3 (M + H) |
| 13 | 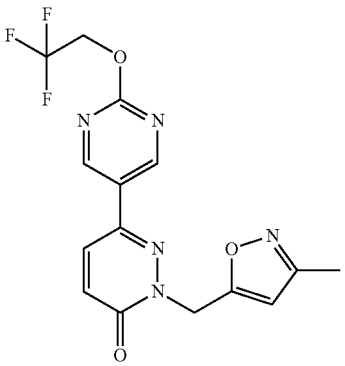 | 2-((3-methylisoxazol-5-yl)methyl)-6-(2-(2,2,2-trifluoroethoxy)pyrimidin-5-yl)pyridazin-3(2H)-one | [M + H]+ 404.1 |

TABLE 1-continued

| Cmpd No. | Structure | Name | NMR/MS |
|---|---|---|---|
| 14 | 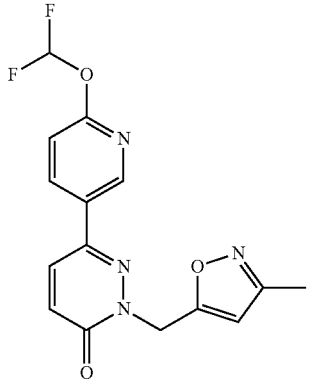 [SMILES: Cc1cc(Cn2nc(-c3ccc(OC(F)F)nc3)ccc2=O)on1] | 6-(6-(difluoromethoxy)pyridin-3-yl)-2-((3-methylisoxazol-5-yl)methyl)pyridazin-3(2H)-one | 368.2 |
| 15 | 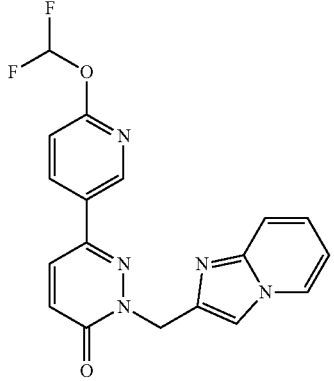 [SMILES: O=c1ccc(-c2ccc(OC(F)F)nc2)nn1Cc1cn2ccccc2n1] | 6-(6-(difluoromethoxy)pyridin-3-yl)-2-(imidazo[1,2-a]pyridin-2-ylmethyl)pyridazin-3(2H)-one | 335.3 |
| 16 | 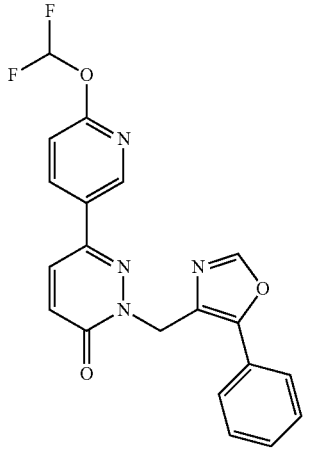 [SMILES: O=c1ccc(-c2ccc(OC(F)F)nc2)nn1Cc1ncoc1-c1ccccc1] | 6-(6-(difluoromethoxy)pyridin-3-yl)-2-((5-phenyloxazol-4-yl)methyl)pyridazin-3(2H)-one | 370.2 |
| 17 | 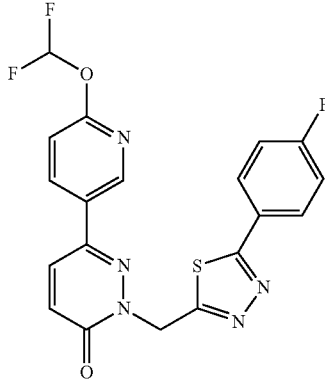 | 6-(6-(difluoromethoxy)pyridin-3-yl)-2-((5-(4-fluorophenyl)-1,3,4-thiadiazol-2-yl)methyl)pyridazin-3(2H)-one | $^1$H NMR (DMSO-d6, 300 MHz): δ 8.81 (d, $J_1$ = 2.4 Hz, 1H), 8.42 (dd, $J_1$ = 8.7 Hz, $J_2$ = 2.7 Hz, 1H), 8.20 (d, $J_1$ = 9.9 Hz, 1H), 8.07-8.04 (m, 2H), 7.78 (t, J = 72.6 Hz, 1H), 7.39-7.37 (m, 2H), 7.27-7.23 (m, 2H), 5.82 (s, 2H); [M + H]+ 397.1 |

TABLE 1-continued

| Cmpd No. | Structure | Name | NMR/MS |
|---|---|---|---|
| 18 | 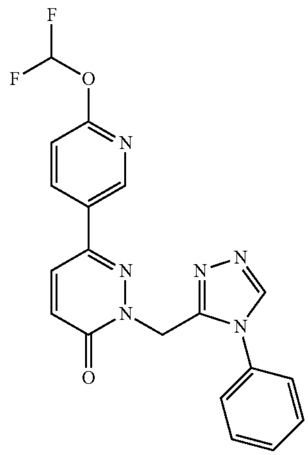 [SMILES: O=c1ccc(-c2ccc(OC(F)F)nc2)nn1Cc1nncn1-c1ccccc1] | 6-(6-(difluoromethoxy)pyridin-3-yl)-2-((4-phenyl-4H-1,2,4-triazol-3-yl)methyl)pyridazin-3(2H)-one | LC/MS (ESI): 432 [M + H]+ |
| 19 | 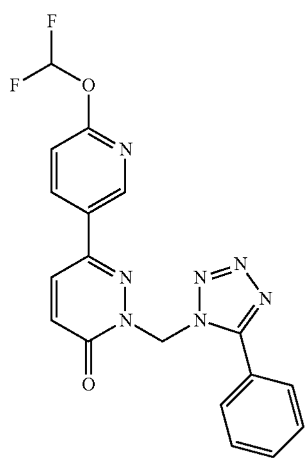 [SMILES: O=c1ccc(-c2ccc(OC(F)F)nc2)nn1Cn1nnnc1-c1ccccc1] | 6-(6-(difluoromethoxy)pyridin-3-yl)-2-((5-phenyl-1H-tetrazol-1-yl)methyl)pyridazin-3(2H)-one | [M + H]+ 397.2 |
| 20 | 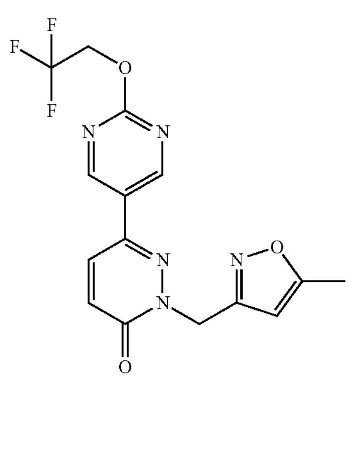 | 2-((5-methylisoxazol-3-yl)methyl)-6-(2-(2,2,2-trifluoroethoxy)pyrimidin-5-yl)pyridazin-3(2H)-one | [M + H]+ 398.2 |

TABLE 1-continued

| Cmpd No. | Structure | Name | NMR/MS |
|---|---|---|---|
| 22 | 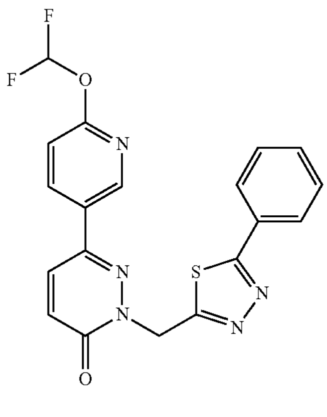 [SMILES: O=c1ccc(-c2ccc(OC(F)F)nc2)nn1Cc1nnc(-c2ccccc2)s1] | 6-(6-(difluoromethoxy)pyridin-3-yl)-2-((5-phenyl-1,3,4-thiadiazol-2-yl)methyl)pyridazin-3(2H)-one | $^1$H NMR (DMSO-d6, 400 MHz): δ 8.81 (d, $J_1$ = 2.4 Hz, 1H), 8.42 (dd, $J_1$ = 8.4 Hz, $J_2$ = 2.4 Hz, 1H), 8.21 (d, $J_1$ = 10.0 Hz, 1H), 7.99-7.97 (m, 2H), 7.79 (t, J = 73.2 Hz, 1H), 7.59-7.53 (m, 3H), 7.27-7.24 (m, 2H), 5.83 (s, 2H); LC/MS (ESI): 414 [M + H]$^+$ |
| 23 | 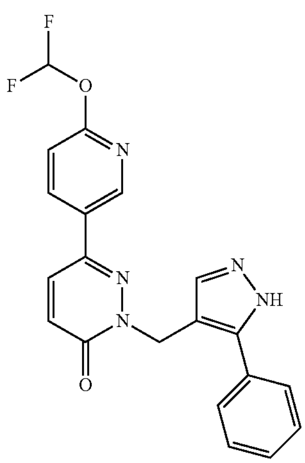 [SMILES: O=c1ccc(-c2ccc(OC(F)F)nc2)nn1Cc1cn[nH]c1-c1ccccc1] | 6-(6-(difluoromethoxy)pyridin-3-yl)-2-((5-phenyl-1H-pyrazol-4-yl)methyl)pyridazin-3(2H)-one | [M + H]+ 396.2 |
| 24 | 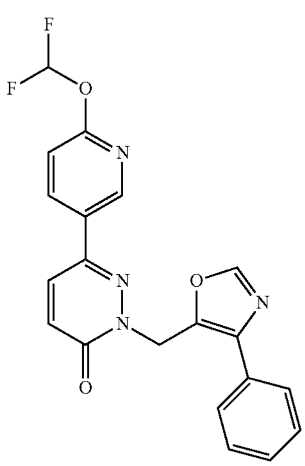 [SMILES: O=c1ccc(-c2ccc(OC(F)F)nc2)nn1Cc1ocnc1-c1ccccc1] | 6-(6-(difluoromethoxy)pyridin-3-yl)-2-((4-phenyloxazol-5-yl)methyl)pyridazin-3(2H)-one | [M + H]+ 397.2 |

TABLE 1-continued

| Cmpd No. | Structure | Name | NMR/MS |
|---|---|---|---|
| 25 | 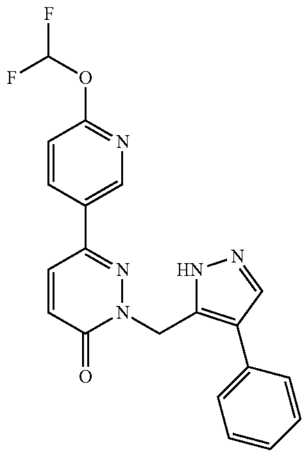 [SMILES: O=c1ccc(-c2ccc(OC(F)F)nc2)nn1Cc1[nH]ncc1-c1ccccc1] | 6-(6-(difluoromethoxy)pyridin-3-yl)-2-((4-phenyl-1H-pyrazol-5-yl)methyl)pyridazin-3(2H)-one | [M + H]+ 396.1 |
| 26 | 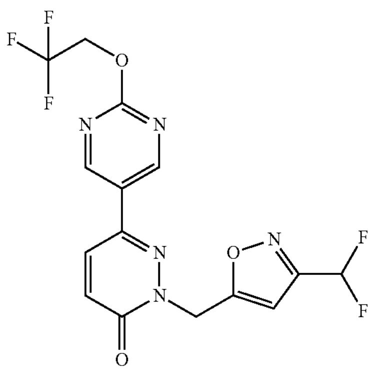 [SMILES: O=c1ccc(-c2cnc(OCC(F)(F)F)nc2)nn1Cc1cc(C(F)F)no1] | 2-((3-(difluoromethyl)isoxazol-5-yl)methyl)-6-(2-(2,2,2-trifluoroethoxy)pyrimidin-5-yl)pyridazin-3(2H)-one | [M + H]+ 404.1 |
| 27 | 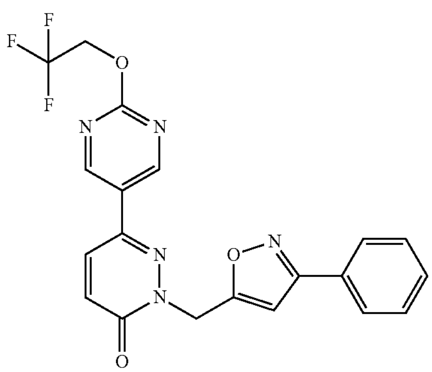 [SMILES: O=c1ccc(-c2cnc(OCC(F)(F)F)nc2)nn1Cc1cc(-c2ccccc2)no1] | 2-((3-phenylisoxazol-5-yl)methyl)-6-(2-(2,2,2-trifluoroethoxy)pyrimidin-5-yl)pyridazin-3(2H)-one | [M + H]+ 430.1 |
| 28 | 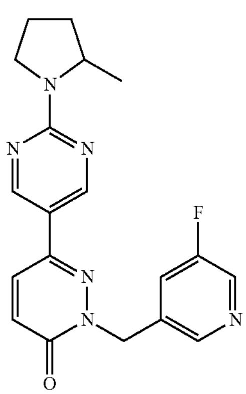 [SMILES: CC1CCCN1c1ncc(-c2ccc(=O)n(Cc3cncc(F)c3)n2)cn1] | 2-((5-fluoropyridin-3-yl)methyl)-6-(2-(2-methylpyrrolidin-1-yl)pyrimidin-5-yl)pyridazin-3(2H)-one | [M + H]+ 367.1 |

TABLE 1-continued

| Cmpd No. | Structure | Name | NMR/MS |
|---|---|---|---|
| 30 | 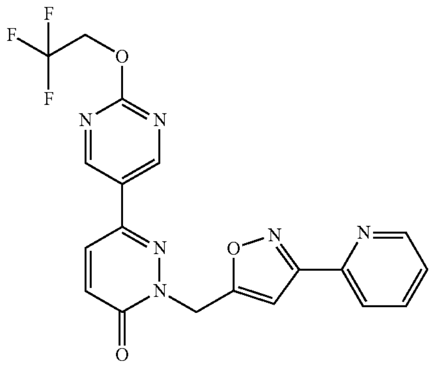 [SMILES: O=c1ccc(-c2cnc(OCC(F)(F)F)nc2)nn1Cc1cc(-c2ccccn2)no1] | 2-((3-(pyridin-2-yl)isoxazol-5-yl)methyl)-6-(2-(2,2,2-trifluoroethoxy)pyrimidin-5-yl)pyridazin-3(2H)-one | [M + H]+ 431.2 |
| 31 | 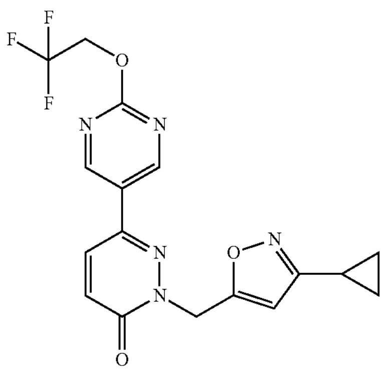 [SMILES: O=c1ccc(-c2cnc(OCC(F)(F)F)nc2)nn1Cc1cc(C2CC2)no1] | 2-((3-cyclopropylisoxazol-5-yl)methyl)-6-(2-(2,2,2-trifluoroethoxy)pyrimidin-5-yl)pyridazin-3(2H)-one | [M + H]+ 394.1 |
| 32 | 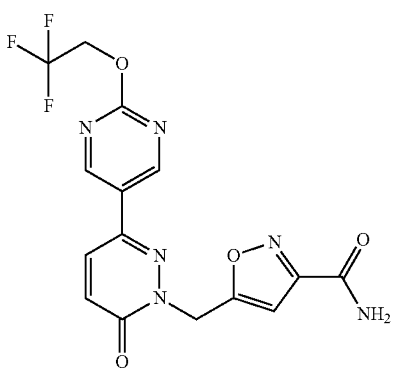 [SMILES: NC(=O)c1cc(Cn2nc(-c3cnc(OCC(F)(F)F)nc3)ccc2=O)on1] | 5-((6-oxo-3-(2-(2,2,2-trifluoroethoxy)pyrimidin-5-yl)pyridazin-1(6H)-yl)methyl)isoxazole-3-carboxamide | [M + H]+ 397.1 |
| 33 | 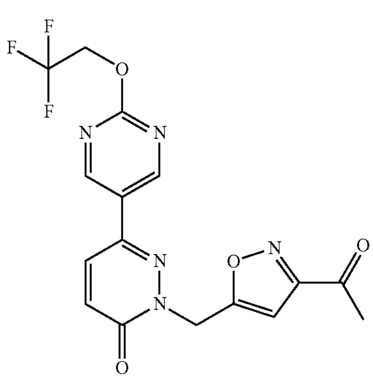 [SMILES: CC(=O)c1cc(Cn2nc(-c3cnc(OCC(F)(F)F)nc3)ccc2=O)on1] | 2-((3-acetylisoxazol-5-yl)methyl)-6-(2-(2,2,2-trifluoroethoxy)pyrimidin-5-yl)pyridazin-3(2H)-one | [M + H]+ 396.1 |

TABLE 1-continued

| Cmpd No. | Structure | Name | NMR/MS |
|---|---|---|---|
| 34 | 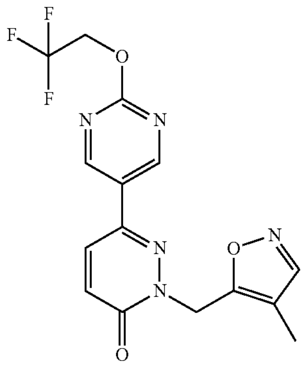 [SMILES: Cc1cnoc1Cn1nc(-c2cnc(OCC(F)(F)F)nc2)ccc1=O] | 2-((4-methylisoxazol-5-yl)methyl)-6-(2-(2,2,2-trifluoroethoxy)pyrimidin-5-yl)pyridazin-3(2H)-one | [M + H]+ 368.1 |
| 36 | 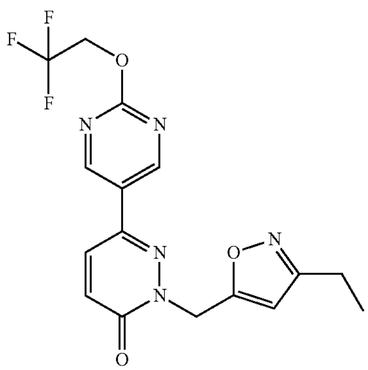 [SMILES: CCc1cc(Cn2nc(-c3cnc(OCC(F)(F)F)nc3)ccc2=O)on1] | 2-((3-ethylisoxazol-5-yl)methyl)-6-(2-(2,2,2-trifluoroethoxy)pyrimidin-5-yl)pyridazin-3(2H)-one | [M + H]+ 382.1 |
| 37 | 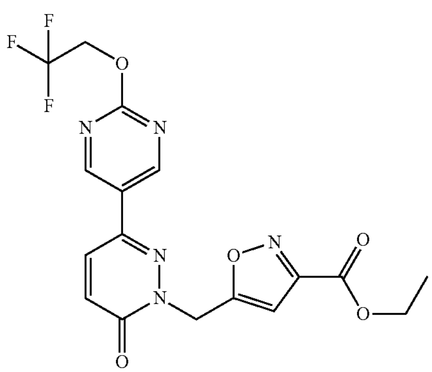 [SMILES: CCOC(=O)c1cc(Cn2nc(-c3cnc(OCC(F)(F)F)nc3)ccc2=O)on1] | ethyl 5-((6-oxo-3-(2-(2,2,2-trifluoroethoxy)pyrimidin-5-yl)pyridazin-1(6H)-yl)methyl)isoxazole-3-carboxylate | [M + H]+ 426.2 |
| 38 | 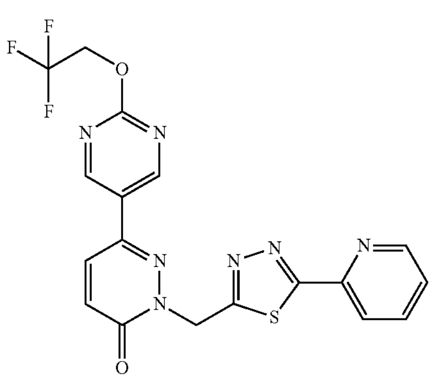 [SMILES: O=c1ccc(-c2cnc(OCC(F)(F)F)nc2)nn1Cc1nnc(-c2ccccn2)s1] | 2-((5-(pyridin-2-yl)-1,3,4-thiadiazol-2-yl)methyl)-6-(2-(2,2,2-trifluoroethoxy)pyrimidin-5-yl)pyridazin-3(2H)-one | [M + H]+ 448.5 |

TABLE 1-continued

| Cmpd No. | Structure | Name | NMR/MS |
|---|---|---|---|
| 39 | 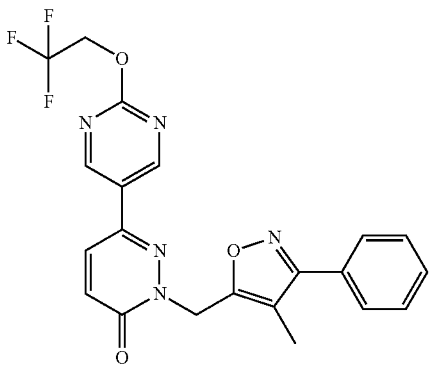 [SMILES: Cc1c(-c2ccccc2)noc1Cn1nc(-c2cnc(OCC(F)(F)F)nc2)ccc1=O] | 2-((4-methyl-3-phenylisoxazol-5-yl)methyl)-6-(2-(2,2,2-trifluoroethoxy)pyrimidin-5-yl)pyridazin-3(2H)-one | [M + H]+ 444.2 |
| 40 | 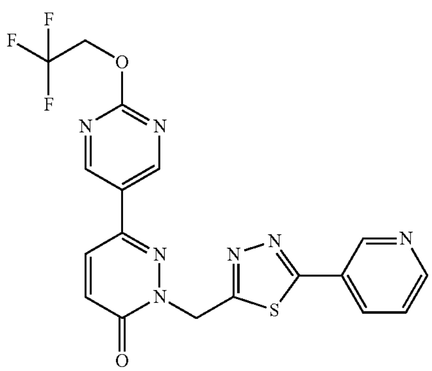 [SMILES: O=c1ccc(-c2cnc(OCC(F)(F)F)nc2)nn1Cc1nnc(-c2cccnc2)s1] | 2-((5-(pyridin-3-yl)-1,3,4-thiadiazol-2-yl)methyl)-6-(2-(2,2,2-trifluoroethoxy)pyrimidin-5-yl)pyridazin-3(2H)-one | [M + H]+ 448.2 |
| 41 | 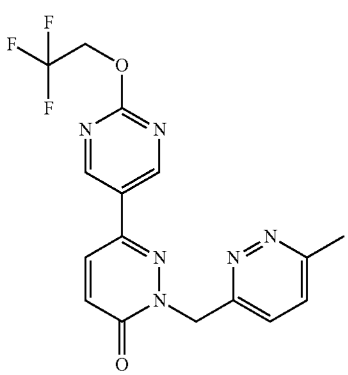 [SMILES: Cc1ccc(Cn2nc(-c3cnc(OCC(F)(F)F)nc3)ccc2=O)nn1] | 2-((6-methylpyridazin-3-yl)methyl)-6-(2-(2,2,2-trifluoroethoxy)pyrimidin-5-yl)pyridazin-3(2H)-one | [M + H]+ 379.2 |
| 42 | 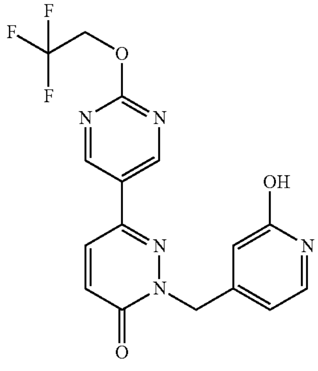 [SMILES: O=c1ccc(-c2cnc(OCC(F)(F)F)nc2)nn1Cc1ccnc(O)c1] | 2-((2-hydroxypyridin-4-yl)methyl)-6-(2-(2,2,2-trifluoroethoxy)pyrimidin-5-yl)pyridazin-3(2H)-one | [M + H]+ 380.2 |

TABLE 1-continued

| Cmpd No. | Structure | Name | NMR/MS |
|---|---|---|---|
| 43 | 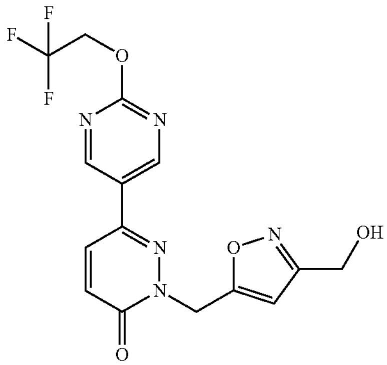 [SMILES: O=c1ccc(-c2cnc(OCC(F)(F)F)nc2)nn1Cc1cc(CO)no1] | 2-((3-(hydroxymethyl)isoxazol-5-yl)methyl)-6-(2-(2,2,2-trifluoroethoxy)pyrimidin-5-yl)pyridazin-3(2H)-one | [M + H]+ 384.1 |
| 44 | 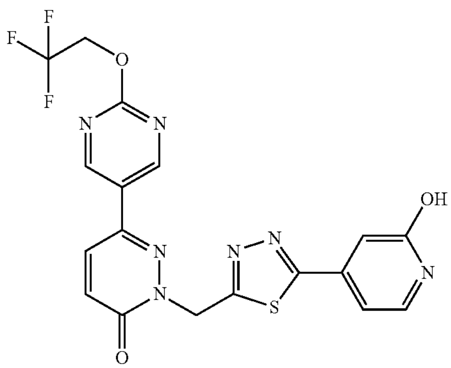 [SMILES: O=c1ccc(-c2cnc(OCC(F)(F)F)nc2)nn1Cc1nnc(-c2ccnc(O)c2)s1] | 2-((5-(2-hydroxypyridin-4-yl)-1,3,4-thiadiazol-2-yl)methyl)-6-(2-(2,2,2-trifluoroethoxy)pyrimidin-5-yl)pyridazin-3(2H)-one | [M + H]+ 464.2 |
| 45 | 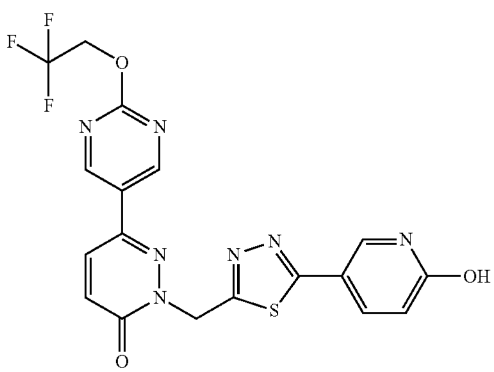 [SMILES: O=c1ccc(-c2cnc(OCC(F)(F)F)nc2)nn1Cc1nnc(-c2ccc(O)nc2)s1] | 2-((5-(6-hydroxypyridin-3-yl)-1,3,4-thiadiazol-2-yl)methyl)-6-(2-(2,2,2-trifluoroethoxy)pyrimidi-5-yl)pyridazin-3(2H)-one | [M + H]+ 464.1 |
| 46 | 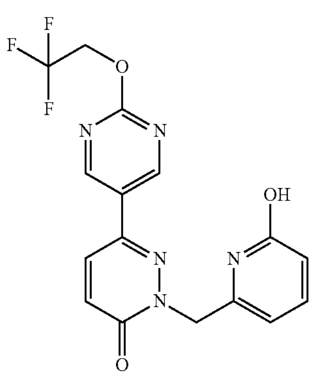 [SMILES: O=c1ccc(-c2cnc(OCC(F)(F)F)nc2)nn1Cc1cccc(O)n1] | 2-((6-hydroxypyridin-2-yl)methyl)-6-(2-(2,2,2-trifluoroethoxy)pyrimidin-5-yl)pyridazin-3(2H)-one | [M + H]+ 380.1 |

TABLE 1-continued

| Cmpd No. | Structure | Name | NMR/MS |
|---|---|---|---|
| 47 | 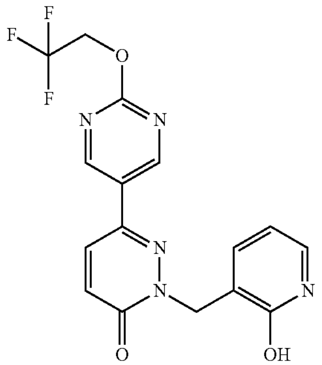 [SMILES: O=c1ccc(-c2cnc(OCC(F)(F)F)nc2)nn1Cc1cccnc1O] | 2-((2-hydroxypyridin-3-yl)methyl)-6-(2-(2,2,2-trifluoroethoxy)pyrimidin-5-yl)pyridazin-3(2H)-one | [M + H]+ 380.2 |
| 48 | 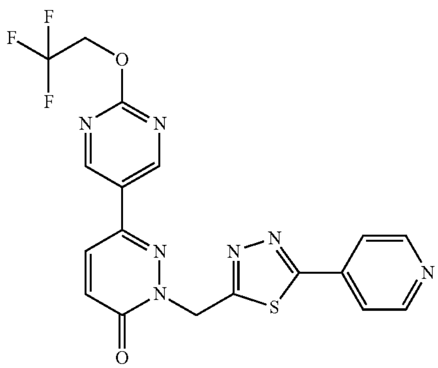 [SMILES: O=c1ccc(-c2cnc(OCC(F)(F)F)nc2)nn1Cc1nnc(-c2ccncc2)s1] | 2-((5-(pyridin-4-yl)-1,3,4-thiadiazol-2-yl)methyl)-6-(2-(2,2,2-trifluoroethoxy)pyrimidin-5-yl)pyridazin-3(2H)-one | [M + H]+ 448.2 |
| 49 | 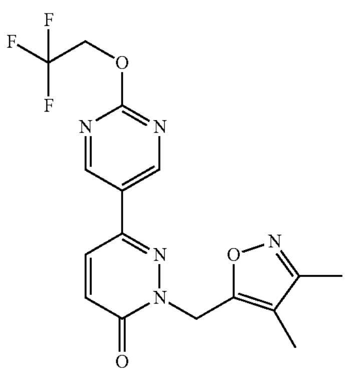 [SMILES: Cc1noc(Cn2nc(-c3cnc(OCC(F)(F)F)nc3)ccc2=O)c1C] | 2-((3,4-dimethylisoxazol-5-yl)methyl)-6-(2-(2,2,2-trifluoroethoxy)pyrimidin-5-yl)pyridazin-3(2H)-one | [M + H]+ 382.1 |
| 50 | 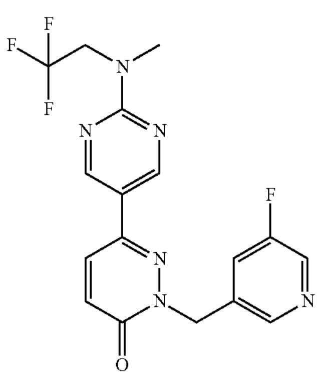 [SMILES: CN(CC(F)(F)F)c1ncc(-c2ccc(=O)n(Cc3cncc(F)c3)n2)cn1] | 2-((5-fluoropyridin-3-yl)methyl)-6-(2-(methyl(2,2,2-trifluoroethyl)amino)pyrimidin-5-yl)pyridazin-3(2H)-one | [M + H]+ 395.2 |

TABLE 1-continued

| Cmpd No. | Structure | Name | NMR/MS |
|---|---|---|---|
| 51 | 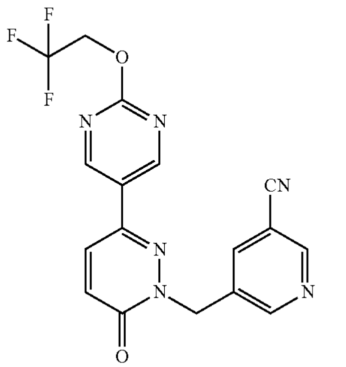 [SMILES: N#Cc1cncc(Cn2nc(-c3cnc(OCC(F)(F)F)nc3)ccc2=O)c1] | 5-((6-oxo-3-(2-(2,2,2-trifluoroethoxy)pyrimidin-5-yl)pyridazin-1(6H)-yl)methyl)nicotinonitrile | [M + H]+ 389.1 |
| 52 | 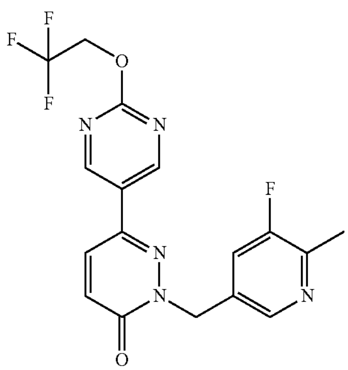 [SMILES: Cc1ncc(Cn2nc(-c3cnc(OCC(F)(F)F)nc3)ccc2=O)cc1F] | 2-((5-fluoro-6-methylpyridin-3-yl)methyl)-6-(2-(2,2,2-trifluoroethoxy)pyrimidin-5-yl)pyridazin-3(2H)-one | [M + H]+ 396.1 |
| 53 | 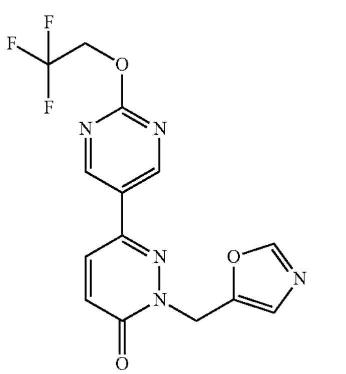 [SMILES: O=c1ccc(-c2cnc(OCC(F)(F)F)nc2)nn1Cc1cnco1] | 2-(oxazol-5-ylmethyl)-6-(2-(2,2,2,-trifluoroethoxy)pyrimidin-5-yl)pyridazin-3(2H)-one | [M + H]+ 354.1 |
| 54 | 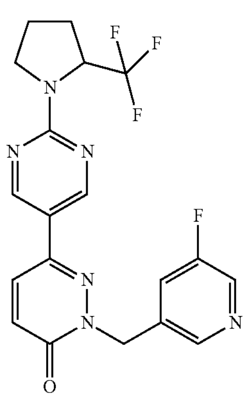 [SMILES: O=c1ccc(-c2cnc(N3CCCC3C(F)(F)F)nc2)nn1Cc1cncc(F)c1] | 2-((5-fluoropyridin-3-yl)methyl)-6-(2-(2-(trifluoromethyl)pyrrolidin-1-yl)pyrimidin-5-yl)pyridazin-3(2H)-one | [M + H]+ 421.2 |

TABLE 1-continued

| Cmpd No. | Structure | Name | NMR/MS |
|---|---|---|---|
| 55 | 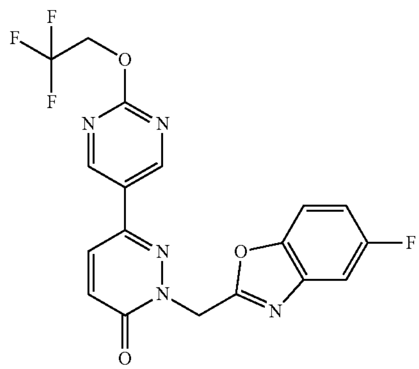 [SMILES: O=c1ccc(-c2cnc(OCC(F)(F)F)nc2)nn1Cc1nc2cc(F)ccc2o1] | 2-((5-fluorobenzo[d]oxazol-2-yl)methyl)-6-(2-(2,2,2,-trifluoroethoxy)pyrimidin-5-yl)pyridazin-3(2H)-one | [M + H]+ 422.2 |
| 56 | 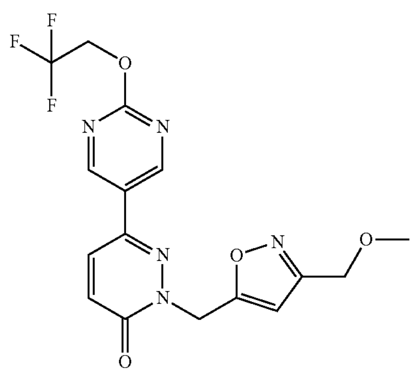 [SMILES: COCc1cc(Cn2nc(-c3cnc(OCC(F)(F)F)nc3)ccc2=O)on1] | 2-((3-(methoxymethyl)isoxazol-5-yl)methyl)-6-(2-(2,2,2-trifluoroethoxy)pyrimidin-5-yl)pyridazin-3(2H)-one | [M + H]+ 398.2 |
| 57 | 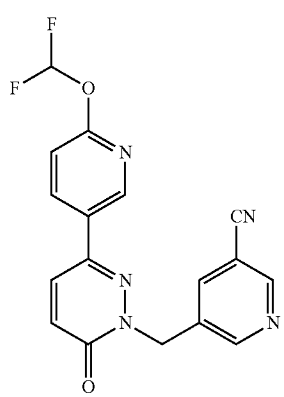 [SMILES: N#Cc1cncc(Cn2nc(-c3ccc(OC(F)F)nc3)ccc2=O)c1] | 5-((3-(6-(difluoromethoxy)pyridin-3-yl)-6-oxopyridazin-1(6H)-yl)methyl)nicotinonitrile | [M + H]+ 356.2 |
| 58 | 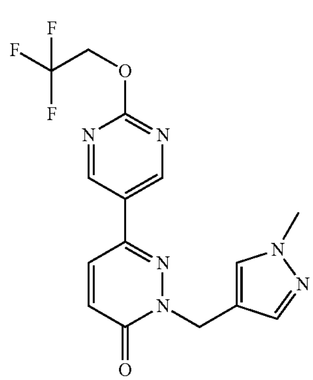 [SMILES: Cn1cc(Cn2nc(-c3cnc(OCC(F)(F)F)nc3)ccc2=O)cn1] | 2-((1-methyl-1H-pyrazol-4-yl)methyl)-6-(2-(2,2,2-trifluoroethoxy)pyrimidin-5-yl)pyridazin-3(2H)-one | [M + H]+ 367.1 |

TABLE 1-continued

| Cmpd No. | Structure | Name | NMR/MS |
|---|---|---|---|
| 59 | 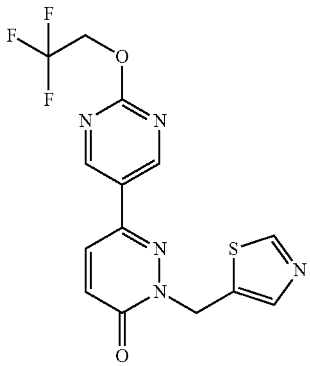 | 2-(thiazol-5-ylmethyl)-6-(2-(2,2,2-trifluoroethoxy)pyrimidin-5-yl)pyridazin-3(2H)-one | [M + H]+ 370.1 |
| 60 | 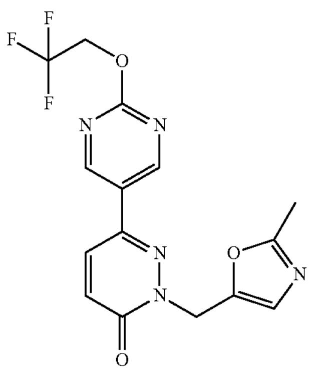 [SMILES: Cc1ncc(Cn2nc(-c3cnc(OCC(F)(F)F)nc3)ccc2=O)o1] | 2-((2-methyloxazol-5-yl)methyl)-6-(2-(2,2,2-trifluoroethoxy)pyrimidin-5-yl)pyridazin-3(2H)-one | [M + H]+ 368.2 |
| 61 | 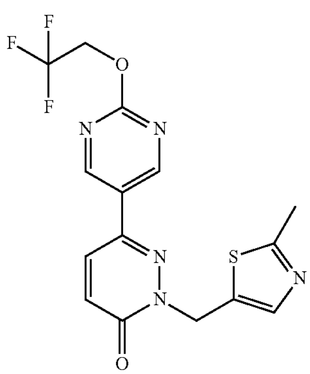 [SMILES: Cc1ncc(Cn2nc(-c3cnc(OCC(F)(F)F)nc3)ccc2=O)s1] | 2-((2-methylthiazol-5-yl)methyl)-6-(2-(2,2,2-trifluoroethoxy)pyrimidin-5-yl)pyridazin-3(2H)-one | [M + H]+ 384.2 |
| 62 | 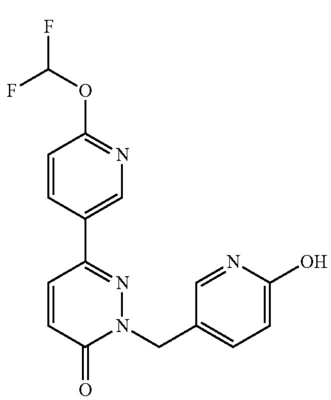 [SMILES: O=c1ccc(-c2ccc(OC(F)F)nc2)nn1Cc1ccc(O)nc1] | 6-(6-(difluoromethoxy)pyridin-3-yl)-2-((6-hydroxypyridin-3-yl)methyl)pyridazin-3(2H)-one | [M + H]+ 380.1 |

TABLE 1-continued

| Cmpd No. | Structure | Name | NMR/MS |
|---|---|---|---|
| 63 | 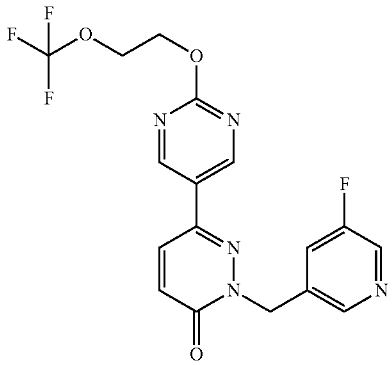 [SMILES: O=c1ccc(-c2cnc(OCCOC(F)(F)F)nc2)nn1Cc1cncc(F)c1] | 2-((5-fluoropyridin-3-yl)methyl)-6-(2-(2-(trifluoromethoxy)ethoxy)pyrimidin-5-yl)pyridazin-3(2H)-one | [M + H]+ 411.2 |
| 64 | 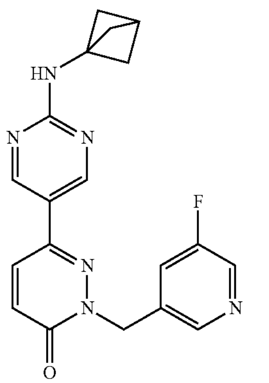 [SMILES: O=c1ccc(-c2cnc(NC34CC(C3)C4)nc2)nn1Cc1cncc(F)c1] | 6-(2-(bicyclo[1.1.1]pentan-1-ylamino)pyrimidin-5-yl)-2-((5-fluoropyridin-3-yl)methyl)pyridazin-3(2H)-one | $^1$H NMR (300 MHz, DMSO-d6) δ 8.81 (s, 2H), 8.54-8.52 (m, 2H), 8.30 (s, 1H), 8.02 (d, J = 9.9 Hz, 1H), 7.77-7.72 (m, 1H), 7.08 (d, J = 9.9 Hz, 1H), 5.36 (s, 2H), 2.46 (s, 1H), 2.09 (s, 6H); LC/MS Rt = 1.556 min; MS m/z: 365 [M + H]$^+$ |
| 65 | 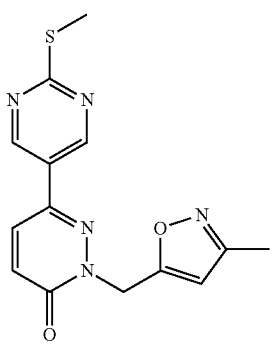 [SMILES: CSc1ncc(-c2ccc(=O)n(Cc3cc(C)no3)n2)cn1] | 2-((3-methylisoxazol-5-yl)methyl)-6-(2-(methylthio)pyrimidin-5-yl)pyridazin-3(2H)-one | $^1$H NMR (400 MHz, DMSO-d$_6$) δ 9.09 (s, 2H), 8.15 (d, J = 9.6 Hz, 1H), 7.21-7.19 (m, 1H), 6.39 (s, 1H), 5.46 (s, 2H), 2.58 (s, 3H), 2.21 (s, 3H); LC/MS Rt = 1.219 min; MS m/z: 316 [M + H]$^+$ |
| 66 | 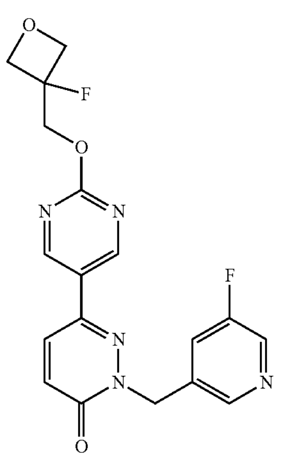 [SMILES: O=c1ccc(-c2cnc(OCC3(F)COC3)nc2)nn1Cc1cncc(F)c1] | 6-(2-((3-fluorooxetan-3-yl)methoxy)pyrimidin-5-yl)-2-((5-fluoropyridin-3-yl)methyl)pyridazin-3(2H)-one | $^1$H NMR (DMSO-d$_6$, 400 MHz) δ 9.13 (s, 2H), 8.54 (d, J = 2.8 Hz, 2H), 8.14 (d, J = 9.6 Hz, 1H), 7.78 (dd, J = 9.6, 2.8 Hz, 1H), 7.17 (d, J = 9.6 Hz, 1H), 5.41 (s, 2H), 4.87 (s, 1H), 4.81 (s, 1H), 4.77 (s, 2H), 4.72 (s, 2H); LC/MS Rt = 0.929 min, MS m/z: 388 [M + H]$^+$ |

TABLE 1-continued

| Cmpd No. | Structure | Name | NMR/MS |
|---|---|---|---|
| 67 | 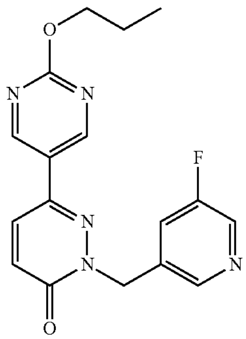 | 2-((5-fluoropyridin-3-yl)methyl)-6-(2-propoxypyrimidin-5-yl)pyridazin-3(2H)-one | $^1$H NMR (400 MHz, DMSO-$d_6$) δ 9.09 (s, 2H), 8.55-8.54 (m, 2H), 8.12 (d, J = 10 Hz, 1H), 7.79-7.76 (m, 1H), 7.17 (d, J = 9.6 Hz, 1H), 5.40 (s, 2H), 4.33 (t, J = 6.4 Hz, 2H), 1.80-1.75 (m, 2H), 0.99 (t, J = 7.2 Hz, 3H); MS m/z: 328 [M + H]$^+$ |
| 68 | 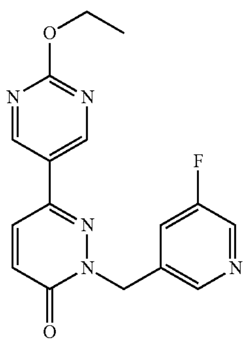 [SMILES: CCOc1ncc(-c2ccc(=O)n(Cc3cncc(F)c3)n2)cn1] | 6-(2-ethoxypyrimidin-5-yl)-2-((5-fluoropyridin-3-yl)methyl)pyridazin-3(2H)-one | $^1$H NMR (300 MHz, DMSO-$d_6$) δ 9.09 (s, 2H), 8.54 (d, J = 2.4 Hz, 2H), 8.11 (d, J = 9.9 Hz, 1H), 7.80-7.75 (m, 1H), 7.16 (d, J = 9.9 Hz, 1H), 5.40 (s, 2H), 4.42 (q, J = 6.9, 7.2 Hz, 2H), 1.36 (t, J = 6.9 Hz, 3H); LC/MS Rt = 0.850 min; MS m/z: 328 [M + H]$^+$ |
| 69 | 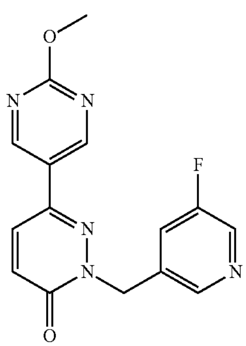 [SMILES: COc1ncc(-c2ccc(=O)n(Cc3cncc(F)c3)n2)cn1] | 2-((5-fluoropyridin-3-yl)methyl)-6-(2-methoxypyrimidin-5-yl)pyridazin-3(2H)-one | $^1$H NMR (400 MHz, DMSO-$d_6$) δ 9.05 (s, 2H), 8.49 (d, J = 2.8 Hz, 2H), 8.05 (d, J = 9.6 Hz, 1H), 7.75-7.71 (m, 1H), 7.12 (d, J = 9.6 Hz, 1H), 5.39 (s, 2H), 3.97 (s, 3H); LC/MS Rt = 2.684 min; MS m/z: 314 [M + H]$^+$ |
| 70 | 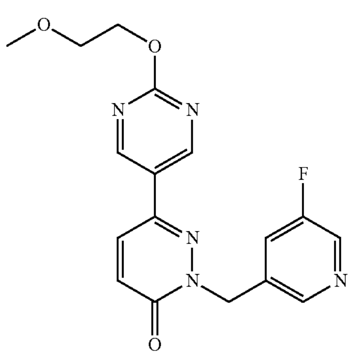 [SMILES: COCCOc1ncc(-c2ccc(=O)n(Cc3cncc(F)c3)n2)cn1] | 2-((5-fluoropyridin-3-yl)methyl)-6-(2-(2-methoxyethoxy)pyrimidin-5-yl)pyridazin-3(2H)-one | $^1$H NMR (DMSO-$d_6$, 400 MHz) δ 9.10 (s, 2H), 8.54 (d, J = 2.4 Hz, 2H), 8.12 (d, J = 10.0 Hz, 1H), 7.82-7.74 (m, 1H), 7.16 (d, J = 9.6 Hz, 1H), 5.40 (s, 2H), 4.52-4.45 (m, 2H), 3.73-3.66 (m, 2H), 3.31 (s, 3H); LC/MS: Rt = 0.810 min, MS m/z: 358 [M + H]$^+$ |

TABLE 1-continued

| Cmpd No. | Structure | Name | NMR/MS |
|---|---|---|---|
| 71 | 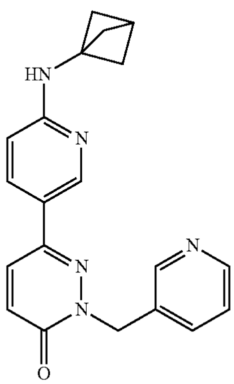 [SMILES: O=c1ccc(-c2ccc(NC34CC(C3)C4)nc2)nn1Cc1cccnc1] | 6-(6-(bicyclo[1.1.1]pentan-1-ylamino)pyridin-3-yl)-2-(pyridin-3-ylmethyl)pyridazin-3(2H)-one | $^1$H NMR (300 MHz, Methanol-$d_4$) δ 8.68 (s, 1H), 8.51-8.49 (m, 2H), 8.02-7.94 (m, 3H), 7.47-7.43 (m, 1H), 7.07 (d, J = 9.9 Hz, 1H), 6.73 (d, J = 9.0 Hz, 1H), 5.46 (s, 2H), 2.50 (s, 1H), 2.18 (s, 6H); LC/MS Rt = 0.732 min; MS m/z: 346 [M + H]$^+$ |
| 72 | 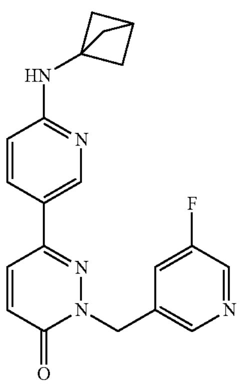 [SMILES: O=c1ccc(-c2ccc(NC34CC(C3)C4)nc2)nn1Cc1cncc(F)c1] | 6-(6-(bicyclo[1.1.1]pentan-1-ylamino)pyridin-3-yl)-2-((5-fluoropyridin-3-yl)methyl)pyridazin-3(2H)-one | [M + H]+ 364.1 |
| 73 | 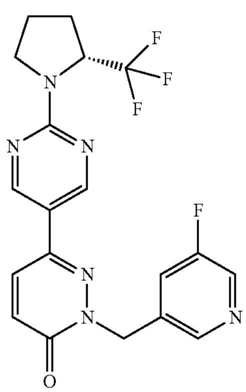 [SMILES: O=c1ccc(-c2cnc(N3CCC[C@@H]3C(F)(F)F)nc2)nn1Cc1cncc(F)c1] | (R)-2-((5-fluoropyridin-3-yl)methyl)-6-(2-(2-(trifluoromethyl)pyrrolidin-1-yl)pyrimidin-5-yl)pyridazin-3(2H)-one | [M + H]+ 421.2 |
| 74 | 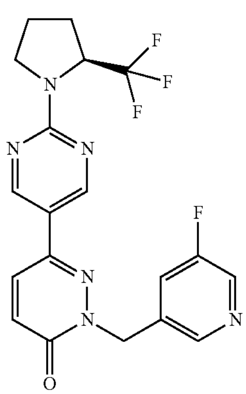 [SMILES: O=c1ccc(-c2cnc(N3CCC[C@H]3C(F)(F)F)nc2)nn1Cc1cncc(F)c1] | (S)-2-((5-fluoropyridin-3-yl)methyl)-6-(2-(2-(trifluoromethyl)pyrrolidin-1-yl)pyrimidin-5-yl)pyridazin-3(2H)-one | [M + H]+ 421.1 |

TABLE 1-continued

| Cmpd No. | Structure | Name | NMR/MS |
|---|---|---|---|
| 75 | 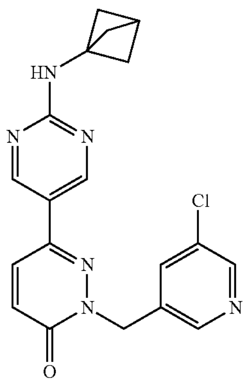 [SMILES: O=c1ccc(-c2cnc(NC34CC(C3)C4)nc2)nn1Cc1cncc(Cl)c1] | 6-(2-(bicyclo[1.1.1]pentan-1-ylamino)pyrimidin-5-yl)-2-((5-chloropyridin-3-yl)methyl)pyridazin-3(2H)-one | [M + H]+ 381.2 |
| 76 | 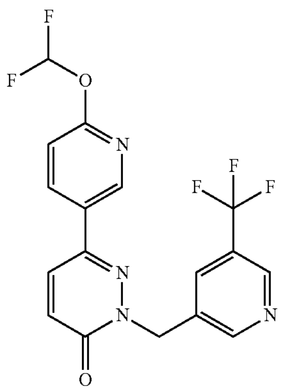 [SMILES: O=c1ccc(-c2ccc(OC(F)F)nc2)nn1Cc1cncc(C(F)(F)F)c1] | 6-(6-(difluoromethoxy)pyridin-3-yl)-2-((5-(trifluoromethyl)pyridin-3-yl)methyl)pyridazin-3(2H)-one | [M + H]+ 399.1 |
| 77 | 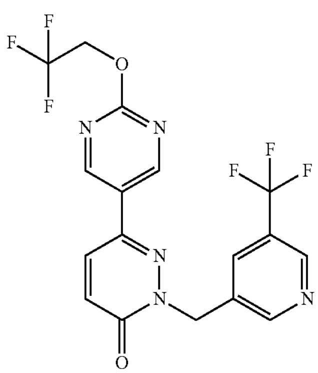 [SMILES: O=c1ccc(-c2cnc(OCC(F)(F)F)nc2)nn1Cc1cncc(C(F)(F)F)c1] | 6-(2-(2,2,2-trifluoroethoxy)pyrimidin-5-yl)-2-((5-(trifluoromethyl)pyridin-3-yl)methyl)pyridazin-3(2H)-one | [M + H]+ 432.1 |
| 78 | 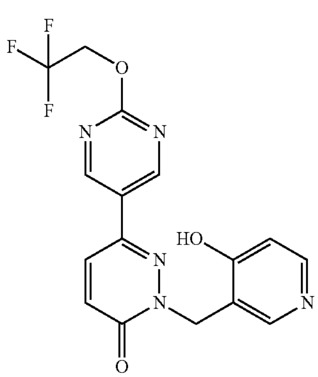 [SMILES: O=c1ccc(-c2cnc(OCC(F)(F)F)nc2)nn1Cc1cnccc1O] | 2-((4-hydroxypyridin-3-yl)methyl)-6-(2-(2,2,2-trifluoroethoxy)pyrimidin-5-yl)pyridazin-3(2H)-one | [M + H]+ 380.2 |

TABLE 1-continued

| Cmpd No. | Structure | Name | NMR/MS |
|---|---|---|---|
| 79 | 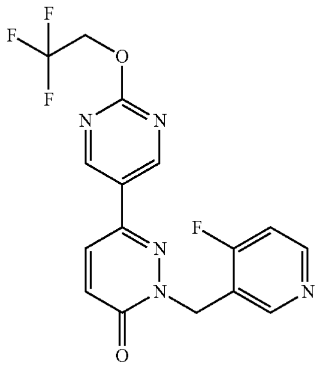 [SMILES: O=c1ccc(-c2cnc(OCC(F)(F)F)nc2)nn1Cc1cnccc1F] | 2-((4-fluoropyridin-3-yl)methyl)-6-(2-(2,2,2-trifluoroethoxy)pyrimidin-5-yl)pyridazin-3(2H)-one | [M + H]+ 382.1 |
| 80 | 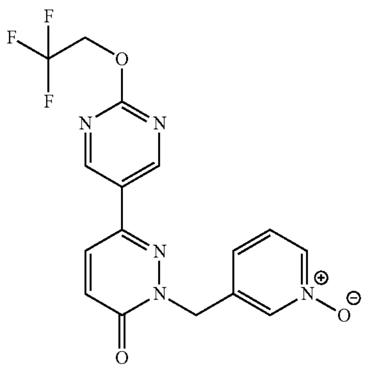 [SMILES: O=c1ccc(-c2cnc(OCC(F)(F)F)nc2)nn1Cc1ccc[n+]([O-])c1] | 3-((6-oxo-3-(2-(2,2,2-trifluoroethoxy)pyrimidin-5-yl)pyridazin-1(6H)-yl)methyl)pyridine 1-oxide | [M + H]+ 380.1 |
| 81 | 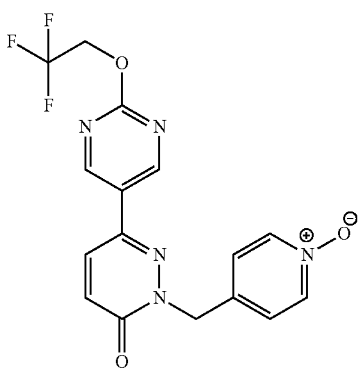 [SMILES: O=c1ccc(-c2cnc(OCC(F)(F)F)nc2)nn1Cc1cc[n+]([O-])cc1] | 4-((6-oxo-3-(2-(2,2,2-trifluoroethoxy)pyrimidin-5-yl)pyridazin-1(6H)-yl)methyl)pyridine 1-oxide | [M + H]+ 380.1 |
| 82 | 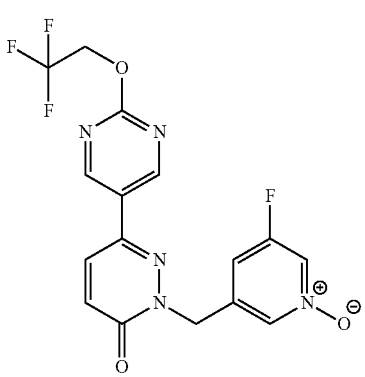 [SMILES: O=c1ccc(-c2cnc(OCC(F)(F)F)nc2)nn1Cc1cc(F)c[n+]([O-])c1] | 3-fluoro-5-((6-oxo-3-(2-(2,2,2-trifluoroethoxy)pyrimidin-5-yl)pyridazin-1(6H)-yl)methyl)pyridine 1-oxide | [M + H]+ 398.3 |

TABLE 1-continued

| Cmpd No. | Structure | Name | NMR/MS |
|---|---|---|---|
| 83 | 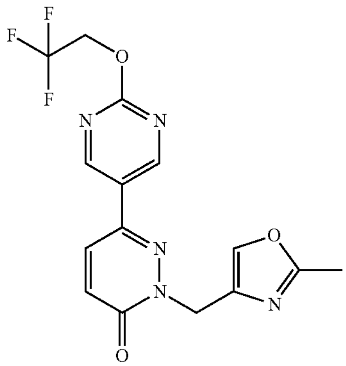 [SMILES: Cc1nc(Cn2nc(-c3cnc(OCC(F)(F)F)nc3)ccc2=O)co1] | 2-((2-methyloxazol-4-yl)methyl)-6-(2-(2,2,2-trifluoroethoxy)pyrimidin-5-yl)pyridazin-3(2H)-one | [M + H]+ 368.1 |
| 84 | 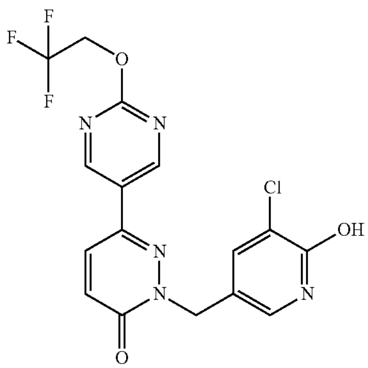 [SMILES: O=c1ccc(-c2cnc(OCC(F)(F)F)nc2)nn1Cc1cnc(O)c(Cl)c1] | 2-((5-chloro-6-hydroxypyridin-3-yl)methyl)-6-(2-(2,2,2-trifluoroethoxy)pyrimidin-5-yl)pyridazin-3(2H)-one | [M + H]+ 414.1 |
| 85 | 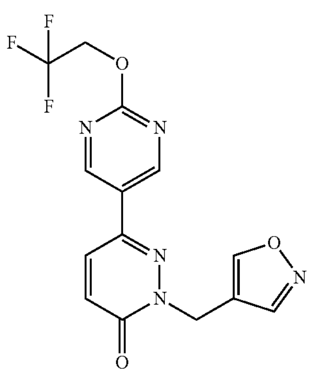 [SMILES: O=c1ccc(-c2cnc(OCC(F)(F)F)nc2)nn1Cc1cnoc1] | 2-(isoxazol-4-ylmethyl)-6-(2-(2,2,2-trifluoroethoxy)pyrimidin-5-yl)pyridazin-3(2H)-one | [M + H]+ 354.1 |
| 86 | 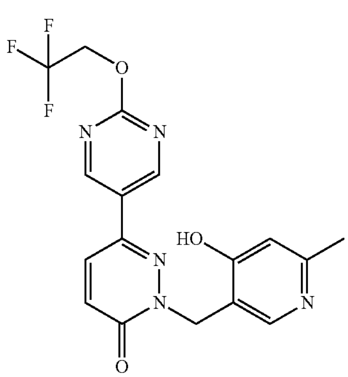 [SMILES: Cc1cc(O)c(Cn2nc(-c3cnc(OCC(F)(F)F)nc3)ccc2=O)cn1] | 2-((4-hydroxy-6-methylpyridin-3-yl)methyl)-6-(2-(2,2,2-trifluoroethoxy)pyrimidin-5-yl)pyridazin-3(2H)-one | [M + H]+ 394.1 |

TABLE 1-continued

| Cmpd No. | Structure | Name | NMR/MS |
|---|---|---|---|
| 87 | 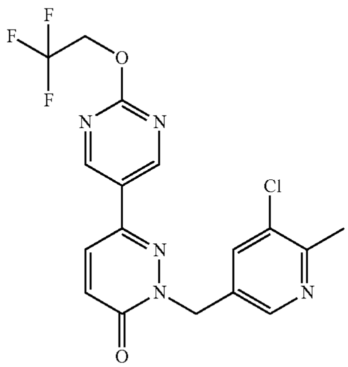 [SMILES: Cc1ncc(Cn2nc(-c3cnc(OCC(F)(F)F)nc3)ccc2=O)cc1Cl] | 2-((5-chloro-6-methylpyridin-3-yl)methyl)-6-(2-(2,2,2-trifluoroethoxy)pyrimidin-5-yl)pyridazin-3(2H)-one | [M + H]+ 412.1 |
| 88 | 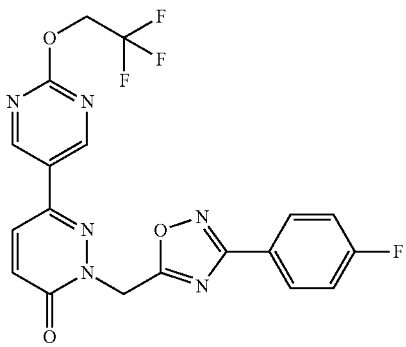 [SMILES: O=c1ccc(-c2cnc(OCC(F)(F)F)nc2)nn1Cc1nc(-c2ccc(F)cc2)no1] | 2-((3-(4-fluorophenyl)-1,2,4-oxadiazol-5-yl)methyl)-6-(2-(2,2,2-trifluoroethoxy)pyrimidin-5-yl)pyridazin-3(2H)-one | H NMR (300 MHz, DMSO-d6): δ 9.15 (s, 2H), 8.13 (d, J = 6.3 Hz, 1H), 8.11-8.05 (m, 2H), 7.30-7.21 (m, 3H), 5.81 (s, 2H), 5.03 (q, J = 8.7 Hz, 2H), LC/MS (ESI): 449 [M + H]+ |
| 89 | 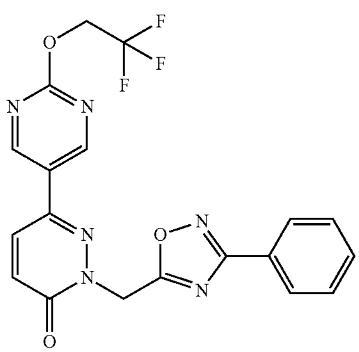 [SMILES: O=c1ccc(-c2cnc(OCC(F)(F)F)nc2)nn1Cc1nc(-c2ccccc2)no1] | 2-((3-phenyl-1,2,4-oxadiazol-5-yl)methyl)-6-(2-(2,2,2-trifluoroethoxy)pyrimidin-5-yl)pyridazin-3(2H)-one | 1H NMR (300 MHz, DMSO-d6): δ 9.16 (s, 2H), 8.15 (d, J = 9.9 Hz, 1H), 8.06-8.02 (m, 2H), 7.59-7.48 (m, 3H), 7.23 (d, J = 9.9 Hz, 1H), 5.81 (s, 2H), 5.03 (q, J = 8.4 Hz, 2H): LC/MS (ESI): 432 [M + H]+ |
| 90 | 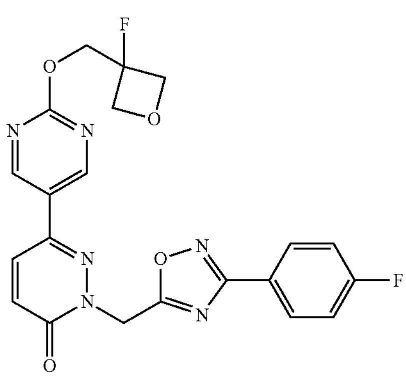 [SMILES: O=c1ccc(-c2cnc(OCC3(F)COC3)nc2)nn1Cc1nc(-c2ccc(F)cc2)no1] | 6-(2-((3-fluorooxetan-3-yl)methoxy)pyrimidin-5-yl)-2-((3-(4-fluorophenyl)-1,2,4-oxadiazol-5-yl)methyl)pyridazin-3(2H)-one | 1H NMR (CD30D, 300 MHz): δ 9.13 (s, 2H), 8.17-8.05 (m, 3H), 7.30-7.21 (m, 3H), 5.80 (s, 2H), 5.03-4.75 (m, 6H); LC/MS (ESI): 456 [M + H]+ |

TABLE 1-continued

| Cmpd No. | Structure | Name | NMR/MS |
|---|---|---|---|
| 91 | 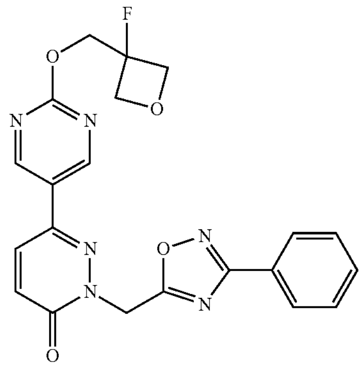 [SMILES: O=c1ccc(-c2cnc(OCC3(F)COC3)nc2)nn1Cc1nc(-c2ccccc2)no1] | 6-(2-((3-fluorooxetan-3-yl)methoxy)pyrimidin-5-yl)-2-((3-phenyl-1,2,4-oxadiazol-5-yl)methyl)pyridazin-3(2H)-one | 1H NMR (DMSO-d6, 300 MHz): δ 9.13 (s, 2H), 8.24 (d, J = 9.6 Hz, 1H), 8.00-7.97 (m, 2H), 7.60-7.56 (m, 3H), 7.27 (d, J = 9.6 Hz, 1H), 5.80 (s, 2H), 4.88-4.71 (m, 6H); LC/MS (ESI): 437 [M + H]+ |
| 92 | 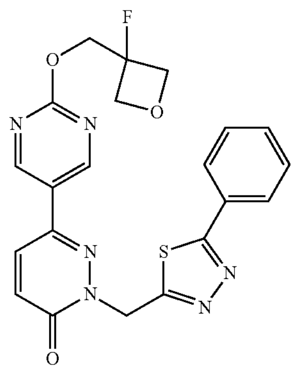 [SMILES: O=c1ccc(-c2cnc(OCC3(F)COC3)nc2)nn1Cc1nnc(-c2ccccc2)s1] | 6-(2-((3-fluorooxetan-3-yl)methoxy)pyrimidin-5-yl)-2-((5-phenyl-1,3,4-thiadiazol-2-yl)methyl)pyridazin-3(2H)-one | 1H NMR (DMSO-d6, 300 MHz): δ 9.14 (s, 2H), 8.20 (d, J\ = 9.6 Hz, 1H), 8.00-7.97 (m, 2H), 7.59-7.53 (m, 3H), 7.26 (d, J\ = 9.9 Hz, 1H), 5.83 (s, 2H), 4.88-4.71 (m, 6H); LC/MS (ESI): 453 [M + H]+ |
| 93 | 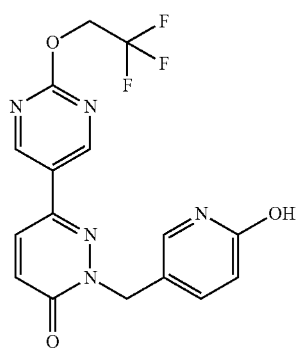 [SMILES: O=c1ccc(-c2cnc(OCC(F)(F)F)nc2)nn1Cc1ccc(O)nc1] | 2-((6-hydroxypyridin-3-yl)methyl)-6-(2-(2,2,2-trifluoroethoxy)pyrimidin-5-yl)pyridazin-3(2H)-one | [M + H]+ 380.2 |
| 94 | 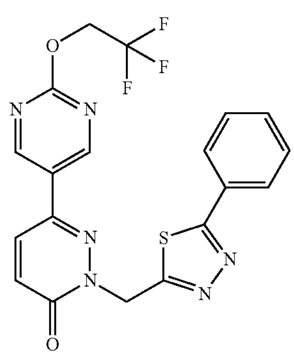 [SMILES: O=c1ccc(-c2cnc(OCC(F)(F)F)nc2)nn1Cc1nnc(-c2ccccc2)s1] | 2-((5-phenyl-1,3,4-thiadiazol-2-yl)methyl)-6-(2-(2,2,2-trifluoroethoxy)pyrimidin-5-yl)pyridazin-3(2H)-one | [M + H]+ 447.2 |

TABLE 1-continued

| Cmpd No. | Structure | Name | NMR/MS |
|---|---|---|---|
| 95 | 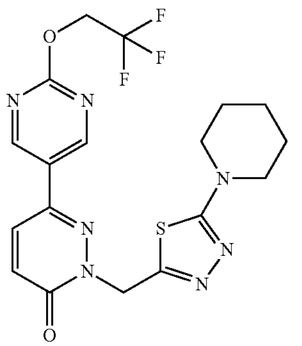 [SMILES: O=c1ccc(-c2cnc(OCC(F)(F)F)nc2)nn1Cc1nnc(N2CCCCC2)s1] | 2-((5-(piperidin-1-yl)-1,3,4-thiadiazol-2-yl)methyl)-6-(2-(2,2,2-trifluoroethoxy)pyrimidin-5-yl)pyridazin-3(2H)-one | [M + H]+ 454.2 |
| 96 | 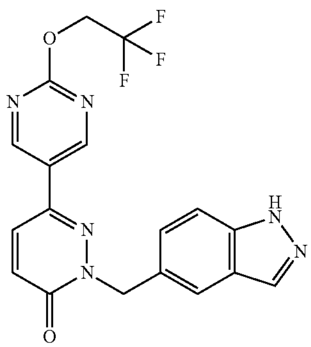 [SMILES: O=c1ccc(-c2cnc(OCC(F)(F)F)nc2)nn1Cc1ccc2[nH]ncc2c1] | 2-((1H-indazol-5-yl)methyl)-6-(2-(2,2,2-trifluoroethoxy)pyrimidin-5-yl)pyridazin-3(2H)-one | [M + H]+ 403.2 |
| 97 | 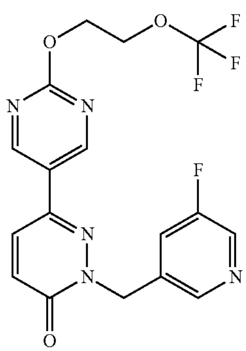 [SMILES: O=c1ccc(-c2cnc(OCCOC(F)(F)F)nc2)nn1Cc1cncc(F)c1] | 2-((5-fluoropyridin-3-yl)methyl)-6-(2-(2-(trifluoromethoxy)ethoxy)pyrimidin-5-yl)pyridazin-3(2H)-one | 1H NMR (300 MHz, DMSO-d6) δ 9.12 (s, 2H), 8.54 (d, J = 2.4 Hz, 2H), 8.13 (d, J = 9.9 Hz, 1H), 7.83-7.73 (m, 1H), 7.17 (d, J = 9.9 Hz, 1H), 5.40 (s, 2H), 4.63 (t, J = 3.9 Hz, 2H), 4.52-4.43 (m, 2H); LC/MS Rt = 1.677 min; MS m/z: 412 [M + H]+ |
| 99 | 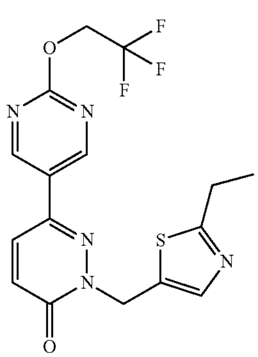 [SMILES: CCc1ncc(Cn2nc(-c3cnc(OCC(F)(F)F)nc3)ccc2=O)s1] | 2-((2-ethylthiazol-5-yl)methyl)-6-(2-(2,2,2-trifluoroethoxy)pyrimidin-5-yl)pyridazin-3(2H)-one | 1H NMR (400 MHz, DMSO-d$_6$): δ 9.16 (s, 2H), 8.12 (d, J = 9.6 Hz, 1H), 7.75 (s, 1H), 7.17 (d, J = 9.6 Hz, 1H), 5.48 (s, 2H), 5.12 (q, J = 8.8 Hz, 2H), 2.92 (q, J = 7.6 Hz, 2H), 1.24 (t, J = 7.6 Hz, 3H); LC?MS Rt = 1.873 min; MS m/z: 398 [M + H]+ |

TABLE 1-continued

| Cmpd No. | Structure | Name | NMR/MS |
|---|---|---|---|
| 100 | 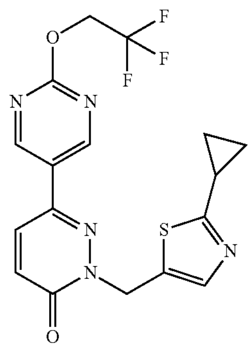 [SMILES: O=c1ccc(-c2cnc(OCC(F)(F)F)nc2)nn1Cc1cnc(C2CC2)s1] | 2-((2-cyclopropylthiazol-5-yl)methyl)-6-(2-(2,2,2-trifluoroethoxy)pyrimidin-5-yl)pyridazin-3(2H)-one | $^1$H NMR (DMSO-$d_6$, 300 MHz) δ 9.17 (s, 2H), 8.13 (d, J = 9.9 Hz, 1H), 7.68 (s, 1H), 7.18 (d, J = 9.9 Hz, 1H), 5.45 (s, 2H), 5.13 (q, J = 9.0 Hz, 2H), 2.39-2.30 (m, 1H), 1.10-1.01 (m, 2H), 0.94-0.89 (m, 2H); LC/MS Rt = 1.370 min; MS m/z: 410 [M + H]$^+$ |
| 101 | 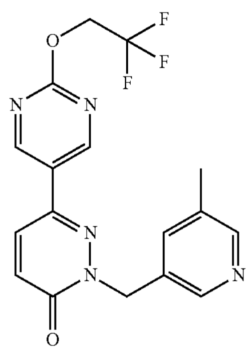 [SMILES: Cc1cncc(Cn2nc(-c3cnc(OCC(F)(F)F)nc3)ccc2=O)c1] | 2-((5-methylpyridin-3-yl)methyl)-6-(2-(2,2,2-trifluoroethoxy)pyrimidin-5-yl)pyridazin-3(2H)-one | $^1$H NMR (DMSO-$d_6$, 300 MHz) δ 9.17 (s, 2H), 8.46 (d, J = 3.0 Hz, 1H), 8.35 (d, J = 3.0 Hz, 1H), 8.14 (d, J = 9.6 Hz, 1H), 7.63 (t, J = 2.4 Hz, 1H), 7.17 (d, J = 9.6 Hz, 1H), 5.33 (s, 2H), 5.12 (m, 2H), 2.28 (s, 3H); LC/MS Rt = 0.734 min; MS m/z: 378 [M + H]$^+$ |
| 102 | 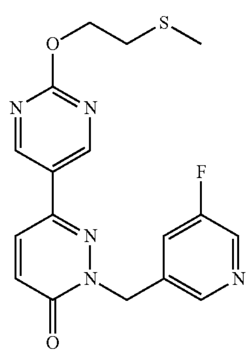 [SMILES: CSCCOc1ncc(-c2ccc(=O)n(Cc3cncc(F)c3)n2)cn1] | 2-((5-fluoropyridin-3-yl)methyl)-6-(2-(2-(methylthio)ethoxy)pyrimidin-5-yl)pyridazin-3(2H)-one | 1H NMR (400 MHz, DMSO-d6) δ 9.11 (s, 2H), 8.54 (d, J = 3.2 Hz, 2H), 8.12 (d, J = 10.0 Hz, 1H), 7.98-7.76 (m, 1H), 7.17 (d, J = 9.6 Hz, 1H), 5.40 (s, 2H), 4.54 (t, J = 6.4 Hz, 2H), 2.90 (t, J = 6.8 Hz, 2H), 2.16 (s, 3H); LC/MS Rt = 1.424 min; MS m/z: 374 [M + H]+ |
| 103 | 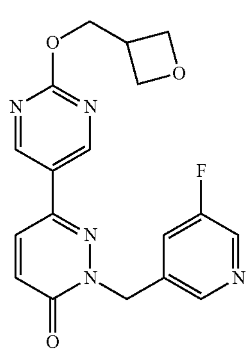 [SMILES: O=c1ccc(-c2cnc(OCC3COC3)nc2)nn1Cc1cncc(F)c1] | 2-((5-fluoropyridin-3-yl)methyl)-6-(2-(oxetan-3-ylmethoxy)pyrimidin-5-yl)pyridazin-3(2H)-one | 1H NMR (300 MHz, DMSO-d6) δ 9.11 (s, 2H), 8.54 (d, J = 3.0 Hz, 2H), 8.13 (d, J = 9.9 Hz, 1H), 7.78 (dt, J = 9.4, 2.3 Hz, 1H), 7.17 (d, J = 9.9 Hz, 1H), 5.40 (s, 2H), 4.72 (dd, J = 7.8, 6.1 Hz, 2H), 4.60 (d, J = 6.9 Hz, 2H), 4.45 (t, J = 6.0 Hz, 2H), 3.49-3.39 (m, 1H); LC/MS Rt = 1.021 min; MS m/z: 370.3 [M + H]+ |

TABLE 1-continued

| Cmpd No. | Structure | Name | NMR/MS |
|---|---|---|---|
| 104 | 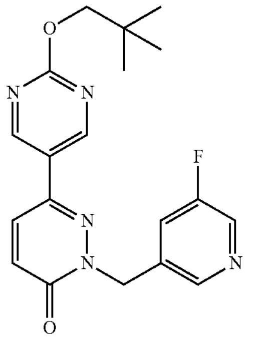 [SMILES: CC(C)(C)COc1ncc(-c2ccc(=O)n(Cc3cncc(F)c3)n2)cn1] | 2-((5-fluoropyridin-3-yl)methyl)-6-(2-(neopentyloxy)pyrimidin-5-yl)pyridazin-3(2H)-one | 1H NMR (400 MHz, DMSO-d6) δ 9.08 (s, 2H), 8.57-8.50 (m, 2H), 8.13 (d, J = 9.7 Hz, 1H), 7.79-7.75 (m, 1H), 7.17 (d, J = 9.6 Hz, 1H), 5.41 (s, 2H), 4.08 (s, 2H), 1.02 (s, 9H); LC/MS Rt = 1.721 min; MS m/z: 370 [M + H]+ |
| 105 | 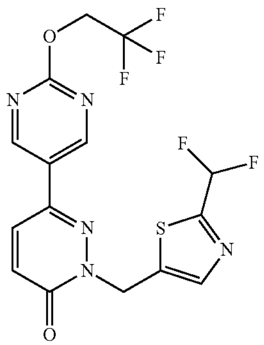 [SMILES: O=c1ccc(-c2cnc(OCC(F)(F)F)nc2)nn1Cc1cnc(C(F)F)s1] | 2-((2-(difluoromethyl)thiazol-5-yl)methyl)-6-(2-(2,2,2-trifluoroethoxy)pyrimidin-5-yl)pyridazin-3(2H)-one | $^1$H NMR (DMSO-d$_6$, 400 MHz) δ 9.18 (s, 2H), 8.16 (d, J = 9.6 Hz, 2H), 7.21 (d, J = 10.0 Hz, 1H), 7.44, 7.30, 7.17 (t, J = 54 Hz, 1H), 5.62 (s, 2H), 5.13 (q, J = 8.8 Hz, 2H); LC/MS Rt = 1.653 min; MS m/z: 420 [M + H]$^+$ |
| 106 | 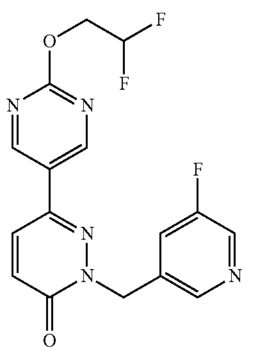 [SMILES: O=c1ccc(-c2cnc(OCC(F)F)nc2)nn1Cc1cncc(F)c1] | 6-(2-(2,2-difluoroethoxy)pyrimidin-5-yl)-2-((5-fluoropyridin-3-yl)methyl)pyridazin-3(2H)-one | 1H NMR (DMSO-d6, 400 MHz) δ 9.15 (s, 2H), 8.54 (d, J = 2.4 Hz, 2H), 8.14 (d, J = 9.6 Hz, 1H), 7.83-7.75 (m, 1H), 7.18 (d, J = 9.6 Hz, 1H), 6.45 (t, J = 3.2 Hz, 0H), 5.41 (s, 2H), 4.70 (td, J = 15.2, 3.6 Hz, 2H); LC/MS Rt = 1.228 min; MS m/z: 364 [M + H]+ |
| 107 | 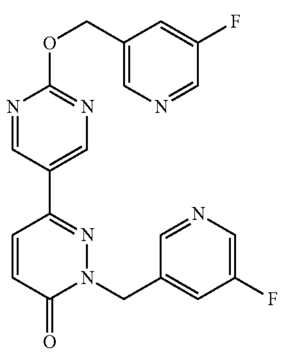 [SMILES: O=c1ccc(-c2cnc(OCc3cncc(F)c3)nc2)nn1Cc1cncc(F)c1] | 6-(2-((5-fluoropyridin-3-yl)methoxy)pyrimidin-5-yl)-2-((5-fluoropyridin-3-yl)methyl)pyridazin-3(2H)-one | |

TABLE 1-continued

| Cmpd No. | Structure | Name | NMR/MS |
|---|---|---|---|
| 108 | 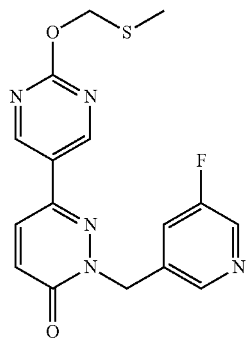 [SMILES: CSCOc1ncc(-c2ccc(=O)n(Cc3cncc(F)c3)n2)cn1] | 2-((5-fluoropyridin-3-yl)methyl)-6-(2-((methylthio)methoxy)pyrimidin-5-yl)pyridazin-3(2H)-one | 1H NMR (300 MHz, DMSO-d6) δ 9.14 (s, 2H), 8.54 (d, J = 2.7 Hz, 2H), 8.13 (d, J = 9.9 Hz, 1H), 7.79 (d, J = 9.6 Hz, 1H), 7.17 (d, J = 9.6 Hz, 1H), 5.58 (s, 2H), 5.40 (s, 2H), 2.27 (s, 3H); LC/MS Rt = 5.971 min; MS m/z: 360 [M + H]+ |
| 109 | 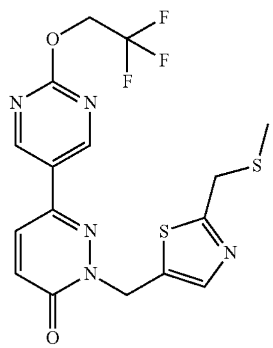 | 2-((2-((methylthio)methyl)thiazol-5-yl)methyl)-6-(2-(2,2,2-trifluoroethoxy)pyrimidin-5-yl)pyridazin-3(2H)-one | $^1$H NMR (DMSO-d$_6$, 300 MHz) δ 9.17 (s, 2H), 8.14 (d, J = 9.6 Hz, 1H), 7.79 (s, 1H), 7.19 (d, J = 9.6 Hz, 1H), 5.51 (s, 2H), 5.13 (q, J = 9.0 Hz, 2H), 4.00 (s, 2H), 2.08 (s, 3H); Rt = 1.458 min; MS m/z: 430 [M + H]$^+$ |
| 110 | 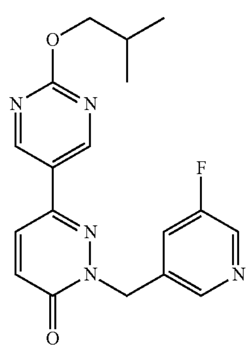 [SMILES: CC(C)COc1ncc(-c2ccc(=O)n(Cc3cncc(F)c3)n2)cn1] | 2-((5-fluoropyridin-3-yl)methyl)-6-(2-isobutoxypyrimidin-5-yl)pyridazin-3(2H)-one | 1H NMR (300 MHz, DMSO-d6) δ 9.09 (s, 2H), 8.55-8.53 (m, 2H), 8.12 (d, J = 9.9 Hz, 1H), 7.80-7.76 (m, 1H), 7.17 (d, J = 9.6 Hz, 1H), 5.40 (s, 2H), 4.16 (d, J = 6.9 Hz, 2H), 2.12-2.03 (m, 1H), 0.99 (d, J = 6.6 Hz, 6H); LC/MS Rt = 1.317 min; MS m/z: 356 [M + H]+ |
| 111 | 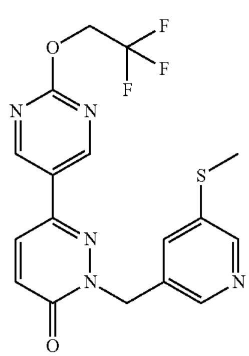 [SMILES: CSc1cncc(Cn2nc(-c3cnc(OCC(F)(F)F)nc3)ccc2=O)c1] | 2-((5-(methylthio)pyridin-3-yl)methyl)-6-(2-(2,2,2-trifluoroethoxy)pyrimidin-5-yl)pyridazin-3(2H)-one | $^1$H NMR (300 MHz, Methanol-d$_4$) δ 9.14 (s, 2H), 8.41 (dd, J = 12.9, 2.1 Hz, 2H), 8.06 (d, J = 9.6 Hz, 1H), 7.87 (t, J = 2.1 Hz, 1H), 7.16 (d, J = 9.9 Hz, 1H), 5.47 (s, 2H), 5.04 (q, J = 8.7 Hz, 2H), 2.55 (s, 3H); LC/MS Rt = 2.406 min; MS m/z: 410 [M + H]$^+$ |

TABLE 1-continued

| Cmpd No. | Structure | Name | NMR/MS |
|---|---|---|---|
| 112 | 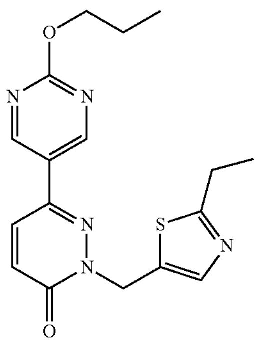 [SMILES: CCCOc1ncc(-c2ccc(=O)n(Cc3cnc(CC)s3)n2)cn1] | 2-((2-ethylthiazol-5-yl)methyl)-6-(2-propoxypyrimidin-5-yl)pyridazin-3(2H)-one | $^1$H NMR (DMSO-$d_6$, 300 MHz) δ 9.08 (s, 2H), 8.10 (d, J = 9.6 Hz, 1H), 7.75 (s, 1H), 7.16 (d, J = 9.6 Hz, 1H), 5.48 (s, 2H), 4.33 (t, J = 6.9 Hz, 2H), 2.93 (q, J = 7.5 Hz, 2H), 1.812-1.742 (m, 2H), 1.25 (t, J = 7.5 Hz, 3H), 0.99 (t, J = 7.5 Hz, 3H); LC/MS Rt = 1.349 min; MS m/z: 358 [M + H]$^+$ |
| 113 | 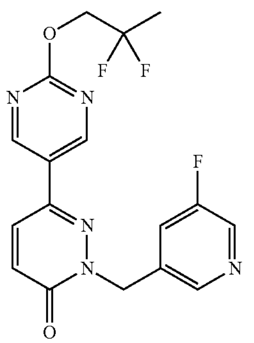 [SMILES: CC(F)(F)COc1ncc(-c2ccc(=O)n(Cc3cncc(F)c3)n2)cn1] | 6-(2-(2,2-difluoropropoxy)pyrimidin-5-yl)-2-((5-fluoropyridin-3-yl)methyl)pyridazin-3(2H)-one | 1H NMR (DMSO-d6, 300 MHz) δ 9.15 (s, 2H), 8.54 (d, J = 2.4 Hz, 2H), 8.15 (d, J = 9.9 Hz, 1H), 7.84-7.73 (m, 1H), 7.18 (d, J = 9.9 Hz, 1H), 5.41 (s, 2H), 4.69 (t, J = 13.2 Hz, 2H), 1.83-1.70 (t, J = 19.5 Hz, 3H); LC/MS Rt = 1.271 min; MS m/z: 378 [M + H]+ |
| 114 | 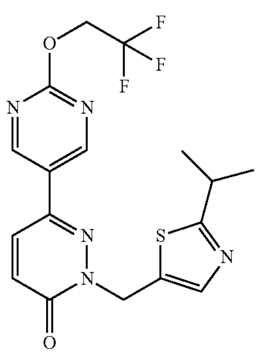 [SMILES: CC(C)c1ncc(Cn2nc(-c3cnc(OCC(F)(F)F)nc3)ccc2=O)s1] | 2-((2-isopropylthiazol-5-yl)methyl)-6-(2-(2,2,2-trifluoroethoxy)pyrimidin-5-yl)pyridazin-3(2H)-one | $^1$H NMR (DMSO-$d_6$, 300 MHz) δ 9.17 (s, 2H), 8.13 (d, J = 9.9 Hz, 1H), 7.77 (s, 1H), 7.18 (d, J = 9.6 Hz, 1H), 5.49 (s, 2H), 5.13 (q, J = 9.0 Hz, 2H), 3.29-3.15 (m, 1H), 1.28 (d, J = 6.9 Hz, 6H); LC/MS Rt = 2.462 min; MS m/z 412 [M + H]$^+$ |
| 115 | 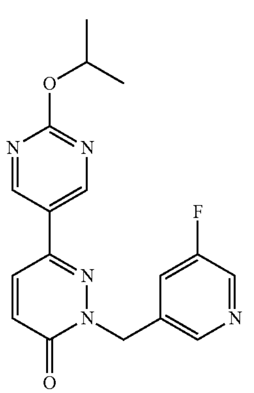 [SMILES: CC(C)Oc1ncc(-c2ccc(=O)n(Cc3cncc(F)c3)n2)cn1] | 2-((5-fluoropyridin-3-yl)methyl)-6-(2-isopropoxypyrimidin-5-yl)pyridazin-3(2H)-one | 1H NMR (DMSO-d6, 300 MHz) δ 9.08 (s, 2H), 8.54 (d, J = 3.3 Hz, 2H), 8.11 (d, J = 9.9 Hz, 1H), 7.78 (m, 1H), 7.16 (d, J = 9.6 Hz, 1H), 5.40 (s, 2H), 5.27 (m, 1H), 1.36 (s, 3H), 1.34 (s, 3H); LC/MS Rt = 1.318 min; MS m/z: 342 [M + H]+ |

TABLE 1-continued

| Cmpd No. | Structure | Name | NMR/MS |
|---|---|---|---|
| 116 | 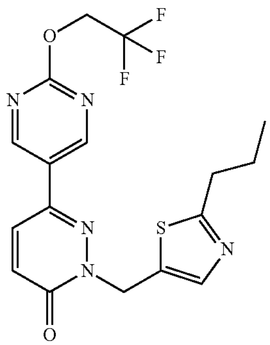 [SMILES: CCCc1ncc(Cn2nc(-c3cnc(OCC(F)(F)F)nc3)ccc2=O)s1] | 2-((2-propylthiazol-5-yl)methyl)-6-(2-(2,2,2-trifluoroethoxy)pyrimidin-5-yl)pyridazin-3(2H)-one | $^1$H NMR (DMSO-$d_6$, 300 MHz) δ 9.17 (s, 2H), 8.13 (d, J = 9.6 Hz, 1H), 7.76 (s, 1H), 7.18 (d, J = 9.9 Hz, 1H), 5.49 (s, 2H), 5.13 (q, J = 9.0 Hz, 2H), 2.88 (t, J = 7.5 Hz, 2H), 1.76-1.63 (m, 2H), 0.92 (t, J = 7.2 Hz, 3H); LC/MS Rt = 1.432 min; MS m/z: 412 [M + H]$^+$ |
| 117 | 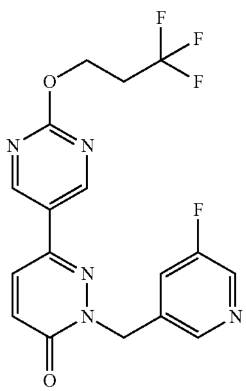 [SMILES: O=c1ccc(-c2cnc(OCCC(F)(F)F)nc2)nn1Cc1cncc(F)c1] | 2-((5-fluoropyridin-3-yl)methyl)-6-(2-(3,3,3-trifluoropropoxy)pyrimidin-5-yl)pyridazin-3(2H)-one | 1H NMR (300 MHz, DMSO-d6) δ 9.13 (s, 2H), 8.54 (d, J = 3.0 Hz, 2H), 8.13 (d, J = 9.6 Hz, 1H), 7.81-7.76 (m, 1H), 7.17 (d, J = 9.9 Hz, 1H), 5.40 (s, 2H), 4.60 (t, J = 6.0 Hz, 2H), 2.95-2.73 (m, 2H); LC/MS Rt = 1.315 min; MS m/z: 396 [M + H]+ |
| 118 | 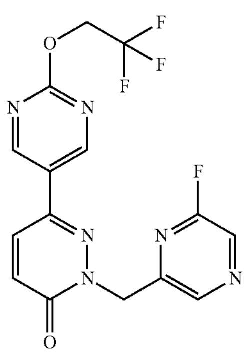 [SMILES: O=c1ccc(-c2cnc(OCC(F)(F)F)nc2)nn1Cc1cncc(F)n1] | 2-((6-fluoropyrazin-yl)methyl)-6-(2-(2,2,2-trifluoroethoxy)pyrimidin-5-yl)pyridazin-3(2H)-one | |
| 119 | 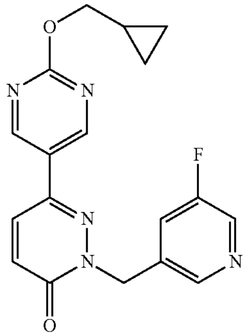 [SMILES: O=c1ccc(-c2cnc(OCC3CC3)nc2)nn1Cc1cncc(F)c1] | 6-(2-(cyclopropylmethoxy)pyrimidin-5-yl)-2-((5-fluoropyridin-3-yl)methyl)pyridazin-3(2H)-one | 1H NMR (300 MHz, DMSO-d6) δ 9.09 (s, 2H), 8.54 (d, J = 2.7 Hz, 2H), 8.12 (d, J = 9.6 Hz, 1H), 7.80-7.77 (m, 1H), 7.17 (d, J = 9.9 Hz, 1H), 5.40 (s, 2H), 4.21 (d, J = 7.5 Hz, 2H), 1.34-1.25 (m, 1H), 0.64-0.52 (m, 2H), 0.43-0.32 (m, 2H); LC/MS Rt = 1.280 min; MS m/z: 354 [M + H]+ |

TABLE 1-continued

| Cmpd No. | Structure | Name | NMR/MS |
|---|---|---|---|
| 120 | 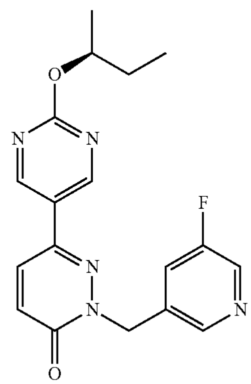 [SMILES: CC[C@H](C)Oc1ncc(-c2ccc(=O)n(Cc3cncc(F)c3)n2)cn1] | (S)-6-(2-(sec-butoxy)pyrimidin-5-yl)-2-((5-fluoropyridin-3-yl)methyl)pyridazin-3(2H)-one | 1H NMR (400 MHz, DMSO-d6) δ 9.07 (s, 2H), 8.54 (d, J = 2.8 Hz, 2H), 8.11 (d, J = 10.0 Hz, 1H), 7.77 (d, J = 9.6 Hz, 1H), 7.16 (d, J = 9.6 Hz, 1H), 5.39 (s, 2H), 5.15-5.07 (m, 1H), 1.77-1.62 (m, 2H), 1.31 (d, J = 6.0 Hz, 3H), 0.92 (t, J = 7.2 Hz, 3H); LC/MS Rt = 1.674 min; MS m/z: 356 [M + H]+ |
| 121 | 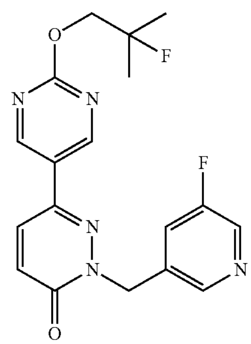 [SMILES: CC(C)(F)COc1ncc(-c2ccc(=O)n(Cc3cncc(F)c3)n2)cn1] | 6-(2-(2-fluoro-2-methylpropoxy)pyrimidin-5-yl)-2-((5-fluoropyridin-3-yl)methyl)pyridazin-3(2H)-one | 1H NMR (300 MHz, DMSO-d6) δ 9.11 (s, 2H), 8.54 (d, J = 3.0 Hz, 2H), 8.13 (d, J = 6.6 Hz, 1H), 7.80-7.76 (m, 1H), 7.17 (d, J = 6.6 Hz, 1H), 5.41 (s, 2H), 4.47, 4.40 (d, J = 41.4 Hz, 2H), 1.48 (s, 3H), 1.41 (s, 3H); LC/MS Rt = 0.985 min; MS m/z: 374 [M + H]+ |
| 122 | 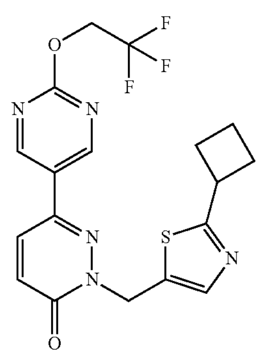 [SMILES: O=c1ccc(-c2cnc(OCC(F)(F)F)nc2)nn1Cc1cnc(C2CCC2)s1] | 2-((2-cyclobutylthiazol-5-yl)methyl)-6-(2-(2,2,2-trifluoroethoxy)pyrimidin-5-yl)pyridazin-3(2H)-one | $^1$H NMR (300 MHz, DMSO-d$_6$) δ 9.17 (s, 2H), 8.13 (d, J = 9.9 Hz, 1H), 7.78 (s, 1H), 7.18 (d, J = 9.6 Hz, 1H), 5.49 (s, 2H), 5.13 (q, J = 9.0 Hz, 2H), 3.86-3.74 (m, 1H), 2.40-1.80 (m, 6H); LC/MS Rt = 1.581 min; MS m/z: 424 [M + H]$^+$ |
| 123 | 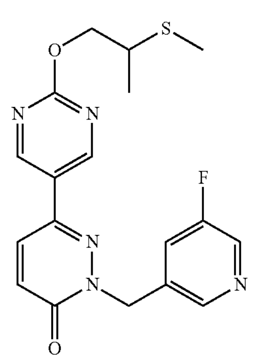 [SMILES: CSC(C)COc1ncc(-c2ccc(=O)n(Cc3cncc(F)c3)n2)cn1] | 2-((5-fluoropyridin-3-yl)methyl)-6-(2-(2-(methylthio)propoxy)pyrimidin-5-yl)pyridazin-3(2H)-one | 1H NMR (300 MHz, DMSO-d$_6$) δ 9.08 (s, 2H), 8.56 (s, 1H), 8.45 (d, J = 2.7 Hz, 1H), 8.05 (d, J = 9.9 Hz, 1H), 7.80-7.75 (m, 1H), 7.15 (d, J = 9.6 Hz, 1H), 5.52 (s, 2H), 4.65 (dd, J$_1$ = 10.8 Hz, J$_2$ = 5.4 Hz, 1H), 4.37 (dd, J$_1$ = 10.8 Hz, J$_2$ = 7.8 Hz, 1H), 3.13 (m, 2H), 2.2 (s, 3H), 1.38 (d, J = 6.9 Hz, 3H); LC/MS Rt = 1.137 min; MS m/z: 388 [M + H]$^+$ |

TABLE 1-continued

| Cmpd No. | Structure | Name | NMR/MS |
|---|---|---|---|
| 124 | 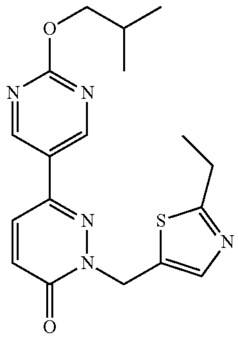 [SMILES: CCc1ncc(Cn2nc(-c3cnc(OCC(C)C)nc3)ccc2=O)s1] | 2-((2-ethylthiazol-5-yl)methyl)-6-(2-isobutoxypyrimidin-5-yl)pyridazin-3(2H)-one | $^1$H NMR (300 MHz, DMSO-$d_6$) δ 9.08 (s, 2H), 8.10 (d, J = 9.9 Hz, 1H), 7.75 (s, 1H), 7.16 (d, J = 9.9 Hz, 1H), 5.48 (s, 2H), 4.16 (d, J = 6.6 Hz, 2H), 2.93 (q, J = 7.5 Hz, 2H), 2.13-2.02 (m, 1H), 1.25 (t, J = 7.5 Hz, 3H), 0.99 (d, J = 6.7 Hz, 6H); LC/MS Rt = 1.462 min; MS m/z: 372 [M + H]$^+$ |
| 125 | 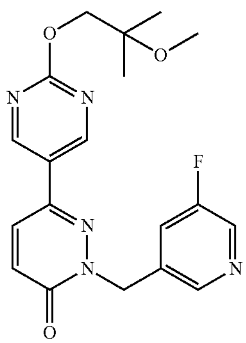 [SMILES: COC(C)(C)COc1ncc(-c2ccc(=O)n(Cc3cncc(F)c3)n2)cn1] | 2-((5-fluoropyridin-3-yl)methyl)-6-(2-(2-methoxy-2-methylpropoxy)pyrimidin-5-yl)pyridazin-3(2H)-one | $^1$H NMR (400 MHz, DMSO-$d_6$) δ 9.09 (s, 2H), 8.55-8.53 (m, 2H), 8.14 (d, J = 10.0 Hz, 1H), 7.78-7.76 (m, 1H), 7.17 (d, J = 9.6 Hz, 1H), 5.40 (s, 2H), 4.28 (s, 2H), 3.16 (s, 3H), 1.22 (s, 6H); LC/MS Rt = 1.151 min; MS m/z: 386 [M + H]$^+$ |
| 126 | 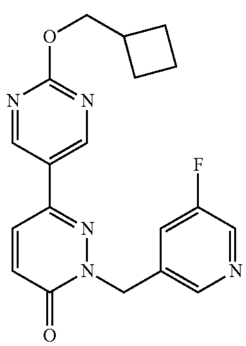 [SMILES: O=c1ccc(-c2cnc(OCC3CCC3)nc2)nn1Cc1cncc(F)c1] | 6-(2-(cyclobutylmethoxy)pyrimidin-5-yl)-2-((5-fluoropyridin-3-yl)methyl)pyridazin-3(2H)-one | 1H NMR (300 MHz, DMSO-$d_6$) δ 9.08 (s, 2H), 8.54-8.53 (m, 2H), 8.15 (d, J = 9.9 Hz, 1H), 7.80-7.76 (m, 1H), 7.16 (d, J = 9.6 Hz, 1H), 5.40 (s, 2H), 4.35 (d, J = 6.9 Hz, 2H), 2.81-2.75 (m, 1H), 2.09-2.04 (m, 2H), 2.03-1.85 (m, 2H); LC/MS Rt = 1.484 min; MS m/z: 368 [M + H]$^+$ |
| 127 | 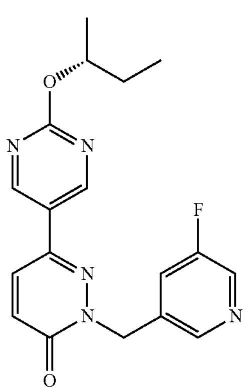 [SMILES: CC[C@@H](C)Oc1ncc(-c2ccc(=O)n(Cc3cncc(F)c3)n2)cn1] | (R)-6-(2-(sec-butoxy)pyrimidin-5-yl)-2-((5-fluoropyridin-3-yl)methyl)pyridazin-3(2H)-one | $^1$H NMR (300 MHz, DMSO-$d_6$) δ 9.07 (s, 2H), 8.54 (t, J = 3.0 Hz, 2H), 8.11 (d, J = 9.9 Hz, 1H), 7.79-7.76 (m, 1H), 7.16 (d, J = 9.9 Hz, 1H), 5.40 (s, 2H), 5.10-5.06 (m,1H), 1.78-1.58 (m, 2H), 1.31 (d, J = 6.3 Hz, 3H), 0.93 (t, J = 7.5 Hz, 3H); LC/MS Rt = 2.219 min; MS m/z: 356 [M + H]$^+$ |

TABLE 1-continued

| Cmpd No. | Structure | Name | NMR/MS |
|---|---|---|---|
| 128 | 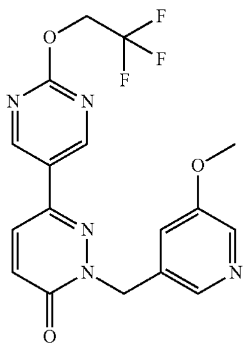 [SMILES: COc1cncc(Cn2nc(-c3cnc(OCC(F)(F)F)nc3)ccc2=O)c1] | 2-((5-methoxypyridin-3-yl)methyl)-6-(2-(2,2,2-trifluoroethoxy)pyrimidin-5-yl)pyridazin-3(2H)-one | $^1$H NMR (300 MHz, DMSO-$d_6$) δ 9.17 (s, 2H), 8.25-8.23 (m, 2H), 8.15 (d, J = 9.6 Hz, 1H), 7.42-7.41 (m, 1H), 7.18 (d, J = 9.6 Hz, 1H), 5.36 (s, 2H), 5.12 (q, J = 9.0 Hz, 2H), 3.82 (s, 3H); LC/MS Rt = 1.301 min; MS m/z: 394 [M + H]$^+$ |
| 129 | 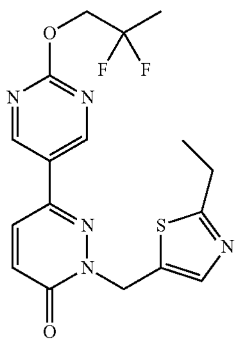 [SMILES: CCc1ncc(Cn2nc(-c3cnc(OCC(C)(F)F)nc3)ccc2=O)s1] | 6-(2-(2,2-difluoropropoxy)pyrimidin-5-yl)-2-((2-ethylthiazol-5-yl)methyl)pyridazin-3(2H)-one | $^1$H NMR (300 MHz, DMSO-$d_6$) δ 9.14 (s, 2H), 8.12 (d, J = 9.9 Hz, 1H), 7.76 (s, 1H), 7.17 (d, J = 9.9 Hz, 1H), 5.49 (s, 2H), 4.70 (t, J = 13.2 Hz, 2H), 2.93 (q, J = 7.5 Hz, 2H), 1.77 (t, J = 19.5 Hz, 3H), 1.25 (t, J = 7.5 Hz, 3H); LC/MS Rt = 1.803 min; MS m/z: 394 [M + H]$^+$ |
| 130 | 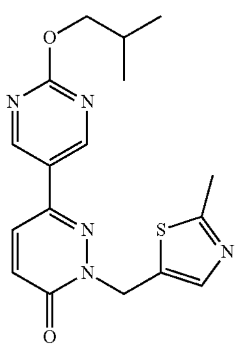 [SMILES: Cc1ncc(Cn2nc(-c3cnc(OCC(C)C)nc3)ccc2=O)s1] | 6-(2-isobutoxypyrimidin-5-yl)-2-((2-methylthiazol-5-yl)methyl)pyridazin-3(2H)-one | $^1$H NMR (300 MHz, DMSO-$d_6$) δ 9.08 (s, 2H), 8.10 (d, J = 9.9 Hz, 1H), 7.72 (s, 1H), 7.16 (d, J = 9.9 Hz, 1H), 5.47 (s, 2H), 4.16 (d, J = 6.6 Hz, 2H), 2.60 (s, 3H), 2.27-2.04 (m, 1H), 1.00 (d, J = 6.6 Hz, 6H); LC/MS Rt = 1.817 min; MS m/z: 358 [M + H]$^+$ |
| 131 | 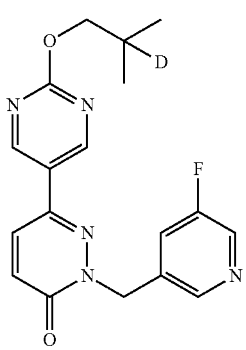 [SMILES: [2H]C(C)(C)COc1ncc(-c2ccc(=O)n(Cc3cncc(F)c3)n2)cn1] | 2-((5-fluoropyridin-3-yl)methyl)-6-(2-(2-methylpropoxy-2-d)pyrimidin-5-yl)pyridazin-3(2H)-one | $^1$H NMR (400 MHz, DMSO-$d_6$) δ 9.09 (s, 2H), 8.55-8.53 (m, 2H), 8.12 (d, J = 10.0 Hz, 1H), 7.77 (d, J = 9.6 Hz, 1H), 7.16 (d, J = 10.0 Hz, 1H), 5.40 (s, 2H), 4.15 (s, 2H), 0.98 (s, 6H); LC/MS Rt = 1.676 min; MS m/z: 357 [M + H]$^+$ |

TABLE 1-continued

| Cmpd No. | Structure | Name | NMR/MS |
|---|---|---|---|
| 132 | 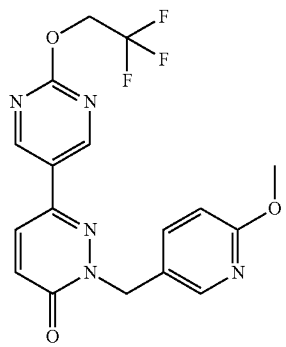 [SMILES: COc1ccc(Cn2nc(-c3cnc(OCC(F)(F)F)nc3)ccc2=O)cn1] | 2-((6-methoxypyridin-3-yl)methyl)-6-(2-(2,2,2-trifluoroethoxy)pyrimidin-5-yl)pyridazin-3(2H)-one | $^1$H NMR (300 MHz, DMSO-$d_6$) δ 9.17 (d, J = 6.0 Hz, 2H), 8.28 (d, J = 1.8 Hz, 1H), 8.12 (d, J = 9.6 Hz, 1H), 7.82-7.78 (m, 1H), 7.15 (d, J = 9.9 Hz, 1H), 6.81 (d, J = 8.7 Hz, 1H), 5.27 (s, 2H), 5.12 (q, J = 9.0 Hz, 2H), 3.82 (s, 3H); LC/MS Rt = 1.460 min; MS m/z: 394 [M + H]$^+$ |
| 133 | 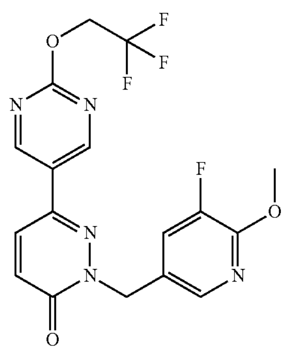 [SMILES: COc1ncc(Cn2nc(-c3cnc(OCC(F)(F)F)nc3)ccc2=O)cc1F] | 2-((5-fluoro-6-methoxypyridin-3-yl)methyl)-6-(2-(2,2,2-trifluoroethoxy)pyrimidin-5-yl)pyridazin-3(2H)-one | $^1$H NMR (400 MHz, DMSO-$d_6$) δ 9.18 (s, 2H), 8.16-8.08 (m, 2H), 7.78 (dd, J = 11.2, 2.0 Hz, 1H), 7.16 (d, J = 9.6 Hz, 1H), 5.30 (s, 2H), 5.12 (q, J = 8.8 Hz, 2H), 3.93 (s, 3H); LC/MS Rt = 1.298 min; MS m/z: 412 [M + H]$^+$ |
| 134 | 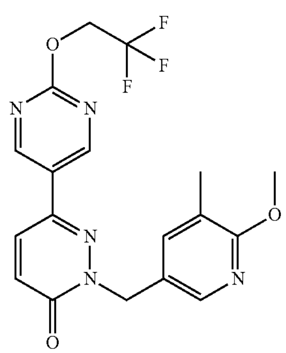 [SMILES: COc1ncc(Cn2nc(-c3cnc(OCC(F)(F)F)nc3)ccc2=O)cc1C] | 2-((6-methoxy-5-methylpyridin-3-yl)methyl)-6-(2-(2,2,2-trifluoroethoxy)pyrimidin-5-yl)pyridazin-3(2H)-one | $^1$H NMR (400 MHz, DMSO-$d_6$) δ 9.17 (s, 2H), 8.11 (d, J = 9.6 Hz, 2H), 7.64-7.59 (m, 1H), 7.14 (d, J = 9.6 Hz, 1H), 5.24 (s, 2H), 5.12 (q, J = 8.8 Hz, 2H), 3.85 (s, 3H), 2.12 (s, 3H); LC/MS Rt = 1.961 min; MS m/z: 408 [M + H]$^+$ |
| 135 | 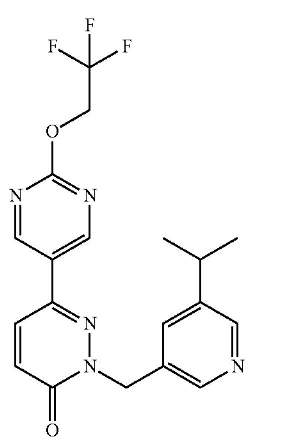 [SMILES: CC(C)c1cncc(Cn2nc(-c3cnc(OCC(F)(F)F)nc3)ccc2=O)c1] | 2-((5-isopropylpyridin-3-yl)methyl)-6-(2-(2,2,2-trifluoroethoxy)pyrimidin-5-yl)pyridazin-3(2H)-one | $^1$H NMR (300 MHz, DMSO-d6) δ 9.17 (s, 2H), 8.47-8.45 (m, 2H), 8.14 (d, J = 9.7 Hz, 1H), 7.76 (d, J = 2.2 Hz, 1H), 7.18 (d, J = 9.7 Hz, 1H), 5.36 (s, 2H), 5.12 (q, J = 8.9 Hz, 2H), 3.00-2.91 (m, 1H), 1.21 (d, J = 6.9 Hz, 6H); LC/MS Rt = 2.011 min; MS m/z: 406 [M + H]$^+$ |

TABLE 1-continued

| Cmpd No. | Name | NMR/MS |
|---|---|---|
| 136 | 2-((5-fluoro-2-methylpyridin-3-yl)methyl)-6-(2-(2,2,2-trifluoroethoxy)pyrimidin-5-yl)pyridazin-3(2H)-one | $^1$H NMR (400 MHz, DMSO-d$_6$) δ 9.12 (s, 2H), 8.39 (d, J = 2.8 Hz, 1H), 8.17 (d, J = 9.6 Hz, 1H), 7.51 (dd, J = 9.6, 2.9 Hz, 1H), 7.20 (d, J = 9.6 Hz, 1H), 5.38 (s, 2H), 5.12 (q, J = 8.8 Hz, 2H), 2.57 (s, 3H); LC/MS Rt = 1.524 min; MS m/z: 396 [M + H]$^+$ |
| 137 | 2-((5-ethylpyridin-3-yl)methyl)-6-(2-(2,2,2-trifluoroethoxy)pyridazinemidin-5-yl)pyridazin-3(2H)-one | $^1$H NMR (300 MHz, DMSO-d$_6$) δ 9.17-9.16 (m, 2H), 8.47 (d, J = 2.1 Hz, 1H), 8.39 (d, J = 2.1 Hz, 1H), 8.14 (d, J = 9.9 Hz, 1H), 7.69 (t, J = 2.1 Hz, 1H), 7.17 (d, J = 9.9 Hz, 1H), 5.35 (s, 2H), 5.16-5.08 (m, 2H), 2.61 (q, J = 7.5 Hz, 2H), 1.17 (td, J = 7.2 Hz, 3H); LC/MS Rt = 0.704 min; MS m/z: 392 [M + H]$^+$ |
| 138 | 6-(2-(benzyloxy)pyrimidin-5-yl)-2-((5-fluoropyridazine-yl)methyl)pyridazin-3(2H)-one | $^1$H NMR (300 MHz, DMSO-d6) δ 9.13 (s, 2H), 8.55-8.53 (m, 2H), 8.13 (d, J = 9.8 Hz, 1H), 7.86-7.71 (m, 1H), 7.52-7.45 (m, 2H), 7.44-7.31 (m, 3H), 7.17 (d, J = 9.8 Hz, 1H), 5.47 (s, 2H), 5.40 (s, 2H); LC/MS Rt = 1.944 min; MS m/z: 390 [M + H]$^+$ |
| 139 | 2-((6-ethyl-5-fluoropyridin-3-yl)methyl)-6-(2-(2,2,2-trifluoroethoxy)pyridazinemidin-5-yl)pyridazin-3(2H)-one | $^1$H NMR (300 MHz, DMSO-d6) δ 9.18 (s, 2H), 8.44 (s, 1H), 8.14 (d, J = 9.6 Hz, 1H), 7.74-7.64 (m, 1H), 7.17 (d, J = 9.9 Hz, 1H), 5.36 (s, 2H), 5.12 (q, J = 9.0 Hz, 2H), 2.82-2.74 (m, 2H), 1.20 (t, J = 7.5 Hz, 3H); LC/MS Rt = 1.626 min; MS m/z: 410 [M + H]$^+$ |

TABLE 1-continued

| Cmpd No. | Structure | Name | NMR/MS |
|---|---|---|---|
| 140 | 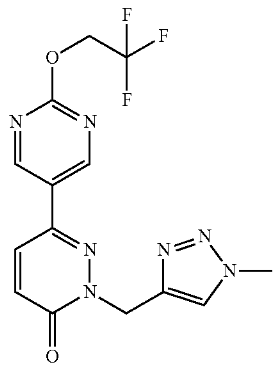 [SMILES: Cn1cc(Cn2nc(-c3cnc(OCC(F)(F)F)nc3)ccc2=O)nn1] | 2-((1-methyl-1H-1,2,3-triazol-4-yl)methyl)-6-(2-(2,2,2-trifluoroethoxy)pyridazinemidin-5-yl)pyridazin-3(2H)-one | $^1$H NMR (300 MHz, DMSO-d$_6$) δ 9.15 (s, 2H), 8.13-8.10 (m, 2H), 7.16 (d, J = 9.6 Hz, 1H), 5.39 (s, 2H), 5.16-5.07 (m, 2H), 4.01 (s, 3H); LC/MS Rt = 0.904 min; MS m/z: 368 [M + H]$^+$ |

In some embodiments, compounds of the disclosure are below in Table 2.

TABLE 2

| Cmpd No. | Structure | Name | NMR/MS |
|---|---|---|---|
| 201 | 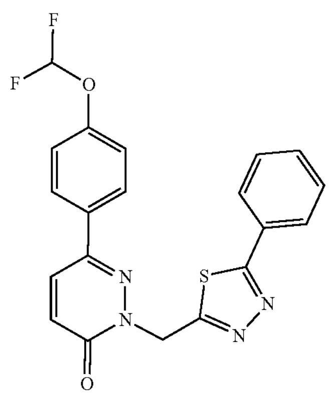 [SMILES: O=c1ccc(-c2ccc(OC(F)F)cc2)nn1Cc1nnc(-c2ccccc2)s1] | 6-(4-(difluoromethoxy)phenyl)-2-((5-phenyl-1,3,4-thiadiazol-2-yl)methyl)pyridazin-3(2H)-one | 413.3 |
| 202 | 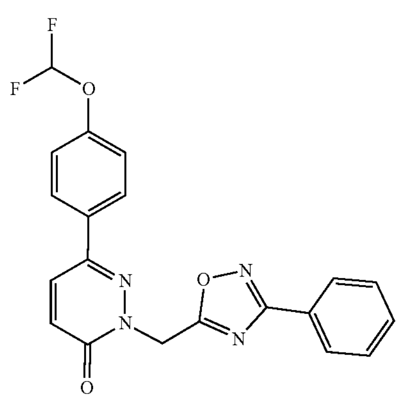 [SMILES: O=c1ccc(-c2ccc(OC(F)F)cc2)nn1Cc1nc(-c2ccccc2)no1] | 6-(4-(difluoromethoxy)phenyl)-2-((3-phenyl-1,2,4-thiadiazol-5-yl)methyl)pyridazin-3(2H)-one | $^1$H NMR (300 MHz, DMSO-d$_6$): δ 8.20 (d, J = 9.6 Hz, 1H), 7.98 (d, J = 7.6 Hz, 4H), 7.60-7.53 (m, 3H), 7.46-7.16 (m, 4H), 5.79 (s, 3H); LC/MS (ESI): 397 [M + H]$^+$ |

TABLE 2-continued

| Cmpd No. | Structure | Name | NMR/MS |
|---|---|---|---|
| 203 | 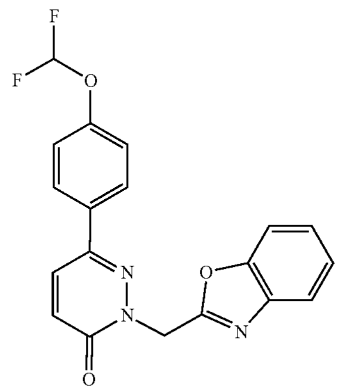 [SMILES: O=c1ccc(-c2ccc(OC(F)F)cc2)nn1Cc1nc2ccccc2o1] | 2-(benzo[d]oxazol-2-ylmethyl)-6-(4-(difluoromethoxy)phenyl)-pyridazin-3(2H)-one | $^1$H NMR (300 MHz, DMSO-$d_6$): δ 8.17 (d, J = 9.9 Hz, 1H), 7.97-7.94 (m, 2H), 7.75-7.71 (m, 2H), 7.58-7.09 (m, 6H), 5.69 (s, 2H); LC/MS (ESI): 370 [M + H]$^+$ |
| 204 | 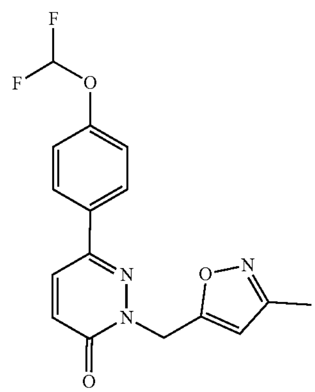 [SMILES: Cc1cc(Cn2nc(-c3ccc(OC(F)F)cc3)ccc2=O)on1] | 6-(4-(difluoromethoxy)phenyl)-2-((3-methylisoxazol-5-yl)methyl)pyridazin-3(2H)-one | $^1$H NMR (400 MHz, DMSO-$d_6$): δ 8.11 (d, J = 10.0 Hz, 1H), 7.94 (d, J = 8.0 Hz, 2H), 7.52-7.12 (m, 4H), 6.34 (s, 1H), 5.46 (s, 2H), 2.21 (s, 3H); LC/MS (ESI): 334 [M + H]$^+$ |
| 205 | 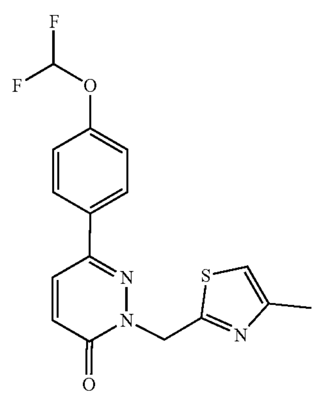 [SMILES: Cc1csc(Cn2nc(-c3ccc(OC(F)F)cc3)ccc2=O)n1] | 6-(4-(difluoromethoxy)phenyl)-2-((4-methylthizol-2-yl)methyl)pyridazin-3(2H)-one | $^1$H NMR (300 MHz, DMSO-$d_6$): δ 8.14-7.95 (d, J = 9.9 Hz, 1H), 7.98-7.95 (m, 2H), 7.58-7.09 (m, 5H), 5.58 (s, 2H), 2.34 (s, 3H); LC/MS (ESI): 350 [M + H]$^+$ |
| 206 | 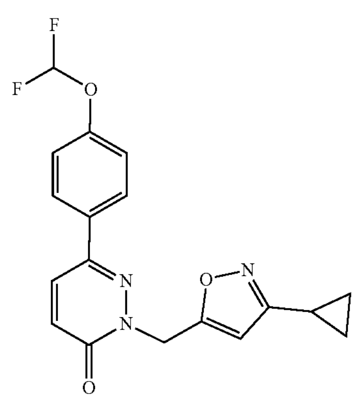 [SMILES: O=c1ccc(-c2ccc(OC(F)F)cc2)nn1Cc1cc(C2CC2)no1] | 2-((3-cyclopropylisoxazol-5-yl)methyl)-6-(4-(difluoromethoxy)phenyl)pyridazin-3(2H)-one | $^1$H NMR (300 MHz, DMSO-$d_6$): δ 8.11 (d, J = 9.6 Hz, 1H), 7.97-7.92 (m, 2H), 7.58-7.09 (m, 4H), 6.24 (s, 1H), 5.42 (s, 2H), 2.02-1.93 (m, 1H), 1.01-0.95 (m, 2H), 0.77-0.74 (m, 2H); LC/MS (ESI): 360 [M + H]$^+$ |

TABLE 2-continued

| Cmpd No. | Structure | Name | NMR/MS |
|---|---|---|---|
| 208 | 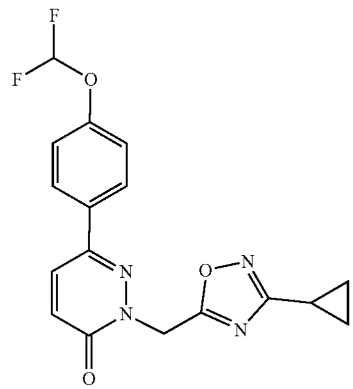 | 2-((3-cyclopropyl-1,2,4-oxadiazol-5-yl)methyl)-6-(4-(difluoromethoxy)phenyl)pyridazin-3(2H)-one | $^1$H NMR (300 MHz, DMSO-$d_6$): δ 8.15 (d, J = 9.9 Hz, 1H), 7.96-7.93 (m, 2H), 7.58-7.09 (m, 4H), 5.62 (s, 2H), 2.16-2.07 (m, 1H), 1.09-1.00 (m, 2H), 0.88-0.86 (m, 2H); LC/MS (ESI): 361 [M + H]$^+$ |
| 209 | 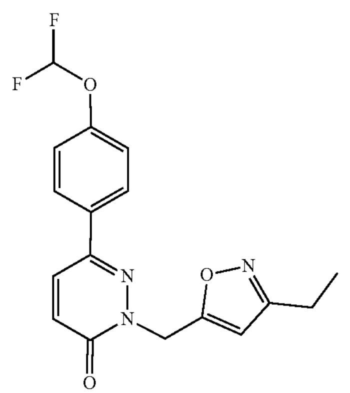 [SMILES: CCc1cc(Cn2nc(-c3ccc(OC(F)F)cc3)ccc2=O)on1] | 6-(4-(difluoromethoxy)phenyl)-2-((3-ethylisoxazol-5-yl)methyl)pyridazin-3(2H)-one | $^1$H NMR (DMSO-d6, 400 MHz): δ 8.16 (d, 1H), 8.02-7.97 (m, 2H), 7.58-7.16 (m, 4H), 6.45 (s, 1H), 5.51 (s, 2H), 2.65 (q, 2H), 1.22 (t, 3H); 348.2 |
| 210 | 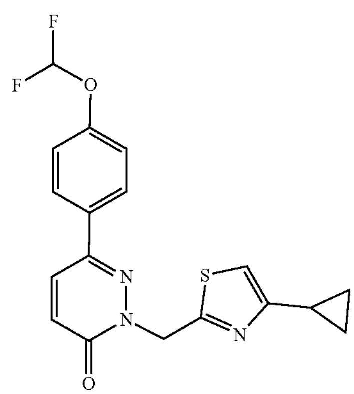 [SMILES: O=c1ccc(-c2ccc(OC(F)F)cc2)nn1Cc1nc(C2CC2)cs1] | 2-((4-cyclopropylthiazol-2-yl)methyl)-6-(4-(difluoromethoxy)phenyl)pyridazin-3(2H)-one | $^1$H NMR (300 MHz, DMSO-$d_6$): δ 8.13 (d, J = 9.9 Hz, 1H), 7.96 (d, J = 8.7 Hz, 2H), 7.60-7.05 (m, 5H), 5.55 (s, 2H), 2.10-2.01 (m, 1H), 0.91-0.76 (m, 4H); LC/MS (ESI): 376 [M + H]$^+$ |
| 211 | 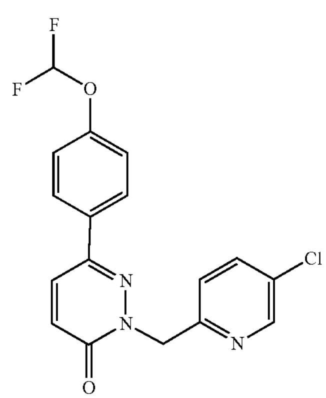 [SMILES: O=c1ccc(-c2ccc(OC(F)F)cc2)nn1Cc1ccc(Cl)cn1] | 2-((5-chloropyridin-2-yl)methyl)-6-(4-(difluoromethoxy)phenyl)pyridazin-3(2H)-one | $^1$H NMR (CDCl$_3$, 400 MHz): δ 8.56 (d, 1H), 8.12 (d, 1H), 7.95-7.91 (m, 3H), 7.52-7.12 (m, 5H), 5.46 (s, 2H); 364.2 |

TABLE 2-continued

| Cmpd No. | Structure | Name | NMR/MS |
|---|---|---|---|
| 212 | 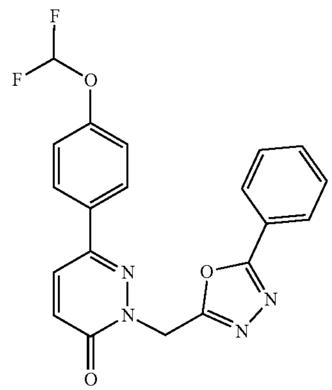 [SMILES: O=c1ccc(-c2ccc(OC(F)F)cc2)nn1Cc1nnc(-c2ccccc2)o1] | 6-(4-(difluoromethoxy)phenyl)-2-((5-phenyl-1,3,4-oxadiazol-2-yl)methyl)pyridazin-3(2H)-one | $^1$H NMR (DMSO-d6, 400 MHz): δ 8.21 (d, 1H), 8.05-7.98 (m, 4H), 7.71-7.62 (m, 3H), 7.58-7.19 (m, 4H), 5.77 (s, 2H); 397.3 |
| 213 | 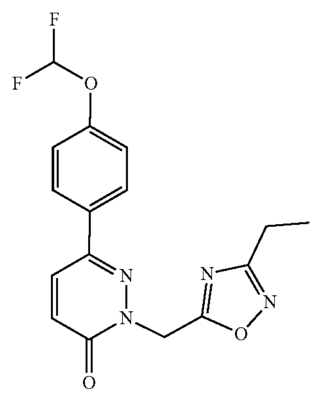 [SMILES: CCc1noc(Cn2nc(-c3ccc(OC(F)F)cc3)ccc2=O)n1] | 6-(4-(difluoromethoxy)phenyl)-2-((3-ethyl-1,2,4-oxadiazol-5-yl)methyl)pyridazin-3(2H)-one | $^1$H NMR (CDCl$_3$, 400 MHz): δ 7.79-7.70 (m, 3H), 7.23-7.18 (m, 2H), 7.12-7.07 (m, 1H), 6.57 (t, 1H), 5.61 (s, 2H), 2.76 (q, 2H), 1.31 (t, 3H); 349.3 |
| 214 | 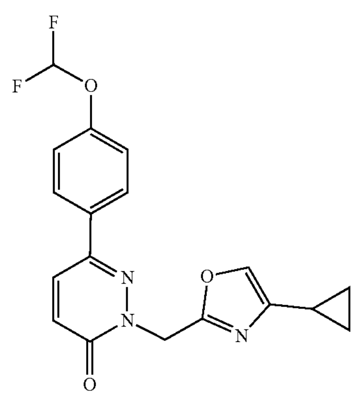 [SMILES: O=c1ccc(-c2ccc(OC(F)F)cc2)nn1Cc1nc(C2CC2)co1] | 2-((4-cyclopropyloxazol-2-yl)methyl)-6-(4-(difluoromethoxy)phenyl)-pyridazin-3(2H)-one | $^1$H NMR (DMSO-d6, 400 MHz): δ 7.77-7.74 (m, 2H), 7.68 (d, 1H), 7.34 (s, 1H), 7.21-7.18 (m, 2H), 7.07 (d, 1H), 6.56 (t, 1H), 5.46 (s, 2H), 1.80-1.73 (m, 1H), 0.88-0.83 (m, 2H), 0.77-0.72 (m, 2H); 360.3 |
| 215 | 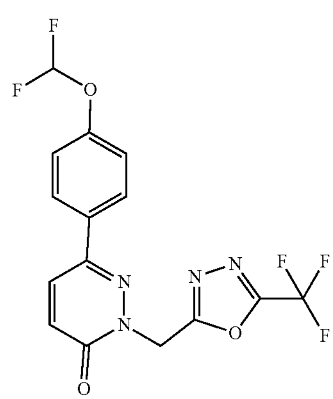 [SMILES: O=c1ccc(-c2ccc(OC(F)F)cc2)nn1Cc1nnc(C(F)(F)F)o1] | 6-(4-(difluoromethoxy)phenyl)-2-((5-(trifluoromethyl)-1,3,4-oxadiazol-2-yl)methyl)pyridazin-3(2H)-one | $^1$H NMR (CDCl$_3$, 400 MHz): δ 7.78-7.71 (m, 3H), 7.24-7.19 (m, 2H), 7.11 (d, 1H), 6.57 (t, 1H), 5.71 (s, 2H); 389.2 |

| Cmpd No. | Structure | Name | NMR/MS |
|---|---|---|---|
| 216 | 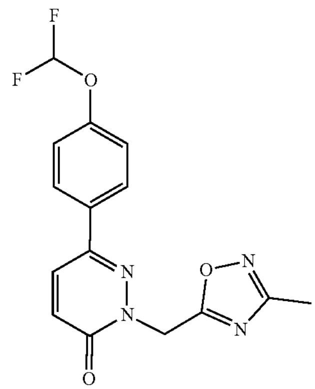 | 6-(4-(difluoromethoxy)phenyl)-2-((3-methyl-1,2,4-oxadiazol-5-yl)methyl)pyridazin-3(2H)-one | [M + H]+ 335.1 |
| 217 | 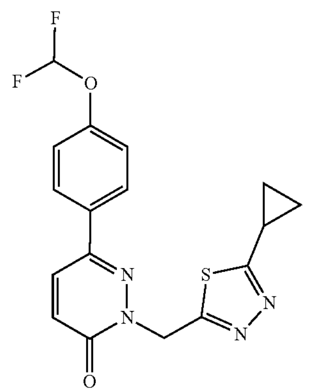 [SMILES: O=c1ccc(-c2ccc(OC(F)F)cc2)nn1Cc1nnc(C2CC2)s1] | 2-((5-cyclopropyl-1,3,4-thiadiazol-2-yl)methyl)-6-(4-(difluoromethoxy)phenyl)-pyridazin-3(2H)-one | $^1$H NMR (DMSO-d6, 400 MHz): δ 8.14 (d, 1H), 7.98-7.95 (m, 2H), 7.54-7.16 (m, 4H), 5.70-5.68 (m, 2H), 2.50-2.47 (m, 1H), 1.22-1.17 (m, 2H), 1.03-0.99 (m, 2H); 377.2 |
| 218 | 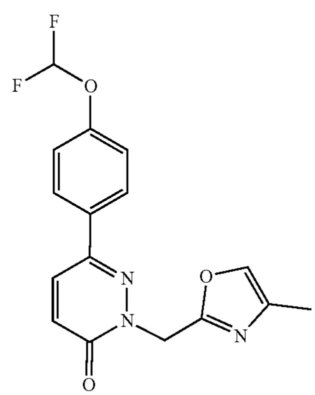 | 6-(4-(difluoromethoxy)phenyl)-2-((4-methyloxazol-2-yl)methyl)pyridazin-3(2H)-one | %). $^1$H NMR (DMSO-d6,400 MHz): δ 8.17 (d, 1H), 8.00-7.96 (m, 2H), 7.83 (s, 1H), 7.58-7.16 (m, 4H), 5.47 (s, 2H), 2.10 (s, 3H); 334.3 |
| 219 | 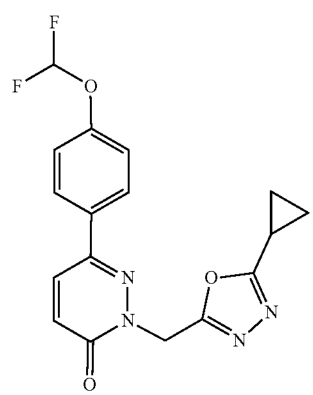 [SMILES: O=c1ccc(-c2ccc(OC(F)F)cc2)nn1Cc1nnc(C2CC2)o1] | 2-((5-cyclopropyl-1,3,4-oxadiazol-2-yl)methyl)-6-(4-(difluoromethoxy)phenyl-pyridazin-3(2H)-one | $^1$H NMR (DMSO-d6, 400 MHz): δ 8.15 (d, 1H), 7.94-7.92 (m, 2H), 7.55-7.15 (m, 4H), 5.55 (s, 2H), 2.28-2.20 (m, 1H), 1.17-1.11 (m, 2H), 1.00-0.95 (m, 2H); 361.2 |

TABLE 2-continued

| Cmpd No. | Structure | Name | NMR/MS |
|---|---|---|---|
| 220 | 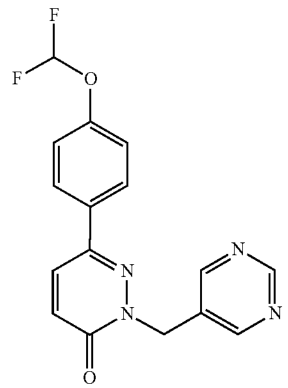 [SMILES: O=c1ccc(-c2ccc(OC(F)F)cc2)nn1Cc1cncnc1] | 6-(4-(difluoromethoxy)phenyl)-2-(pyrimidin-5-ylmethyl)pyridazin-3(2H)-one | [M + H]+ 331.1 |
| 221 | 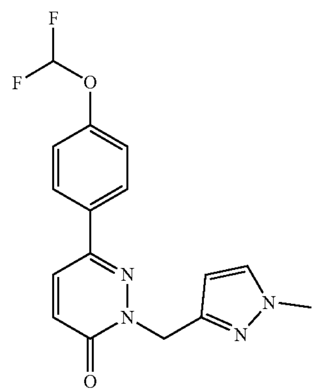 [SMILES: Cn1ccc(Cn2nc(-c3ccc(OC(F)F)cc3)ccc2=O)n1] | 6-(4-(difluoromethoxy)phenyl)-2-((1-methyl-1H-pyrazol-3-yl)methyl)pyridazin-3(2H)-one | [M + H]+ 331.1 |
| 222 | 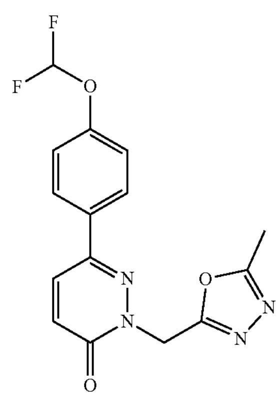 [SMILES: Cc1nnc(Cn2nc(-c3ccc(OC(F)F)cc3)ccc2=O)o1] | 6-(4-(difluoromethoxy)phenyl)-2-((5-methyl-1,3,4-oxadiazol-2-yl)methyl)pyridazin-3(2H)-one | $^1$H NMR (DMSO-d6, 400 MHz): δ 8.19 (d, 1H), 8.00-7.95 (m, 2H), 7.58-7.19 (m, 4H), 5.63 (s, 2H), 2.54 (s, 3H); 335.2 |
| 223 | 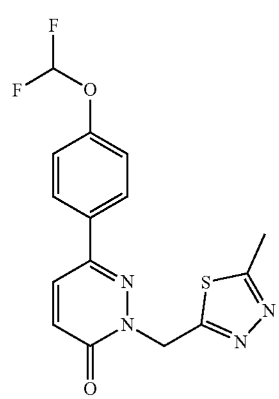 | 6-(4-(difluoromethoxy)phenyl)-2-((5-methyl-1,3,4-thiadiazol-2-yl)methyl)pyridazin-3(2H)-one | $^1$H NMR (DMSO-d6, 400 MHz): δ 8.14 (d, 1H), 8.00-7.95 (m, 2H), 7.54-7.17 (m, 4H), 5.72 (s, 2H), 2.70 (s, 3H); 351.2 |

TABLE 2-continued

| Cmpd No. | Structure | Name | NMR/MS |
|---|---|---|---|
| 224 | 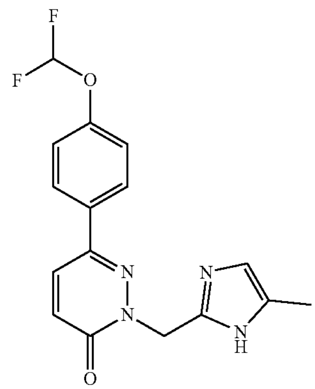 [SMILES: Cc1cnc(Cn2nc(-c3ccc(OC(F)F)cc3)ccc2=O)[nH]1] | 6-(4-(difluoromethoxy)phenyl)-2-((5-methyl-1H-imidazol-2-yl)methyl)pyridazin-3(2H)-one | m/z = 333.2 (M + H) |
| 225 | 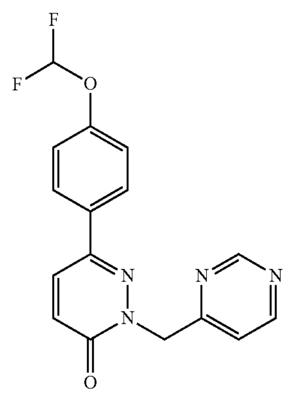 [SMILES: O=c1ccc(-c2ccc(OC(F)F)cc2)nn1Cc1ccncn1] | 6-(4-(difluoromethoxy)phenyl)-2-(pyrimidin-4-ylmethyl)pyridazin-3(2H)-one | [M + H]+ 331.1 |
| 226 | 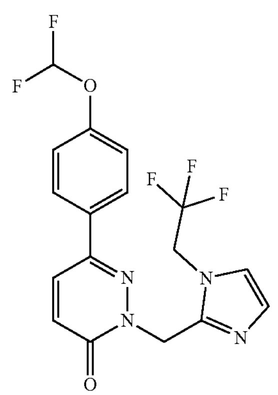 [SMILES: O=c1ccc(-c2ccc(OC(F)F)cc2)nn1Cc1nccn1CC(F)(F)F] | 6-(4-(difluoromethoxy)phenyl)-2-((1-(2,2,2-trifluoroethyl)-1H-imidazol-2-yl)methyl)pyridazin-3(2H)-one | [M + H]+ 401.1 |
| 227 | 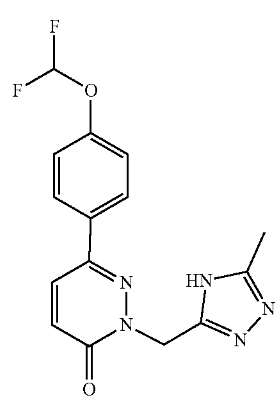 [SMILES: Cc1nnc(Cn2nc(-c3ccc(OC(F)F)cc3)ccc2=O)[nH]1] | 6-(4-(difluoromethoxy)phenyl)-2-((5-methyl-4H-1,2,4-triazol-3-yl)methyl)pyridazin-3(2H)-one | [M + H]+ 334.1 |

TABLE 2-continued

| Cmpd No. | Structure | Name | NMR/MS |
|---|---|---|---|
| 228 | 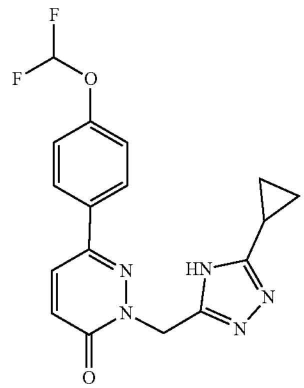 [SMILES: O=c1ccc(-c2ccc(OC(F)F)cc2)nn1Cc1nnc(C2CC2)[nH]1] | 2-((5-cyclopropyl-4H-1,2,4-triazol-3-yl)methyl)-6-(4-(difluoromethoxy)phenyl)-pyridazin-3(2H)-one | [M + H]+ 360.1 |
| 229 | 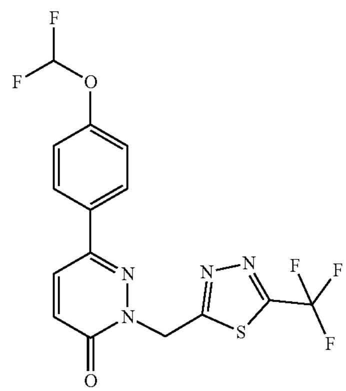 [SMILES: O=c1ccc(-c2ccc(OC(F)F)cc2)nn1Cc1nnc(C(F)(F)F)s1] | 6-(4-(difluoromethoxy)phenyl)-2-((5-(trifluoromethyl)-1,3,4-thiadiazol-2-yl)methyl)pyridazin-3(2H)-one | $^1$H NMR (DMSO-d6, 400 MHz): δ 8.21 (d, 1H), 8.05-8.00 (m, 2H), 7.59-7.21 (m, 4H), 5.95 (s, 2H); 405.1 |
| 230 | 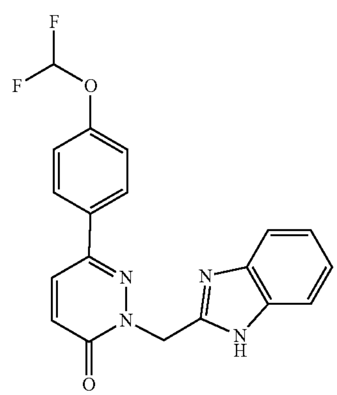 [SMILES: O=c1ccc(-c2ccc(OC(F)F)cc2)nn1Cc1nc2ccccc2[nH]1] | 2-((1H-benzo[d]imidazol-2-yl)methyl)-6-(4-(difluoromethoxy)phenyl)-pyridazin-3(2H)-one | m/z = 369.2 (M + H) |
| 231 | 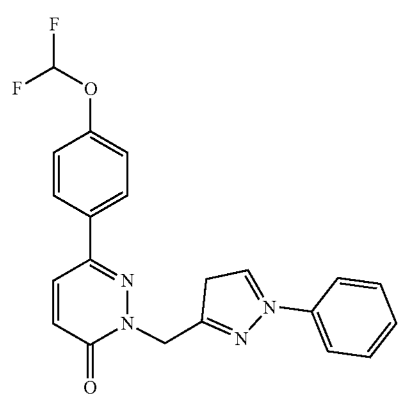 | 6-(4-(difluoromethoxy)phenyl)-2-((1-phenyl-1H-pyrazol-3-yl)methyl)pyridazin-3(2H)-one | [M + H]+ 395.2 |

TABLE 2-continued

| Cmpd No. | Structure | Name | NMR/MS |
|---|---|---|---|
| 232 | 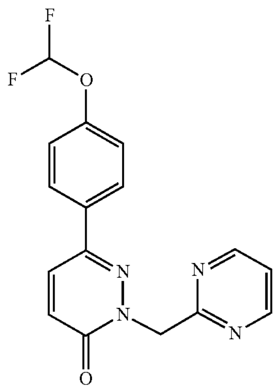 [SMILES: O=c1ccc(-c2ccc(OC(F)F)cc2)nn1Cc1ncccn1] | 6-(4-(difluoromethoxy)phenyl)-2-(pyrimidin-2-ylmethyl)pyridazin-3(2H)-one | [M + H]+ 331.1 |
| 233 | 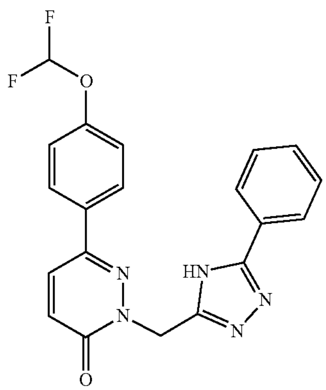 [SMILES: O=c1ccc(-c2ccc(OC(F)F)cc2)nn1Cc1nnc(-c2ccccc2)[nH]1] | 6-(4-(difluoromethoxy)phenyl)-2-((5-phenyl-4H-1,2,4-triazol-3-yl)methyl)pyridazin-3(2H)-one | [M + H]+ 331.1 |
| 234 | 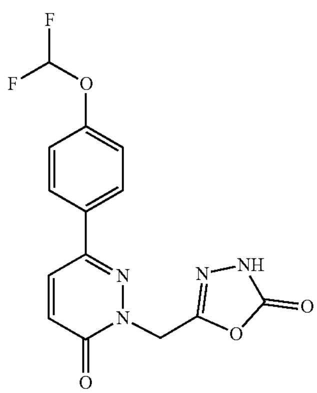 [SMILES: O=c1[nH]nc(Cn2nc(-c3ccc(OC(F)F)cc3)ccc2=O)o1] | 5-((3-(4-(difluoromethoxy)phenyl)-6-oxopyridazin-1(6H)-yl)methyl)-1,3,4-oxadiazol-2(3H)-one | m/z = 337.2 (M + H) |
| 235 | 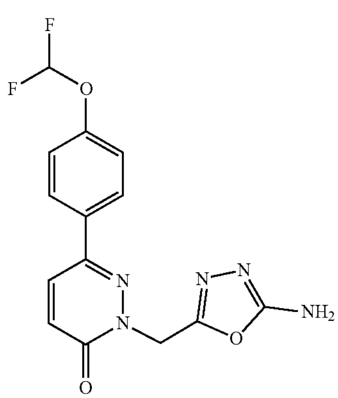 [SMILES: Nc1nnc(Cn2nc(-c3ccc(OC(F)F)cc3)ccc2=O)o1] | 2-((5-amino-1,3,4-oxadiazol-2-yl)methyl)-6-(4-(difluoromethoxy)phenyl)-pyridazin-3(2H)-one | m/z = 336.1 (M + H) |

TABLE 2-continued

| Cmpd No. | Structure | Name | NMR/MS |
|---|---|---|---|
| 236 | 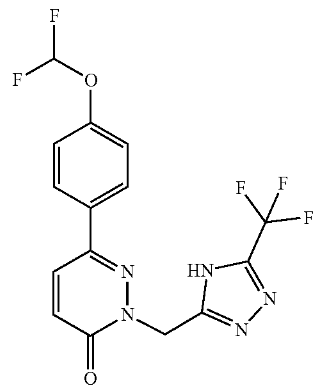 [SMILES: O=c1ccc(-c2ccc(OC(F)F)cc2)nn1Cc1nnc(C(F)(F)F)[nH]1] | 6-(4-(difluoromethoxy)phenyl)-2-((5-(trifluoromethyl)-4H-1,2,4-triazol-3-yl)methyl)pyridazin-3(2H)-one | [M + H]+ 388.1 |
| 237 | 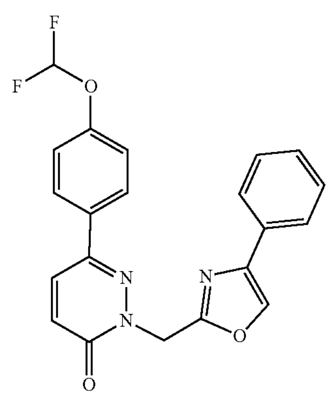 [SMILES: O=c1ccc(-c2ccc(OC(F)F)cc2)nn1Cc1nc(-c2ccccc2)co1] | 6-(4-(difluoromethoxy)phenyl)-2-((4-phenyloxazol-2-yl)methyl)pyridazin-3(2H)-one | m/z = 396.3 (M + H) |
| 238 | 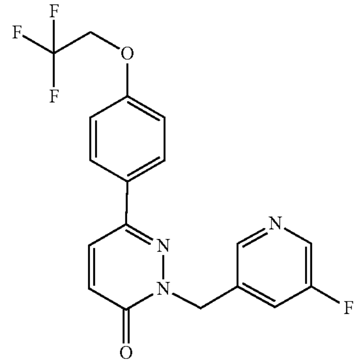 [SMILES: O=c1ccc(-c2ccc(OCC(F)(F)F)cc2)nn1Cc1cncc(F)c1] | 2-((5-fluoropyridin-3-yl)methyl)-6-(4-(2,2,2-trifluoroethoxy)phenyl)pyridazin-3(2H)-one | [M + H]+ 380.1 |

In certain embodiments, compounds of the methods described herein may be selected from commercially available compounds including those described in Table 3. Compounds of Table 3 and 4 were tested and $IC_{50}$ data appears in Table 5 and 6 herein. A=$IC_{50}$ is less than or equal to 10 µM; B=$IC_{50}$ is greater than 10 µM and less than 100 µM; C=$IC_{50}$ is greater than 100 µM.

TABLE 3

| Cmpd No. | Structure | Name |
| --- | --- | --- |
| 301 | 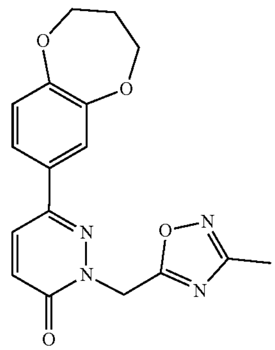 [SMILES: Cc1noc(Cn2nc(-c3ccc4c(c3)OCCCO4)ccc2=O)n1] | 6-(3,4-dihydro-2H-benzo[b][1,4]dioxepin-7-yl)-2-((3-methyl-1,2,4-oxadiazol-5-yl)methyl)pyridazin-3(2H)-one |
| 302 | 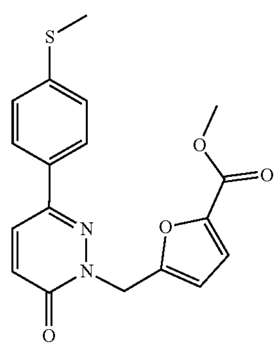 [SMILES: COC(=O)c1ccc(Cn2nc(-c3ccc(SC)cc3)ccc2=O)o1] | methyl 5-((3-(4-(methylthio)phenyl)-6-oxopyridazin-1(6H)-yl)methyl)furan-2-carboxylate |
| 303 | 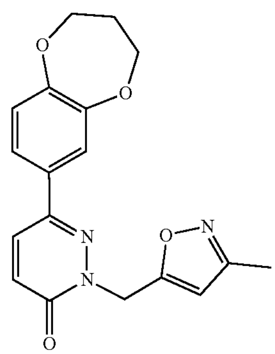 [SMILES: Cc1cc(Cn2nc(-c3ccc4c(c3)OCCCO4)ccc2=O)on1] | 6-(3,4-dihydro-2H-benzo[b][1,4]dioxepin-7-yl)-2-((3-methylisoxazol-5-yl)methyl)pyridazin-3(2H)-one |
| 304 | 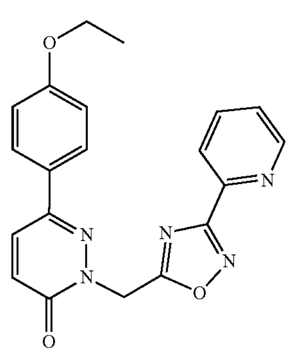 [SMILES: CCOc1ccc(-c2ccc(=O)n(Cc3nc(-c4ccccn4)no3)n2)cc1] | 6-(4-ethoxyphenyl)-2-((3-(pyridin-2-yl)-1,2,4-oxadiazol-5-yl)methyl)pyridazin-3(2H)-one |

TABLE 3-continued

| Cmpd No. | Structure | Name |
|---|---|---|
| 305 | 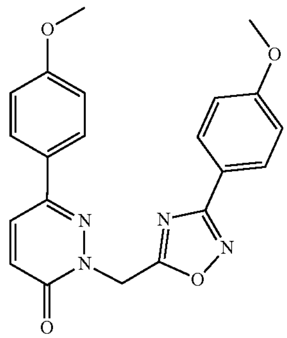 [SMILES: COc1ccc(-c2ccc(=O)n(Cc3nc(-c4ccc(OC)cc4)no3)n2)cc1] | 6-(4-methoxyphenyl)-2-((3-(4-methoxyphenyl)-1,2,4-oxadiazol-5-yl)methyl)pyridazin-3(2H)-one |
| 306 | 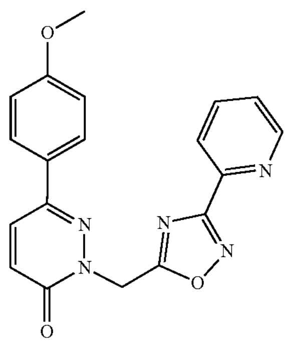 [SMILES: COc1ccc(-c2ccc(=O)n(Cc3nc(-c4ccccn4)no3)n2)cc1] | 6-(4-methoxyphenyl)-2-((3-(pyridin-2-yl)-1,2,4-oxadiazol-5-yl)methyl)pyridazin-3(2H)-one |
| 307 | 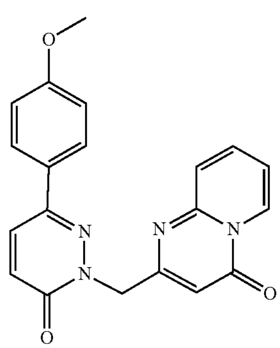 [SMILES: COc1ccc(-c2ccc(=O)n(Cc3cc(=O)n4ccccc4n3)n2)cc1] | 2-((3-(4-methoxyphenyl)-6-oxopyridazin-1(6H)-yl)methyl)-4H-pyrido[1,2-a]pyrimidin-4-one |
| 308 | 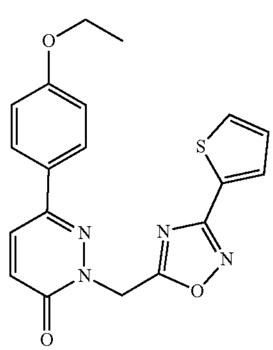 [SMILES: CCOc1ccc(-c2ccc(=O)n(Cc3nc(-c4cccs4)no3)n2)cc1] | 6-(4-ethoxyphenyl)-2-((3-(thiophen-2-yl)-1,2,4-oxadiazol-5-yl)methyl)pyridazin-3(2H)-one |

TABLE 3-continued

| Cmpd No. | Structure | Name |
|---|---|---|
| 309 | 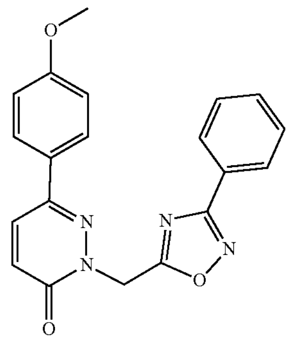 [SMILES: COc1ccc(-c2ccc(=O)n(Cc3nc(-c4ccccc4)no3)n2)cc1] | 6-(4-methoxyphenyl)-2-((3-phenyl-1,2,4-oxadiazol-5-yl)methyl)pyridazin-3(2H)-one |
| 310 | 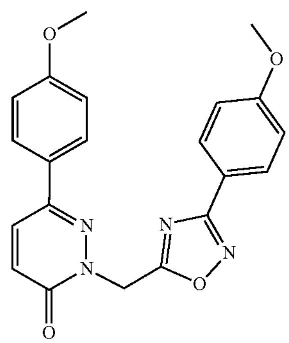 [SMILES: COc1ccc(-c2ccc(=O)n(Cc3nc(-c4ccc(OC)cc4)no3)n2)cc1] | 6-(4-methoxyphenyl)-2-((3-(4-methoxyphenyl)-1,2,4-oxadiazol-5-yl)methyl)pyridazin-3(2H)-one |
| 311 | 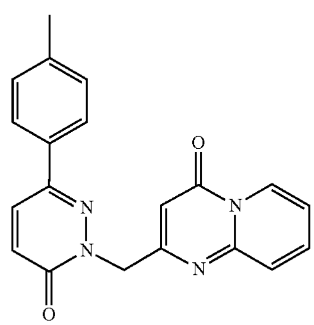 [SMILES: Cc1ccc(-c2ccc(=O)n(Cc3cc(=O)n4ccccc4n3)n2)cc1] | 2-((6-oxo-3-(p-tolyl)pyridazin-1(6H)-yl)methyl)-4H-pyrido[1,2-a]pyrimidin-4-one |
| 312 | 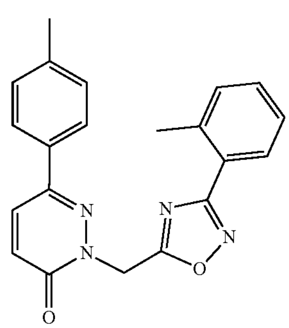 [SMILES: Cc1ccc(-c2ccc(=O)n(Cc3nc(-c4ccccc4C)no3)n2)cc1] | 6-(p-tolyl)-2-((3-(o-tolyl)-1,2,4-oxadiaxol-5-yl)methyl)pyridazin-3(2H)-one |

TABLE 3-continued

| Cmpd No. | Structure | Name |
| --- | --- | --- |
| 313 | 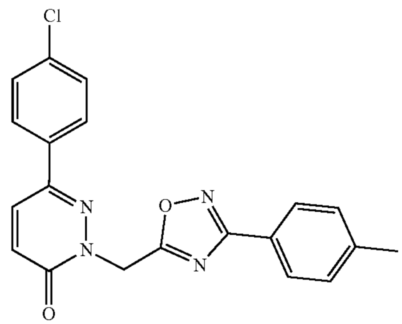 [SMILES: Cc1ccc(-c2noc(Cn3nc(-c4ccc(Cl)cc4)ccc3=O)n2)cc1] | 6-(4-chlorophenyl)-2-((3-(p-tolyl)-1,2,4-oxadiazol-5-yl)methyl)pyridazin-3(2H)-one |
| 314 | 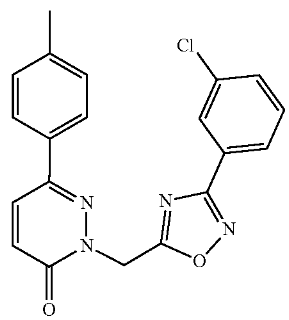 [SMILES: Cc1ccc(-c2ccc(=O)n(Cc3nc(-c4cccc(Cl)c4)no3)n2)cc1] | 2-((3-(3-chlorophenyl)-1,2,4-oxadiazol-5-yl)methyl)-6-(p-tolyl)pyridazin-3(2H)-one |
| 315 | 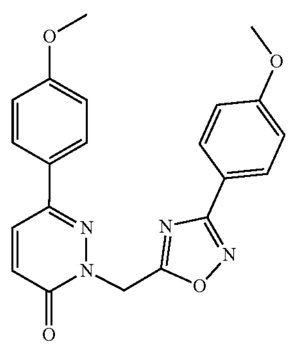 [SMILES: COc1ccc(-c2ccc(=O)n(Cc3nc(-c4ccc(OC)cc4)no3)n2)cc1] | 6-(4-methoxyphenyl)-2-((3-(4-methoxyphenyl)-1,2,4-oxadiazol-5-yl)methyl)pyridazin-3(2H)-one |

In certain embodiments, compounds for use in the methods described herein include those in Table 4 or salts thereof.

TABLE 4

| Compound No. | Structure | Name |
| --- | --- | --- |
| 350 | 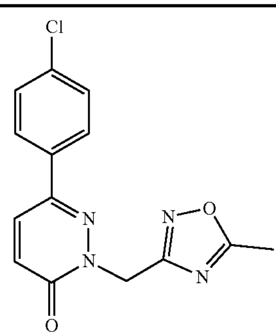 | 6-(4-chlorophenyl)-2-((5-methyl-1,2,4-oxadiazol-3-yl)methyl)pyridazin-3(2H)-one |

TABLE 4-continued

| Compound No. | Structure | Name |
|---|---|---|
| 351 | 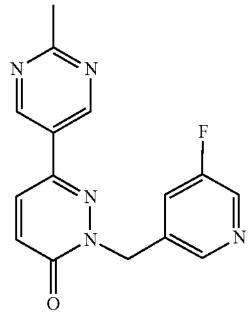 [SMILES: Cc1ncc(-c2ccc(=O)n(Cc3cncc(F)c3)n2)cn1] | 2-((5-fluoropyridin-3-yl)methyl)-6-(2-methylpyrimidin-5-yl)pyridazin-3(2H)-one |
| 352 | 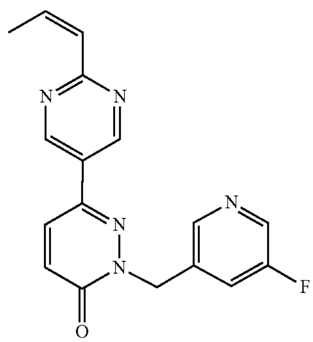 [SMILES: C/C=C\c1ncc(-c2ccc(=O)n(Cc3cncc(F)c3)n2)cn1] | (Z)-2-((5-fluoropyridin-3-yl)methyl)-6-(2-(prop-1-en-1-yl)pyrimidin-5-yl)pyridazin-3(2H)-one |

Skeletal IC$_{50}$ values of compounds of the disclosure appear in Table 5.

TABLE 5

| Cmpd No. | IC$_{50}$ |
|---|---|
| 1 | A |
| 2 | A |
| 3 | A |
| 4 | A |
| 5 | A |
| 6 | A |
| 7 | A |
| 8 | A |
| 9 | A |
| 10 | B |
| 11 | A |
| 12 | A |
| 13 | A |
| 14 | A |
| 15 | C |
| 16 | C |
| 17 | A |
| 18 | C |
| 19 | C |
| 20 | B |
| 22 | A |
| 23 | C |
| 24 | C |
| 25 | C |
| 26 | A |
| 27 | A |
| 28 | A |
| 30 | A |
| 31 | A |
| 32 | A |
| 33 | A |
| 34 | A |
| 36 | A |
| 37 | A |
| 38 | A |

TABLE 5-continued

| Cmpd No. | IC$_{50}$ |
|---|---|
| 39 | A |
| 40 | A |
| 41 | A |
| 42 | B |
| 43 | B |
| 44 | B |
| 45 | B |
| 46 | C |
| 47 | C |
| 49 | C |
| 50 | A |
| 51 | A |
| 52 | A |
| 53 | A |
| 54 | A |
| 55 | A |
| 56 | A |
| 57 | B |
| 58 | A |
| 59 | A |
| 60 | A |
| 61 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | C |
| 79 | A |
| 80 | C |

TABLE 5-continued

| Cmpd No. | IC$_{50}$ |
|---|---|
| 81 | C |
| 82 | B |
| 83 | B |
| 84 | C |
| 85 | B |
| 86 | C |
| 87 | A |
| 88 | A |
| 89 | A |
| 90 | A |
| 91 | A |
| 92 | A |
| 94 | A |
| 95 | A |
| 96 | A |
| 97 | A |
| 99 | A |
| 100 | A |
| 101 | A |
| 102 | A |
| 103 | A |
| 104 | A |
| 105 | A |
| 106 | A |
| 107 | C |
| 108 | A |
| 109 | A |
| 110 | A |
| 111 | A |
| 112 | A |
| 113 | A |
| 114 | A |
| 115 | A |
| 116 | A |
| 117 | A |
| 118 | A |
| 119 | A |
| 120 | A |
| 121 | A |
| 122 | A |
| 123 | A |
| 124 | A |
| 125 | A |
| 126 | A |
| 127 | A |
| 128 | A |
| 129 | A |
| 130 | A |
| 131 | A |
| 132 | A |
| 137 | A |
| 138 | A |
| 201 | A |
| 202 | A |
| 203 | A |
| 204 | A |
| 205 | A |
| 206 | A |
| 208 | A |
| 209 | A |
| 210 | A |
| 211 | B |
| 212 | B |
| 213 | B |
| 214 | B |
| 215 | B |
| 216 | B |
| 217 | B |
| 218 | B |
| 219 | B |
| 220 | B |
| 221 | B |
| 222 | B |
| 223 | B |
| 224 | C |
| 225 | C |
| 226 | C |
| 227 | C |
| 228 | C |
| 229 | C |
| 230 | C |
| 231 | C |
| 232 | C |
| 233 | C |
| 234 | C |
| 235 | C |
| 236 | C |
| 237 | B |
| 238 | A |
| 301 | C |
| 302 | B |
| 304 | A |
| 305 | A |
| 306 | B |
| 307 | B |
| 308 | A |
| 309 | A |
| 310 | A |
| 311 | B |
| 312 | A |
| 313 | B |
| 314 | C |
| 315 | A |
| 350 | C |
| 351 | B |
| 352 | A |

A = IC$_{50}$ is less than or equal to 10 μM;
B = IC$_{50}$ is greater than 10 μM and less than 100 μM;
C = IC$_{50}$ is greater than 100 μM.

Certain compounds of the disclosure have cardiac IC$_{50}$ values as in Table 6.

TABLE 6

| Cmpd No. | IC$_{50}$ |
|---|---|
| 1 | B |
| 2 | C |
| 3 | C |
| 4 | C |
| 5 | C |
| 6 | C |
| 7 | B |
| 8 | C |
| 9 | C |
| 10 | C |
| 11 | C |
| 12 | B |
| 13 | C |
| 14 | C |
| 15 | C |
| 16 | C |
| 17 | C |
| 18 | C |
| 19 | C |
| 20 | C |
| 22 | C |
| 23 | C |
| 24 | C |
| 25 | C |
| 26 | B |
| 27 | A |
| 28 | B |
| 30 | B |
| 31 | C |
| 32 | C |
| 33 | C |
| 34 | C |
| 36 | C |
| 37 | C |
| 38 | A |
| 39 | C |
| 40 | C |

TABLE 6-continued

| Cmpd No. | IC$_{50}$ |
|---|---|
| 41 | C |
| 42 | C |
| 43 | C |
| 44 | C |
| 45 | C |
| 46 | C |
| 47 | C |
| 48 | C |
| 49 | C |
| 50 | B |
| 51 | C |
| 52 | B |
| 53 | C |
| 54 | C |
| 55 | B |
| 56 | C |
| 57 | C |
| 58 | C |
| 59 | C |
| 60 | C |
| 61 | C |
| 65 | C |
| 66 | C |
| 67 | B |
| 68 | B |
| 69 | B |
| 70 | C |
| 71 | C |
| 72 | C |
| 73 | C |
| 74 | C |
| 75 | C |
| 76 | C |
| 77 | B |
| 78 | C |
| 79 | C |
| 80 | C |
| 81 | C |
| 82 | C |
| 83 | C |
| 84 | C |
| 86 | C |
| 87 | B |
| 88 | C |
| 89 | C |
| 90 | C |
| 91 | C |
| 92 | C |
| 94 | A |
| 95 | B |
| 96 | C |
| 99 | C |
| 100 | C |
| 101 | C |
| 102 | C |
| 103 | C |
| 104 | C |
| 105 | C |
| 106 | B |
| 109 | C |
| 110 | C |
| 111 | C |
| 112 | B |
| 113 | C |
| 114 | C |
| 115 | B |
| 116 | C |
| 117 | C |
| 118 | C |
| 119 | B |
| 120 | B |
| 121 | C |
| 122 | C |
| 123 | C |
| 124 | C |
| 125 | C |
| 126 | C |
| 127 | C |
| 128 | C |
| 129 | C |
| 130 | C |
| 131 | C |
| 132 | B |
| 137 | C |
| 138 | C |
| 201 | C |
| 202 | C |
| 203 | C |
| 204 | C |
| 205 | B |
| 206 | C |
| 208 | C |
| 209 | C |
| 210 | B |
| 211 | C |
| 212 | C |
| 213 | C |
| 214 | C |
| 215 | C |
| 216 | C |
| 217 | C |
| 218 | C |
| 219 | C |
| 220 | C |
| 221 | C |
| 222 | C |
| 223 | C |
| 224 | C |
| 225 | C |
| 226 | C |
| 227 | C |
| 228 | C |
| 229 | C |
| 230 | C |
| 231 | C |
| 232 | C |
| 233 | C |
| 234 | C |
| 235 | C |
| 236 | C |
| 237 | C |
| 238 | C |
| 301 | C |
| 302 | C |
| 304 | D |
| 305 | D |
| 306 | D |
| 307 | D |
| 308 | C |
| 309 | C |
| 310 | C |
| 311 | D |
| 312 | C |
| 313 | C |
| 314 | C |
| 315 | C |
| 350 | C |
| 352 | C |

A = IC$_{50}$ is less than or equal to 10 µM;
B = IC$_{50}$ is greater than 10 µM and less than 100 µM;
C = IC$_{50}$ is greater than 100 µM;
D is greater than 60 µM.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating activity-induced muscle damage, a neuromuscular condition, a metabolic myopathy, or a movement disorder,
wherein the neuromuscular condition is selected from Duchenne Muscular Dystrophy, Becker muscular dystrophy, myotonic dystrophy 1, myotonic dystrophy 2, facioscapulohumeral muscular dystrophy, oculopharyngeal muscular dystrophy, limb girdle muscular dystrophy, tendinitis, and carpal tunnel syndrome;
wherein the movement disorder comprises muscle spasticity associated with multiple sclerosis; Parkinson's disease; Alzheimer's disease; cerebral palsy; injury; or a traumatic event, wherein the traumatic event is selected from stroke, traumatic brain injury, spinal cord injury, hypoxia, meningitis, encephalitis, phenylketonuria, and amyotrophic lateral sclerosis;
wherein the metabolic myopathy is selected from McArdle's syndrome;
the method comprising administering to a subject in need thereof a compound or salt of Formula (III'):

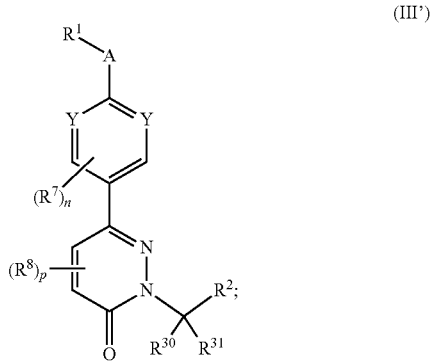

(III')

or a salt thereof, wherein:
each Y is independently selected from $C(R^3)$, N, and $N^+(-O^-)$;
A is absent or selected from —O—, —$NR^4$—, —$CR^5R^6$—, —C(O)—, —S—, —S(O)—, and —$S(O)_2$—;
$R^1$ is selected from:
$C_{1-6}$ alkyl, $C_{2-6}$ alkenyl, and $C_{2-6}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, —CN, $C_{3-10}$ carbocycle, and 3- to 10-membered heterocycle, wherein the $C_{3-10}$ carbocycle and 3- to 10-membered heterocycle are each optionally substituted with one or more $R^9$; and
$C_{3-10}$ carbocycle and 3- to 10-membered heterocycle, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)$ $OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN; or
$R^1$ together with $R^3$ form a 5- to 10-membered heterocycle or $C_{5-10}$ carbocycle, wherein the 5- to 10-membered heterocycle or $C_{5-10}$ carbocycle is optionally substituted with one or more $R^9$; or $R^1$ together with $R^5$ form a 3- to 10-membered heterocycle or saturated $C_{3-10}$ carbocycle, wherein the 3- to 10-membered heterocycle or saturated $C_{3-10}$ carbocycle is optionally substituted with one or more $R^9$; or $R^1$ together with $R^4$ form a 3- to 10-membered heterocycle, wherein the 3- to 10-membered heterocycle is optionally substituted with one or more $R^9$; and
when A is —$NR^4$—, $R^1$ is additionally selected from hydrogen, and when A is —C(O)—, $R^1$ is additionally selected from —$N(R^{10})_2$ and —$OR^{10}$;
when A is absent, $R^1$ is further selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, and —CN;
$R^2$ is a heteroaryl optionally substituted with one or more substituents independently selected from:
halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN; and when $R^2$ is pyridyl or pyrimidyl, a substituent on a nitrogen atom of the pyridyl or pyrimidyl is optionally further selected from —O—;
$C_{1-6}$ alkyl, $C_{2-6}$ alkenyl, and $C_{2-6}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, —CN, $C_{3-10}$ carbocycle and 3- to 10-membered heterocycle, wherein the $C_{3-10}$ carbocycle and 3- to 10-membered heterocycle are each optionally substituted with one or more $R^9$; and
$C_{3-10}$ carbocycle and 3- to 10-membered heterocycle, each of which is optionally substituted with one or more $R^9$;
each $R^3$, $R^5$, and $R^6$ are independently selected from:
hydrogen, halogen, —$OR^{10}$, —$SR^{10}$, —$N(R^{10})_2$, —$NO_2$, —CN, and $C_{1-6}$ alkyl optionally substituted with one or more substituents independently selected from halogen, —$OR^{10}$, —$SR^{10}$, —$N(R^{10})_2$, —$NO_2$, and —CN; or
$R^3$ together with $R^1$ form a 5- to 10-membered heterocycle or $C_{5-10}$ carbocycle, wherein the 5- to 10-membered heterocycle or $C_{5-10}$ carbocycle is optionally substituted with one or more $R^9$; or $R^5$ together with $R^1$ form a 3- to 10-membered heterocycle or $C_{3-10}$ carbocycle, wherein the 3- to 10-membered heterocycle or $C_{3-10}$ carbocycle is optionally substituted with one or more $R^9$;
$R^4$ is independently selected from:
hydrogen; and
$C_{1-6}$ alkyl optionally substituted with one or more substituents independently selected from halogen, —$OR^{10}$, —$SR^{10}$, —$N(R^{10})_2$, —$NO_2$, and —CN; or R⁴ together with R¹ form a 3- to 10-membered heterocycle, which is optionally substituted with one or more R⁹;

each R⁷ and R⁸ is independently selected from:
  halogen, —OR¹⁰, —SR¹⁰, —N(R¹⁰)₂, —NO₂, —CN, and C₁₋₆ alkyl optionally substituted with one or more substituents independently selected from halogen, —OR¹⁰, —SR¹⁰, —N(R¹⁰)₂, —NO₂, and —CN;

each R⁹ is independently selected from:
  halogen, —OR¹⁰, —SR¹⁰, —N(R¹⁰)₂, —C(O)R¹⁰, —C(O)N(R¹⁰)₂, —N(R¹⁰)C(O)R¹⁰, —N(R¹⁰)C(O)N(R¹⁰)₂, —OC(O)N(R¹⁰)₂, —N(R¹⁰)C(O)OR¹⁰, —C(O)OR¹⁰, —OC(O)R¹⁰, —S(O)R¹⁰, —S(O)₂R¹⁰, —NO₂, =O, =S, =N(R¹⁰), and —CN; and
  C₁₋₃ alkyl, C₂₋₃ alkenyl, and C₂₋₃ alkynyl, each of which is optionally substituted with one or more substituents independently selected from halogen, —OR¹⁰, —SR¹⁰, —N(R¹⁰)₂, —C(O)R¹⁰, —C(O)N(R¹⁰)₂, —N(R¹⁰)C(O)R¹⁰, —N(R¹⁰)C(O)N(R¹⁰)₂, —OC(O)N(R¹⁰)₂, —N(R¹⁰)C(O)OR¹⁰, —C(O)OR¹⁰, —OC(O)R¹⁰, —S(O)R¹⁰, —S(O)₂R¹⁰, —NO₂, =O, =S, =N(R¹⁰), and —CN;

each R¹⁰ is independently selected from:
  hydrogen; and
  C₁₋₆ alkyl, C₂₋₆ alkenyl, and C₂₋₆ alkynyl, each of which is optionally substituted with one or more substituents independently selected from halogen, —CN, —OH, —SH, —NO₂, —NH₂, =O, =S, —O—C₁₋₆ alkyl, —S—C₁₋₆ alkyl, —N(C₁₋₆ alkyl)₂, —NH(C₁₋₆ alkyl), C₃₋₁₀ carbocycle, and 3- to 10-membered heterocycle; and
  C₃₋₁₀ carbocycle, and 3- to 10-membered heterocycle, each of which is optionally substituted with one or more substituents independently selected from halogen, —CN, —OH, —SH, —NO₂, —NH₂, =O, =S, —O—C₁₋₆ alkyl, —S—C₁₋₆ alkyl, —N(C₁₋₆ alkyl)₂, —NH(C₁₋₆ alkyl), C₁₋₆ alkyl, C₂₋₆ alkenyl, C₂₋₆ alkynyl, C₃₋₁₀ carbocycle, 3- to 10-membered heterocycle, and haloalkyl;

R³⁰ and R³¹ are independently selected from R¹⁰; or R³⁰ and R³¹ come together to form a C₃₋₇ carbocycle or 3- to 7-membered heterocycle, wherein C₃₋₇ carbocycle or 3- to 7-membered heterocycle is optionally substituted with one or more R⁹;

n is 0, 1, or 2; and
p is 0, 1, or 2.

2. The method of claim 1, wherein each R³⁰ and R³¹ is independently hydrogen.
3. The method of claim 1, wherein A is absent.
4. The method of claim 1, wherein each Y is independently selected from C(R³) and N.
5. The method of claim 1, wherein at least one Y is N or N⁺(—O⁻).
6. The method of claim 1, wherein one Y is N, and one Y is C(R³).
7. The method of claim 1, wherein one Y is N⁺(—O⁻), and one Y is C(R³).
8. The method of claim 1, wherein one Y is N, and one Y is N⁺(—O⁻).
9. The method of claim 1, wherein each Y is N.
10. The method of claim 1, wherein each Y is C(R³).
11. The method of claim 1, wherein the method is for treating a neuromuscular condition.
12. The method of claim 11, wherein the neuromuscular condition is Duchenne muscular dystrophy.
13. The method of claim 11, wherein the neuromuscular condition is Becker muscular dystrophy.
14. The method of claim 1, wherein a movement disorder is treated, wherein the movement disorder comprises muscle spasticity.
15. The method of claim 14, wherein the muscle spasticity is selected from spasticity associated with multiple sclerosis, Parkinson's disease, Alzheimer's disease, and cerebral palsy.
16. The method of claim 1, wherein the compound or salt is administered in an amount sufficient to reduce involuntary muscle contractions.
17. The method of claim 16, wherein the compound or salt is administered in an amount sufficient to reduce involuntary muscle contractions by at least 10%.
18. The method of claim 1, wherein the method further comprises administering to the subject an additional therapeutic agent.
19. The method of claim 18, wherein the additional therapeutic agent is corticosteroid.
20. The method of claim 19, wherein the corticosteroid is deflazacort or prednisone.
21. The method of claim 18, wherein the additional therapeutic agent is vamorolone.
22. The method of claim 18, wherein the additional therapeutic agent is a gene therapy.
23. The method of claim 22, wherein the gene therapy comprises dystrophin gene or a variant or truncated version thereof.
24. The method of claim 22, wherein the gene therapy comprises microdystrophin.
25. The method of claim 18, wherein the additional therapeutic agent is an exon skipping agent.
26. The method of claim 25, wherein the exon skipping agent is eteplirsen.
27. The method of claim 25, wherein the exon skipping agent is ataluren.
28. The method of claim 1, wherein the compound is selected from

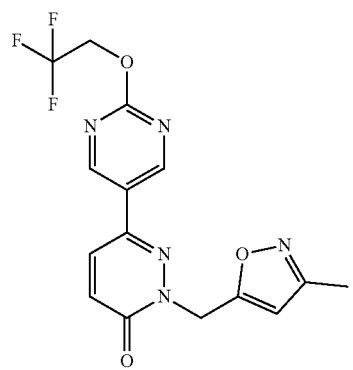 [SMILES: Cc1cc(Cn2nc(-c3cnc(OCC(F)(F)F)nc3)ccc2=O)on1]

or a salt thereof.

29. The method of claim 1, wherein the compound is selected from

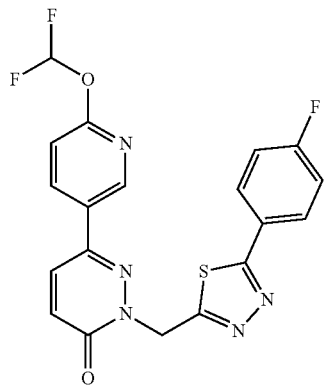

or a salt thereof.

30. The method of claim 1, wherein the compound is selected from

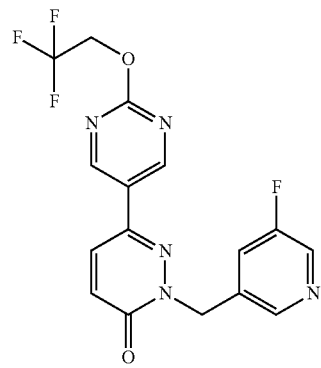 [SMILES: O=c1ccc(-c2cnc(OCC(F)(F)F)nc2)nn1Cc1cncc(F)c1]

or a salt thereof.

31. The method of claim 1, wherein the compound is selected from

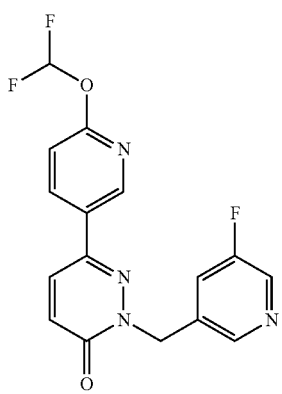

a salt thereof.

32. The method of claim 1, wherein the compound is selected from

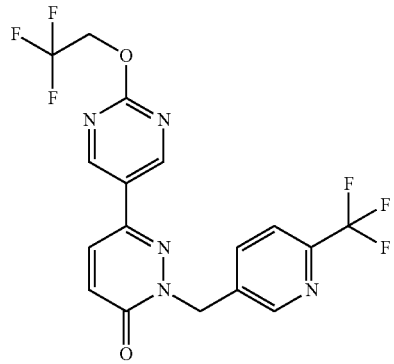 [SMILES: O=c1ccc(-c2cnc(OCC(F)(F)F)nc2)nn1Cc1ccc(C(F)(F)F)nc1]

or a salt thereof.

33. The method of claim 1, wherein the compound is selected from

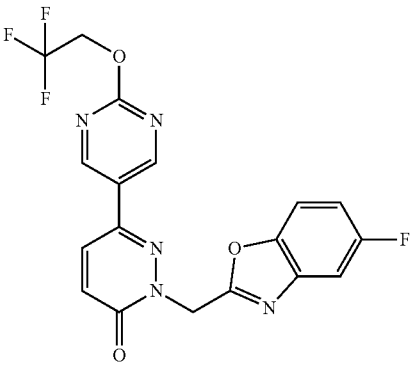 [SMILES: O=c1ccc(-c2cnc(OCC(F)(F)F)nc2)nn1Cc1nc2cc(F)ccc2o1]

or a salt thereof.

34. The method of claim 1, wherein the compound is selected from or

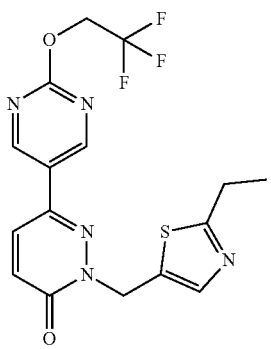 [SMILES: CCc1ncc(Cn2nc(-c3cnc(OCC(F)(F)F)nc3)ccc2=O)s1]

a salt thereof.

35. The method of claim 1, wherein the compound is selected from

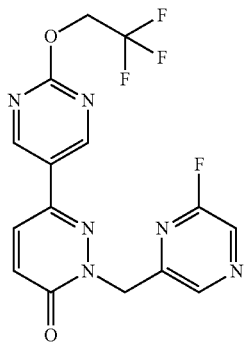

or a salt thereof.

36. The method of claim 1, wherein the compound is selected from

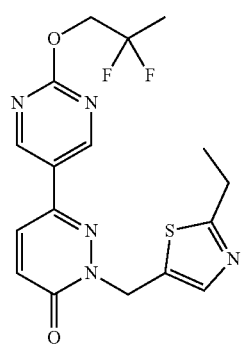 [SMILES: CCc1ncc(Cn2nc(-c3cnc(OCC(C)(F)F)nc3)ccc2=O)s1]

or a salt thereof.

37. The method of claim 31, wherein the compound is selected from

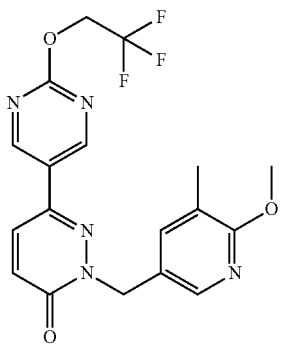 [SMILES: COc1ncc(Cn2nc(-c3cnc(OCC(F)(F)F)nc3)ccc2=O)cc1C]

or a salt thereof.

38. The method of claim 1, wherein the method is for treating a metabolic myopathy, and the metabolic myopathy is selected from McArdle's disease.

39. The method of claim 1, wherein the compound or salt is selected from

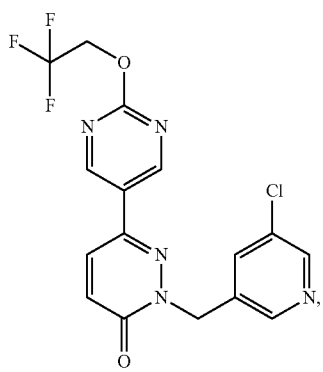

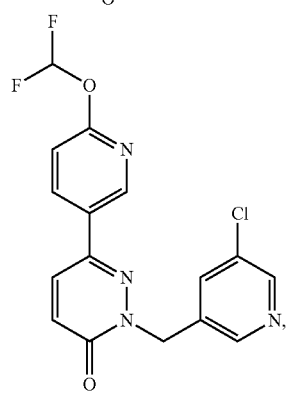

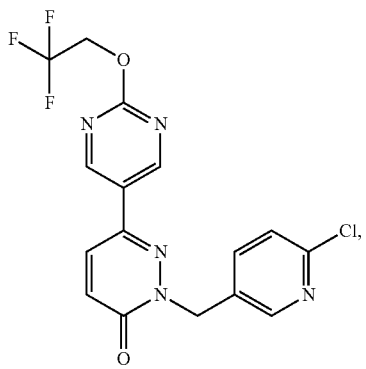

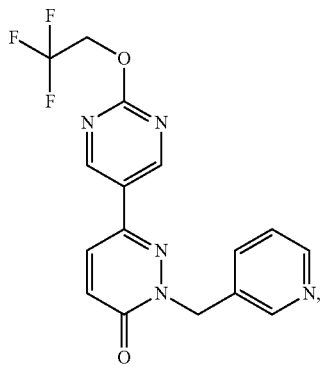

261
-continued
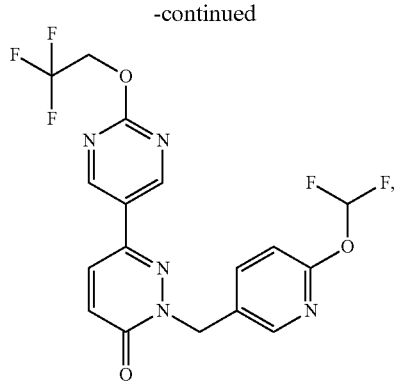
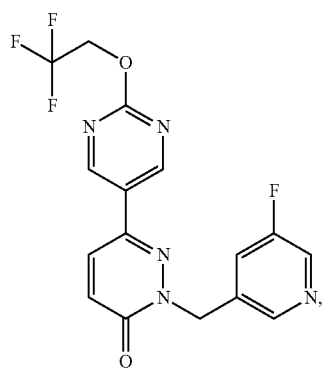
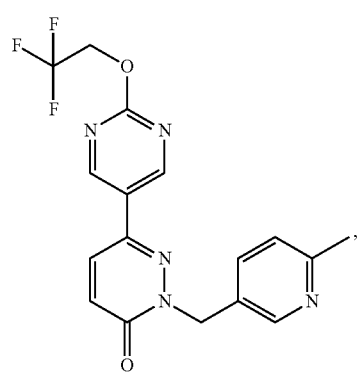
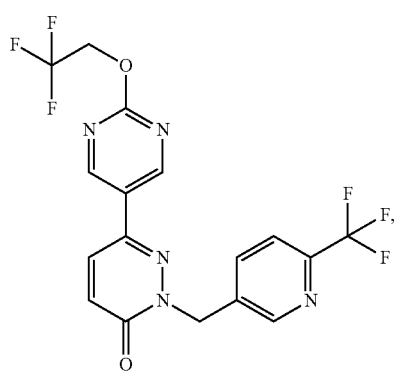
262
-continued
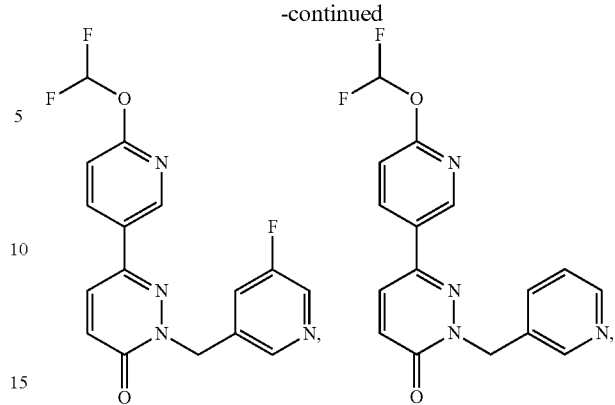
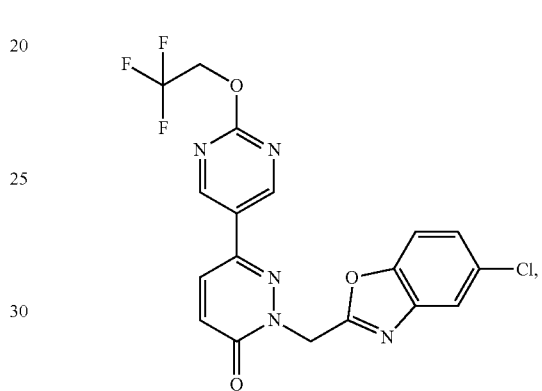
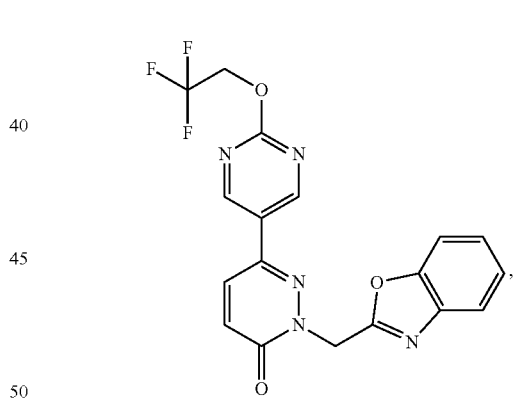
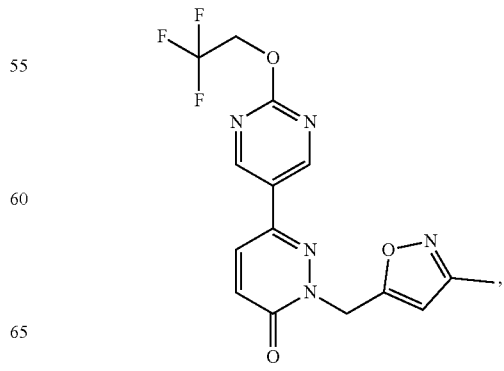

263
-continued
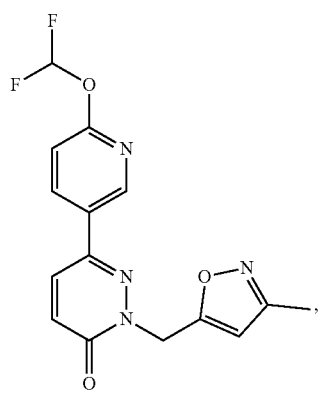
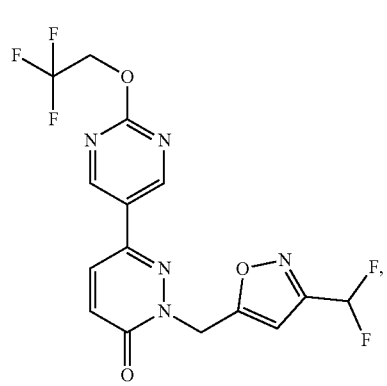
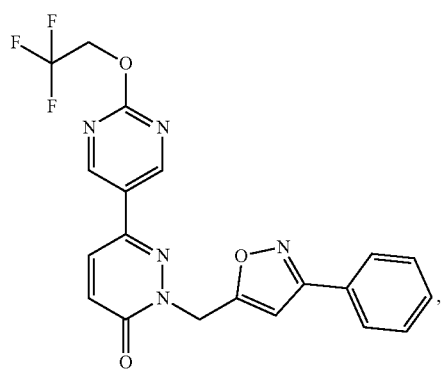
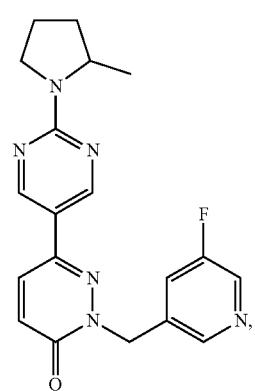
264
-continued
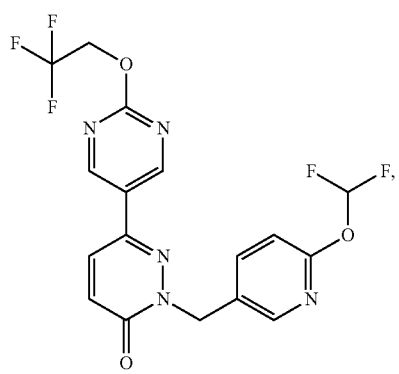
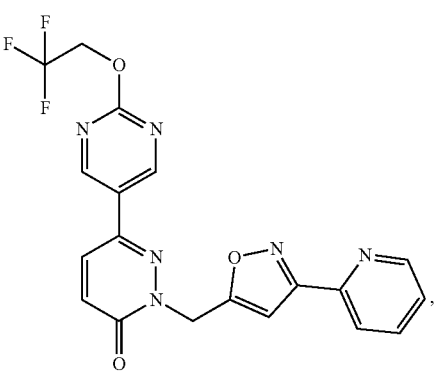
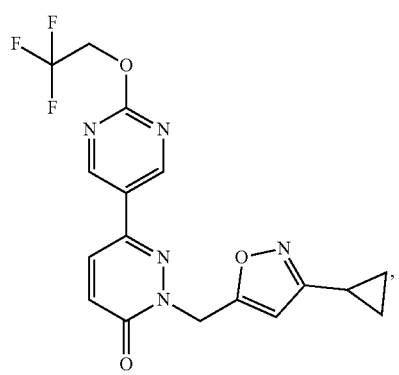

265
-continued
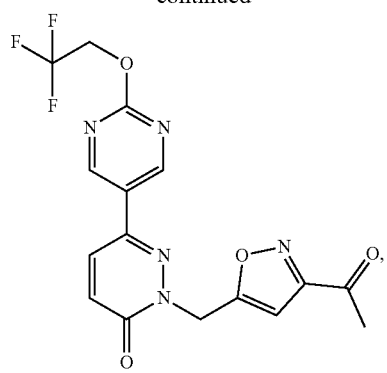
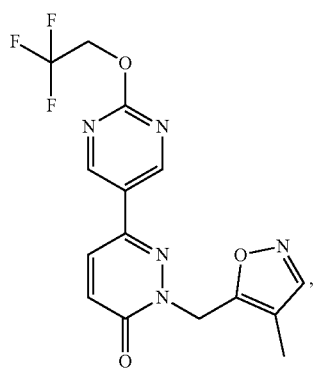
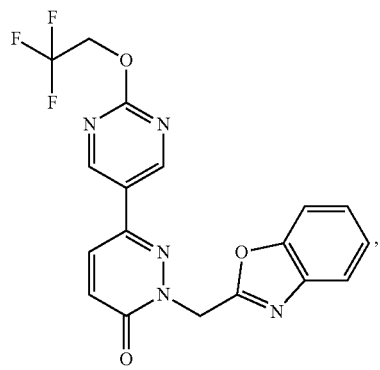
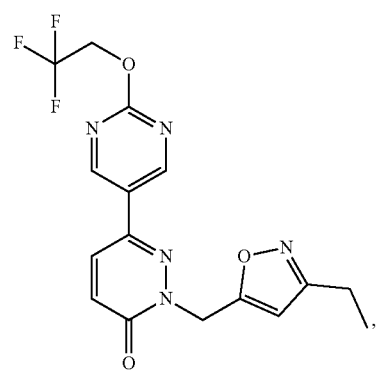
266
-continued
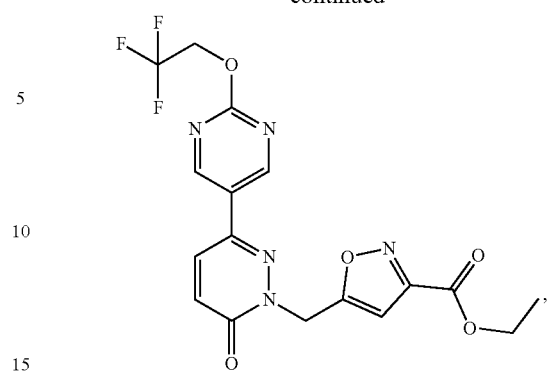
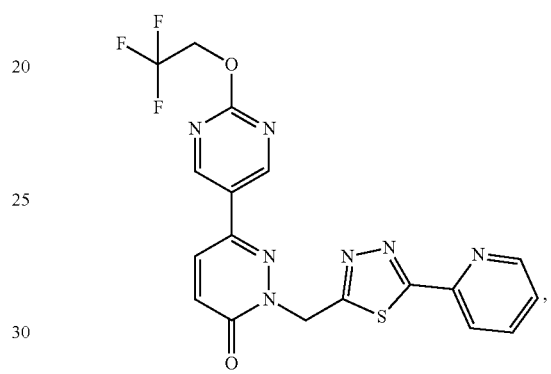
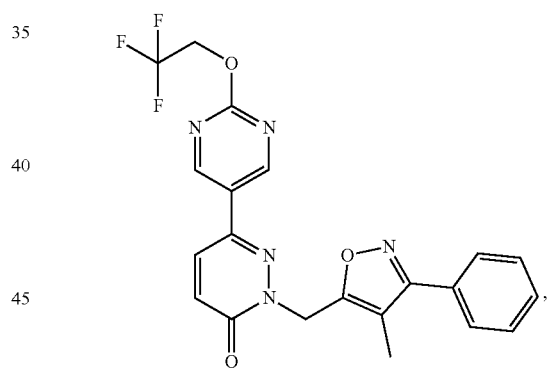
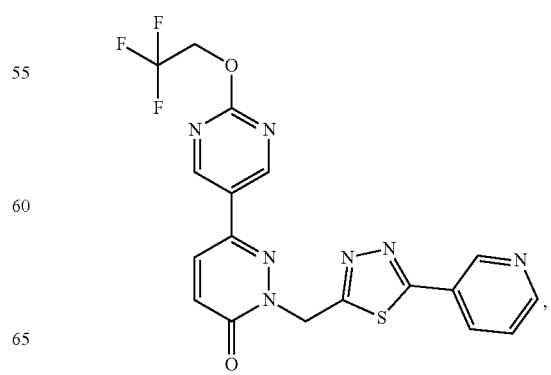

267
-continued
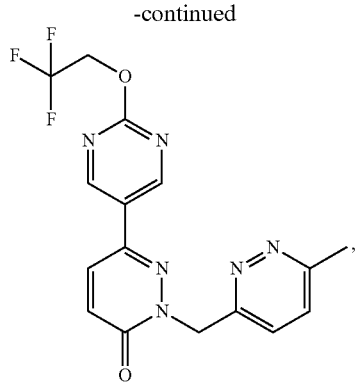
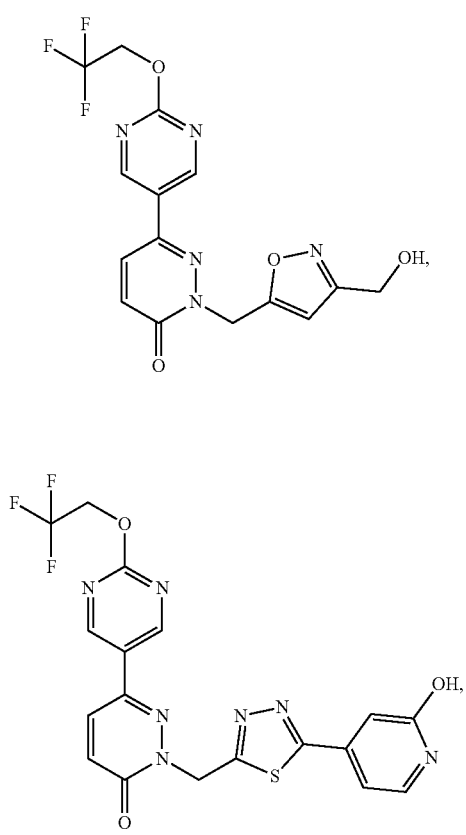
268
-continued
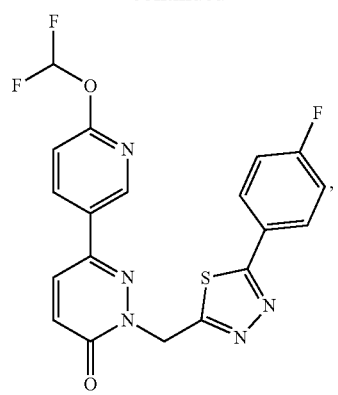
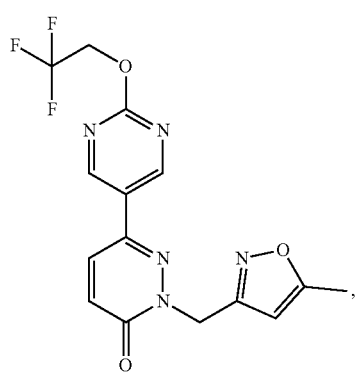
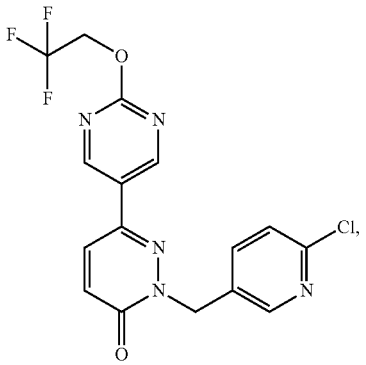
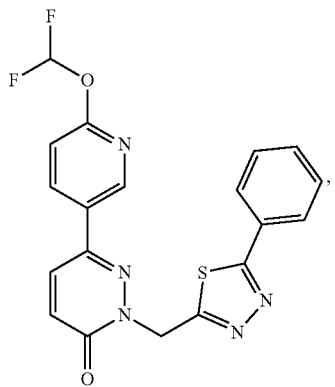

269
-continued
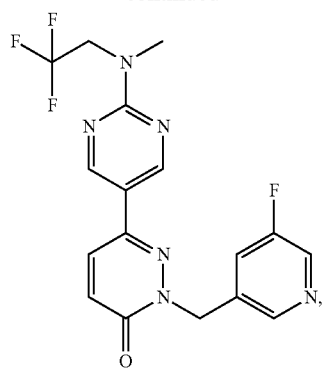
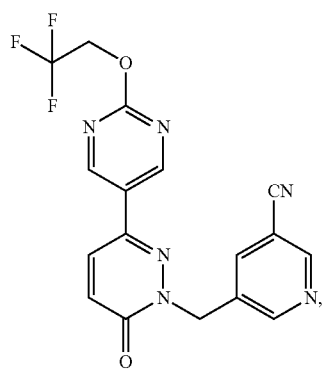
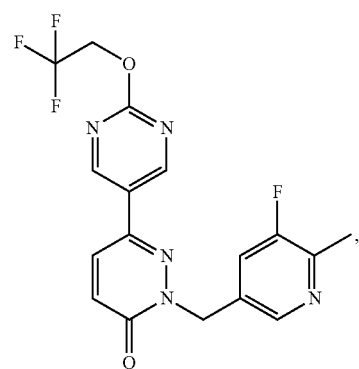
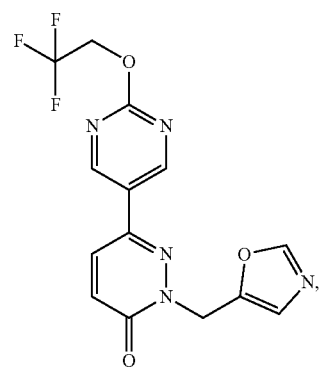
270
-continued
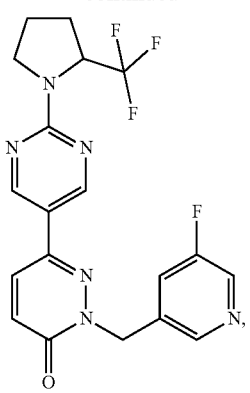
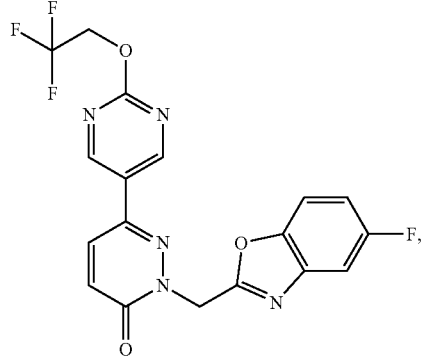
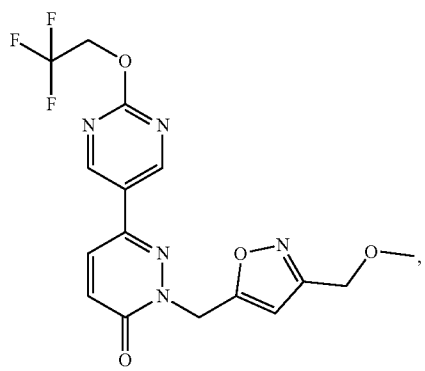
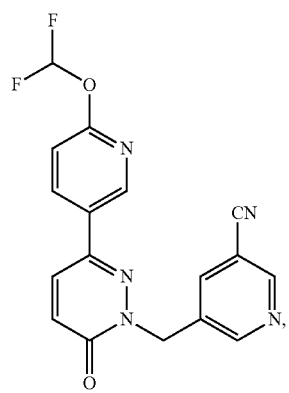

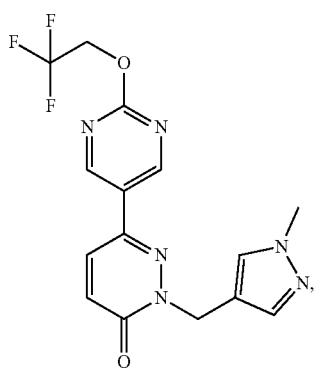
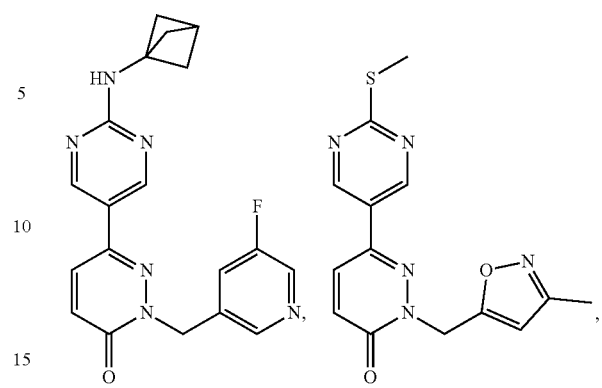
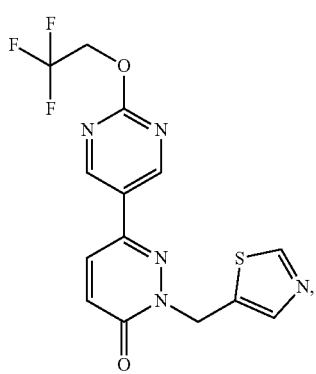
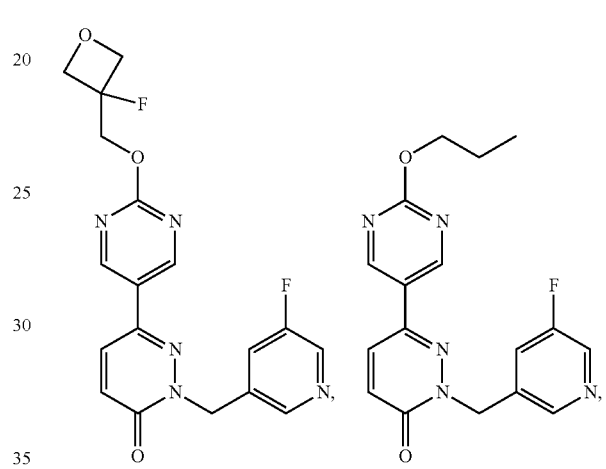
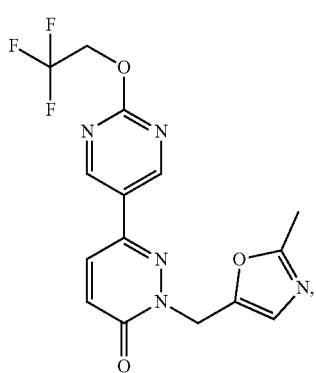
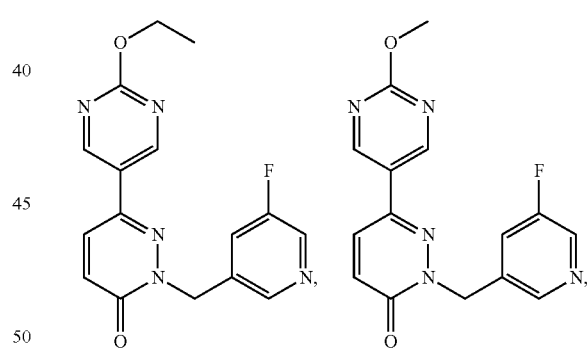
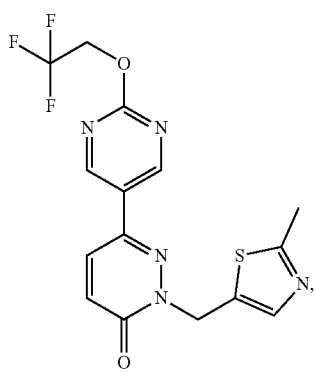
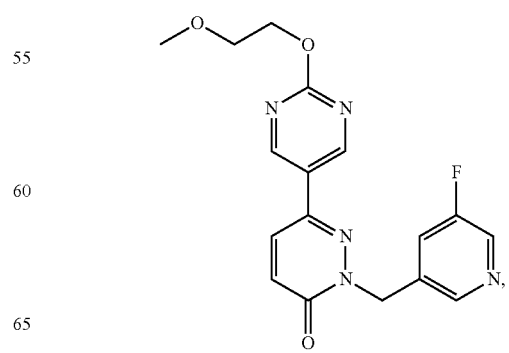

273
-continued
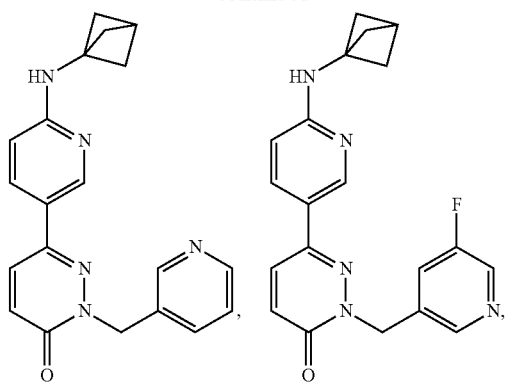
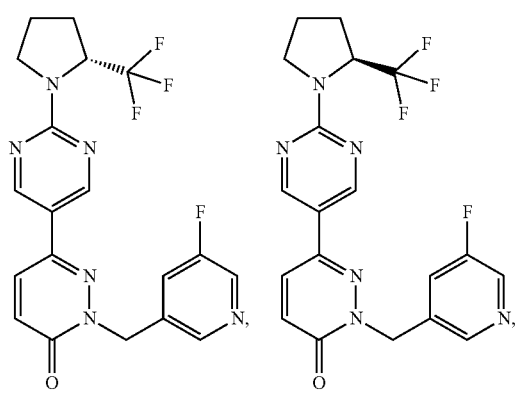
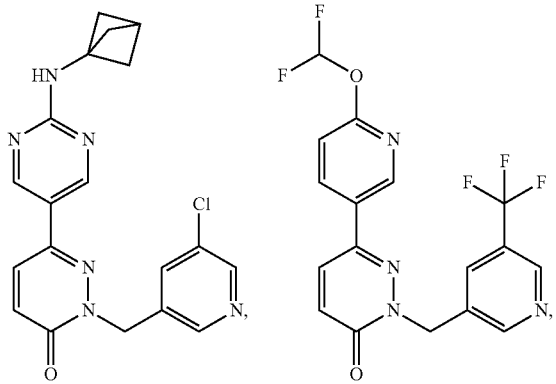
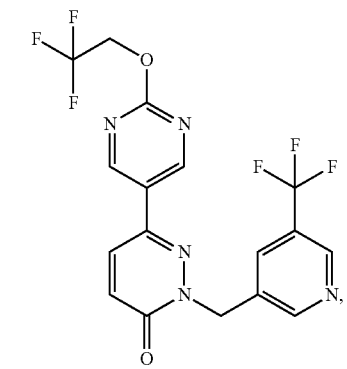
274
-continued
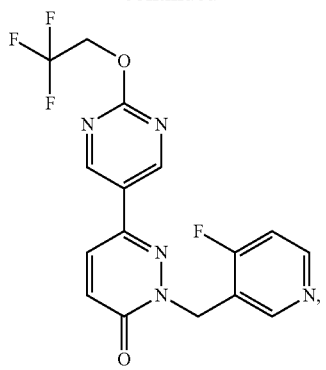
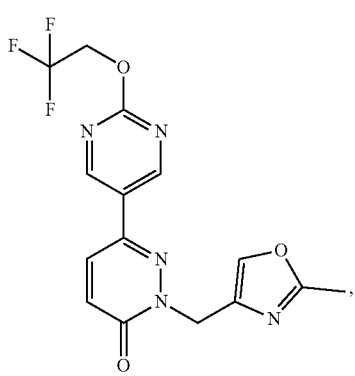
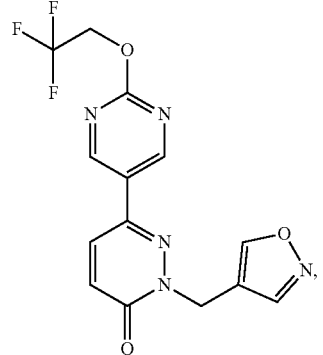
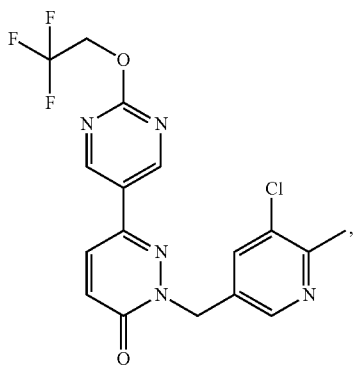

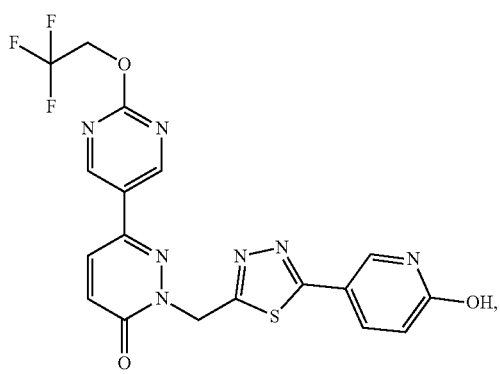
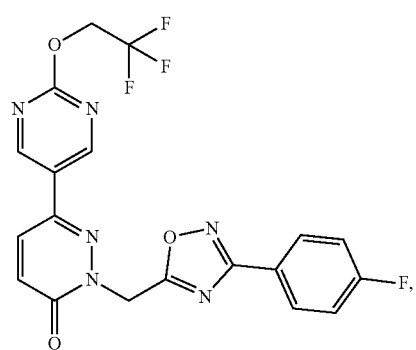
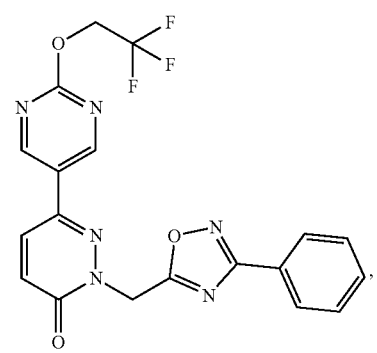
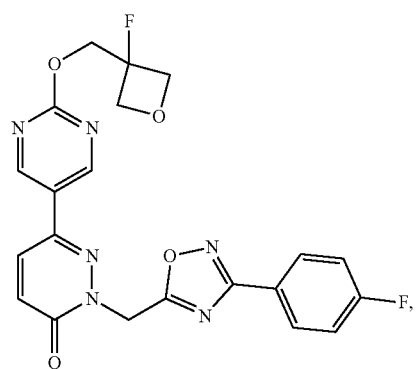
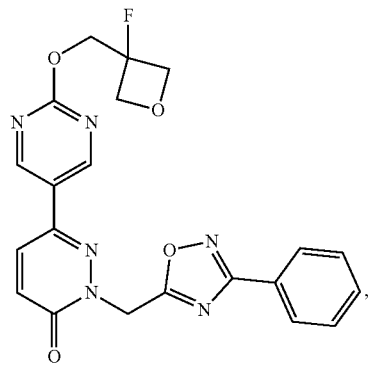
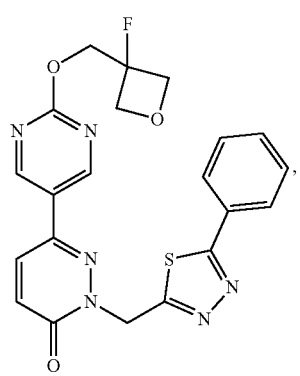
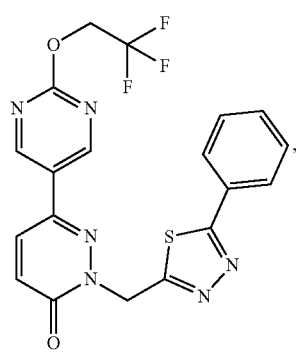
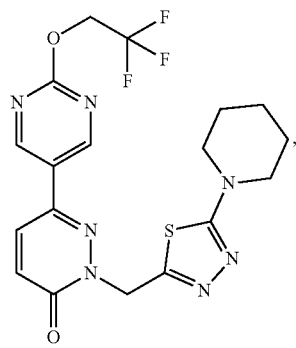

277
-continued
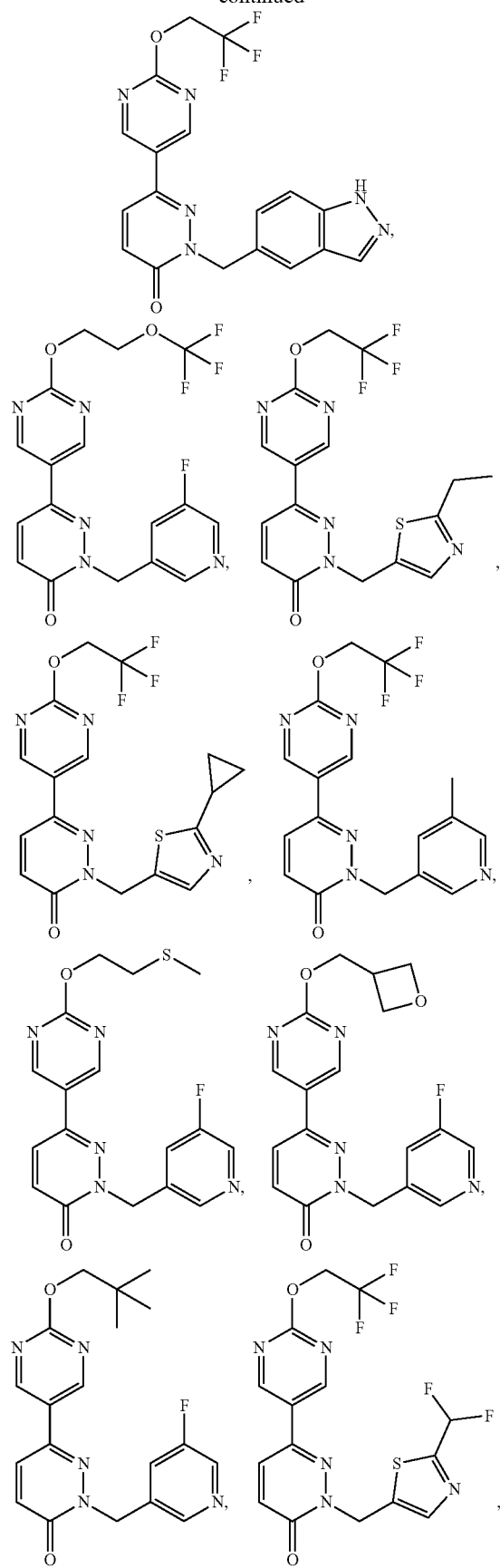
278
-continued
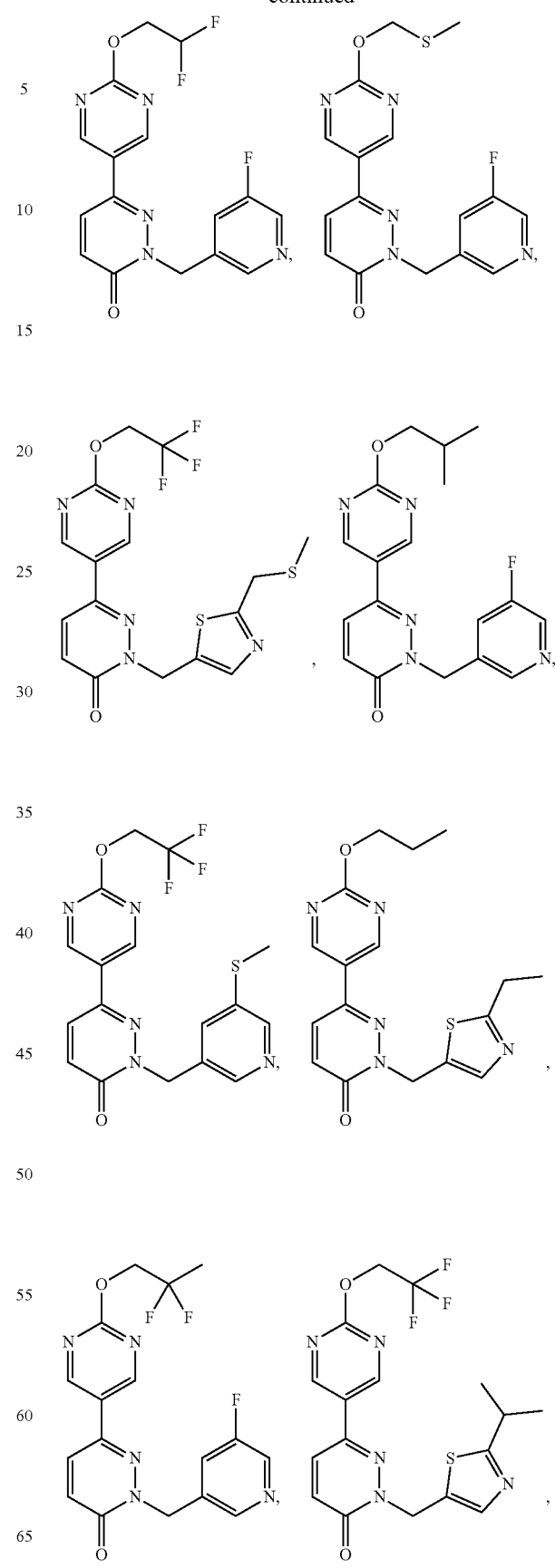

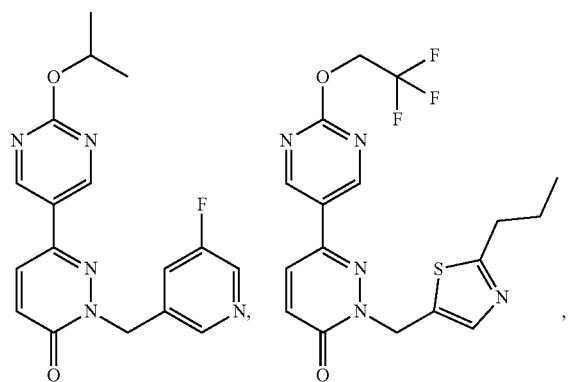
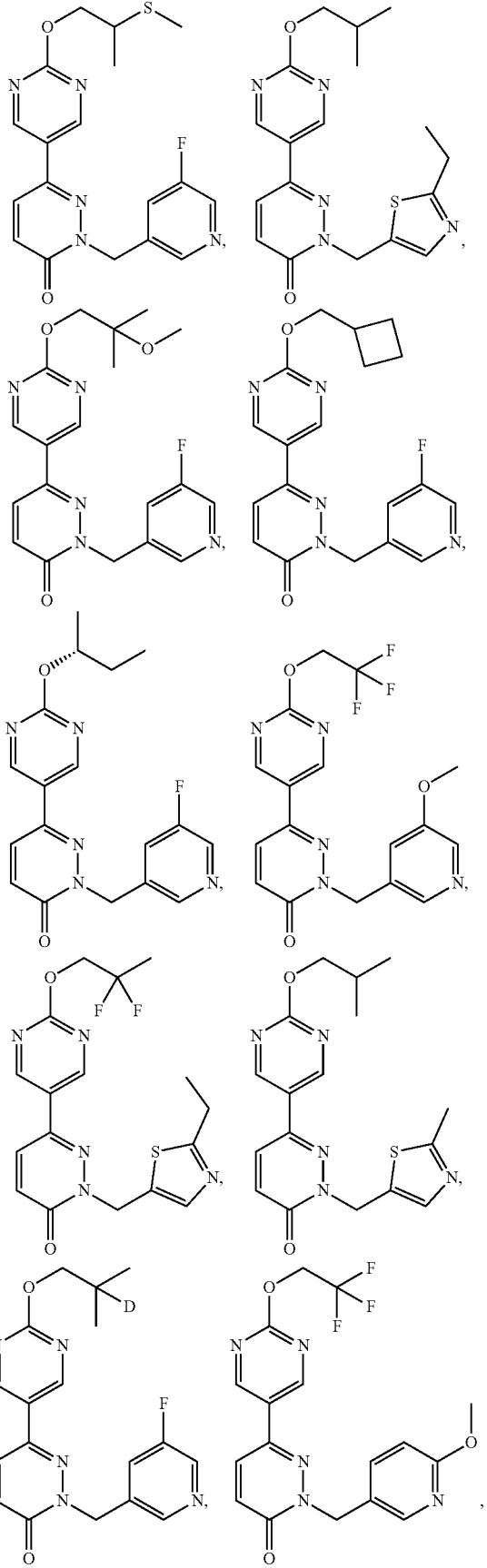

281
-continued

282
-continued

-continued

285
-continued
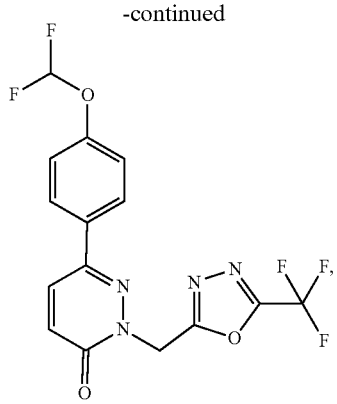
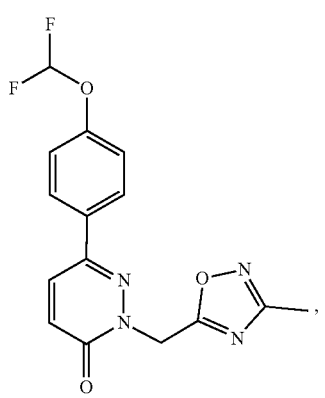
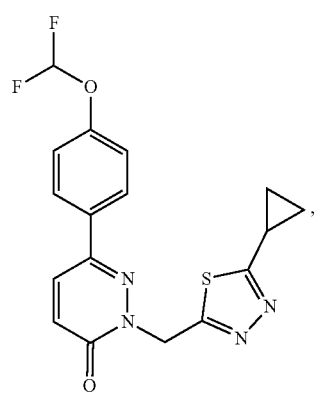
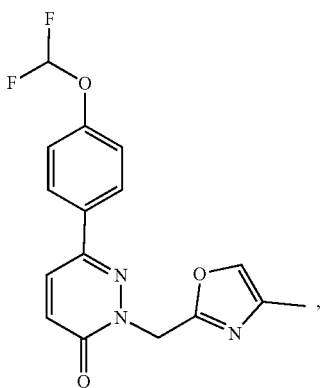
286
-continued
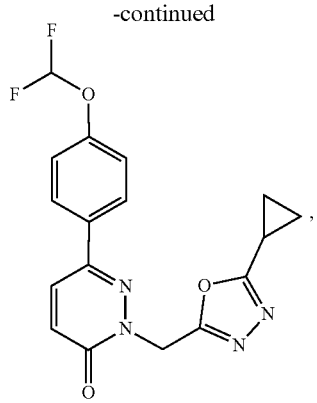
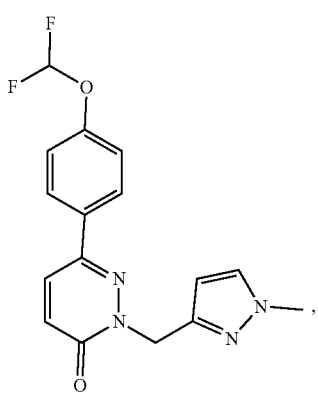

287
-continued
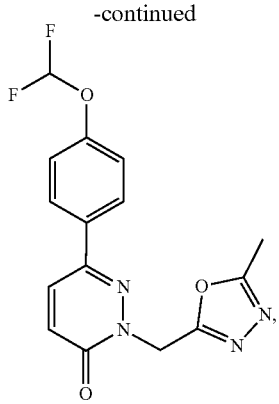
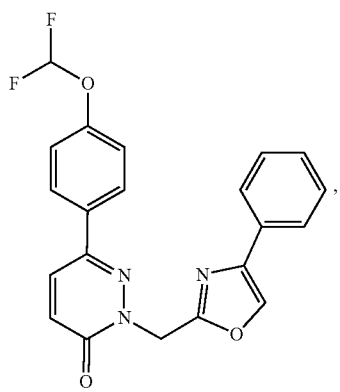
288
-continued
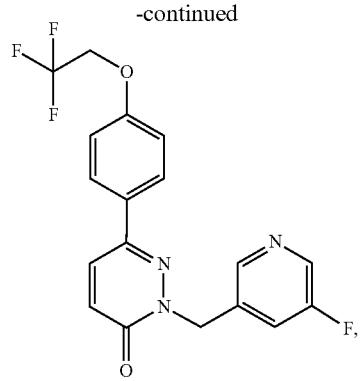
and
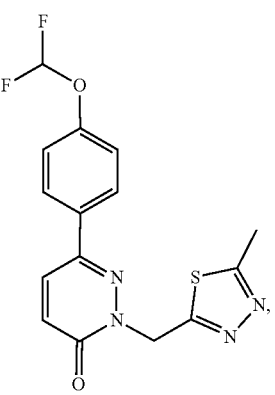 [SMILES: Cc1nnc(Cn2nc(-c3ccc(OC(F)F)cc3)ccc2=O)s1]
or a salt thereof.
* * * * *